US008597892B2

(12) United States Patent
Shelton et al.

(10) Patent No.: US 8,597,892 B2
(45) Date of Patent: Dec. 3, 2013

(54) MIRNA BIOMARKERS OF PROSTATE DISEASE

(75) Inventors: Jeffrey Shelton, Buda, TX (US); Kevin Kelnar, Kyle, TX (US); Stephanie Volz, Austin, TX (US); Alex Adai, Austin, TX (US); David Brown, Austin, TX (US)

(73) Assignee: Asuragen, Inc., Austin, TX (US)

( * ) Notice: Subject to any disclaimer, the term of this patent is extended or adjusted under 35 U.S.C. 154(b) by 459 days.

(21) Appl. No.: 12/785,216

(22) Filed: May 21, 2010

(65) Prior Publication Data

US 2010/0297652 A1 Nov. 25, 2010

Related U.S. Application Data

(60) Provisional application No. 61/180,760, filed on May 22, 2009.

(51) Int. Cl.
*C12Q 1/68* (2006.01)
(52) U.S. Cl.
USPC .......................................... 435/6.14
(58) Field of Classification Search
None
See application file for complete search history.

(56) References Cited

U.S. PATENT DOCUMENTS

| | | | |
|---|---|---|---|
| 6,713,619 B1 | 3/2004 | Weinberg et al. | |
| 2006/0204989 A1 | 9/2006 | Kopreski | |
| 2008/0306006 A1 | 12/2008 | Croce et al. | |
| 2009/0075258 A1 | 3/2009 | Latham et al. | |
| 2009/0131348 A1* | 5/2009 | Labourier et al. | 514/44 |
| 2010/0173288 A1 | 7/2010 | Zhang et al. | |

FOREIGN PATENT DOCUMENTS

| | | |
|---|---|---|
| EP | 2133431 | 12/2009 |
| EP | 2133431 A1 | 12/2009 |
| WO | WO 2005/118806 | 12/2005 |
| WO | WO 2008/112283 A2 | 9/2008 |
| WO | WO 2009/055979 | 5/2009 |
| WO | WO 2009/108860 A2 | 9/2009 |
| WO | WO 2009/108860 A3 | 9/2009 |
| WO | WO 2009/143379 A2 | 11/2009 |
| WO | WO 2010/004562 | 1/2010 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Ambs et al., "Genomic Profiling of MicroRNA and Messenger RNA Reveals Deregulated MicroRNA Expression in Prostate Cancer," *Cancer Res.* 68(15):6162-6170 (2008).
Bianchi, "Circulating Fetal DNA: Its Origin and Diagnostic Potential—A Review," *Placenta* 25 Suppl. A:S93-S101 (2004).
Bremnes et al., "Circulating tumour-derived DNA and RNA markers in blood: a tool for early detection, diagnostics, and follow-up?," *Lung Cancer* 49:1-12 (2005).
Bussemakers et al., "DD3: A New Prostate-specific Gene, Highly Overexpressed in Prostate Cancer[1]," *Canc. Res.* 59:5975-5979 (1999).
Chen et al., "Telomerase RNA as a detection marker in the serum of breast cancer patients," *Clin. Cancer Res.* 6:3823-3826 (2000).
Chen et al., "Real-time quantification of microRNAs by stem-loop RT-PCR," *Nucl. Acids Res.* 33(20):e179 (2005).
Chen et al., "Characterization of microRNAs in serum: a novel class of biomarkers for diagnosis of cancer and other diseases," *Cell Res.* 18:997-1006 (2008).
Chim et al., "Detection and Characterization of Placental MircoRNAs in Maternal Plasma," *Clin. Chem.* 54:482 (2008).
Dasi et al., "Real-time quantification in plasma of human telomerase reverse transcriptase (hTERT) mRNA: a simple blood test to monitor disease in cancer patients," *Lab Invest.* 81:767-769 (2001).
De Kok et al., "DD3$^{PCA3}$, a Very Sensitive and Specific Marker to Detect Prostate Tumors," *Cancer Res.* 62:2695-2698 (2002).
Dodd et al., "Partial AUC Estimation and Regression," *Biometrics* 59:614-623 (2003).
Esquela-Kerscher et al., "The *let-7* microRNA reduces tumor growth in mouse models of lung cancer," *Cell Cycle* 7(6):759-764 (2008).
Fabbri et al., "MicroRNAs," *Cancer J.* 14:1-6 (2008).
Fradet et al., "uPM3, A new molecular urine test for the detection of Prostate Cancer," *Urology* 64:311-316 (2004).
Gandellini et al., "miR-205 Exerts Tumor-Suppressive Functions in Human prostate through Down-regulation of Protein Kinase Cε," *Cancer Res.* 69(6):2287-2295 (2009).
Garofalo et al., "MicroRNA signatures of TRAIL resistance in human non-small cell lung cancer," *Oncogene* 27:3845-3855 (2008).
Hessels et al., "DD3$^{PCA3}$-based Molecular Urine Analysis for the Diagnosis of Prostate Cancer," *Eur. Urol.* 44:8-15, discussion 15-16 (2003).
Jahr et al., "DNA Fragments in the Blood Plasma of Cancer Patients: Quantitations and Evidence for Their Origin from Apoptotic and Necrotic Cells[1]," *Cancer Res.* 61:1659-1665 (2001).
Kurreck et al., "Ántisense technologies: Improvement through novel chemical modifications," *Eur. J. Biochem.* 270:1628-1644 (2003).
Lawrie et al., "Detection of elevated levels of tumour-associated microRNAs in serum of patients with diffuse large B-cell lymphoma," *Br. J. Haematol.* 141:672-675 (2008).
Markou et al., "Prognostic Value of Mature MicroRNA-21 and MicroRNA-205 Overexpression in Non-Small Cell Lung Cancer by Quantitative Real-Time RT-PCR," *Clin. Chem.* 54(10):1696-1704 (2008).
Mattie et al., "Optimized high-throughput microRNA expression profiling provides novel biomarker assessment of clinical prostate and breast cancer biopsies," *Molecular Cancer* 5:24-39 (2006).

(Continued)

*Primary Examiner* — James Martinell
(74) *Attorney, Agent, or Firm* — Finnegan, Henderson, Farabow, Garrett & Dunner, LLP

(57) ABSTRACT

This application describes miRNAs that may be used as serum or plasma biomarkers for characterizing prostate disease in a patient. These miRNA biomarkers may be used alone or in combination with other markers for the diagnosis, prognosis, or monitoring of diseases such as prostate cancer.

9 Claims, 18 Drawing Sheets

(56) References Cited

OTHER PUBLICATIONS

Mitchell et al., "Circulating microRNAs as stable blood-based markers for cancer detection," *Proc. Natl. Acad. Sci. USA* 105(30):10513-10518 (2008); Supporting Information, pp. 1-29.

Okada et al., "Prognostic Significance of Perioperative Serum Carcinoembryonic Antigen in Non-Small Cell Lung Cancer: Analysis of 1,000 Consecutive Resections for Clinical Stage I Disease," *Ann. Thorac. Surg.* 78:216-221 (2004).

Ozen et al., "Widespread deregulation of microRNA expression in human prostate cancer," *Oncogene* 27:1788-1793 (2008).

Pepe et al., "Combining Predictors for Classification Using the Area under the Receiver Operating Characteristic Curve," *Biometrics* 62:221-229 (2006).

Porkka et al., "MicroRNA Expression Profiling in Prostate Cancer," *Cancer Res* 67(13):6130-6135 (2007).

Prueitt et al., "Expression of MicroRNAs and Protein-Coding Genes Associated With Perineural Invasion in Prostate Cancer," *The Prostate* 68:1152-1164 (2008).

Ramirez et al., "Ethylation patterns and K-ras mutations in tumor and paired serum of resected non-small cell lung cancer patients," *Cancer Lett.* 193:207-216 (2003).

Schickel et al., "MicroRNAs: key players in the immune system, differentiation, tumorigenesis and cell death," *Oncogene* 27:5959-5974 (2008).

Schneider et al., "Tumor markers in detection of lung cancer," *Adv. Clin. Chem.* 42:1-41 (2006).

Shi et al., "microRNAs and prostate cancer," *J. Cell. Mol. Med.* 12(5A):1456-1465 (2008).

Siemes et al., "C-Reactive Protein Levels, Variation in the c_reactive Protein Gene, and Cancer Risk: The Rotterdam Study," *J. Clin. Oncol.* 24:16-22 (2006).

Tong et al., "MicroRNA profile analysis of human prostate cancers," *Cancer Gene Therapy* 16:206-216 (2009).

Weiss et al., "EGFR regulation by microRNA in lung cancer: correlation with clinical response and survival to gefitinib and EGFR expression in cell lines," *Ann Oncol.* 19:1053-1059 (2008).

Yanaihara et al. "Unique microRNA molecular profiles in lung cancer diagnosis and prognosis," *Cancer Cell* 9(3):189-198 (2006).

Yu et al., "MicroRNA Signature Predicts Survival and Relapse in Lung Cancer," *Cancer Cell* 13(1):48-57 (2008).

Greenberg et al., "Biomarkers for lung cancer: clinical uses." *Current Opin. Pulm. Med.* 13:249-255 (2007).

Jackson, "Serum-based microRNAs: Are we blinded by potential?" *PNAS* 106:1 (Jan. 6, 2009).

Ji et al., "Plasma miR-208 as a Biomarker of Myocardial Injury," *Clinical Chemistry* 55(11):1944-1949 (2009).

International Search Report and Written Opinion for PCT/US10/035839, dated Jan. 25, 2011.

Li et al., "Serum Circulating Human mRNA Profiling and Its Utility for Oral Cancer Detection," *J. Clinical Oncology* 24(11):1754-1760 (2006).

Lodes et al., "Detection of Cancer with Serum miRNAs on an Oligonucleotide Microarray," *PLoS ONE* 4(7):e6229:1-12 (2009).

Press Release, CombiMATRIX Corporation, "CombiMatrix Announces Positive Preliminary Data on Non-Invasive, Cancer Screening Test," GlobeNewswire via COMTEX News Network, (Feb. 26, 2009).

Tanaka et al., "Down-Regulation of miR-92 in Human Plasma Is a Novel Marker for Acute Leukemia Patients," *PLoS ONE* 4(7):(e5532):1-5 (2009).

Suciu et al., "Detection of Cancer with Serum miRNAs on an Oligonucleotide Microarray" Poster presented at Cambridge Healthtech Institute's 16th International Molecular Medicine Tri-Conference, Feb. 25-27, 2009, in San Francisco.

Alhasan et al., "Scanometric MicroRNA Array Profiling of Prostate Cancer Markers Using Spherical Nucleic Acid—Gold Nanoparticle Conjugates," *Anal. Chem.*, 84:4153-4160 (2012).

Arroyo et al., "Argonaute2 complexes carry a population of circulating microRNAs independent of vesicles in human plasma," *PNAS*, 108(12):5003-5008 (Mar. 22, 2011).

Brase et al., "Circulating miRNAs are correlated with tumor progression in prostate cancer," *Int. J. Cancer*, 128:608-616 (2011).

Chen et al., "A Panel of Five Circulating MicroRNAs as Potential Biomarkers for Prostate Cancer," *The Prostate*, 72:1443-1452 (2012).

International Patent Application No. PCT/CN2007/003463: International Application Status Report, dated Apr. 24, 2009 (2 pages).

Mahn et al., "Circulating microRNAs (miRNA) in Serum of Patients with Prostate Cancer," *Urology*, 77(5):1265.e9-1265e16 (2011).

Moltzahn et al., "Microfluidic-Based Multiplex qRT-PCR Identifies Diagnostic and Prognostic microRNA Signatures in the Sera of Prostate Cancer Patients," *Cancer Res.*, 71(2):550-560 (Jan. 15, 2011).

Nguyen et al., "Expression Differences of Circulating microRNAs in Metastatic Castration Resistant Prostate Cancer and Low-Risk, Localized Prostate Cancer," *The Prostate*, 73:346-354 (2013).

Selth et al, "Discovery of circulating microRNAs associated with human prostate cancer using a mouse model of disease," *Int. J. Cancer*, 131:652-661 (2012).

Selth et al., "Circulating microRNAs: macro-utility as markers of prostate cancer?," *Endocrine-Related Cancer*, 19:R99-R113 (2012).

Tong at al, "MicroRNA profile analysis of human prostate cancers," *Cancer Gene Therapy*, 16:206-216 (2009).

Devere-White et al., "MicroRNAs and their potential for translation in prostate cancer," *Urologic Oncology: Seminars and Original Investigations*, 27:307-311 (2009).

Extended European Search Report for European Patent Application No. 13161685.6, dated Aug. 5, 2013, 17 pages.

Le et al., "MicroRNA-125b is a novel negative regulator of p53," *Genes & Development*, 23:862-876 (2009).

Lee et al., "Depletion of Human Micro-RNA miR-125b Reveals That It Is Critical For the Proliferation of Differentiated Cells but Not for the Down-regulation of Putative Targets during Differentiation," The Journal of Biological Chemistry, 280(17):16635-16641 (2005).

Mirnezami et al., "MicroRNAs: Key players in carcinogenesis and novel therapeutic targets," EJSO, 35:339-347 (2009).

Reynolds et al., "Molecular markers for prostate cancer," Cancer Letters, 249:5-13 (2007).

Shi et al., "An androgen-regulated miRNA suppresses Bak1 expression and induces androgen-independent growth of prostate cancer cells," PNAS, 104(50):19983-19988 (Dec. 11, 2007).

Shi et al., "Suppression of Key Apoptosis-Related Molecules by MIR-125B Contributes to Androgen-Independent Growth of Prostate Cancer Cells," The Journal of Urology, 181(4 Suppl.):93, Abstract 251 (Apr. 26, 2009).

* cited by examiner

| pre-miRNA | Sequence | Mature miRNAs from Tables 1 and 20 |
|---|---|---|
| let-7a-1 | UGGGAUGAGGUAGUAGGUUGUAUAGUUUUAGGGUCACACCCACCAC UGGGAGAUAACUAUACAAUCUACUGUCUUUCCUA | let-7a |
| let-7a-2 | AGGUUGAGGUAGUAGGUUGUAUAGUUUAGAAUUACAUCAAGGGAGA UAACUGUACAGCCUCCUAGCUUUCCU | let-7a |
| let-7a-3 | GGGUGAGGUAGUAGGUUGUAUAGUUUGGGGCUCUGCCCUGCUAUGG GAUAACUAUACAAUCUACUGUCUUUCCU | let-7a |
| let-7b | CGGGGUGAGGUAGUAGGUUGUGUGGUUUCAGGGCAGUGAUGUUGCC CCUCGGAAGAUAACUAUACAACCUACUGCCUUCCCUG | let-7b |
| let-7c | GCAUCCGGGUUGAGGUAGUAGGUUGUAUGGUUUAGAGUUACACCCU GGGAGUUAACUGUACAACCUUCUAGCUUUCCUUGGAGC | let-7c |
| let-7d | CCUAGGAAGAGGUAGUAGGUUGCAUAGUUUUAGGGCAGGGAUUUUG CCCACAAGGAGGUAACUAUACGACCUGCUGCCUUUCUUAGG | let-7d |
| let-7e | CCCGGGCUGAGGUAGGAGGUUGUAUAGUUGAGGAGGACACCCAAGG AGAUCACUAUACGGCCUCCUAGCUUUCCCCAGG | let-7e |
| let-7f-1 | UCAGAGUGAGGUAGUAGAUUGUAUAGUUGUGGGGUAGUGAUUUUAC CCUGUUCAGGAGAUAACUAUACAAUCUAUUGCCUUCCCUGA | let-7f |
| let-7f-2 | UGUGGGAUGAGGUAGUAGAUUGUAUAGUUUUAGGGUCAUACCCCAU CUUGGAGAUAACUAUACAGUCUACUGUCUUUCCCACG | let-7f |
| let-7g | AGGCUGAGGUAGUAGUUUGUACAGUUUGAGGGUCUAUGAUACCACC CGGUACAGGAGAUAACUGUACAGGCCACUGCCUUGCCA | let-7g |
| let-7i | CUGGCUGAGGUAGUAGUUUGUGCUGUUGGUCGGGUUGUGACAUUGC CCGCUGUGGAGAUAACUGCGCAAGCUACUGCCUUGCUA | let-7i |
| miR-1-1 | UGGGAAACAUACUUCUUUAUAUGCCCAUAUGGACCUGCUAAGCUAU GGAAUGUAAAGAAGUAUGUAUCUCA | miR-1 |
| miR-1-2 | ACCUACUCAGAGUACAUACUUCUUUAUGUACCCAUAUGAACAUACA AUGCUAUGGAAUGUAAAGAAGUAUGUAUUUUUGGUAGGC | miR-1 |
| miR-100 | CCUGUUGCCACAAACCCGUAGAUCCGAACUUGUGGUAUUAGUCCGC ACAAGCUUGUAUCUAUAGGUAUGUGUCUGUUAGG | miR-100 |
| miR-101-1 | UGCCCUGGCUCAGUUAUCACAGUGCUGAUGCUGUCUAUUCUAAAGG UACAGUACUGUGAUAACUGAAGGAUGGCA | miR-101 |
| miR-101-2 | ACUGUCCUUUUUCGGUUAUCAUGGUACCGAUGCUGUAUAUCUGAAA GGUACAGUACUGUGAUAACUGAAGAAUGGUGGU | miR-101 |
| miR-103-1 | UACUGCCCUCGGCUUCUUUACAGUGCUGCCUUGUUGCAUAUGGAUC AAGCAGCAUUGUACAGGGCUAUGAAGGCAUUG | miR-103 |
| miR-103-2 | UUGUGCUUUCAGCUUCUUUACAGUGCUGCCUUGUAGCAUUCAGGUC AAGCAGCAUUGUACAGGGCUAUGAAAGAACCA | miR-103 |
| miR-105-1 | UGUGCAUCGUGGUCAAAUGCUCAGACUCCUGUGGUGGCUGCUCAUG CACCACGGAUGUUUGAGCAUGUGCUACGGUGUCUA | miR-105 |
| miR-105-2 | UGUGCAUCGUGGUCAAAUGCUCAGACUCCUGUGGUGGCUGCUUAUG CACCACGGAUGUUUGAGCAUGUGCUAUGGUGUCUA | miR-105 |

Figure 1A

| | | |
|---|---|---|
| miR-106a | CCUUGGCCAUGUAAAAGUGCUUACAGUGCAGGUAGCUUUUUGAGAUCUACUGCAAUGUAAGCACUUCUUACAUUACCAUGG | miR-106a |
| miR-106b | CCUGCCGGGGCUAAAGUGCUGACAGUGCAGAUAGUGGUCCUCUCCGUGCUACCGCACUGUGGGUACUUGCUGCUCCAGCAGG | miR-106b |
| miR-107 | CUCUCUGCUUUCAGCUUCUUUACAGUGUUGCCUUGUGGCAUGGAGUUCAAGCAGCAUUGUACAGGGCUAUCAAAGCACAGA | miR-107 |
| miR-10a | GAUCUGUCUGUCUUCUGUAUAUACCCUGUAGAUCCGAAUUUGUGUAAGGAAUUUUGUGGUCACAAAUUCGUAUCUAGGGGAAUAUGUAGUUGACAUAAACACUCCGCUCU | miR-10a |
| miR-10b | CCAGAGGUUGUAACGUUGUCUAUAUAUACCCUGUAGAACCGAAUUUGUGUGGUAUCCGUAUAGUCACAGAUUCGAUUCUAGGGGAAUAUAUGGUCGAUGCAAAAACUUCA | miR-10b |
| miR-122 | CCUUAGCAGAGCUGUGGAGUGUGACAAUGGUGUUUGUGUCUAAACUAUCAAACGCCAUUAUCACACUAAAUAGCUACUGCUAGGC | miR-122a (also called miR-122) |
| miR-124-1 | AGGCCUCUCUCUCCGUGUUCACAGCGGACCUUGAUUUAAAUGUCCAUACAAUUAAGGCACGCGGUGAAUGCCAAGAAUGGGGCUG | miR-124a (also called miR-124) |
| miR-124-2 | AUCAAGAUUAGAGGCUCUGCUCUCCGUGUUCACAGCGGACCUUGAUUUAAUGUCAUACAAUUAAGGCACGCGGUGAAUGCCAAGAGCGGAGCCUACGGCUGCACUUGAA | miR-124a (also called miR-124) |
| miR-124-3 | UGAGGGCCCCUCUGCGUGUUCACAGCGGACCUUGAUUUAAAUGUCUAUACAAUUAAGGCACGCGGUGAAUGCCAAGAGAGGCGCCUCC | miR-124a (also called miR-124) |
| miR-125a | UGCCAGUCUCUAGGUCCCUGAGACCCUUUAACCUGUGAGGACAUCCAGGGUCACAGGUGAGGUUCUUGGGAGCCUGGCGUCUGGCC | miR-125a |
| miR-125b-1 | UGCGCUCCUCUCAGUCCCUGAGACCCUAACUUGUGAUGUUUACCGUUUAAAUCCACGGGUUAGGCUCUUGGGAGCUGCGAGUCGUGCU | miR-125b |
| miR-125b-2 | ACCAGACUUUUCCUAGUCCCUGAGACCCUAACUUGUGAGGUAUUUUAGUAACAUCACAAGUCAGGCUCUUGGGACCUAGGCGGAGGGGA | miR-125b |
| miR-126 | CGCUGGCGACGGGACAUUAUUACUUUUGGUACGCGCUGUGACACUUCAAACUCGUACCGUGAGUAAUAAUGCGCCGUCCACGGCA | miR-126; miR-126* |
| miR-127 | UGUGAUCACUGUCUCCAGCCUGCUGAAGCUCAGAGGGCUCUGAUUCAGAAAGAUCAUCGGAUCCGUCUGAGCUUGGCUGGUCGGAAGUCUCAUCAUC | miR-127 |
| miR-128-1 | UGAGCUGUUGGAUUCGGGGCCGUAGCACUGUCUGAGAGGUUUACAUUUCUCACAGUGAACCGGUCUCUUUUUCAGCUGCUUC | miR-128a |
| miR-128-2 | UGUGCAGUGGGAAGGGGGGCCGAUACACUGUACGAGAGUGAGUAGCAGGUCUCACAGUGAACCGGUCUCUUUCCCUACUGUGUC | miR-128b |
| miR-129-1 | GGAUCUUUUUGCGGUCUGGGCUUGCUGUUCCUCUCAACAGUAGUCAGGAAGCCCUUACCCCAAAAAGUAUCU | miR-129 |
| miR-129-2 | UGCCCUUCGCGAAUCUUUUUGCGGUCUGGGCUUGCUGUACAUAACUCAAUAGCCGGAAGCCCUUACCCCAAAAAGCAUUUGCGGAGGGCG | miR-129 |
| miR-130a | UGCUGCUGGCCAGAGCUCUUUUCACAUUGUGCUACUGUCUGCACCUGUCACUAGCAGUGCAAUGUUAAAAGGGCAUUGGCCGUGUAGUG | miR-130a |
| miR-130b | GGCCUGCCCGACACUCUUUCCCUGUUGCACUACUAUAGGCCGCUGGGAAGCAGUGCAAUGAUGAAAGGGCAUCGGUCAGGUC | miR-130b |

Figure 1B

| | | |
|---|---|---|
| miR-132 | CCGCCCCCGCGUCUCCAGGGCAACCGUGGCUUUCGAUUGUUACUGU GGGAACUGGAGGUAACAGUCUACAGCCAUGGUCGCCCCGCAGCACG CCCACGCGC | miR-132 |
| miR-133a-1 | ACAAUGCUUUGCUAGAGCUGGUAAAAUGGAACCAAAUCGCCUCUUC AAUGGAUUUGGUCCCCUUCAACCAGCUGUAGCUAUGCAUUGA | miR-133a |
| miR-133a-2 | GGGAGCCAAAUGCUUUGCUAGAGCUGGUAAAAUGGAACCAAAUCGA CUGUCCAAUGGAUUUGGUCCCCUUCAACCAGCUGUAGCUGUGCAUU GAUGGCGCCG | miR-133a |
| miR-133b | CCUCAGAAGAAAGAUGCCCCCUGCUCUGGCUGGUCAAACGGAACCA AGUCCGUCUUCCUGAGAGGUUUGGUCCCCUUCAACCAGCUACAGCA GGGCUGGCAAUGCCCAGUCCUUGGAGA | miR-133b |
| miR-134 | CAGGGUGUGUGACUGGUUGACCAGAGGGGCAUGCACUGUGUUCACC CUGUGGGCCACCUAGUCACCAACCCUC | miR-134 |
| miR-135a-1 | AGGCCUCGCUGUUCUCUAUGGCUUUUUAUUCCUAUGUGAUUCUACU GCUCACUCAUAUAGGGAUUGGAGCCGUGGCGCACGGCGGGGACA | miR-135a |
| miR-135a-2 | AGAUAAAUUCACUCUAGUGCUUUAUGGCUUUUUAUUCCUAUGUGAU AGUAAUAAAGUCUCAUGUAGGGAUGGAAGCCAUGAAAUACAUUGUG AAAAAUCA | miR-135a |
| miR-135b | CACUCUGCUGUGGCCUAUGGCUUUUCAUUCCUAUGUGAUUGCUGUC CCAAACUCAUGUAGGGCUAAAAGCCAUGGGCUACAGUGAGGGCGA GCUCC | miR-135b |
| miR-136 | UGAGCCCUCGGAGGACUCCAUUUGUUUUGAUGAUGGAUUCUUAUGC UCCAUCAUCGUCUCAAAUGAGUCUUCAGAGGGUUCU | miR-136 |
| miR-137 | GGUCCUCUGACUCUCUUCGGUGACGGGUAUUCUUGGGUGGAUAAUA CGGAUUACGUUGUUAUUGCUUAAGAAUACGCGUAGUCGAGGAGAGU ACCAGCGGCA | miR-137 |
| miR-138-1 | CCCUGGCAUGGUGUGGUGGGGCAGCUGGGUGUUGUGAAUCAGGCCGU UGCCAAUCAGAGAACGGCUACUUCACAACACCAGGGCCACACCACA CUACAGG | miR-138 |
| miR-138-2 | CGUUGCUGCAGCUGGUGUUGUGAAUCAGGCCGACGAGCAGCGCAUC CUCUUACCCGGCUAUUUCACGACACCAGGGUUGCAUCA | miR-138 |
| miR-139 | GUGUAUUCUACAGUGCACGUGUCUCCAGUGUGGCUCGGAGGCUGGA GACGCGGCCCUGUUGGAGUAAC | miR-139 |
| miR-140 | UGUGUCUCUCUCUGUGUCCUGCCAGUGGUUUUACCCUAUGGUAGGU UACGUCAUGCUGUUCUACCACAGGGUAGAACCACGGACAGGAUACC GGGGCACC | miR-140 |
| miR-141 | CGGCCGGCCCUGGGUCCAUCUUCCAGUACAGUGUUGGAUGGUCUAA UUGUGAAGCUCCUAACACUGUCUGGUAAAGAUGGCUCCCGGGUGGG UUC | miR-141 |
| miR-142 | GACAGUGCAGUCACCCAUAAAGUAGAAAGCACUACUAACAGCACUG GAGGGUGUAGUGUUUCCUACUUUAUGGAUGAGUGUACUGUG | miR-142-3p; miR-142-5p |
| miR-143 | GCGCAGCGCCCUGUCUCCCAGCCUGAGGUGCAGUGCUGCAUCUCUG GUCAGUUGGGAGUCUGAGAUGAAGCACUGUAGCUCAGGAAGAGAGA AGUUGUUCUGCAGC | miR-143 |
| miR-145 | CACCUUGUCCUCACGGUCCAGUUUUCCCAGGAAUCCCUUAGAUGCU AAGAUGGGGAUUCCUGGAAAUACUGUUCUUGAGGUCAUGGUU | miR-145 |

Figure 1C

| | | |
|---|---|---|
| miR-146a | CCGAUGUGUAUCCUCAGCUUUGAGAACUGAAUUCCAUGGGUUGUGU CAGUGUCAGACCUCUGAAAUUCAGUUCUUCAGCUGGGAUAUCUCUG UCAUCGU | miR-146a |
| miR-146b | CCUGGCACUGAGAACUGAAUUCCAUAGGCUGUGAGCUCUAGCAAUG CCCUGUGGACUCAGUUCUGGUGCCCGG | miR-146b |
| miR-147 | AAUCUAAAGACAACAUUUCUGCACACACACCAGACUAUGGAAGCCA GUGUGUGGAAAUGCUUCUGCUAGAUU | miR-147 |
| miR-147b | UAUAAAUCUAGUGGAAACAUUUCUGCACAAACUAGAUUCUGGACAC CAGUGUGCGGAAAUGCUUCUGCUACAUUUUUAGG | miR-147b |
| miR-148a | GAGGCAAAGUUCUGAGACACUCCGACUCUGAGUAUGAUAGAAGUCA GUGCACUACAGAACUUUGUCUC | miR-148a |
| miR-148b | CAAGCACGAUUAGCAUUUGAGGUGAAGUUCUGUUAUACACUCAGGC UGUGGCUCUCUGAAAGUCAGUGCAUCACAGAACUUUGUCUCGAAAG CUUUCUA | miR-148b |
| miR-149 | GCCGGCGCCCGAGCUCUGGCUCCGUGUCUUCACUCCCGUGCUUGUC CGAGGAGGGAGGGAGGGACGGGGGCUGUGCUGGGGCAGCUGGA | miR-149 |
| miR-150 | CUCCCCAUGGCCCUGUCUCCCAACCCUUGUACCAGUGCUGGGCUCA GACCCUGGUACAGGCCUGGGGGACAGGGACCUGGGGAC | miR-150 |
| miR-151 | UUUCCUGCCCUCGAGGAGCUCACAGUCUAGUAUGUCUCAUCCCCUA CUAGACUGAAGCUCCUUGAGGACAGGGAUGGUCAUACUCACCUC | miR-151 |
| miR-152 | UGUCCCCCCCGGCCCAGGUUCUGUGAUACACUCCGACUCGGGCUCU GGAGCAGUCAGUGCAUGACAGAACUUGGGCCCGGAAGGACC | miR-152 |
| miR-153-1 | CUCACAGCUGCCAGUGUCAUUUUUGUGAUCUGCAGCUAGUAUUCUC ACUCCAGUUGCAUAGUCACAAAAGUGAUCAUUGGCAGGUGUGGC | miR-153 |
| miR-153-2 | AGCGGUGGCCAGUGUCAUUUUUGUGAUGUUGCAGCUAGUAAUAUGA GCCCAGUUGCAUAGUCACAAAAGUGAUCAUUGGAAACUGUG | miR-153 |
| miR-154 | GUGGUACUUGAAGAUAGGUUAUCCGUGUUGCCUUCGCUUUAUUUGU GACGAAUCAUACACGGUUGACCUAUUUUUCAGUACCAA | miR-154; miR-154* |
| miR-155 | CUGUUAAUGCUAAUCGUGAUAGGGGUUUUUGCCUCCAACUGACUCC UACAUAUUAGCAUUAACAG | miR-155 |
| miR-15a | CCUUGGAGUAAAGUAGCAGCACAUAAUGGUUUGUGGAUUUUGAAAA GGUGCAGGCCAUAUUGUGCUGCCUCAAAAAUACAAGG | miR-15a |
| miR-15b | UUGAGGCCUUAAAGUACUGUAGCAGCACAUCAUGGUUUACAUGCUA CAGUCAAGAUGCGAAUCAUUAUUUGCUGCUCUAGAAAUUUAAGGAA AUUCAU | miR-15b |
| miR-16-1 | GUCAGCAGUGCCUUAGCAGCACGUAAAUAUUGGCGUUAAGAUUCUA AAAUUAUCUCCAGUAUUAACUGUGCUGCUGAAGUAAGGUUGAC | miR-16 |
| miR-16-2 | GUUCCACUCUAGCAGCACGUAAAUAUUGGCGUAGUGAAAUAUAUAU UAAACACCAAUAUUACUGUGCUGCUUUAGUGUGAC | miR-16 |
| miR-17 | GUCAGAAUAAUGUCAAAGUGCUUACAGUGCAGGUAGUGAUAUGUGC AUCUACUGCAGUGAAGGCACUUGUAGCAUUAUGGUGAC | miR-17-3p; miR-17-5p |
| miR-181a-1 | UGAGUUUUGAGGUUGCUUCAGUGAACAUUCAACGCUGUCGGUGAGU UUGGAAUUAAAAUCAAAACCAUCGACCGUUGAUUGUACCCUAUGGC UAACCAUCAUCUACUCCA | miR-181a; miR-213 (also called miR-181a*) |

Figure 1D

| | | |
|---|---|---|
| miR-181a-2 | AGAAGGGCUAUCAGGCCAGCCUUCAGAGGACUCCAAGGAACAUUCAACGCUGUCGGUGAGUUUGGGAUUUGAAAAAACCACUGACCGUUGACUGUACCUUGGGGUCCUUA | miR-181a |
| miR-181b-1 | CCUGUGCAGAGAUUAUUUUUUAAAAGGUCACAAUCAACAUUCAUUGCUGUCGGUGGGUUGAACUGUGUGGACAAGCUCACUGAACAAUGAAUGCAACUGUGGCCCCGCUU | miR-181b |
| miR-181b-2 | CUGAUGGCUGCACUCAACAUUCAUUGCUGUCGGUGGGUUUGAGUCUGAAUCAACUCACUGAUCAAUGAAUGCAAACUGCGGACCAAACA | miR-181b |
| miR-181c | CGGAAAAUUUGCCAAGGGUUUGGGGGAACAUUCAACCUGUCGGUGAGUUUGGGCAGCUCAGGCAAACCAUCGACCGUUGAGUGGACCCUGAGGCCUGGAAUUGCCAUCCU | miR-181c |
| miR-181d | GUCCCCUCCCCUAGGCCACAGCCGAGGUCACAAUCAACAUUCAUUGUUGUCGGUGGGUUGUGAGGACUGAGGCCAGACCCACCGGGGGAUGAAUGUCACUGUGGCUGGGCCAGACACGGCUUAAGGGGAAUGGGGAC | miR-181d |
| miR-182 | GAGCUGCUUGCCUCCCCCCGUUUUUGGCAAUGGUAGAACUCACACUGGUGAGGUAACAGGAUCCGGUGGUUCUAGACUUGCCAACUAUGGGCGAGGACUCAGCCGGCAC | miR-182 |
| miR-183 | CCGCAGAGUGUGACUCCUGUUCUGUGUAUGGCACUGGUAGAAUUCACUGUGAACAGUCUCAGUCAGUGAAUUACCGAAGGGCCAUAAACAGAGCAGAGACAGAUCCACGA | miR-183 |
| miR-184 | CCAGUCACGUCCCCUUAUCACUUUUCCAGCCCAGCUUUGUGACUGUAAGUGUUGGACGGAGAACUGAUAAGGGUAGGUGAUUGA | miR-184 |
| miR-185 | AGGGGGCGAGGGAUUGGAGAGAAAGGCAGUUCCUGAUGGUCCCCUCCCCAGGGGCUGGCUUUCCUCUGGUCCUUCCCUCCCA | miR-185 |
| miR-186 | UGCUUGUAACUUUCCAAAGAAUUCUCCUUUUGGGCUUUCUGGUUUUAUUUUAAGCCCAAAGGUGAAUUUUUUGGGAAGUUUGAGCU | miR-186 |
| miR-187 | GGUCGGGCUCACCAUGACACAGUGUGAGACCUCGGGCUACAACACAGGACCCGGGCGCUGCUCUGACCCCUCGUGUCUUGUGUUGCAGCCGGAGGGACGCAGGUCCGCA | miR-187 |
| miR-188 | UGCUCCCUCUCUCACAUCCCUUGCAUGGUGGAGGGUGAGCUUUCUGAAAACCCCUCCCACAUGCAGGGUUUGCAGGAUGGCGAGCC | miR-188 |
| miR-18a | UGUUCUAAGGUGCAUCUAGUGCAGAUAGUGAAGUAGAUUAGCAUCUACUGCCCUAAGUGCUCCUUCUGGCA | miR-18a; miR-18a* |
| miR-18b | UGUGUUAAGGUGCAUCUAGUGCAGUUAGUGAAGCAGCUUAGAAUCUACUGCCCUAAAUGCCCCUUCUGGCA | miR-18b |
| miR-190 | UGCAGGCCUCUGUGUGAUAUGUUUGAUAUAUUAGGUUGUUAUUUAAUCCAACUAUAUAUCAAACAUAUUCCUACAGUGUCUUGCC | miR-190 |
| miR-191 | CGGCUGGACAGCGGGCAACGGAAUCCCAAAAGCAGCUGUUGUCUCCAGAGCAUUCCAGCUGCGCUUGGAUUUCGUCCCCUGCUCUCCUGCCU | miR-191 |
| miR-192 | GCCGAGACCGAGUGCACAGGGCUCUGACCUAUGAAUUGACAGCCAGUGCUCUCGUCUCCCCUCUGGCUGCCAAUUCCAUAGGUCACAGGUAUGUUCGCCUCAAUGCCAGC | miR-192 |
| miR-193a | CGAGGAUGGGAGCUGAGGGCUGGGUCUUUGCGGGCGAGAUGAGGGUGUCGGAUCAACUGGCCUACAAAGUCCCAGUUCUCGGCCCCCG | miR-193a |
| miR-193b | GUGGUCUCAGAACGGGGUUUUGAGGGCGAGAUGAGUUUAUGUUUUAUCCAACUGGCCCUCAAAGUCCCGCUUUUGGGGUCAU | miR-193b |

Figure 1E

| miR-194-1 | AUGGUGUUAUCAAGUGUAACAGCAACUCCAUGUGGACUGUGUACCA AUUUCCAGUGGAGAUGCUGUUACUUUUGAUGGUUACCAA | miR-194 |
|---|---|---|
| miR-194-2 | UGGUUCCCGCCCCCUGUAACAGCAACUCCAUGUGGAAGUGCCCACU GGUUCCAGUGGGGCUGCUGUUAUCUGGGGCGAGGGCCAG | miR-194 |
| miR-195 | AGCUUCCCUGGCUCUAGCAGCACAGAAAUAUUGGCACAGGGAAGCG AGUCUGCCAAUAUUGGCUGUGCUGCUCCAGGCAGGGUGGUG | miR-195 |
| miR-196a-1 | GUGAAUUAGGUAGUUUCAUGUUGUUGGGCCUGGGUUUCUGAACACA ACAACAUUAAACCACCCGAUUCAC | miR-196a |
| miR-196a-2 | UGCUCGCUCAGCUGAUCUGUGGCUUAGGUAGUUUCAUGUUGUUGGG AUUGAGUUUUGAACUCGGCAACAAGAAACUGCCUGAGUUACAUCAG UCGGUUUUCGUCGAGGGC | miR-196a |
| miR-196b | ACUGGUCGGUGAUUUAGGUAGUUUCCUGUUGUUGGGAUCCACCUUU CUCUCGACAGCACGACACUGCCUUCAUUACUUCAGUUG | miR-196b |
| miR-197 | GGCUGUGCCGGGUAGAGAGGGCAGUGGGAGGUAAGAGCUCUUCACC CUUCACCACCUUCUCCACCCAGCAUGGCC | miR-197 |
| miR-198 | UCAUGGUCCAGAGGGGAGAUAGGUUCCUGUGAUUUUUCCUUCUUC UCUAUAGAAUAAAUGA | miR-198 |
| miR-199a-1 | GCCAACCCAGUGUUCAGACUACCUGUUCAGGAGGCUCUCAAUGUGU ACAGUAGUCUGCACAUUGGUUAGGC | miR-199a (also called miR-199-5p); miR-199a* (also called miR-199-3p) |
| miR-199a-2 | AGGAAGCUUCUGGAGAUCCUGCUCCGUCGCCCCAGUGUUCAGACUA CCUGUUCAGGACAAUGCCGUUGUACAGUAGUCUGCACAUUGGUUAG ACUGGGCAAGGGAGAGCA | miR-199a (also called miR-199-5p); miR-199a* (also called miR-199-3p) |
| miR-199b | CCAGAGGACACCUCCACUCCGUCUACCCAGUGUUUAGACUAUCUGU UCAGGACUCCCAAAUUGUACAGUAGUCUGCACAUUGGUUAGGCUGG GCUGGGUUAGACCCUCGG | miR-199b |
| miR-19a | GCAGUCCUCUGUUAGUUUUGCAUAGUUGCACUACAAGAAGAAUGUA GUUGUGCAAAUCUAUGCAAAACUGAUGGUGGCCUGC | miR-19a |
| miR-19b-1 | CACUGUUCUAUGGUUAGUUUUGCAGGUUUGCAUCCAGCUGUGUGAU AUUCUGCUGUGCAAAUCCAUGCAAAACUGACUGUGGUAGUG | miR-19b |
| miR-19b-2 | ACAUUGCUACUUACAAUUAGUUUUGCAGGUUUGCAUUUCAGCGUAU AUAUGUAUAUGUGGCUGUGCAAAUCCAUGCAAAACUGAUUGUGAUA AUGU | miR-19b |
| miR-200a | CCGGGCCCCUGUGAGCAUCUUACCGGACAGUGCUGGAUUUCCCAGC UUGACUCUAACACUGUCUGGUAACGAUGUUCAAAGGUGACCCGC | miR-200a; miR-200a* |
| miR-200b | CCAGCUCGGGCAGCCGUGGCCAUCUUACUGGGCAGCAUUGGAUGGA GUCAGGUCUCUAAUACUGCCUGGUAAUGAUGACGGCGGAGCCCUGC ACG | miR-200b |
| miR-200c | CCCUCGUCUUACCCAGCAGUGUUUGGGUGCGGUUGGGAGUCUCUAA UACUGCCGGGUAAUGAUGGAGG | miR-200c |
| miR-202 | CGCCUCAGAGCCGCCCGCCGUUCCUUUUUCCUAUGCAUAUACUUCU UUGAGGAUCUGGCCUAAAGAGGUAUAGGGCAUGGGAAAACGGGGCG GUCGGGUCCUCCCCAGCG | miR-202; miR-202* |
| miR-203 | GUGUUGGGGACUCGCGCGCUGGGUCCAGUGGUUCUUAACAGUUCAA CAGUUCUGUAGCGCAAUUGUGAAAUGUUUAGGACCACUAGACCCGG CGGGCGCGGCGACAGCGA | miR-203 |

Figure 1F

| | | |
|---|---|---|
| miR-204 | GGCUACAGUCUUUCUUCAUGUGACUCGUGGACUUCCCUUUGUCAUC CUAUGCCUGAGAAUAUAUGAAGGAGGCUGGGAAGGCAAAGGGACGU UCAAUUGUCAUCACUGGC | miR-204 |
| miR-205 | AAAGAUCCUCAGACAAUCCAUGUGCUUCUCUUGUCCUUCAUUCCAC CGGAGUCUGUCUCAUACCCAACCAGAUUUCAGUGGAGUGAAGUUCA GGAGGCAUGGAGCUGACA | miR-205 |
| miR-206 | UGCUUCCCGAGGCCACAUGCUUCUUUAUAUCCCCAUAUGGAUUACU UUGCUAUGGAAUGUAAGGAAGUGUGUGGUUUCGGCAAGUG | miR-206 |
| miR-208a | UGACGGGCGAGCUUUUGGCCCGGGUUAUACCUGAUGCUCACGUAUA AGACGAGCAAAAAGCUUGUUGGUCA | miR-208 (also called miR-208a) |
| miR-20a | GUAGCACUAAAGUGCUUAUAGUGCAGGUAGUGUUUAGUUAUCUACU GCAUUAUGAGCACUUAAAGUACUGC | miR-20a |
| miR-20b | AGUACCAAAGUGCUCAUAGUGCAGGUAGUUUUGGCAUGACUCUACU GUAGUAUGGGCACUUCCAGUACU | miR-20b |
| miR-21 | UGUCGGGUAGCUUAUCAGACUGAUGUUGACUGUUGAAUCUCAUGGC AACACCAGUCGAUGGGCUGUCUGACA | miR-21 |
| miR-210 | ACCCGGCAGUGCCUCCAGGCGCAGGGCAGCCCCUGCCCACCGCACA CUGCGCUGCCCCAGACCCACUGUGCGUGUGACAGCGGCUGAUCUGU GCCUGGGCAGCGCGACCC | miR-210 |
| miR-211 | UCACCUGGCCAUGUGACUUGUGGGCUUCCCUUUGUCAUCCUUCGCC UAGGGCUCUGAGCAGGGCAGGGACAGCAAAGGGGUGCUCAGUUGUC ACUUCCCACAGCACGGAG | miR-211 |
| miR-212 | CGGGGCACCCCGCCCGGACAGCGCGCCGGCACCUUGGCUCUAGACU GCUUACUGCCCGGGCCGCCCUCAGUAACAGUCUCCAGUCACGGCCA CCGACGCCUGGCCCCGCC | miR-212 |
| miR-214 | GGCCUGGCUGGACAGAGUUGUCAUGUGUCUGCCUGUCUACACUUGC UGUGCAGAACAUCCGCUCACCUGUACAGCAGGCACAGACAGGCAGU CACAUGCAAACCCAGCCU | miR-214 |
| miR-215 | AUCAUUCAGAAAUGGUAUACAGGAAAAUGACCUAUGAAUUGACAGA CAAUAUAGCUGAGUUUGUCUGUCAUUUCUUUAGGCCAAUAUUCUGU AUGACUGUGCUACUUCAA | miR-215 |
| miR-216a | GAUGGCUGUGAGUUGGCUUAAUCUCAGCUGGCAACUGUGAGAUGUU CAUACAAUCCCUCACAGUGGUCUCUGGGAUUAUGCUAAACAGAGCA AUUUCCUAGCCCUCACGA | miR-216 (also called miR-216a) |
| miR-217 | AGUAUAAUUAUUACAUAGUUUUGAUGUCGCAGAUACUGCAUCAGG AACUGAUUGGAUAAGAAUCAGUCACCAUCAGUUCCUAAUGCAUUGC CUUCAGCAUCUAAACAAG | miR-217 |
| miR-218-1 | GUGAUAAUGUAGCGAGAUUUUCUGUUGUGCUUGAUCUAACCAUGUG GUUGCGAGGUAUGAGUAAAACAUGGUUCCGUCAAGCACCAUGGAAC GUCACGCAGCUUUCUACA | miR-218 |
| miR-218-2 | GACCAGUCGCUGCGGGCUUUCCUUUGUGCUUGAUCUAACCAUGUG GUGGAACGAUGGAAACGGAACAUGGUUCUGUCAAGCACCGCGGAAA GCACCGUGCUCUCCUGCA | miR-218 |
| miR-219-1 | CCGCCCCGGGCCGCGGCUCCUGAUUGUCCAAACGCAAUUCUCGAGU CUAUGGCUCCGGCCGAGAGUUGAGUCUGGACGUCCCGAGCCGCCGC CCCCAAACCUCGAGCGGG | miR-219 |
| miR-219-2 | ACUCAGGGGCUUCGCCACUGAUUGUCCAAACGCAAUUCUUGUACGA GUCUGCGGCCAACCGAGAAUUGUGGCUGGACAUCUGUGGCUGAGCU CCGGG | miR-219 |

Figure 1G

| | | |
|---|---|---|
| miR-22 | GGCUGAGCCGCAGUAGUUCUUCAGUGGCAAGCUUUAUGUCCUGACC CAGCUAAAGCUGCCAGUUGAAGAACUGUUGCCCUCUGCC | miR-22 |
| miR-220a | GACAGUGUGGCAUUGUAGGGCUCCACACCGUAUCUGACACUUUGGG CGAGGGCACCAUGCUGAAGGUGUUCAUGAUGCGGUCUGGGAACUCC UCACGGAUCUUACUGAUG | miR-220 (also called miR-220a) |
| miR-221 | UGAACAUCCAGGUCUGGGGCAUGAACCUGGCAUACAAUGUAGAUUU CUGUGUUCGUUAGGCAACAGCUACAUUGUCUGCUGGGUUUCAGGCU ACCUGGAAACAUGUUCUC | miR-221 |
| miR-222 | GCUGCUGGAAGGUGUAGGUACCCUCAAUGGCUCAGUAGCCAGUGUA GAUCCUGUCUUUCGUAAUCAGCAGCUACAUCUGGCUACUGGGUCUC UGAUGGCAUCUUCUAGCU | miR-222 |
| miR-223 | CCUGGCCUCCUGCAGUGCCACGCUCCGUGUAUUUGACAAGCUGAGU UGGACACUCCAUGUGGUAGAGUGUCAGUUUGUCAAAUACCCCAAGU GCGGCACAUGCUUACCAG | miR-223 |
| miR-224 | GGGCUUUCAAGUCACUAGUGGUUCCGUUUAGUAGAUGAUUGUGCAU UGUUUCAAAAUGGUGCCCUAGUGACUACAAAGCCC | miR-224 |
| miR-23a | GGCCGGCUGGGGUUCCUGGGGAUGGGAUUUGCUUCCUGUCACAAAU CACAUUGCCAGGGAUUUCCAACCGACC | miR-23a |
| miR-23b | CUCAGGUGCUCUGGCUGCUUGGGUUCCUGGCAUGCUGAUUUGUGAC UUAAGAUUAAAAUCACAUUGCCAGGGAUUACCACGCAACCACGACC UUGGC | miR-23b |
| miR-24-1 | CUCCGGUGCCUACUGAGCUGAUAUCAGUUCUCAUUUUACACACUGG CUCAGUUCAGCAGGAACAGGAG | miR-24; miR-189 (also called miR-24*) |
| miR-24-2 | CUCUGCCUCCCGUGCCUACUGAGCUGAAACACAGUUGGUUUGUGUA CACUGGCUCAGUUCAGCAGGAACAGGG | miR-24 |
| miR-25 | GGCCAGUGUUGAGAGGCGGAGACUUGGGCAAUUGCUGGACGCUGCC CUGGGCAUUGCACUUGUCUCGGUCUGACAGUGCCGGCC | miR-25 |
| miR-26a-1 | GUGGCCUCGUUCAAGUAAUCCAGGAUAGGCUGUGCAGGUCCCAAUG GGCCUAUUCUUGGUUACUUGCACGGGGACGC | miR-26a |
| miR-26a-2 | GGCUGUGGCUGGAUUCAAGUAAUCCAGGAUAGGCUGUUUCCAUCUG UGAGGCCUAUUCUUGAUUACUUGUUUCUGGAGGCAGCU | miR-26a |
| miR-26b | CCGGGACCCAGUUCAAGUAAUUCAGGAUAGGUUGUGUGCUGUCCAG CCUGUUCUCCAUUACUUGGCUCGGGGACCGG | miR-26b |
| miR-27a | CUGAGGAGCAGGGCUUAGCUGCUUGUGAGCAGGGUCCACACCAAGU CGUGUUCACAGUGGCUAAGUUCCGCCCCCCAG | miR-27a |
| miR-27b | ACCUCUCUAACAAGGUGCAGAGCUUAGCUGAUUGGUGAACAGUGAU UGGUUUCCGCUUUGUUCACAGUGGCUAAGUUCUGCACCUGAAGAGA AGGUG | miR-27b |
| miR-28 | GGUCCUUGCCCUCAAGGAGCUCACAGUCUAUUGAGUUACCUUUCUG ACUUUCCCACUAGAUUGUGAGCUCCUGGAGGGCAGGCACU | miR-28 |
| miR-296 | AGGACCCUUCCAGAGGGCCCCCCCUCAAUCCUGUUGUGCCUAAUUC AGAGGGUUGGGUGGAGGCUCUCCUGAAGGGCUCU | miR-296 |
| miR-299 | AAGAAAUGGUUUACCGUCCCACAUACAUUUUGAAUAUGUAUGUGGG AUGGUAAACCGCUUCUU | miR-299-3p; miR-299-5p |
| miR-29a | AUGACUGAUUUCUUUUGGUGUUCAGAGUCAAUAUAAUUUUCUAGCA CCAUCUGAAAUCGGUUAU | miR-29a |

Figure 1H

| | | |
|---|---|---|
| miR-29b-1 | CUUCAGGAAGCUGGUUUCAUAUGGUGGUUUAGAUUUAAAUAGUGAU UGUCUAGCACCAUUUGAAAUCAGUGUUCUUGGGGG | miR-29b |
| miR-29b-2 | CUUCUGGAAGCUGGUUUCACAUGGUGGCUUAGAUUUUUCCAUCUUU GUAUCUAGCACCAUUUGAAAUCAGUGUUUUAGGAG | miR-29b |
| miR-29c | AUCUCUUACACAGGCUGACCGAUUUCUCCUGGUGUUCAGAGUCUGU UUUUGUCUAGCACCAUUUGAAAUCGGUUAUGAUGUAGGGGGA | miR-29c |
| miR-301a | ACUGCUAACGAAUGCUCUGACUUUAUUGCACUACUGUACUUUACAG CUAGCAGUGCAAUAGUAUUGUCAAAGCAUCUGAAAGCAGG | miR-301 (also called miR-301a) |
| miR-302a | CCACCACUUAAACGUGGAUGUACUUGCUUUGAAACUAAAGAAGUAA GUGCUUCCAUGUUUUGGUGAUGG | miR-302a; miR-302a* |
| miR-302b | GCUCCCUUCAACUUUAACAUGGAAGUGCUUUCUGUGACUUUAAAAG UAAGUGCUUCCAUGUUUUAGUAGGAGU | miR-302b; miR-302b* |
| miR-302c | CCUUUGCUUUAACAUGGGGGUACCUGCUGUGUGAAACAAAAGUAAG UGCUUCCAUGUUUCAGUGGAGG | miR-302c; miR-302c* |
| miR-302d | CCUCUACUUUAACAUGGAGGCACUUGCUGUGACAUGACAAAAAUAA GUGCUUCCAUGUUUGAGUGUGG | miR-302d; miR-302d* |
| miR-30a | GCGACUGUAAACAUCCUCGACUGGAAGCUGUGAAGCCACAGAUGGG CUUUCAGUCGGAUGUUUGCAGCUGC | miR-30a-3p; miR-30a-5p |
| miR-30b | ACCAAGUUUCAGUUCAUGUAAACAUCCUACACUCAGCUGUAAUACA UGGAUGGCUGGGAGGUGGAUGUUUACUUCAGCUGACUUGGA | miR-30b |
| miR-30c-1 | ACCAUGCUGUAGUGUGUGUAAACAUCCUACACUCUCAGCUGUGAGC UCAAGGUGGCUGGGAGAGGGUUGUUUACUCCUUCUGCCAUGGA | miR-30c |
| miR-30c-2 | AGAUACUGUAAACAUCCUACACUCUCAGCUGUGGAAAGUAAGAAAG CUGGGAGAAGGCUGUUUACUCUUUCU | miR-30c |
| miR-30d | GUUGUUGUAAACAUCCCCGACUGGAAGCUGUAAGACACAGCUAAGC UUUCAGUCAGAUGUUUGCUGCUAC | miR-30d |
| miR-30e | GGGCAGUCUUUGCUACUGUAAACAUCCUUGACUGGAAGCUGUAAGG UGUUCAGAGGAGCUUUCAGUCGGAUGUUUACAGCGGCAGGCUGCCA | miR-30e-3p; miR-30e-5p |
| miR-31 | GGAGAGGAGGCAAGAUGCUGGCAUAGCUGUUGAACUGGGAACCUGC UAUGCCAACAUAUUGCCAUCUUUCC | miR-31 |
| miR-32 | GGAGAUAUUGCACAUUACUAAGUUGCAUGUUGUCACGGCCUCAAUG CAAUUUAGUGUGUGUGAUAUUUC | miR-32 |
| miR-320a | GCUUCGCUCCCCUCCGCCUUCUCUUCCCGGUUCUUCCCGGAGUCGG GAAAAGCUGGGUUGAGAGGGCGAAAAAGGAUGAGGU | miR-320 (also called miR-320a) |
| miR-323 | UUGGUACUUGGAGAGAGGUGGUCCGUGGCGCGUUCGCUUUAUUUAU GGCGCACAUUACACGGUCGACCUCUUUGCAGUAUCUAAUC | miR-323 |
| miR-324 | CUGACUAUGCCUCCCCGCAUCCCCUAGGGCAUUGGUGUAAAGCUGG AGACCCACUGCCCCAGGUGCUGCUGGGGGUUGUAGUC | miR-324-3p; miR-324-5p |
| miR-325 | AUACAGUGCUUGGUUCCUAGUAGGUGUCCAGUAAGUGUUUGUGACA UAAUUUGUUUAUUGAGGACCUCCUAUCAAUCAAGCACUGUGCUAGG CUCUGG | miR-325 |
| miR-326 | CUCAUCUGUCUGUUGGGCUGGAGGCAGGGCCUUUGUGAAGGCGGGU GGUGCUCAGAUCGCCUCUGGGCCCUUCCUCCAGCCCCGAGGCGGAU UCA | miR-326 |

Figure 1I

| | | |
|---|---|---|
| miR-328 | UGGAGUGGGGGGGCAGGAGGGGCUCAGGGAGAAAGUGCAUACAGCCCCUGGCCCUCUCUGCCCUUCCGUCCCCUG | miR-328 |
| miR-329-1 | GGUACCUGAAGAGAGGUUUUCUGGGUUUCUGUUUCUUUAAUGAGGACGAAACACACCUGGUUAACCUCUUUUCCAGUAUC | miR-329 |
| miR-329-2 | GUGGUACCUGAAGAGAGGUUUUCUGGGUUUCUGUUUCUUUAUUGAGGACGAAACACACCUGGUUAACCUCUUUUCCAGUAUCAA | miR-329 |
| miR-33a | CUGUGGUGCAUUGUAGUUGCAUUGCAUGUUCUGGUGGUACCCAUGCAAUGUUUCCACAGUGCAUCACAG | miR-33 (also called miR-33a) |
| miR-330 | CUUUGGCGAUCACUGCCUCUCUGGGCCUGUGUCUUAGGCUCUGCAAGAUCAACCGAGCAAAGCACACGGCCUGCAGAGAGGCAGCGCUCUGCCC | miR-330 |
| miR-331 | GAGUUUGGUUUUGUUUGGGUUUGUUCUAGGUAUGGUCCCAGGGAUCCCAGAUCAAACCAGGCCCCUGGGCCUAUCCUAGAACCAACCUAAGCUC | miR-331 |
| miR-335 | UGUUUUGAGCGGGGGUCAAGAGCAAUAACGAAAAAUGUUUGUCAUAAACCGUUUUUCAUUAUUGCUCCUGACCUCCUCUCAUUUGCUAUAUUCA | miR-335 |
| miR-337 | GUAGUCAGUAGUUGGGGGGUGGGAACGGCUUCAUACAGGAGUUGAUGCACAGUUAUCCAGCUCCUAUAUGAUGCCUUUCUUCAUCCCCUUCAA | miR-337 |
| miR-338 | UCUCCAACAAUAUCCUGGUGCUGAGUGAUGACUCAGGCGACUCCAGCAUCAGUGAUUUUGUUGAAGA | miR-338 |
| miR-339 | CGGGGCGGCCGCUCUCCCUGUCCUCCAGGAGCUCACGUGUGCCUGCCUGUGAGCGCCUCGACGACAGAGCCGGCGCCUGCCCCAGUGUCUGCGC | miR-339 |
| miR-340 | UUGUACCUGGUGUGAUUAUAAAGCAAUGAGACUGAUUGUCAUAUGUCGUUUGUGGGAUCCGUCUCAGUUACUUUAUAGCCAUACCUGGUAUCUUA | miR-340 |
| miR-342 | GAAACUGGGCUCAAGGUGAGGGGUGCUAUCUGUGAUUGAGGGACAUGGUUAAUGGAAUUGUCUCACACAGAAAUCGCACCCGUCACCUUGGCCUACUUA | miR-342 |
| miR-345 | ACCCAAACCCUAGGUCUGCUGACUCCUAGUCCAGGGCUCGUGAUGGCUGGUGGGCCCUGAACGAGGGGUCUGGAGGCCUGGGUUUGAAUAUCGACAGC | miR-345 |
| miR-346 | GGUCUCUGUGUUGGGCGUCUGUCUGCCCGCAUGCCUGCCUCUCUGUUGCUCUGAAGGAGGCAGGGGCUGGGCCUGCAGCUGCCUGGGCAGAGCGG | miR-346 |
| miR-34a | GGCCAGCUGUGAGUGUUUCUUUGGCAGUGUCUUAGCUGGUUGUUGUGAGCAAUAGUAAGGAAGCAAUCAGCAAGUAUACUGCCCUAGAAGUGCUGCACGUUGUGGGGCCC | miR-34a |
| miR-34b | GUGCUCGGUUUGUAGGCAGUGUCAUUAGCUGAUUGUACUGUGGUGGUUACAAUCACUAACUCCACUGCCAUCAAAACAAGGCAC | miR-34b |
| miR-34c | AGUCUAGUUACUAGGCAGUGUAGUUAGCUGAUUGCUAAUAGUACCAAUCACUAACCACACGGCCAGGUAAAAAGAUU | miR-34c |
| miR-361 | GGAGCUUAUCAGAAUCUCCAGGGGUACUUUAUAAUUUCAAAAAGUCCCCCAGGUGUGAUUCUGAUUUGCUUC | miR-361 |
| miR-362 | CUUGAAUCCUUGGAACCUAGGUGUGAGUGCUAUUUCAGUGCAACACACCUAUUCAAGGAUUCAAA | miR-362 |

Figure 1J

| | | |
|---|---|---|
| miR-365-1 | ACCGCAGGGAAAAUGAGGGACUUUUGGGGGCAGAUGUGUUUCCAUU CCACUAUCAUAAUGCCCCUAAAAAUCCUUAUUGCUCUUGCA | miR-365 |
| miR-365-2 | AGAGUGUUCAAGGACAGCAAGAAAAAUGAGGGACUUUCAGGGGCAG CUGUGUUUUCUGACUCAGUCAUAAUGCCCCUAAAAAUCCUUAUUGU UCUUGCAGUGUGCAUCGGG | miR-365 |
| miR-367 | CCAUUACUGUUGCUAAUAUGCAACUCUGUUGAAUAUAAAUUGGAAU UGCACUUUAGCAAUGGUGAUGG | miR-367 |
| miR-369 | UUGAAGGGAGAUCGACCGUGUUAUAUUCGCUUUAUUGACUUCGAAU AAUACAUGGUUGAUCUUUUCUCAG | miR-369-3p; miR-369-5p |
| miR-370 | AGACAGAGAAGCCAGGUCACGUCUCUGCAGUUACACAGCUCACGAG UGCCUGCUGGGGUGGAACCUGGUCUGUCU | miR-370 |
| miR-371 | GUGGCACUCAAACUGUGGGGGCACUUUCUGCUCUCUGGUGAAAGUG CCGCCAUCUUUUGAGUGUUAC | miR-371 |
| miR-372 | GUGGGCCUCAAAUGUGGAGCACUAUUCUGAUGUCCAAGUGGAAAGU GCUGCGACAUUUGAGCGUCAC | miR-372 |
| miR-373 | GGGAUACUCAAAAUGGGGGCGCUUUCCUUUUUGUCUGUACUGGGAA GUGCUUCGAUUUUGGGGUGUCCC | miR-373; miR-373* |
| miR-374a | UACAUCGGCCAUUAUAAUACAACCUGAUAAGUGUUAUAGCACUUAU CAGAUUGUAUUGUAAUUGUCUGUGUA | miR-374 (also called miR-374a) |
| miR-375 | CCCCGCGACGAGCCCCUCGCACAAACCGGACCUGAGCGUUUUGUUC GUUCGGCUCGCGUGAGGC | miR-375 |
| miR-376a-1 | UAAAAGGUAGAUUCUCCUUCUAUGAGUACAUUAUUUAUGAUUAAUC AUAGAGGAAAAUCCACGUUUUC | miR-376a; miR-376a* |
| miR-376a-2 | GGUAUUUAAAAGGUAGAUUUUCCUUCUAUGGUUACGUGUUUGAUGG UUAAUCAUAGAGGAAAAUCCACGUUUUCAGUAUC | miR-376a |
| miR-376b | CAGUCCUUCUUUGGUAUUUAAAACGUGGGAUAUUCCUUCUAUGUUUA CGUGAUUCCUGGUUAAUCAUAGAGGAAAAUCCAUGUUUUCAGUAUC AAAUGCUG | miR-376b |
| miR-376c | AAAAGGUGGAUAUUCCUUCUAUGUUUAUGUUAUUUAUGGUUAAACA UAGAGGAAAUUCCACGUUUU | miR-368 (also called miR-376c) |
| miR-377 | UUGAGCAGAGGUUGCCCUUGGUGAAUUCGCUUUAUUUAUGUUGAAU CACACAAAGGCAACUUUUGUUUG | miR-377 |
| miR-378 | AGGGCUCCUGACUCCAGGUCCUGUGUGUUACCUAGAAAUAGCACUG GACUUGGAGUCAGAAGGCCU | miR-378; miR-422b (also called miR-378*) |
| miR-379 | AGAGAUGGUAGACUAUGGAACGUAGGCGUUAUGAUUUCUGACCUAU GUAACAUGGUCCACUAACUCU | miR-379 |
| miR-380 | AAGAUGGUUGACCAUAGAACAUGCGCUAUCUCUGUGUCGUAUGUAA UAUGGUCCACAUCUU | miR-380 |
| miR-381 | UACUUAAAGCGAGGUUGCCCUUUGUAUAUUCGGUUUAUUGACAUGG AAUAUACAAGGGCAAGCUCUCUGUGAGUA | miR-381 |
| miR-382 | UACUUGAAGAGAAGUUGUUCGUGGUGGAUUCGCUUUACUUAUGACG AAUCAUUCACGGACAACACUUUUUUCAGUA | miR-382 |
| miR-383 | CUCCUCAGAUCAGAAGGUGAUUGUGGCUUUGGGUGGAUAUUAAUCA GCCACAGCACUGCCUGGUCAGAAAGAG | miR-383 |
| miR-409 | UGGUACUCGGGGAGAGGUUACCCGAGCAACUUUGCAUCUGGACGAC GAAUGUUGCUCGGUGAACCCCUUUUCGGUAUCA | miR-409-5p |

Figure 1K

| | | |
|---|---|---|
| miR-410 | GGUACCUGAGAAGAGGUUGUCUGUGAUGAGUUCGCUUUUAUUAAUG ACGAAUAUAACACAGAUGGCCUGUUUUCAGUACC | miR-410 |
| miR-412 | CUGGGGUACGGGGAUGGAUGGUCGACCAGUUGGAAAGUAAUUGUUU CUAAUGUACUUCACCUGGUCCACUAGCCGUCCGUAUCCGCUGCAG | miR-412 |
| miR-422a | GAGAGAAGCACUGGACUUAGGGUCAGAAGGCCUGAGUCUCUCUGCU GCAGAUGGGCUCUCUGUCCCUGAGCCAAGCUUUGUCCUCCCUGG | miR-422a |
| miR-423 | AUAAAGGAAGUUAGGCUGAGGGGCAGAGAGCGAGACUUUUCUAUUU UCCAAAAGCUCGGUCUGAGGCCCCUCAGUCUUGCUUCCUAACCCGC GC | miR-423 |
| miR-424 | CGAGGGGAUACAGCAGCAAUUCAUGUUUUGAAGUGUUCUAAAUGGU UCAAAACGUGAGGCGCUGCUAUACCCCCUCGUGGGGAAGGUAGAAG GUGGGG | miR-424 |
| miR-425 | GAAAGCGCUUUGGAAUGACACGAUCACUCCCGUUGAGUGGGCACCC GAGAAGCCAUCGGGAAUGUCGUGUCCGCCCAGUGCUCUUUC | miR-425 |
| miR-429 | CGCCGGCCGAUGGGCGUCUUACCAGACAUGGUUAGACCUGGCCCUC UGUCUAAUACUGUCUGGUAAAACCGUCCAUCCGCUGC | miR-429 |
| miR-432 | UGACUCCUCCAGGUCUUGGAGUAGGUCAUUGGGUGGAUCCUCUAUU UCCUUACGUGGGCCACUGGAUGGCUCCUCCAUGUCUUGGAGUAGAU CA | miR-432; miR-432* |
| miR-433 | CCGGGGAGAAGUACGGUGAGCCUGUCAUUAUUCAGAGAGGCUAGAU CCUCUGUGUUGAGAAGGAUCAUGAUGGGCUCCUCGGUGUUCUCCAG G | miR-433 |
| miR-448 | GCCGGGAGGUUGAACAUCCUGCAUAGUGCUGCCAGGAAAUCCCUAU UUCAUAUAAGAGGGGGCUGGCUGGUUGCAUAUGUAGGAUGUCCCAU CUCCCAGCCCACUUCGUCA | miR-448 |
| miR-449a | CUGUGUGUGAUGAGCUGGCAGUGUAUUGUUAGCUGGUUGAAUAUGU GAAUGGCAUCGGCUAACAUGCAACUGCUGUCUUAUUGCAUAUACA | miR-449 (also called miR-449a) |
| miR-450a-1 | AAACGAUACUAAACUGUUUUUGCGAUGUGUUCCUAAUAUGCACUAU AAAUAUAUUGGGAACAUUUUGCAUGUAUAGUUUUGUAUCAAUAUA | miR-450 (also called miR-450a) |
| miR-450a-2 | CCAAAGAAAGAUGCUAAACUAUUUUUUGCGAUGUGUUCCUAAUAUGU AAUAUAAAUGUAUGGGGACAUUUUGCAUUCAUAGUUUUGUAUCAA UAAUAUGG | miR-450 (also called miR-450a) |
| miR-451 | CUUGGGAAUGGCAAGGAAACCGUUACCAUUACUGAGUUUAGUAAUG GUAAUGGUUCUCUUGCUAUACCCAGA | miR-451 |
| miR-452 | GCUAAGCACUUACAACUGUUUGCAGAGGAAACUGAGACUUUGUAAC UAUGUCUCAGUCUCAUCUGCAAAGAAGUAAGUGCUUUGC | miR-452; miR-452* |
| miR-453 | GCAGGAAUGCUGCGAGCAGUGCCACCUCAUGGUACUCGGAGGGAGG UUGUCCGUGGUGAGUUCGCAUUAUUUAAUGAUGC | miR-453 |
| miR-455 | UCCCUGGCGUGAGGGUAUGUGCCUUUGGACUACAUCGUGGAAGCCA GCACCAUGCAGUCCAUGGGCAUAUACACUUGCCUCAAGGCCUAUGU CAUC | miR-455 |
| miR-483 | GAGGGGGAAGACGGGAGGAAAGAAGGGAGUGGUUCCAUCACGCCUC CUCACUCCUCUCCUCCCGUCUUCUCCUCUC | miR-483 |
| miR-485 | ACUUGGAGAGAGGCUGGCCGUGAUGAAUUCGAUUCAUCAAAGCGAG UCAUACACGGCUCUCCUCUCUUUUAGU | miR-485-3p; miR-485-5p |

Figure 1L

| | | |
|---|---|---|
| miR-486 | GCAUCCUGUACUGAGCUGCCCCGAGGCCCUUCAUGCUGCCCAGCUCGGGGCAGCUCAGUACAGGAUAC | miR-486 |
| miR-487a | GGUACUUGAAGAGUGGGUUAUCCCUGCUGUGUUCGCUUAAUUUAUGACGAAUCAUACAGGGACAUCCAGUUUUUCAGUAUC | miR-487a |
| miR-487b | UUGGUACUUGGAGAGUGGUUAUCCCUGUCCUGUUCGUUUUGCUCAUGUCGAAUCGUACAGGGUCAUCCACUUUUUCAGUAUCAA | miR-487b |
| miR-488 | GAGAAUCAUCUCUCCCAGAUAAUGGCACUCUCAAACAAGUUUCCAAAUUGUUUGAAAGGCUAUUUCUUGGUCAGAUGACUCUC | miR-488 |
| miR-489 | GUGGCAGCUUGGUGGUCGUAUGUGUGACGCCAUUUACUUGAACCUUUAGGAGUGACAUCACAUAUACGGCAGCUAAACUGCUAC | miR-489 |
| miR-490 | UGGAGGCCUUGCUGGUUUGGAAAGUUCAUUGUUCGACACCAUGGAUCUCCAGGUGGGUCAAGUUUAGAGAUGCACCAACCUGGAGGACUCCAUGCUGUUGAGCUGUUCACAAGCAGCGGACACUUCCA | miR-490 |
| miR-491 | UUGACUUAGCUGGGUAGUGGGAACCCUUCCAUGAGGAGUAGAACACUCCUUAUGCAAGAUUCCCUUCUACCUGGCUGGGUUGG | miR-491 |
| miR-492 | CAACUACAGCCACUACUACAGGACCAUCGAGGACCUGCGGGACAAGAUUCUUGGUGCCACCAUUGAGAACGCCAGGAUUGUCCUGCAGAUCAACAAUGCUCAACUGGCUGCAGAUG | miR-492 |
| miR-493 | CUGGCCUCCAGGGCUUUGUACAUGGUAGGCUUUCAUUCAUUCGUUUGCACAUUCGUGAAGGUCUACUGUGUGCCAGGCCCUGUGCCAG | miR-493 (also called miR-493-3p); miR-493* (also called miR-493-5p) |
| miR-494 | GAUACUCGAAGGAGAGGUUGUCCGUGUUGUCUUCUCUUUAUUUAUGAUGAAACAUACACGGGAAACCUCUUUUUUAGUAUC | miR-494 |
| miR-495 | UGGUACCUGAAAAGAAGUUGCCCAUGUUAUUUUCGCUUUAUAUGUGACGAAACAAACAUGGUGCACUUCUUUUUCGGUAUCA | miR-495 |
| miR-496 | CCCAAGUCAGGUACUCGAAUGGAGGUUGUCCAUGGUGUGUUCAUUUUAUUUAUGAUGAGUAUUACAUGGCCAAUCUCCUUUCGGUACUCAAUUCUUCUUGGG | miR-496 |
| miR-497 | CCACCCCGGUCCUGCUCCCGCCCCAGCAGCACACUGUGGUUUGUACGGCACUGUGGCCACGUCCAAACCACACUGUGGUGUUAGAGCGAGGGUGGGGGAGGCACCGCCGAGG | miR-497 |
| miR-498 | AACCCUCCUUGGGAAGUGAAGCUCAGGCUGUGAUUUCAAGCCAGGGGGCGUUUUCUAUAACUGGAUGAAAAGCACCUCCAGAGCUUGAAGCUCACAGUUUGAGAGCAAUCGUCUAAGGAAGUU | miR-498 |
| miR-499 | GCCCUGUCCCCUGUGCCUUGGGCGGGCGGCUGUUAAGACUUGCAGUGAUGUUUAACUCCUCUCCACGUGAACAUCACAGCAAGUCUGUGCUCUUCCCGUCCCUACGCUGCCUGGGCAGGGU | miR-499 |
| miR-500 | GCUCCCCCUCUCUAAUCCUUGCUACCUGGGUGAGAGUGCUGUCUGAAUGCAAUGCACCUGGGCAAGGAUUCUGAGAGCGAGAGC | miR-500 |
| miR-501 | GCUCUUCCUCUCUAAUCCUUUGUCCCUGGGUGAGAGUGCUUUCUGAAUGCAAUGCACCCGGGCAAGGAUUCUGAGAGGGUGAGC | miR-501 |
| miR-502 | UGCUCCCCCUCUCUAAUCCUUGCUAUCUGGGUGCUAGUGCUGGCUCAAUGCAAUGCACCUGGGCAAGGAUUCAGAGAGGGGGAGCU | miR-502 |
| miR-503 | UGCCCUAGCAGCGGGAACAGUUCUGCAGUGAGCGAUCGGUGCUCUGGGGUAUUGUUUCCGCUGCCAGGGUA | miR-503 |
| miR-504 | GCUGCUGUUUGGGAGACCCUGGUCUGCACUCUAUCUGUAUUCUUACUGAAGGGAGUGCAGGGCAGGGUUUCCCAUACAGAGGGC | miR-504 |

Figure 1M

| | | |
|---|---|---|
| miR-505 | GAUGCACCCAGUGGGGGAGCCAGGAAGUAUUGAUGUUUCUGCCAGU UUAGCGUCAACACUUGCUGGUUUCCUCUCUGGAGCAUC | miR-505 |
| miR-506 | GCCACCACCAUCAGCCAUACUAUGUGUAGUGCCUUAUUCAGGAAGG UGUUACUUAAUAGAUUAAUAUUUGUAAGGCACCCUUCUGAGUAGAG UAAUGUGCAACAUGGACAACAUUUGUGGUGGC | miR-506 |
| miR-507 | GUGCUGUGUGUAGUGCUUCACUUCAAGAAGUGCCAUGCAUGUGUCU AGAAAUAUGUUUUGCACCUUUUGGAGUGAAAUAAUGCACAACAGAU AC | miR-507 |
| miR-508 | CCACCUUCAGCUGAGUGUAGUGCCCUACUCCAGAGGGCGUCACUCA UGUAAACUAAAACAUGAUUGUAGCCUUUUGGAGUAGAGUAAUACAC AUCACGUAACGCAUAUUUGGUGG | miR-508 |
| miR-509-1 | CAUGCUGUGUGUGGUACCCUACUGCAGACAGUGGCAAUCAUGUAUA AUUAAAAAUGAUUGGUACGUCUGUGGGUAGAGUACUGCAUGACACA UG | miR-509 |
| miR-509-2 | CAUGCUGUGUGUGGUACCCUACUGCAGACAGUGGCAAUCAUGUAUA AUUAAAAAUGAUUGGUACGUCUGUGGGUAGAGUACUGCAUGACAC | miR-509 |
| miR-509-3 | GUGGUACCCUACUGCAGACGUGGCAAUCAUGUAUAAUUAAAAAUGA UUGGUACGUCUGUGGGUAGAGUACUGCAU | miR-509 |
| miR-510 | GUGGUGUCCUACUCAGGAGAGUGGCAAUCACAUGUAAUUAGGUGUG AUUGAAACCUCUAAGAGUGGAGUAACAC | miR-510 |
| miR-511-1 | CAAUAGACACCCAUCGUGUCUUUUGCUCUGCAGUCAGUAAAUAUUU UUUUGUGAAUGUGUAGCAAAAGACAGAAUGGUGGUCCAUUG | miR-511 |
| miR-511-2 | CAAUAGACACCCAUCGUGUCUUUUGCUCUGCAGUCAGUAAAUAUUU UUUUGUGAAUGUGUAGCAAAAGACAGAAUGGUGGUCCAUUG | miR-511 |
| miR-512-1 | UCUCAGUCUGUGGCACUCAGCCUUGAGGGCACUUUCUGGUGCCAGA AUGAAAGUGCUGUCAUAGCUGAGGUCCAAUGACUGAGG | miR-512-5p |
| miR-512-2 | GGUACUUCUCAGUCUGUGGCACUCAGCCUUGAGGGCACUUUCUGGU GCCAGAAUGAAAGUGCUGUCAUAGCUGAGGUCCAAUGACUGAGGCG AGCACC | miR-512-5p |
| miR-513a-1 | GGGAUGCCACAUUCAGCCAUUCAGCGUACAGUGCCUUUCACAGGGA GGGUGUCAUUUAUGUGAACUAAAAUAUAAAUUUCACCUUUCUGAGAA GGGUAAUGUACAGCAUGCACUGCAUAUGUGGGUGUCCC | miR-513 (also called miR-513a) |
| miR-513a-2 | GGAUGCCACACAUUCAGCCAUUCAGUGUGCAGUGCCUUUCACAGGGAG GUGUCAUUUAUGUGAACUAAAAUAUAAAUUUCACCUUUCUGAGAAG GGUAAUGUACAGCAUGCACUGCAUAUGUGGUGUCC | miR-513 (also called miR-513a) |
| miR-514-1 | AACAUGUUGUCUGUGGUACCCUACUCUGGAGAGUGACAAUCAUGUA UAAUUAAAAUUUGAUUGACACUUCUGUGAGUAGAGUAACGCAUGACA CGUACG | miR-514 |
| miR-514-2 | GUUGUCUGUGGUACCCUACUCUGGAGAGUGACAAUCAUGUAUAACU AAAUUUGAUUGACACUUCUGUGAGUAGAGUAACGCAUGACAC | miR-514 |
| miR-514-3 | GUUGUCUGUGGUACCCUACUCUGGAGAGUGACAAUCAUGUAUAACU AAAUUUGAUUGACACUUCUGUGAGUAGAGUAACGCAUGACAC | miR-514 |
| miR-515-1 | UCUCAUGCAGUCAUUCUCCAAAAGAAAGCACUUUCUGUUGUCUGAA AGCAGAGUGCCUUCUUUUGGAGCGUUACUGUUUGAGA | miR-515-3p; miR-515-5p |
| miR-515-2 | UCUCAUGCAGUCAUUCUCCAAAAGAAAGCACUUUCUGUUGUCUGAA AGCAGAGUGCCUUCUUUUGGAGCGUUACUGUUUGAGA | miR-515-2 |

Figure 1N

| miR-516a-1 | UCUCAGGCUGUGACCUUCUCGAGGAAAGAAGCACUUUCUGUUGUCU GAAAGAAAAGAAAGUGCUUCCUUUCAGAGGGUUACGGUUUGAGA | miR-516 (also called miR-516a) |
|---|---|---|
| miR-516a-2 | UCUCAGGUUGUGACCUUCUCGAGGAAAGAAGCACUUUCUGUUGUCU GAAAGAAAAGAAAGUGCUUCCUUUCAGAGGGUUACGGUUUGAGA | miR-516 (also called miR-516a) |
| miR-517a | UCUCAGGCAGUGACCCUCUAGAUGGAAGCACUGUCUGUUGUAUAAA AGAAAAGAUCGUGCAUCCCUUUAGAGUGUUACUGUUUGAGA | miR-517a; miR-517* |
| miR-517b | GUGACCCUCUAGAUGGAAGCACUGUCUGUUGUCUAAGAAAAGAUCG UGCAUCCCUUUAGAGUGUUAC | miR-517b; miR-517* |
| miR-517c | GAAGAUCUCAGGCAGUGACCCUCUAGAUGGAAGCACUGUCUGUUGU CUAAGAAAAGAUCGUGCAUCCUUUUAGAGUGUUACUGUUUGAGAAA AUC | miR-517c; miR-517* |
| mir-518a-1 | UCUCAAGCUGUGACUGCAAAGGGAAGCCCUUUCUGUUGUCUGAAAG AAGAGAAAGCGCUUCCCUUUGCUGGAUUACGGUUUGAGA | mir-518a |
| mir-518a-2 | UCUCAAGCUGUGGGUCUGCAAAGGGAAGCCCUUUCUGUUGUCUAAA AGAAGAGAAAGCGCUUCCCUUUGCUGGAUUACGGUUUGAGA | mir-518a |
| miR-518b | UCAUGCUGUGGCCCUCCAGAGGGAAGCGCUUUCUGUUGUCUGAAAG AAAACAAAGCGCUCCCCUUUAGAGGUUUACGGUUUGA | miR-518b |
| miR-518c | GCGAGAAGAUCUCAUGCUGUGACUCUCUGGAGGGAAGCACUUUCUG UUGUCUGAAAGAAAACAAAGCGCUUCUCUUUAGAGUGUUACGGUUU GAGAAAAGC | miR-518c; miR-518c* |
| miR-518d | UCCCAUGCUGUGACCCUCUAGAGGGAAGCACUUUCUGUUGUCUGAA AGAAACCAAAGCGCUUCCCUUUGGAGCGUUACGGUUUGAGA | miR-518d |
| miR-518e | UCUCAGGCUGUGACCCUCUAGAGGGAAGCGCUUUCUGUUGGCUAAA AGAAAAGAAAGCGCUUCCCUUCAGAGUGUUAACGCUUUGAGA | miR-518e |
| miR-518f | UCUCAUGCUGUGACCCUCUAGAGGGAAGCACUUUCUCUUGUCUAAA AGAAAAGAAAGCGCUUCUCUUUAGAGGAUUACUCUUUGAGA | miR-518f |
| miR-519a-1 | CUCAGGCUGUGACACUCUAGAGGGAAGCGCUUUCUGUUGUCUGAAA GAAAGGAAAGUGCAUCCUUUUAGAGUGUUACUGUUUGAG | miR-519a |
| miR-519a-2 | UCUCAGGCUGUGUCCCUCUACAGGGAAGCGCUUUCUGUUGUCUGAA AGAAAGGAAAGUGCAUCCUUUUAGAGUGUUACUGUUUGAGA | miR-519a |
| miR-519b | CAUGCUGUGACCCUCUAGAGGGAAGCGCUUUCUGUUGUCUGAAAGA AAAGAAAGUGCAUCCUUUUAGAGGUUUACUGUUUG | miR-519b |
| miR-519c | UCUCAGCCUGUGACCCUCUAGAGGGAAGCGCUUUCUGUUGUCUGAA AGAAAAGAAAGUGCAUCUUUUUAGAGGAUUACAGUUUGAGA | miR-519c |
| miR-519d | UCCCAUGCUGUGACCCUCCAAAGGGAAGCGCUUUCUGUUUGUUUUC UCUUAAACAAAGUGCCUCCCUUUAGAGUGUUACCGUUUGGGA | miR-519d |
| miR-519e | UCUCAUGCAGUCAUUCUCCAAAAGGGAGCACUUUCUGUUUGAAAGA AAACAAAGUGCCUCCUUUUAGAGUGUUACUGUUUGAGA | miR-519e; miR-519e* |
| miR-520a | CUCAGGCUGUGACCCUCCAGAGGGAAGUACUUUCUGUUGUCUGAGA GAAAAGAAAGUGCUUCCCUUUGGACUGUUUCGGUUUGAG | miR-520a; miR-520a* |
| miR-520b | CCCUCUACAGGGAAGCGCUUUCUGUUGUCUGAAAGAAAAGAAAGUG CUUCCUUUUAGAGGG | miR-520b |
| miR-520c | UCUCAGGCUGUCGUCCUCUAGAGGGAAGCACUUUCUGUUGUCUGAA AGAAAAGAAAGUGCUUCCUUUUAGAGGGUUACCGUUUGAGA | miR-520c |

Figure 1O

| | | |
|---|---|---|
| miR-520d | UCUCAAGCUGUGAGUCUACAAAGGGAAGCCCUUUCUGUUGUCUAAA AGAAAAGAAAGUGCUUCUCUUUGGUGGGUUACGGUUUGAGA | miR-520d; miR-520d* |
| miR-520e | UCUCCUGCUGUGACCCUCAAGAUGGAAGCAGUUUCUGUUGUCUGAA AGGAAAGAAAGUGCUUCCUUUUUGAGGGUUACUGUUUGAGA | miR-520e |
| miR-520f | UCUCAGGCUGUGACCCUCUAAAGGGAAGCGCUUUCUGUGGUCAGAA AGAAAAGCAAGUGCUUCCUUUUAGAGGGUUACCGUUUGGGA | miR-520f |
| miR-520g | UCCCAUGCUGUGACCCUCUAGAGGAAGCACUUUCUGUUUGUUGUCU GAGAAAAAACAAAGUGCUUCCCUUUAGAGUGUUACCGUUUGGGA | miR-520g |
| miR-520h | UCCCAUGCUGUGACCCUCUAGAGGAAGCACUUUCUGUUUGUUGUCU GAGAAAAAACAAAGUGCUUCCCUUUAGAGUUACUGUUUGGGA | miR-520h |
| miR-521-1 | UCUCAGGCUGUGACCCUCCAAAGGGAAGAACUUUCUGUUGUCUAAA AGAAAAGAACGCACUUCCCUUUAGAGUGUUACCGUGUGAGA | miR-521 |
| miR-521-2 | UCUCGGGCUGUGACUCUCCAAAGGGAAGAAUUUUCUCUUGUCUAAA AGAAAAGAACGCACUUCCCUUUAGAGUGUUACCGUGUGAGA | miR-521 |
| miR-522 | UCUCAGGCUGUGUCCCUCUAGAGGGAAGCGCUUUCUGUUGUCUGAA AGAAAAGAAAAUGGUUCCCUUUAGAGUGUUACGCUUUGAGA | miR-522 |
| miR-523 | UCUCAUGCUGUGACCCUCUAGAGGGAAGCGCUUUCUGUUGUCUGAA AGAAAAGAACGCGCUUCCCUAUAGAGGGUUACCCUUUGAGA | miR-523 |
| miR-525 | CUCAAGCUGUGACUCUCCAGAGGGAUGCACUUUCUCUUAUGUGAAA AAAAAGAAGGCGCUUCCCUUUAGAGCGUUACGGUUUGGG | miR-525; miR-525* |
| miR-526a-1 | CUCAGGCUGUGACCCUCUAGAGGGAAGCACUUUCUGUUGCUUGAAA GAAGAGAAAGCGCUUCCUUUUAGAGGAUUACUCUUUGAG | miR-526a |
| miR-526a-2 | GUGACCCUCUAGAGGGAAGCACUUUCUGUUGAAAGAAAAGAACAUG CAUCCUUUCAGAGGGUUAC | miR-526a |
| miR-526b | UCAGGCUGUGACCCUCUUGAGGGAAGCACUUUCUGUUGUCUGAAAG AAGAGAAAGUGCUUCCUUUUAGAGGCUUACUGUCUGA | miR-526b; miR-526b* |
| miR-527 | UCUCAAGCUGUGACUGCAAAGGGAAGCCCUUUCUGUUGUCUAAAAG AAAAGAAAGUGCUUCCCUUUGGUGAAUUACGGUUUGAGA | miR-527 |
| miR-532 | CGACUUGCUUUCUCUCCUCCAUGCCUUGAGUGUAGGACCGUUGGCA UCUUAAUUACCCUCCCACACCCAAGGCUUGCAAAAAAGCGAGCCU | miR-532 |
| miR-539 | AUACUUGAGGAGAAAUUAUCCUUGGUGUGUUCGCUUUAUUUAUGAU GAAUCAUACAAGGACAAUUUCUUUUUGAGUAU | miR-539 |
| miR-542 | CAGAUCUCAGACAUCUCGGGGAUCAUCAUGUCACGAGAUACCAGUG UGCACUUGUGACAGAUUGAUAACUGAAAGGUCUGGGAGCCACUCAU CUUCA | miR-542-3p; miR-542-5p |
| miR-552 | AACCAUUCAAAUAUACCACAGUUUGUUUAACCUUUUGCCUGUUGGU UGAAGAUGCCUUUCAACAGGUGACUGGUUAGACAAACUGUGGUAUA UACA | miR-552 |
| miR-561 | CUUCAUCCACCAGUCCUCCAGGAACAUCAAGGAUCUUAAACUUUGC CAGAGCUACAAAGGCAAAGUUUAAGAUCCUUGAAGUUCCUGGGGGA ACCAU | miR-561 |
| miR-565 | CCAGUGGCGCAAUGGAUAACGCGUCUGACUACGGAUCAGAAGAUUC UAGGUUCGACUCCUGGCUGGCUCGCGAUGUCUGUUUUGCCACACUU GACCC | miR-565 |

Figure 1P

| miR-566 | GCUAGGCGUGGUGGCGGGCGCCUGUGAUCCCAACUACUCAGGAGGC UGGGGCAGCAGAAUCGCUUGAACCCGGGAGGCGAAGGUUGCAGUGA GC | miR-566 |
|---|---|---|
| miR-575 | AAUUCAGCCCUGCCACUGGCUUAUGUCAUGACCUUGGGCUACUCAG GCUGUCUGCACAAUGAGCCAGUUGGACAGGAGCAGUGCCACUCAAC UC | miR-575 |
| miR-576 | UACAAUCCAACGAGGAUUCUAAUUUCUCCACGUCUUUGGUAAUAAG GUUUGGCAAAGAUGUGGAAAAAUUGGAAUCCUCAUUCGAUUGGUUA UAACCA | miR-576 |
| miR-584 | UAGGGUGACCAGCCAUUAUGGUUUGCCUGGGACUGAGGAAUUUGCU GGGAUAUGUCAGUUCCAGGCCAACCAGGCUGGUUGGUCUCCCUGAA GCAAC | miR-584 |
| miR-592 | UAUUAUGCCAUGACAUUGUGUCAAUAUGCGAUGAUGUGUUGUGAUG GCACAGCGUCAUCACGUGGUGACGCAACAUCAUGACGUAAGACGUC ACAAC | miR-592 |
| miR-605 | GCCCUAGCUUGGUUCUAAAUCCCAUGGUGCCUUCUCCUUGGGAAAA ACAGAGAAGGCACUAUGAGAUUUAGAAUCAAGUUAGG | miR-605 |
| miR-618 | CUCUUGUUCACAGCCAAACUCUACUUGUCCUUCUGAGUGUAAUUAC GUACAUGCAGUAGCUCAGGAGACAAGCAGGUUUACCCUGUGGAUGA GUCUGA | miR-618 |
| miR-622 | AGAGAAGCUGGACAAGUACUGGUCUCAGCAGAUUGAGGAGAGCACC ACAGUGGUCAUCACACAGUCUGCUGAGGUUGGAGCUGCUGAGAUGA CACU | miR-622 |
| miR-638 | GUGAGCGGGCGCGGCAGGGAUCGCGGGCGGGUGGCGGCCUAGGGCG CGGAGGGCGGACCGGGAAUGGCGCGCCGUGCGCCGCCGGCGUAACU GCGGCGCU | miR-638 |
| miR-652 | ACGAAUGGCUAUGCACUGCACAACCCUAGGAGAGGGUGCCAUUCAC AUAGACUAUAAUUGAAUGGCGCCACUAGGGUUGUGCAGUGCACAAC CUACAC | miR-652 |
| mir-660 | CUGCUCCUUCUCCCAUACCCAUUGCAUAUCGGAGUUGUGAAUUCUC AAAACACCUCCUGUGUGCAUGGAUUACAGGAGGGUGAGCCUUGUCA UCGUG | mir-660 |
| miR-7-1 | UUGGAUGUUGGCCUAGUUCUGUGUGGAAGACUAGUGAUUUUGUUGU UUUUAGAUAACUAAAUCGACAACAAAUCACAGUCUGCCAUAUGGCA CAGGCCAUGCCUCUACAG | miR-7 |
| miR-7-2 | CUGGAUACAGAGUGGACCGGCUGGCCCCAUCUGGAAGACUAGUGAU UUUGUUGUUGUCUUACUGCGCUCAACAACAAAUCCCAGUCUACCUA AUGGUGCCAGCCAUCGCA | miR-7 |
| miR-7-3 | AGAUUAGAGUGGCUGUGGUCUAGUGCUGUGUGGAAGACUAGUGAUU UUGUUGUUCUGAUGUACUACGACAACAAGUCACAGCCGGCCUCAUA GCGCAGACUCCCUUCGAC | miR-7 |
| miR-9-1 | CGGGGUUGGUUGUUAUCUUUGGUUAUCUAGCUGUAUGAGUGGUGUG GAGUCUUCAUAAAGCUAGAUAACCGAAAGUAAAAAUAACCCCA | miR-9; miR-9* |
| miR-9-2 | GGAAGCGAGUUGUUAUCUUUGGUUAUCUAGCUGUAUGAGUGUAUUG GUCUUCAUAAAGCUAGAUAACCGAAAGUAAAAACUCCUUCA | miR-9; miR-9* |
| miR-9-3 | GGAGGCCCGUUUCUCUCUUUGGUUAUCUAGCUGUAUGAGUGCCACA GAGCCGUCAUAAAGCUAGAUAACCGAAAGUAGAAAUGAUUCUCA | miR-9; miR-9* |
| miR-92a-1 | CUUUCUACACAGGUUGGGAUCGGUUGCAAUGCUGUGUUUCUGUAUG GUAUUGCACUUGUCCCGGCCUGUUGAGUUUGG | miR-92 (also called miR-92a) |

Figure 1Q

| | | |
|---|---|---|
| miR-92a-2 | UCAUCCCUGGGUGGGGAUUUGUUGCAUUACUUGUGUUCUAUAUAAA GUAUUGCACUUGUCCCGGCCUGUGGAAGA | miR-92 (also called miR-92a) |
| miR-93 | CUGGGGGCUCCAAAGUGCUGUUCGUGCAGGUAGUGUGAUUACCCAA CCUACUGCUGAGCUAGCACUUCCCGAGCCCCGG | miR-93 |
| miR-95 | AACACAGUGGGCACUCAAUAAAUGUCUGUUGAAUUGAAAUGCGUUA CAUUCAACGGGUAUUUAUUGAGCACCCACUCUGUG | miR-95 |
| miR-96 | UGGCCGAUUUUGGCACUAGCACAUUUUUGCUUGUGUCUCUCCGCUC UGAGCAAUCAUGUGCAGUGCCAAUAUGGGAAA | miR-96 |
| miR-98 | AGGAUUCUGCUCAUGCCAGGGUGAGGUAGUAAGUUGUAUUGUUGUG GGGUAGGGAUAUUAGGCCCCAAUUAGAAGAUAACUAUACAACUUAC UACUUUCCCUGGUGUGUGGCAUAUUCA | miR-98 |
| miR-99a | CCCAUUGGCAUAAACCCGUAGAUCCGAUCUUGUGGUGAAGUGGACC GCACAAGCUCGCUUCUAUGGGUCUGUGUCAGUGUG | miR-99a |
| miR-99b | GGCACCCACCCGUAGAACCGACCUUGCGGGGCCUUCGCCGCACACA AGCUCGUGUCUGUGGGUCCGUGUC | miR-99b |

Figure 1R

MIRNA BIOMARKERS OF PROSTATE DISEASE

This application claims priority to U.S. Provisional Application No. 61/180,760, filed May 22, 2009, which is incorporated by reference in its entirety.

Work described in this application was partially funded by the Federal government under National Cancer Institution/NIH Grant No. 1R43CA135917-01. Accordingly, the Federal government may have certain rights in this invention.

Prostate cancer (PrCa) is the most commonly diagnosed cancer and the second leading cause of cancer deaths in men, following only by lung cancer (Jemal et al., *CA Cancer J Clin.* 58(2):71-96 (2008)). The detection, diagnosis, and monitoring of PrCa involves a combination of assays (e.g., detection of prostate specific antigen (PSA) in blood), physical examination (e.g., digital rectal examination (DRE)), and observation of prostate tissue biopsy samples for cancerous cells.

Currently, a definitive diagnosis of PrCa requires the direct observation of cancerous cells in a prostate tissue biopsy. A prostate biopsy is typically acquired with the aid of a transrectal ultrasound probe, in which six to twelve tissue fragments are collected. Once collected, the tissue is fixed in a formalin solution and embedded in paraffin for sectioning. Formalin-fixed, paraffin embedded (FFPE) tissue sections are stained and analyzed by a pathologist. If cancerous cells are observed, the pathologist will most commonly identify the two most common architectural patterns of differentiation within the lesion and assign a grade (1 through 5) to each of these two differentiation patterns. A Gleason Score (GS) is calculated as the sum of the grade for the most common pattern (which must represent at least 50% of the tumor) and the grade for the second most common pattern (representing 5-50% of the tumor), thereby resulting in a GS ranging from 2 to 10 (Gleason, *Cancer Chemother Rep* 50:125-128 (1966), Gleason, *Hum Pathol* 23:273-279 (1992)). Higher Gleason Scores, particularly those ≥5, are correlated with less favorable patient prognoses (Egevad et al., *BJU Int* 89:538-542 (2002)). The GS is the most widespread method of PrCa tissue grading in use today, and the accurate assessment of Gleason grades and score is currently the most useful factor in predicting the course of the disease and the probable outcome.

The adoption of PSA testing, in addition to DRE, has dramatically increased the number of prostate cancers that are identified at a point early enough so that radical prostatectomy can be curative. However, the PSA assay still fails to detect ~15% of patients with cancer (Daneshgari et al., *Urology* 45:604-609 (1995)). In addition, PSA testing has a relatively high false positive rate that is caused by the normal fluctuation of PSA levels due to a patient's age or to the presence of conditions such as prostatitis or benign prostatic hyperplasia (BPH). Early detection, due in part to PSA testing, has reduced detected tumor size to the point where PSA contribution from BPH is nearly indistinguishable from PrCa tumors (Stamey et al., *J Urol* 172:1297-1301 (2004)). Therefore, at the time of tumor detection, PSA measurements are not reliable for distinguishing between BPH and prostate cancer. Additionally, data suggests that the PSA-based PrCa screening may result in the diagnosis of PrCa in approximately 36.5% of men who are not destined to have clinical progression of the cancer (Etzioni et al., *J Natl Cancer Inst* 94:981-990 (2002)). In most of these patients, the disease is indolent.

A nucleic acid-based diagnostic assay has been developed as an alternative to PSA testing. This assay measures levels of PCA3 mRNA using qRT-PCR (de Kok et al., *Cancer Res* 62:2695-2698 (2002); Hessels et al., *Eur Urol* 44:8-15; discussion 15-16 (2003)). PCA3 is over-expressed in prostate tumors (Bussemakers et al., *Cancer Res* 59:5975-5979 (1999)). In clinical trials, the PCA3 test achieved 66-82% sensitivity and 76-89% specificity for PrCa (Fradet et al., *Urology* 64:311-316 (2004)). PCA3 diagnostic assays are available but have yet to be approved by the FDA. Unfortunately, as with PSA, PCA3 testing exhibits disappointingly high false-positive and false-negative rates. The apparent best application of the PCA3 test is as a reflex for the PSA test. Also, a major impediment to the adoption of the PCA3 test is that it requires a urine sample from patients following a prostatic massage, which may be poorly tolerated. It also requires that an individual submit both blood and urine samples to accommodate both the PSA and PCA3 tests.

Additional diagnostic assay alternatives are therefore needed. An assay that performs better than the PSA and PCA3 tests in one or more criteria would be a welcome addition to clinicians and patients who are seeking to diagnose and manage prostate cancer.

We herein describe methods for diagnosing prostate disease by measuring miRNAs from serum or plasma.

In some embodiments, the invention relates to the characterization of prostate diseases such as cancer or BPH by detecting miRNAs from serum or plasma. The methods of the invention include both diagnosing disease, and evaluating the prognosis or aggressiveness of a prostate disease. Further, the methods may be used to characterize the progression of a prostate disease. The patients tested using the methods of the invention may also be tested using PSA or PCA3 assays.

In certain embodiments of the invention, the diagnosis or prognosis may be achieved by amplifying and detecting the amount of certain miRNAs that are present in elevated or reduced levels in the serum or plasma of a subject with prostate disease. In some instances, one serum or plasma miRNA may be amplified and measured to characterize prostate disease, while in other embodiments, two or more miRNAs are detected from serum or plasma. Some embodiments include amplifying and measuring a pair of miRNAs. In some instances, one miRNA in the pair is elevated in serum or plasma of patients with prostate disease, and the other miRNA in the pair is reduced. In other circumstances, both miRNAs in the pair can be elevated or both reduced. In certain embodiments, non-miRNA biomarkers such as PSA may also be measured. Some embodiments of the invention relate to diagnosis or prognosis of prostate cancer. Other embodiments of the invention include diagnosing BPH in a patient.

Additional embodiments of the invention are discussed throughout this application. Other objects, features, and advantages of the present invention will become apparent from the following detailed description. Any embodiment discussed with respect to one aspect of the invention applies to other aspects of the invention as well and vice versa. The embodiments in the Example section are understood to be embodiments of the invention that are applicable to all aspects of the invention.

It should be understood, however, that the detailed description and the specific examples, while indicating specific embodiments of the invention, are given by way of illustration only, since various changes and modifications within the spirit and scope of the invention will become apparent to those skilled in the art from this application.

BRIEF DESCRIPTION OF THE DRAWINGS

FIGS. 1A-1R show human precursor miRNA (pre-miRNA) sequences (SEQ ID NOS 1-340, respectively, in order of appearance), as provided by Release 13.0 of the miRBase::Sequences Database (http://microrna.sanger.ac.uk; Griffiths-Jones et al., Nucleic Acids Research, 2008, 36, Database Issue, D154-D158; Griffiths-Jones et al., Nucleic Acids Research, 2006, 34, Database Issue, D140-D144; Griffiths-Jones, Nucleic Acids Research, 2004, 32, Database Issue, D109-D111). The names of mature miRNAs from Tables 1 and 20 are also provided for each precursor sequence.

EXEMPLARY EMBODIMENTS

In certain aspects, the methods of the invention provide assays for amplifying and measuring the amount of a miRNA in a serum or plasma sample, thereby characterizing a prostate disease.

To assist in understanding the present invention, certain terms are first defined. Additional definitions are provided throughout the application.

As used herein, the term "microRNA" (miRNA or miR) includes human miRNAs, mature single stranded miRNAs, precursor miRNAs (pre-miR), and variants thereof, which may be naturally occurring. In some instances, the term "miRNA" also includes primary miRNA transcripts and duplex miRNAs. Unless otherwise noted, when used herein, the name of a specific miRNA refers to the mature miRNA. For example, miR-122a refers to a mature miRNA sequence derived from pre-miR-122. The sequences for particular miRNAs, including human mature and precursor sequences, are reported in the miRBase::Sequences Database (http://microrna.sanger.ac.uk (version 15 released April 2010); Griffiths-Jones et al., Nucleic Acids Research, 2008, 36, Database Issue, D154-D158; Griffiths-Jones et al., Nucleic Acids Research, 2006, 34, Database Issue, D140-D144; Griffiths-Jones, Nucleic Acids Research, 2004, 32, Database Issue, D109-D111). For certain miRNAs, a single precursor contains more than one mature miRNA sequence. In other instances, multiple precursor miRNAs contain the same mature sequence. In some instances, mature miRNAs have been re-named based on new scientific consensus. For example, miR-213, as used herein, refers to a mature miRNA from pre-miR-181a-1, and is also called miR-181a*. Other miRNAs that have been re-named include miR-189 (also called miR-24*), which comes from pre-miR-24-1; miR-368 (also called miR-376c); and miR-422b (also called miR-378*). The skilled artisan will appreciate that scientific consensus regarding the precise nucleic acid sequence for a given miRNA, in particular for mature forms of the miRNAs, may change with time. MiRNAs detected by assays of this application include naturally occurring sequences for the miR-NAs.

The term "characterizing" includes making diagnostic or prognostic determinations or predictions of disease. In some instances, "characterizing" includes identifying whether a subject has a disease such as cancer or BPH. Additionally, "characterizing" includes distinguishing patients with prostate cancer from patients having other prostate diseases. In other circumstances, "characterizing" includes determining the stage or aggressiveness of a disease state such as prostate cancer, or determining an appropriate treatment method for prostate disease.

The use of the word "a", "an" or "the" when used in conjunction with the term "comprising" in the claims and/or the specification may mean "one," but it is also consistent with the meaning of "one or more," "at least one," and "one or more than one."

I. SAMPLES

Serum is typically the fluid, non-cellular portion of coagulated blood. Plasma is also a non-cellular blood sample, but unlike serum, plasma contains clotting factors. In some embodiments, serum or plasma samples may be obtained from a human patient previously screened for prostate disease using PSA or PCA3 assays, or other diagnostic methods. In other embodiments, the patient has undergone a physical exam or biopsy to detect prostate disease. Additional embodiments include measuring miRNA in samples from patients previously or currently undergoing treatment for a prostate disease. The volume of plasma or serum obtained and used for the assay may be varied depending upon clinical intent.

One of skill in the art will recognize that many methods exist for obtaining and preparing serum samples. Generally, blood is drawn into a collection tube using standard methods and allowed to clot. The serum is then separated from the cellular portion of the coagulated blood. In some methods, clotting activators such as silica particles are added to the blood collection tube. In other methods, the blood is not treated to facilitate clotting. Blood collection tubes are commercially available from many sources and in a variety of formats (e.g., Becton Dickenson Vacutainer® tubes—SST™, glass serum tubes, or plastic serum tubes).

In some methods, the blood is collected by venipuncture and processed within three hours after drawing to minimize hemolysis and minimize the release of miRNAs from intact cells in the blood. In some methods, blood is kept on ice until use. The blood may be fractionated by centrifugation to remove cellular components. In some embodiments, centrifugation to prepare serum can be at a speed of at least 500, 1000, 2000, 3000, 4000, or 5000×G. In certain embodiments, the blood can be incubated for at least 10, 20, 30, 40, 50, 60, 90, 120, or 150 minutes to allow clotting. In other embodiments, the blood is incubated for at most 3 hours. When using plasma, the blood is not permitted to coagulate prior to separation of the cellular and acellular components. Serum or plasma can be frozen after separation from the cellular portion of blood until further assayed.

Before analysis, RNA may be extracted from serum or plasma and purified using methods known in the art. Many methods are known for isolating total RNA, or to specifically extract small RNAs, including miRNAs. The RNA may be extracted using commercially-available kits (e.g., Perfect RNA Total RNA Isolation Kit, Five Prime-Three Prime, Inc.; mirVana™ kits, Ambion, Inc.). Alternatively, RNA extraction methods previously published for the extraction of mammalian intracellular RNA or viral RNA may be adapted, either as published or with modification, for extraction of RNA from plasma and serum. RNA may be extracted from plasma or serum using silica particles, glass beads, or diatoms, as in the method or adaptations described in U.S. Publication No. 2008/0057502.

II. miRNA MARKERS FOR PROSTATE DISEASE

Certain embodiments of the invention provide serum or plasma miRNAs as markers for prostate disease. In some embodiments, miRNAs that are present at elevated levels in the serum or plasma of patients with prostate disease are used as markers. In other embodiments, miRNAs that have reduced levels are used as markers. In some embodiments, more than one miRNA from serum or plasma will be used as markers. When more than one miRNA biomarker is used, the miRNAs may all have elevated levels, all have reduced levels, or a mixture of miRNAs with elevated and reduced levels may be used.

The terms "reduced levels" or "elevated levels" refer to the amount of a miRNA in a serum or plasma sample from a patient compared to the amount of the miRNA in serum or plasma from a cohort or cohorts that do not have the prostate disease that the patient is being tested for. For instance, a miRNA that has reduced levels in the sera of prostate cancer patients is present at lower amounts in prostate cancer patient sera than in serum from a donor who does not have prostate cancer. For certain miRNAs, elevated levels in a patient serum or plasma sample indicates presence or prognosis for a prostate disease. Other miRNAs are present in reduced levels in patients with prostate disease.

Prostate disease can be classified as BPH or prostate cancer. In some embodiments, prostate cancer can be further characterized based on histopathology, aggressiveness, Gleason score, PSA measurements, and other methods known in the art. In some embodiments, the methods described herein can be used to characterize a patient with at least 80, 85, 90, 91, 92, 93, 94, 95, 96, 97, 98, or 99% sensitivity. The degree of sensitivity indicates the percentage of patients with a disease who are positively characterized as having the disease. In additional embodiments, the methods have at least 80, 85, 90, 91, 92, 93, 94, 95, 96, 97, 98, or 99% specificity (e.g., the percentage of non-diseased patients who are correctly characterized). The assay parameters can be adjusted to optimize for both sensitivity and specificity.

In some cases, the level of the miRNA marker will be compared to a control to determine whether the level is reduced or elevated. The control may be an external control, such as a miRNA in a serum or plasma sample from a patient known to be free of prostate disease. In other circumstances, the external control may be a miRNA from a non-serum sample like a tissue sample or a known amount of a synthetic RNA. An internal control may be a miRNA from the same serum or plasma sample being tested. The identity of a miRNA control may be the same as or different from the patient serum or plasma miRNA being measured.

Table 1 lists miRNAs that have elevated or reduced levels in serum from patients with prostate disease. These miRNAs may be used in accordance with the invention. Some of the miRNAs are useful for characterizing prostate cancer, including distinguishing cancer from BPH. Other miRNAs are suitable markers for identifying patients with BPH. In addition, some miRNAs may be used to predict the aggressiveness or outcome of prostate cancer.

TABLE 1 miRNAs with elevated or reduced levels in serum from patients with prostate disease. Levels are of miRNA in prostate cancer patients compared to patients with BPH or normal prostate.

| miRNA | Level | miRNA | Level | miRNA | Level |
|---|---|---|---|---|---|
| let-7i | Elevated | miR-502 | elevated | miR-331 | reduced |
| miR-100 | Elevated | miR-504 | elevated | miR-335 | reduced |
| miR-101 | Elevated | miR-505 | elevated | miR-340 | reduced |
| miR-105 | Elevated | miR-507 | elevated | miR-346 | reduced |
| miR-106b | Elevated | miR-511 | elevated | miR-365 | reduced |
| miR-10a | Elevated | miR-516-3p | elevated | miR-367 | reduced |
| miR-10b | Elevated | miR-517c | elevated | miR-372 | reduced |
| miR-122a | Elevated | miR-520a | elevated | miR-373* | reduced |
| miR-125a | Elevated | miR-520g | elevated | miR-380-3p | reduced |
| miR-125b | elevated | miR-522 | elevated | miR-412 | reduced |
| miR-126 | elevated | miR-523 | elevated | miR-425 | reduced |
| miR-126* | elevated | miR-526b* | elevated | miR-432* | reduced |
| miR-127 | elevated | miR-532 | elevated | miR-449 | reduced |
| miR-128a | elevated | miR-576 | elevated | miR-452* | reduced |
| miR-133a | elevated | miR-592 | elevated | miR-489 | reduced |
| miR-133b | elevated | miR-92 | elevated | miR-490 | reduced |
| miR-136 | elevated | miR-95 | elevated | miR-492 | reduced |
| miR-137 | elevated | miR-96 | elevated | miR-493* | reduced |
| miR-138 | elevated | miR-99a | elevated | miR-494 | reduced |
| miR-139 | elevated | miR-99b | elevated | miR-503 | reduced |
| miR-141 | elevated | miR-181a | elevated v normal | miR-509 | reduced |
| miR-146a | elevated | miR-185 | elevated v normal | miR-512-5p | reduced |
| miR-146b | elevated | miR-424 | elevated v normal | miR-514 | reduced |
| miR-147 | elevated | miR-0 | elevated v normal, reduced v BPH | miR-515-5p | reduced |
| miR-148b | elevated | miR-124a | elevated v normal, reduced v BPH | miR-516-5p | reduced |
| miR-151 | elevated | miR-130a | elevated v normal, reduced v BPH | miR517a | reduced |
| miR-152 | elevated | miR-130b | elevated v normal, reduced v BPH | miR-518c | reduced |
| miR-154 | elevated | miR-142-3p | elevated v normal, reduced v BPH | miR-518d | reduced |
| miR-17-3p | elevated | miR-142-5p | elevated v normal, reduced v BPH | miR-518e | reduced |
| miR-181b | elevated | miR-148a | elevated v normal, reduced v BPH | miR-518f | reduced |
| miR-181d | elevated | miR-149 | elevated v normal, reduced v BPH | miR-519c | reduced |
| miR-182* | elevated | miR-15a | elevated v normal, reduced v BPH | miR-519d | reduced |
| miR-186 | elevated | miR-184 | elevated v normal, reduced v BPH | miR-519e | reduced |

TABLE 1-continued miRNAs with elevated or reduced levels in serum from patients with prostate disease. Levels are of miRNA in prostate cancer patients compared to patients with BPH or normal prostate.

| miRNA | Level | miRNA | Level | miRNA | Level |
|---|---|---|---|---|---|
| miR-187 | elevated | miR-189 | elevated v normal, reduced v BPH | miR-519e* | reduced |
| miR-18a | elevated | miR-18b | elevated v normal, reduced v BPH | miR-520a* | reduced |
| miR-190 | elevated | miR-193a | elevated v normal, reduced v BPH | miR-520b | reduced |
| miR-192 | elevated | miR-194 | elevated v normal, reduced v BPH | miR-520d | reduced |
| miR-193b | elevated | miR-208 | elevated v normal, reduced v BPH | miR-520d* | reduced |
| miR-199a | elevated | miR-213 | elevated v normal, reduced v BPH | miR-520e | reduced |
| miR-199a* | elevated | miR-216 | elevated v normal, reduced v BPH | miR-520f | reduced |
| miR-199b | elevated | miR-23a | elevated v normal, reduced v BPH | miR-520h | reduced |
| miR-19a | elevated | miR-27a | elevated v normal, reduced v BPH | miR-521 | reduced |
| miR-19b | elevated | miR-27b | elevated v normal, reduced v BPH | miR-525* | reduced |
| miR-200a | elevated | miR-302b | elevated v normal, reduced v BPH | miR-526b | reduced |
| miR-200b | elevated | miR-302c* | elevated v normal, reduced v BPH | miR-527 | reduced |
| miR-200c | elevated | miR-326 | elevated v normal, reduced v BPH | miR-542-3p | reduced |
| miR-204 | elevated | miR-338 | elevated v normal, reduced v BPH | miR-542-5p | reduced |
| miR-205 | elevated | miR-339 | elevated v normal, reduced v BPH | miR-552 | reduced |
| miR-206 | elevated | miR-345 | elevated v normal, reduced v BPH | miR-565 | reduced |
| miR-21 | elevated | miR-34b | elevated v normal, reduced v BPH | miR-566 | reduced |
| miR-210 | elevated | miR-361 | elevated v normal, reduced v BPH | miR-575 | reduced |
| miR-214 | elevated | miR-374 | elevated v normal, reduced v BPH | miR-584 | reduced |
| miR-215 | elevated | miR-377 | elevated v normal, reduced v BPH | miR-605 | reduced |
| miR-217 | elevated | miR-378 | elevated v normal, reduced v BPH | miR-638 | reduced |
| miR-218 | elevated | miR-422a | elevated v normal, reduced v BPH | miR-652 | reduced |
| miR-219 | elevated | miR-422b | elevated v normal, reduced v BPH | miR-9* | reduced |
| miR-221 | elevated | miR-506 | elevated v normal, reduced v BPH | miR-103 | reduced v normal |
| miR-23b | elevated | miR-517* | elevated v normal, reduced v BPH | miR-519b | reduced v normal |
| miR-25 | elevated | miR-518c* | elevated v normal, reduced v BPH | miR-93 | reduced v normal |
| miR-296 | elevated | miR-520c | elevated v normal, reduced v BPH | miR-98 | reduced v normal |
| miR-29a | elevated | miR-618 | elevated v normal, reduced v BPH | let-7b | reduced v normal, elevated v BPH |
| miR-29b | elevated | miR-622 | elevated v normal, reduced v BPH | let-7c | reduced v normal, elevated v BPH |
| miR-29c | elevated | mir660 | elevated v normal, reduced v BPH | let-7e | reduced v normal, elevated v BPH |
| miR-302b* | elevated | let-7a | reduced | miR-1 | reduced v normal, elevated v BPH |
| miR-30a-5p | elevated | let-7d | reduced | miR-106a | reduced v normal, elevated v BPH |
| miR-30e-5p | elevated | let-7f | reduced | miR-107 | reduced v normal, elevated v BPH |
| miR-320 | elevated | let-7g | reduced | miR-128b | reduced v normal, elevated v BPH |
| miR-324-3p | elevated | miR-132 | reduced | miR-129 | reduced v normal, elevated v BPH |
| miR-324-5p | elevated | miR-135a | reduced | miR-134 | reduced v normal, elevated v BPH |
| miR-325 | elevated | miR-135b | reduced | miR-145 | reduced v normal, elevated v BPH |

TABLE 1-continued miRNAs with elevated or reduced levels in serum from patients with prostate disease. Levels are of miRNA in prostate cancer patients compared to patients with BPH or normal prostate.

| miRNA | Level | miRNA | Level | miRNA | Level |
|---|---|---|---|---|---|
| miR-329 | elevated | miR-140 | reduced | miR-155 | reduced v normal, elevated v BPH |
| miR-33 | elevated | miR-143 | reduced | miR-183 | reduced v normal, elevated v BPH |
| miR-337 | elevated | miR-153 | reduced | miR-18a* | reduced v normal, elevated v BPH |
| miR-34a | elevated | miR-154* | reduced | miR-196b | reduced v normal, elevated v BPH |
| miR-34c | elevated | miR-15b | reduced | miR-20b | reduced v normal, elevated v BPH |
| miR-362 | elevated | miR-16 | reduced | miR-211 | reduced v normal, elevated v BPH |
| miR-368 | elevated | miR-17-5p | reduced | miR-222 | reduced v normal, elevated v BPH |
| miR-370 | elevated | miR-181c | reduced | miR-224 | reduced v normal, elevated v BPH |
| miR-371 | elevated | miR-182 | reduced | miR-28 | reduced v normal, elevated v BPH |
| miR-373 | elevated | miR-188 | reduced | miR-299-3p | reduced v normal, elevated v BPH |
| miR-375 | elevated | miR-191 | reduced | miR-299-5p | reduced v normal, elevated v BPH |
| miR-376a | elevated | miR-195 | reduced | miR-302a | reduced v normal, elevated v BPH |
| miR-376a* | elevated | miR-196a | reduced | miR-302d | reduced v normal, elevated v BPH |
| miR-376b | elevated | miR-197 | reduced | miR-31 | reduced v normal, elevated v BPH |
| miR-380-5p | elevated | miR198 | reduced | miR-328 | reduced v normal, elevated v BPH |
| miR-381 | elevated | miR-200a* | reduced | miR-330 | reduced v normal, elevated v BPH |
| miR-382 | elevated | miR-202 | reduced | miR-342 | reduced v normal, elevated v BPH |
| miR-383 | elevated | miR-202* | reduced | miR-369-3p | reduced v normal, elevated v BPH |
| miR-4 | elevated | miR-203 | reduced | miR-369-5p | reduced v normal, elevated v BPH |
| miR-409-5p | elevated | miR-20a | reduced | miR-379 | reduced v normal, elevated v BPH |
| miR-410 | elevated | miR-212 | reduced | miR-423 | reduced v normal, elevated v BPH |
| miR-429 | elevated | miR-22 | reduced | miR-432 | reduced v normal, elevated v BPH |
| miR-433 | elevated | miR-220 | reduced | miR-452 | reduced v normal, elevated v BPH |
| miR-448 | elevated | miR-223 | reduced | miR-485-3p | reduced v normal, elevated v BPH |
| miR-451 | elevated | miR-24 | reduced | miR-487b | reduced v normal, elevated v BPH |
| miR-453 | elevated | miR-26a | reduced | miR-488 | reduced v normal, elevated v BPH |
| miR-455 | elevated | miR-26b | reduced | miR-493 | reduced v normal, elevated v BPH |
| miR-483 | elevated | miR-301 | reduced | miR-508 | reduced v normal, elevated v BPH |
| miR-485-5p | elevated | miR-302a* | reduced | miR-510 | reduced v normal, elevated v BPH |
| miR-486 | elevated | miR-30-a-3p | reduced | miR-515-3p | reduced v normal, elevated v BPH |
| miR-487a | elevated | miR-30b | reduced | mir-518a | reduced v normal, elevated v BPH |
| miR-491 | elevated | miR-30c | reduced | miR-518b | reduced v normal, elevated v BPH |
| miR-495 | elevated | miR-30d | reduced | miR-525 | reduced v normal, elevated v BPH |
| miR-496 | elevated | miR-30e-3p | reduced | miR-526a | reduced v normal, elevated v BPH |
| miR-497 | elevated | miR-32 | reduced | miR-539 | reduced v normal, elevated v BPH |
| miR-498 | elevated | miR-323 | reduced | miR-9 | reduced v normal, elevated v BPH |
| miR-499 | elevated | | | | |

In some embodiments, a single miRNA may be used to characterize prostate cancer. For example, any one of the following miRNAs may be used to characterize prostate cancer, either alone or in combination with other markers: let-7a, let-7c, let-7d, let-7e, let-7f, let-7g, let-7i, miR-100, miR-101, miR-103, miR-105, miR-106a, miR-106b, miR-107, miR-10a, miR-10b, miR-122a, miR-125a, miR-125b, miR-126, miR-126*, miR-128a, miR-128b, miR-129, miR-130b, miR-132, miR-133a, miR-133b, miR-136, miR-138, miR-139, miR-140, miR-141, miR-142-3p, miR-142-5p, miR-143, miR-146a, miR-146b, miR-147, miR-148a, miR-148b, miR-151, miR-152, miR-154, miR-154*, miR-15b, miR-16, miR-17-3p, miR-17-5p, miR-181a, miR-181b, miR-181d, miR-182, miR-184, miR-186, miR-189, miR-190, miR-191, miR-192, miR-193a, miR-193b, miR-194, miR-195, miR-196a, miR-196b, miR-197, miR198, miR-199a*, miR-199b, miR-19a, miR-19b, miR-200a, miR-200a*, miR-200b, miR-200c, miR-202, miR-202*, miR-204, miR-205, miR-206, miR-208, miR-20a, miR-20b, miR-21, miR-210, miR-212, miR-215, miR-218, miR-219, miR-220, miR-222, miR-223, miR-224, miR-23a, miR-23b, miR-24, miR25, miR-26a, miR-26b, miR-27a, miR-27b, miR-296, miR-29a, miR-29b, miR-29c, miR-302a, miR-302b*, miR-302d, miR-30-a-3p, miR-30a-5p, miR-30b, miR-30c, miR-30d, miR-30e-3p, miR-30e-5p, miR-32, miR-320, miR-323, miR-324-3p, miR-326, miR-328, miR-33, miR-331, miR-335, miR-338, miR-339, miR-340, miR-342, miR-345, miR-346, miR-34a, miR-34b, miR-361, miR-368, miR-369-5p, miR-370, miR-372, miR-373*, miR-375, miR-376a, miR-376a*, miR-376b, miR-377, miR-379, miR-380-5p, miR-381, miR-383, miR-409-5p, miR-412, miR-423, miR-424, miR-429, miR-432*, miR-448, miR-451, miR-452*, miR-455, miR-483, miR-485-3p, miR-487b, miR-488, miR-489, miR-490, miR-491, miR-492, miR-494, miR-496, miR-497, miR-498, miR-499, miR-501, miR-502, miR-503, miR-504, miR-505, miR-507, miR-510, miR-512-5p, miR-515-3p, miR-515-5p, miR-518b, miR-518d, miR-518e, miR-518f, miR-519c, miR-519d, miR-519e, miR-520a*, miR-520b, miR-520d, miR-520h, miR-521, miR-523, miR-525*, miR-526a, miR-526b, miR-526b*, miR-527, miR-532, miR-542-5p, miR-552, miR-565, miR-566, miR-575, miR-576, miR-584, miR-592, miR-638, mir660, miR-9, miR-9*, miR-92, miR-93, miR-95, miR-98, miR-99a, and miR-99b.

In other embodiments, any one of the following miRNAs may be used to characterize prostate cancer, either alone or in combination with other markers: let-7c, let-7d, let-7f, let-7g, let-7i, miR-101, miR-106b, miR-10a, miR-10b, miR-122a, miR-125a, miR-125b, miR-126, miR-126*, miR-128a, miR-130b, miR-133b, miR-136, miR-138, miR-139, miR-140, miR-141, miR-142-5p, miR-143, miR-147, miR-148a, miR-151, miR-152, miR-154, miR-15b, miR-17-3p, miR-17-5p, miR-181b, miR-181d, miR-192, miR-193a, miR-195, miR-196a, miR198, miR-199a*, miR-199b, miR-200a, miR-200b, miR-200c, miR-202, miR-204, miR-205, miR-206, miR-212, miR-219, miR-220, miR-223, miR-23b, miR-24, miR25, miR-26a, miR-27a, miR-296, miR-29b, miR-302b*, miR-30-a-3p, miR-30b, miR-30c, miR-30e-3p, miR-32, miR-324-3p, miR-326, miR-33, miR-331, miR-335, miR-340, miR-345, miR-34a, miR-361, miR-368, miR-369-5p, miR-370, miR-375, miR-376a, miR-376a*, miR-376b, miR-379, miR-380-5p, miR-409-5p, miR-412, miR-423, miR-429, miR-432*, miR-448, miR-451, miR-452*, miR-483, miR-489, miR-490, miR-494, miR-496, miR-497, miR-499, miR-502, miR-503, miR-505, miR-507, miR-515-3p, miR-515-5p, miR-518e, miR-519c, miR-519d, miR-519e, miR-520a*, miR-520h, miR-523, miR-526b*, miR-527, miR-532, miR-542-5p, miR-552, miR-584, miR-9, miR-9*, miR-92, miR-99a, and miR-99b.

In some embodiments, a miRNA for characterizing prostate cancer is chosen from let-7d, miR-10b, miR-122a, miR-139, miR-24, miR-204, miR-205, miR-206, miR-375, and miR-99b, and may be used alone or in combination with other markers. In other embodiments, the miRNA used for characterizing prostate cancer may be chosen from let-7d, miR-122a, miR-139, miR-204, miR-205, miR-206, and miR-375.

In certain methods, miRNAs that have reduced levels in serum from patients with prostate disease are used as biomarkers. Certain miRNAs at reduced levels in serum can be used to distinguish patients with prostate cancer from normal patients or patients with BPH. These miRNA markers include let-7d, let-7f, let-7g, miR-132, miR-135a, miR-135b, miR-140, miR-143, miR-153, miR-154*, miR-15b, miR-16, miR-17-5p, miR-181c, miR-182, miR-188, miR-195, miR-196a, miR-197, miR198, miR-200a*, miR-202, miR-202*, miR-203, miR-20a, miR-212, miR-22, miR-220, miR-223, miR-24, miR-26b, miR-301, miR-302a*, miR-30-a-3p, miR-30b, miR-30c, miR-30d, miR-30e-3p, miR-32, miR-323, miR-331, miR-335, miR-346, miR-365, miR-367, miR-372, miR-373*, miR-380-3p, miR-412, miR-425, miR-432*, miR-449, miR-452*, miR-489, miR-490, miR-492, miR-493*, miR-494, miR-503, miR-504, miR-505, miR-512-5p, miR-514, miR-515-5p, miR-516-5p, miR517a, miR-518c, miR-518d, miR-518e, miR-518f, miR-519c, miR-519d, miR-519e, miR-519e*, miR-520a*, miR-520b, miR-520d, miR-520d*, miR-520e, miR-520f, miR-520h, miR-521, miR-525*, miR-526b, miR-527, miR-542-3p, miR-542-5p, miR-552, miR-565, miR-566, miR-575, miR-584, miR-605, miR-638, miR-652, miR-9, miR-9*, miR-340, miR-26a, miR-191, let-7a, miR-103, miR-519b, miR-93, miR-98, let-7b, let-7e, miR-1, miR-107, miR-128b, miR-129, miR-134, miR-145, miR-183, miR-18a*, miR-196b, miR-20b, miR-211, miR-224, miR-28, miR-299-3p, miR-299-5p, miR-302a, miR-302d, miR-31, miR-328, miR-330, miR-342, miR-369-3p, miR-369-5p, miR-379, miR-423, miR-432, miR-452, miR-485-3p, miR-487b, miR-488, miR-493, miR-501, miR-510, miR-515-3p, mir-518a, miR-518b, miR-525, miR-526a, miR-539, miR-508, miR-155, let-7c, miR-106a, and miR-222.

In certain embodiments, two or more miRNAs are used to characterize prostate disease. Any one of the following miRNAs may be used in combination with at least one other serum miRNA in the methods of the invention: let-7a, let-7c, let-7d, let-7f, let-7g, miR-1, miR-103, miR-106a, miR-106b, miR-107, miR-10b, miR-122a, miR-125a, miR-125b, miR-126, miR-126*, miR-130a, miR-130b, miR-132, miR-133b, miR-135a, miR-139, miR-140, miR-142-3p, miR-142-5p, miR-143, miR-145, miR-146a, miR-146b, miR-148a, miR-148b, miR-152, miR-154*, miR-155, miR-15a, mir-15b, miR-16, miR-17-5p, miR-181, miR-181c, miR-181d, miR-185, miR-187, miR-188, miR-18a, miR-18a*, miR-191, miR-192, miR-193a, miR-194, miR-195, miR-196b, miR-197, miR-199a*, miR-199b, miR-19a, miR-200a, miR-200c, miR-204, miR-206, miR-20a, miR-20b, miR-212, miR-214, miR-218, miR-22, miR-221, miR-222, miR-223, miR-224, miR-23a, miR-23b, miR-24, miR25, miR-26a, miR-26b, miR-27a, miR-27b, miR-28, miR-29a, miR-29c, miR-301, miR-30a-5p, miR-30b, miR-30c, miR-30d, miR-30e-3p, miR-32, miR-328, miR-331, miR-335, miR-339, miR-340, miR-342, miR-345, miR-346, miR-34a, miR-361, miR-365, miR-374, miR-375, miR-378, miR-422b, miR-423, miR-425, miR-432, miR-432*, miR-483, miR-495, miR-501, miR-539, miR-565, miR-566, miR-576, miR-584, miR-618, miR-638, mir-660, miR-92, miR-93, miR-98, and miR-99b.

In other embodiments, any miRNA chosen from the following list can be used in combination with another serum miRNA biomarker to characterize prostate cancer: let-7a, let-7c, let-7d, let-7f, let-7g, miR-1, miR-103, miR-106a, miR-107, miR-10b, miR-122a, miR-125a, miR-125b, miR-126, miR-126*, miR-130a, miR-130b, miR-132, miR-139, miR-140, miR-142-5p, miR-143, miR-145, miR-146a, miR-148a, miR-155, miR-15a, miR-15b, miR-16, miR-17-5p, miR-181c, miR-185, miR-188, miR-18a, miR-18a*, miR-191, miR-192, miR-193a, miR-194, miR-195, miR-196b, miR-197, miR-199a*, miR-19a, miR-200a, miR-200c, miR-204, miR-206, miR-20a, miR-20b, miR-212, miR-214, miR-22, miR-222, miR-223, miR-224, miR-23a, miR-23b, miR-24, miR25, miR-26a, miR-26b, miR-28, miR-29a, miR-29c, miR-301, miR-30a-5p, miR-30b, miR-30c, miR-30d, miR-30e-3p, miR-32, miR-328, miR-331, miR-335, miR-339, miR-340, miR-342, miR-345, miR-346, miR-34a, miR-361, miR-365, miR-374, miR-375, miR-422b, miR-423, miR-425, miR-432*, miR-483, miR-501, miR-565, miR-566, miR-576, miR-584, miR-638, mir-660, miR-92, miR-93, miR-98, and miR-99b.

Some embodiments of the invention relate to amplifying and measuring at least a pair of miRNAs from serum. Table 2 includes pairs that may be used to characterize prostate cancer.

TABLE 2 miRNA pairs for diagnosis of prostate cancer from serum samples.
miRNA pairs

| | | |
|---|---|---|
| let-7a, miR-125b | miR-125b, miR-214 | miR-16, miR-192 |
| let-7c, miR-125b | miR-125b, miR-22 | miR-16, miR-200a |
| let-7c, miR-154* | miR-125b, miR-222 | miR-16, miR-200c |
| let-7d, miR-125b | miR-125b, miR-223 | miR-16, miR-26a |
| let-7d, miR-200c | miR-125b, miR-224 | miR-16, miR-34a |
| let-7d, miR-204 | miR-125b, miR-23a | miR-17-5p, miR-139 |
| let-7d, miR-206 | miR-125b, miR-23b | miR-17-5p, miR-375 |
| let7d, miR-26a | miR-125b, miR-24 | miR-181, let7d |
| let-7d, miR-375 | miR-125b, miR25 | miR-181c, miR-375 |
| let-7f, miR-10b | miR-125b, miR-26a | miR-188, miR-483 |
| let-7f, miR-125b | miR-125b, miR-26b | miR-195, miR-139 |
| let-7f, miR-204 | miR-125b, miR-28 | miR-195, miR-155 |
| let-7g, miR-125b | miR-125b, miR-29a | miR-195, miR-17-5p |
| miR-1, miR-125b | miR-125b, miR-29c | miR-195, miR-181 |
| miR-103, miR-125b | miR-125b, miR-301 | miR-195, miR-26a |
| miR-103, miR-375 | miR-125b, miR-30a-5p | miR-199a*, miR-24 |
| miR-106a, miR-125b | miR-125b, miR-30b | miR-200a, let7d |
| miR-107, miR-125b | miR-125b, miR-30c | miR-200a, miR-103 |
| miR-10b, let7d | miR-125b, miR-30d | miR-200a, mir-15b |
| miR-10b, let-7f | miR-125b, miR-30e-3p | miR-200a, miR-17-5p |
| miR-10b, let-7g | miR-125b, miR-32 | miR-200a, miR-195 |
| miR-10b, mir-15b | miR-125b, miR-328 | miR-200a, miR-20a |
| miR-10b, miR-16 | miR-125b, miR-331 | miR-200a, miR-22 |
| miR-10b, miR-17-5p | miR-125b, miR-335 | miR-200a, miR-24 |
| miR-10b, miR-195 | miR-125b, miR-339 | miR-200c, let7d |
| miR-10b, miR-20a | miR-125b, miR-340 | miR-200c, mir-15b |
| miR-10b, miR-24 | miR-125b, miR-342 | miR-200c, miR-195 |
| miR-10b, miR-30b | miR-125b, miR-345 | miR-200c, miR-24 |
| miR-10b, miR-32 | miR-125b, miR-361 | miR-204, miR-24 |
| miR-10b, miR-335 | miR-125b, miR-365 | miR-204, miR-30b |
| miR-122a, let7d | miR-125b, miR-374 | miR-204, miR-30c |
| miR-122a, mir-15b | miR-125b, miR-422b | miR-204, miR-340 |
| miR-122a, miR-16 | miR-125b, miR-423 | miR206, let7d |
| miR-122a, miR-17-5p | miR-125b, miR-425 | miR206, mir-15b |
| miR-122a, miR-192 | miR-125b, miR-565 | miR206, miR-16 |
| miR-122a, miR-195 | miR-125b, miR-576 | miR206, miR-195 |
| miR-122a, miR-20a | miR-125b, miR-584 | miR206, miR-20a |
| miR-122a, miR-22 | miR-125b, miR-638 | miR206, miR-22 |
| miR-125a, miR-125b | miR-125b, mir660 | miR-206, miR-24 |
| miR-125b, let7d | miR-125b, miR-92 | miR-206, miR-29a |
| miR-125b, let-7f | miR-125b, miR-93 | miR-206, miR-29c |
| miR-125b, let-7g | miR-125b, miR-98 | miR-206, miR-30e-3p |
| miR-125b, miR-103 | miR-126, miR-24 | miR-206, miR-340 |
| miR-125b, miR-126 | miR-130a, miR-375 | miR-20a, miR-139 |

TABLE 2-continued miRNA pairs for diagnosis of prostate cancer from serum samples.
miRNA pairs

| | | |
|---|---|---|
| miR-125b, miR-126* | miR-130b, miR-375 | miR-20a, miR-155 |
| miR-125b, miR-130a | miR-132, miR-200c | miR-20a, miR-26a |
| miR-125b, miR-130b | miR-132, miR-375 | miR-212, miR-375 |
| miR-125b, miR-132 | miR-139, let7d | miR-22, miR-139 |
| miR-125b, miR-140 | miR-139, let-7f | miR-24, miR-139 |
| miR-125b, miR-142-5p | miR-139, let-7g | miR-24, miR-375 |
| miR-125b, miR-143 | miR-139, miR-103 | miR-29a, miR-16 |
| miR-125b, miR-145 | miR-139, miR-15b | miR-29c, miR-122a |
| miR-125b, miR-148a | miR-139, miR-191 | miR-29c, miR-200a |
| miR-125b, miR-155 | miR-139, miR-24 | miR-30b, miR-375 |
| miR-125b, miR-15a | miR-139, miR-26a | miR-30c, miR-375 |
| miR-125b, miR-15b | miR-146a, miR-375 | miR-30e-3p, miR-375 |
| miR-125b, miR-16 | miR-155, let7d | miR-340, miR-375 |
| miR-125b, miR-17-5p | miR-155, miR-191 | miR-346, miR-483 |
| miR-125b, miR-181c | miR-155, miR-24 | miR-34a, miR-195 |
| miR-125b, miR-185 | miR-15a, miR-375 | miR-361, miR-375 |
| miR-125b, miR-18a | mir-15b, miR-139 | miR-375, miR-422b |
| miR-125b, miR-18a* | mir-15b, miR-155 | miR-375, miR-425 |
| miR-125b, miR-191 | miR-15b, miR-200c | miR-432*, miR-483 |
| miR-125b, miR-192 | miR-15b, miR-204 | miR-483, miR-566 |
| miR-125b, miR-193a | mir-15b, miR-26a | miR-483, miR-584 |
| miR-125b, miR-194 | miR-15b, miR-375 | miR-99b, let7d |
| miR-125b, miR-195 | miR-15b, miR-483 | miR-99b, mir-15b |
| miR-125b, miR-196b | miR-16, miR-103 | miR-99b, miR-16 |
| miR-125b, miR-197 | miR-16, miR-139 | miR-99b, miR-191 |
| miR-125b, miR-199a* | miR-16, miR-155 | miR-99b, miR-195 |
| miR-125b, miR-19a | miR-16, miR-17-5p | miR-99b, miR-20a |
| miR-125b, miR-20a | miR-16, miR-181 | miR-99b, miR-24 |
| miR-125b, miR-20b | miR-16, miR-191 | |

In certain embodiments, pairs of miRNA markers from serum can be used to predict the aggressiveness or stage of prostate cancer. For example, one of the miRNA pairs in Table 3 may be used to determine cancer aggressiveness.

TABLE 3

Biomarker pairs that can be used to identify serum from prostate cancer patients with high Gleason scores.
miRNA Pairs

| | |
|---|---|
| miR-27a, miR-495 | miR-148a, miR-495 |
| miR-27b, miR-495 | miR-148b, miR-495 |
| miR-152, miR-495 | let-7c, miR-154* |
| miR-133b, miR-495 | miR-194, miR-495 |
| miR-29a, miR-495 | miR-130b, miR-495 |
| miR-199b, miR-495 | miR-181c, miR-495 |
| miR-29c, miR-495 | miR-199a*, miR-495 |
| miR-146a, miR-495 | miR-223, miR-495 |
| miR-106b, miR-495 | miR-221, miR-495 |
| miR-15a, miR-495 | miR-155, miR-495 |
| miR-142-3p, miR-495 | miR-28, miR-495 |
| miR-135a, miR-495 | miR-187, miR-618 |
| miR-146b, miR-495 | miR-301, miR-495 |
| miR-218, miR-432 | miR-218, miR-378 |
| miR-23a, miR-495 | miR-142-5p, miR-495 |
| miR-188, miR-218 | miR-132, miR-495 |
| miR-181d, miR-495 | miR-130a, miR-495 |
| miR-146a, miR-539 | |

Other miRNAs and groups of miRNAs that can be used in the methods of the invention will be apparent from the Examples described herein.

III. METHODS TO MEASURE THE LEVEL OF A miRNA

Many methods of measuring the levels or amounts of miRNAs are contemplated. Any reliable, sensitive, and specific method can be used. In some embodiments, a miRNA is amplified prior to measurement. In other embodiments, the level of miRNA is measured during the amplification process. In still other methods, the miRNA is not amplified prior to measurement.

A. Amplification Reactions

Many methods exist for amplifying miRNA nucleic acid sequences such as mature miRNAs, precursor miRNAs, and primary miRNAs. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method is used, such as reverse transcription followed by real time quantitative PCR (qRT-PCR) (Chen et al., Nucleic Acids Research, 33(20):e179 (2005)).

A typical PCR reaction includes multiple amplification steps, or cycles that selectively amplify target nucleic acid species: a denaturing step in which a target nucleic acid is denatured; an annealing step in which a set of PCR primers (forward and reverse primers) anneal to complementary DNA strands; and an elongation step in which a thermostable DNA polymerase elongates the primers. By repeating these steps multiple times, a DNA fragment is amplified to produce an amplicon, corresponding to the target DNA sequence. Typical PCR reactions include 20 or more cycles of denaturation, annealing, and elongation. In many cases, the annealing and elongation steps can be performed concurrently, in which case the cycle contains only two steps. Since mature miRNAs are single-stranded, a reverse transcription reaction (which produces a complementary cDNA sequence) may be performed prior to PCR reactions. Reverse transcription reactions include the use of, e.g., a RNA-based DNA polymerase (reverse transcriptase) and a primer.

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than 15, 20, 25, 30, or 35 nucleotides in length. In additional embodiments, a primer is at least 35 nucleotides in length.

In a further aspect, a forward primer can comprise at least one sequence that anneals to a miRNA biomarker and alternatively can comprise an additional 5' non-complementary region. In another aspect, a reverse primer can be designed to anneal to the complement of a reverse transcribed miRNA. The reverse primer may be independent of the miRNA biomarker sequence, and multiple miRNA biomarkers may be amplified using the same reverse primer. Alternatively, a reverse primer may be specific for a miRNA biomarker.

In some embodiments, two or more miRNAs are amplified in a single reaction volume. One aspect includes multiplex q-PCR, such as qRT-PCR, which enables simultaneous amplification and quantification of at least two miRNAs of interest in one reaction volume by using more than one pair of primers and/or more than one probe. The primer pairs comprise at least one amplification primer that uniquely binds each miRNA, and the probes are labeled such that they are distinguishable from one another, thus allowing simultaneous quantification of multiple miRNAs. Multiplex qRT-PCR has research and diagnostic uses, including but not limited to detection of miRNAs for diagnostic, prognostic, and therapeutic applications.

The qRT-PCR reaction may further be combined with the reverse transcription reaction by including both a reverse transcriptase and a DNA-based thermostable DNA polymerase. When two polymerases are used, a "hot start" approach may be used to maximize assay performance (U.S. Pat. Nos. 5,411,876 and 5,985,619). For example, the components for a reverse transcriptase reaction and a PCR reaction may be sequestered using one or more thermoactivation methods or chemical alteration to improve polymerization efficiency (U.S. Pat. Nos. 5,550,044, 5,413,924, and 6,403,341).

B. Detection of miRNAs

In certain embodiments, labels, dyes, or labeled probes and/or primers are used to detect amplified or unamplified miRNAs. The skilled artisan will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where miRNA amplification is preferred.

A probe or primer may include Watson-Crick bases or modified bases. Modified bases include, but are not limited to, the AEGIS bases (from Eragen Biosciences), which have been described, e.g., in U.S. Pat. Nos. 5,432,272, 5,965,364, and 6,001,983. In certain aspects, bases are joined by a natural phosphodiester bond or a different chemical linkage. Different chemical linkages include, but are not limited to, a peptide bond or a Locked Nucleic Acid (LNA) linkage, which is described, e.g., in U.S. Pat. No. 7,060,809.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan™) probes (see U.S. Pat. No. 5,538,848), stem-loop molecular beacons (see, e.g., U.S. Pat. Nos. 6,103,476 and 5,925,517), stemless or linear beacons (see, e.g., WO 9921881, U.S. Pat. Nos. 6,485,901 and 6,649,349), peptide nucleic acid (PNA) Molecular Beacons (see, e.g., U.S. Pat. Nos. 6,355,421 and 6,593,091), linear PNA beacons (see, e.g. U.S. Pat. No. 6,329,144), non-FRET probes (see, e.g., U.S. Pat. No. 6,150,097), Sunrise™/ AmplifluorB™probes (see, e.g., U.S. Pat. No. 6,548,250), stem-loop and duplex Scorpion™ probes (see, e.g., U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB Eclipse™ probe (Epoch Biosciences), hairpin probes (see, e.g., U.S. Pat. No. 6,596,490), PNA light-up probes, antiprimer quench probes (Li et al., Clin. Chem. 53:624-633 (2006)), self-assembled nanoparticle probes, and ferrocene-modified probes described, for example, in U.S. Pat. No. 6,485,901.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels.

In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g., biotin-avidin). In still other aspects, use of labels can be accomplished using any one of a large number of known techniques employing known labels, linkages, linking groups, reagents, reaction conditions, and analysis and purification methods.

MiRNAs can be detected by direct or indirect methods. In a direct detection method, one or more miRNAs are detected by a detectable label that is linked to a nucleic acid molecule. In such methods, the miRNAs may be labeled prior to binding to the probe. Therefore, binding is detected by screening for the labeled miRNA that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified miRNAs, are detected using FlexMAP Microspheres (Luminex) conjugated with probes to capture the desired nucleic acids.

Some methods may involve detection with polynucleotide probes modified with fluorescent labels or branched DNA (bDNA) detection, for example.

In other embodiments, nucleic acids are detected by indirect detection methods. For example, a biotinylated probe may be combined with a stretavidin-conjugated dye to detect the bound nucleic acid. The streptavidin molecule binds a biotin label on amplified miRNA, and the bound miRNA is detected by detecting the dye molecule attached to the streptavidin molecule. In one embodiment, the streptavidin-conjugated dye molecule comprises Phycolink® Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal (see, e.g., Kricka, L., Nonisotopic DNA Probe Techniquies, Academic Press, San Diego (1992) and Garman A., Non-Radioactive Labeling, Academic Press (1997).). Fluorescent reporter dyes useful as labels include, but are not limited to, fluoresceins (see, e.g., U.S. Pat. Nos. 5,188,934, 6,008,379, and 6,020,481), rhodamines (see, e.g., U.S. Pat. Nos. 5,366,860, 5,847,162, 5,936,087, 6,051,719, and 6,191,278), benzophenoxazines (see, e.g., U.S. Pat. No. 6,140,500), energy-transfer fluorescent dyes, comprising pairs of donors and acceptors (see, e.g., U.S. Pat. Nos. 5,863,727; 5,800,996; and 5,945,526), and cyanines (see, e.g., WO 9745539), lissamine, phycoerythrin, Cy2, Cy3, Cy3.5, Cy5, Cy5.5, Cy7, FluorX (Amersham), Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, Tetramethylrhodamine, and/or Texas Red, as well as any other fluorescent moiety capable of generating a detectable signal. Examples of fluorescein dyes include, but are not limited to, 6-carboxyfluorescein; 2',4',1,4,-tetrachlorofluorescein, and 2',4',5',7',1, 4-hexachlorofluorescein. In certain aspects, the fluorescent label is selected from SYBR-Green, 6-carboxyfluorescein ("FAM"), TET, ROX, VICTM, and JOE. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In still a further aspect, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g., Blackburn et al., eds. "DNA and RNA Structure" in Nucleic Acids in Chemistry and Biology (1996)).

In further aspects, methods relying on hybridization and/or ligation to quantify miRNAs may be used, including oligonucleotide ligation (OLA) methods and methods that allow a distinguishable probe that hybridizes to the target nucleic acid sequence to be separated from an unbound probe. As an example, HARP-like probes, as disclosed in U.S. Publication No. 2006/0078894 may be used to measure the quantity of miRNAs. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

In an additional embodiment of the method, a probe ligation reaction may be used to quantify miRNAs. In a Multiplex Ligation-dependent Probe Amplification (MLPA) technique (Schouten et al., Nucleic Acids Research 30:e57 (2002)), pairs of probes which hybridize immediately adjacent to each other on the target nucleic acid are ligated to each other only in the presence of the target nucleic acid. In some aspects, MLPA probes have flanking PCR primer binding sites. MLPA probes can only be amplified if they have been ligated, thus allowing for detection and quantification of miRNA biomarkers.

IV. EXAMPLES

The following examples illustrate various embodiments of the invention and are not intended to limit the scope of the invention.

The examples described herein include the use of qRT-PCR, which includes real-time monitoring of PCR products during the exponential phase instead of by an end-point measurement. The threshold cycle ($C_t$) measurements in the examples refer to the number of cycles it takes to reach a pre-defined point in the fluorescent signal.

Example 1

MicroRNA Serum Biomarkers of Prostate Cancer and BPH miRNAs potentially relevant to carcinogenesis frequently exhibit differential expression in cancerous versus normal samples. In certain instances, differential expression in a disease sample leads to reduced or elevated levels of the miRNA in serum or plasma isolated from the individual. In addition, miRNAs with reduced or elevated levels in normal and cancerous samples may be used in the diagnosis of cancerous lesions and in patient prognosis. To identify miRNAs present in serum, that may be useful markers for diagnosis of prostate cancer and for establishing patient prognosis, the inventors evaluated miRNA levels in serum samples from twelve normal male donors, twelve PrCa patients, and twelve patients with BPH (Table 4). Patient and normal serum samples were purchased from ProteoGenex, Inc. (Culver City, Calif., USA).

TABLE 4

Histopathological data and patient information.

| Patient Diagnosis | Patient Age | Smoker | Stage (Greene et al., 2002) | PSA | Gleason Score |
|---|---|---|---|---|---|
| BPH | 53 | Yes | | 2.2 | NA |
| BPH | 71 | No | PIN II | 9.2 | NA |
| BPH | 46 | No | | 8.3 | NA |
| BPH | 66 | Yes | PIN III | 4 | NA |
| BPH | 51 | No | | 9.2 | NA |
| BPH | 66 | No | PIN II | 5.2 | NA |
| BPH | 47 | No | | 7.3 | NA |
| BPH | 66 | Yes | | 6.5 | NA |
| BPH | 45 | No | | 9 | NA |
| BPH | 41 | Yes | | 3.2 | NA |
| BPH | 53 | Yes | | 4 | NA |
| BPH | 50 | No | | 7 | NA |
| PrCa | 71 | No | T1c | 5.1 | 5 (2 + 3) |
| PrCa | 73 | No | T1c | 8.2 | 7 (3 + 4) |
| PrCa | 78 | No | T2 | 18 | |
| PrCa | 75 | No | T1c | 13 | 5 (3 + 2) |
| PrCa | 65 | No | T3 | 30 | 7 (3 + 4) |
| PrCa | 62 | Yes | T1c | 16 | 7 (3 + 4) |
| PrCa | 67 | No | T2 | 12 | 4 (2 + 2) |
| PrCa | 61 | No | T2 | 4.4 | 5 (2 + 3) |
| PrCa | 69 | No | T1c | 6.4 | 5 (2 + 3) |
| PrCa | 61 | No | T3 | 52.6 | 8 (4 + 4) |
| PrCa | 62 | No | T1c | 10.6 | 4 (2 + 2) |
| PrCa | 77 | No | T3 | 31 | Unknown |
| Normal | 50 | No | NA | 0.44 | NA |
| Normal | 49 | No | NA | 0.34 | NA |
| Normal | 49 | No | NA | 0.37 | NA |
| Normal | 48 | No | NA | 0.36 | NA |
| Normal | 48 | Yes | NA | 0.36 | NA |
| Normal | 48 | No | NA | 0.54 | NA |
| Normal | 51 | No | NA | Unknown | NA |
| Normal | 48 | No | NA | Unknown | NA |
| Normal | 46 | Yes | NA | Unknown | NA |
| Normal | 52 | No | NA | Unknown | NA |
| Normal | 53 | No | NA | Unknown | NA |
| Normal | 47 | No | NA | Unknown | NA |

PIN, prostate intraepithelial neoplasia.
NA, not available.

For serum preparation, ten (10) ml of whole blood was collected from patients and normal donors using a BD Vacutainer® glass serum tube (Becton, Dickinson and Company; Franklin Lakes, N.J., USA; cat. no. 366441). Following blood collection, tubes were incubated at room temperature for up to 2.5 hours to allow the blood to clot. Tubes were centrifuged for ten minutes at 2,000×g. Serum was transferred to a new tube using a serological pipette and frozen at −80° C. until it was processed for RNA isolation.

Serum RNA was purified using the organic extraction of the mirVana PARIS™ Kit (Part No. AM1556; Applied Biosystems/Ambion; Austin, Tex., USA), with the following modifications. Following the addition of acid phenol:chloroform and vortexing, samples were incubated on ice for 5 min then centrifuged at 13,000×g for 10 min at 4° C. The aqueous layer was removed, extracted with chloroform, and centrifuged again. The aqueous layer was removed from the second extraction, and 3M NaOAc (1/10 volume), glycogen (5 mg/ml), and 100% ethanol (1.5 volume) were added to the samples. Lysate/ethanol mixtures were passed through a mirVana PARIS filter cartridge, and filters were washed once with 650 µl of Wash 1 buffer and twice with 650 µl of Wash 2/3 buffer, RNA was eluted with two aliquots of nuclease free water (50 µl) and stored at −80° C.

Levels of 329 miRNAs in serum samples were determined by qRT-PCR using TaqMan® MicroRNA Assays (Applied Biosystems; Foster City, Calif., USA) specific for each miRNA. Reverse transcription (RT) reaction components (Table 5) were assembled on ice prior to the addition of RNA template. Serum RNA (0.25 µl per reaction) was added and mixed. RT reactions were incubated in a 384-well GeneAmp® PCR System 9700 (Applied Biosystems) at 16° C. for 30 minutes, then at 42° C. for 30 minutes, then at 85° C. for 5 minutes. RT reactions were then frozen at −20° C. All reaction components were as provided by the manufacturer (Applied Biosystems; Foster City, Calif., USA) unless otherwise specified.

TABLE 5

Reverse transcription reaction components.

| Component | µl per 10 µl rxn | Final Concentration |
|---|---|---|
| Nuclease-free water | 5.85 | |
| 10× Reverse Transcription Buffer | 1.0 | 1X |
| dNTP mix (100 mM) | 0.1 | 1 mM |
| 1.25X RT Primer | 2.0 | 0.25X |
| RNase Inhibitor (20 U/µl) | 0.13 | 0.26 U/µl |
| Multiscribe ™ Recombinant Moloney Murine Leukemia Virus Reverse Transcriptase (MMLV-RT) (50U/ul) | 0.67 | 3.35 U/µl |
| Human Serum RNA | 0.25 | |

PCR components (Table 6) were assembled on ice prior to the addition of cDNA (4 µl) from the RT reaction. Reactions were incubated in an ABI PRISM™ 7900HT Fast Real-Time PCR system (Applied Biosystems) at 95° C. for 1 minute, then for 50 cycles at 95° C. for 5 seconds and 60° C. for 30 seconds. Results were analyzed with the 7900HT Fast Real-Time PCR system SDS V2.3 software (Applied Biosystems). All reaction components were as provided by the manufacturer (Applied Biosystems; Foster City, Calif., USA) unless otherwise specified.

TABLE 6

PCR components.

| Component | µl per 15 µl rxn | Final Concentration |
|---|---|---|
| Nuclease-free water | 4.1 | |
| MgCl$_2$ (50 mM) | 1.5 | 5 mM |
| 10X Platinum PCR Buffer, Minus Mg (Invitrogen Corp.; Carlsbad, CA, USA) | 1.5 | 1 X |
| dNTP mix (2.5 mM each) (Ambion, Inc.; Austin, TX USA) | 1.5 | 0.25 mM each |
| 3X TaqMan Assay Buffer | 2.0 | 0.4 X |
| 50X ROX Internal Marker | 0.3 | 1 X |
| Platinum ® Taq DNA Polymerase (5 U/µl) (Invitrogen) | 0.1 | 0.033 U/µl |
| cDNA from RT reaction | 4.0 | |

The qRT-PCR data were initially assessed for outliers. All miRNAs in a given sample with raw Ct readings of 50 were eliminated from further analyses. All data from samples having fewer than 150 miRNAs with raw Ct values <50 were eliminated. The average raw Ct for 50 miRNAs that were detected in each sample analyzed was calculated for each of the individual samples. The average Ct for a given sample was subtracted from the raw Ct readings for each miRNA in the corresponding sample to produce a dCt for each miRNA that was detected.

The average dCt values for each miRNA in the normal donor, BPH, and PrCa patient samples were calculated. The average dCt values for the PrCa patient samples were subtracted from the average dCt values for the normal donor or BPH samples, and the average dCt values for the BPH samples were subtracted from the average dCt values for normal donor samples to determine the variance in the miRNA levels between the three patient sets. Student's t-test was then used to determine the potential of various miRNAs to distinguish the sera of PrCa patients from sera of normal donors or patients with BPH. Table 7 provides the average dCt values, the difference in miRNA levels between patient sets, and p-values for each miRNA tested. miRNAs that are present at reduced or elevated levels in PrCa patients compared to BPH or normal patients represent biomarkers of prostate cancer that can be used to diagnose prostate cancer using the serum from a patient.

TABLE 7

Normalized qRT-PCR data for quantification of 329 miRNAs in serum from PrCa patients, BPH patients, and normal donors (norm).

| miRNA | Avg BPH | Avg Norm | Avg PrCa | BPH − norm | BPH − PrCa | norm − PrCa | p value (BPH vs norm) | p value (BPH vs PrCa) | p value (Norm vs PrCa) |
|---|---|---|---|---|---|---|---|---|---|
| let-7a | 0.83 ± 1.13 | −0.28 ± 0.41 | 1.08 ± 1.2 | 1.11 | −0.24 | −1.36 | 3.95E-03 | 6.11E-01 | 1.19E-03 |
| let-7b | 1.18 ± 0.96 | 0.45 ± 0.67 | 0.51 ± 0.56 | 0.73 | 0.66 | −0.06 | 4.29E-02 | 5.08E-02 | 8.04E-01 |
| let-7c | 4.47 ± 1 | 3.68 ± 0.69 | 3.97 ± 0.69 | 0.79 | 0.49 | −0.29 | 3.56E-02 | 1.74E-01 | 3.10E-01 |
| let-7d | 3.37 ± 0.74 | 2.51 ± 0.59 | 3.8 ± 0.64 | 0.86 | −0.43 | −1.29 | 4.59E-03 | 1.43E-01 | 3.76E-05 |
| let-7e | 9.3 ± 1.12 | 7.99 ± 0.76 | 9.14 ± 0.91 | 1.31 | 0.16 | −1.15 | 2.86E-03 | 7.02E-01 | 2.77E-03 |
| let-7f | 3.76 ± 1.17 | 2.56 ± 0.29 | 4.31 ± 1.31 | 1.2 | −0.55 | −1.75 | 2.24E-03 | 2.94E-01 | 1.71E-04 |
| let-7g | 0.56 ± 0.8 | −0.46 ± 0.61 | 0.86 ± 1.07 | 1.02 | −0.29 | −1.31 | 1.97E-03 | 4.57E-01 | 1.28E-03 |
| let-7i | 1.52 ± 0.91 | 1.47 ± 0.66 | 1.23 ± 0.79 | 0.05 | 0.3 | 0.25 | 8.78E-01 | 4.02E-01 | 4.16E-01 |
| miR-500 | 8.04 ± 1.29 | 9.24 ± 2.91 | 9.08 ± 1.92 | −1.2 | −1.05 | 0.15 | 2.05E-01 | 1.44E-01 | 8.89E-01 |
| miR-501 | 6.26 ± 0.68 | 6.82 ± 1.15 | 6.25 ± 0.69 | −0.56 | 0.01 | 0.56 | 1.63E-01 | 9.75E-01 | 1.58E-01 |
| miR-1 | 1.25 ± 0.91 | 0.76 ± 0.54 | 0.87 ± 0.8 | 0.49 | 0.37 | −0.11 | 1.27E-01 | 2.99E-01 | 6.86E-01 |
| miR-100 | 6.21 ± 1.22 | 7.05 ± 1.05 | 5.97 ± 0.58 | −0.84 | 0.24 | 1.08 | 8.18E-02 | 5.46E-01 | 4.78E-03 |
| miR-101 | 2.14 ± 0.8 | 2.32 ± 0.65 | 1.84 ± 0.93 | −0.18 | 0.3 | 0.48 | 5.57E-01 | 4.06E-01 | 1.58E-01 |
| miR-103 | 0.65 ± 0.49 | 0.3 ± 0.34 | 0.65 ± 0.54 | 0.35 | 0 | −0.35 | 5.75E-02 | 9.98E-01 | 7.26E-02 |
| miR-105 | 12.53 ± 2.13 | 13.39 ± 3.63 | 12.41 ± 2.75 | −0.86 | 0.12 | 0.98 | 5.15E-01 | 9.13E-01 | 4.63E-01 |
| miR-106a | 0.89 ± 0.59 | 0.29 ± 0.26 | 0.81 ± 0.42 | 0.61 | 0.08 | −0.52 | 3.74E-03 | 7.01E-01 | 1.25E-03 |
| miR-106b | −0.44 ± 0.84 | 0.03 ± 0.4 | −0.88 ± 0.93 | −0.47 | 0.44 | 0.91 | 9.37E-02 | 2.37E-01 | 5.16E-03 |
| miR-107 | 7.1 ± 1.18 | 6.28 ± 0.48 | 6.9 ± 0.69 | 0.82 | 0.21 | −0.62 | 3.54E-02 | 6.05E-01 | 1.90E-02 |
| miR-10a | 7.26 ± 0.95 | 7.32 ± 0.79 | 6.74 ± 0.76 | −0.06 | 0.52 | 0.58 | 8.67E-01 | 1.51E-01 | 8.00E-02 |
| miR-10b | 6.93 ± 1.26 | 7.17 ± 1.13 | 5.93 ± 0.9 | −0.23 | 1.01 | 1.24 | 6.37E-01 | 3.38E-02 | 7.00E-03 |
| miR-122a | 10.2 ± 3.69 | 11.92 ± 3.56 | 7.22 ± 1.74 | −1.71 | 2.98 | 4.7 | 2.84E-01 | 2.36E-02 | 9.75E-04 |
| miR-124a | 11.59 ± 3.99 | 14.16 ± 3.93 | 13.68 ± 4.76 | −2.57 | −2.09 | 0.47 | 2.20E-01 | 4.02E-01 | 8.16E-01 |
| miR-125a | 3.38 ± 0.73 | 3.17 ± 0.65 | 2.89 ± 1.03 | 0.2 | 0.49 | 0.29 | 4.82E-01 | 1.93E-01 | 4.22E-01 |
| miR-125b | 5.86 ± 0.6 | 6.51 ± 0.39 | 4.19 ± 0.89 | −0.66 | 1.66 | 2.32 | 4.46E-03 | 2.33E-05 | 3.74E-08 |
| miR-126 | −0.58 ± 0.37 | −0.63 ± 0.33 | −0.85 ± 0.47 | 0.06 | 0.27 | 0.21 | 6.96E-01 | 1.32E-01 | 2.11E-01 |
| miR-126* | 0.57 ± 0.42 | 0.46 ± 0.37 | 0.23 ± 0.41 | 0.11 | 0.34 | 0.23 | 5.04E-01 | 5.80E-02 | 1.66E-01 |
| miR-127 | 5.39 ± 1.35 | 5.06 ± 1.08 | 4.84 ± 1.71 | 0.33 | 0.56 | 0.23 | 5.13E-01 | 3.84E-01 | 7.02E-01 |
| miR-128a | 11.56 ± 3.78 | 10.25 ± 1.01 | 9.54 ± 0.95 | 1.31 | 2.02 | 0.71 | 3.02E-01 | 1.61E-01 | 1.50E-01 |
| miR-128b | 16.03 ± 3.6 | 13.76 ± 3.52 | 15.2 ± 4.18 | 2.27 | 0.83 | −1.44 | 1.51E-01 | 6.50E-01 | 4.27E-01 |
| miR-129 | 16.31 ± 3.57 | 14.43 ± 3.65 | 15.78 ± 2.57 | 1.87 | 0.53 | −1.35 | 2.27E-01 | 7.01E-01 | 3.45E-01 |
| miR-130a | 1.18 ± 0.52 | 1.39 ± 0.39 | 1.37 ± 0.58 | −0.21 | −0.18 | 0.03 | 2.75E-01 | 4.27E-01 | 8.90E-01 |
| miR-130b | 2.43 ± 0.6 | 2.89 ± 0.42 | 2.68 ± 0.7 | −0.47 | −0.26 | 0.21 | 3.87E-02 | 3.46E-01 | 3.89E-01 |
| miR-132 | 4.72 ± 0.71 | 4.16 ± 0.47 | 4.78 ± 0.31 | 0.56 | −0.06 | −0.61 | 3.42E-01 | 8.00E-01 | 9.32E-04 |
| miR-133a | 6.54 ± 1.15 | 7.23 ± 1.09 | 6.31 ± 0.79 | −0.69 | 0.23 | 0.92 | 1.48E-01 | 5.71E-01 | 2.77E-02 |
| miR-133b | 4.55 ± 1.14 | 4.87 ± 1.07 | 4.24 ± 1.01 | −0.31 | 0.32 | 0.63 | 4.98E-01 | 4.82E-01 | 1.55E-01 |
| miR-134 | 5.76 ± 1.34 | 5.35 ± 0.8 | 5.37 ± 1.71 | 0.4 | 0.38 | −0.02 | 3.81E-01 | 5.46E-01 | 9.73E-01 |
| miR-135a | 8.93 ± 1.15 | 9.01 ± 1.18 | 9.46 ± 2.81 | −0.08 | −0.53 | −0.45 | 8.66E-01 | 5.53E-01 | 6.32E-01 |
| miR-135b | 12.77 ± 2.77 | 13.08 ± 3.96 | 13.6 ± 4.41 | −0.31 | −0.83 | −0.52 | 8.43E-01 | 6.26E-01 | 7.89E-01 |
| miR-136 | 15.81 ± 3.41 | 18.45 ± 3.25 | 14.15 ± 4.39 | −2.63 | 1.66 | 4.29 | 1.32E-01 | 3.92E-01 | 5.95E-02 |
| miR-137 | 14.64 ± 2.93 | 14 ± 3.13 | 13.68 ± 4.09 | 0.64 | 0.97 | 0.33 | 6.10E-01 | 5.18E-01 | 8.30E-01 |
| miR-138 | 10.06 ± 1.38 | 10.67 ± 1.54 | 8.9 ± 1.33 | −0.62 | 1.16 | 1.77 | 3.11E-01 | 5.34E-02 | 7.63E-03 |
| miR-139 | 5.92 ± 0.69 | 6.38 ± 0.57 | 5.31 ± 0.33 | −0.46 | 0.61 | 1.07 | 8.84E-02 | 1.09E-02 | 1.07E-05 |
| miR-140 | 2.08 ± 0.87 | 2.2 ± 0.2 | 2.31 ± 0.42 | −0.12 | −0.23 | −0.11 | 6.51E-01 | 4.26E-01 | 4.28E-01 |
| miR-141 | 9.38 ± 1.02 | 10.3 ± 2.2 | 8.61 ± 2.03 | −0.92 | 0.76 | 1.69 | 2.00E-01 | 2.63E-01 | 7.07E-02 |
| miR-142-3p | −0.91 ± 0.55 | −0.46 ± 0.44 | −0.74 ± 0.78 | −0.44 | −0.17 | 0.28 | 4.09E-02 | 5.55E-01 | 2.98E-01 |
| miR-142-5p | 3.08 ± 0.98 | 3.67 ± 0.66 | 3.48 ± 0.55 | −0.59 | −0.4 | 0.19 | 9.63E-02 | 2.27E-01 | 4.53E-01 |
| miR-143 | 7.7 ± 1.41 | 8.06 ± 0.6 | 8.65 ± 2.66 | −0.36 | −0.95 | −0.59 | 4.20E-01 | 2.87E-01 | 4.64E-01 |
| miR-145 | 4.84 ± 0.68 | 4.51 ± 0.82 | 4.62 ± 1.06 | 0.33 | 0.22 | −0.11 | 3.01E-01 | 5.59E-01 | 7.79E-01 |
| miR-146a | −0.96 ± 0.61 | −0.76 ± 0.53 | −1.05 ± 0.9 | −0.21 | 0.08 | 0.29 | 3.84E-01 | 7.92E-01 | 3.43E-01 |
| miR-146b | 0.53 ± 0.56 | 0.75 ± 0.59 | 0.43 ± 0.99 | −0.22 | 0.1 | 0.32 | 3.66E-01 | 7.60E-01 | 3.49E-01 |
| miR-147 | 11.14 ± 1.65 | 11.78 ± 3.63 | 10.25 ± 1.54 | −0.64 | 0.89 | 1.53 | 5.81E-01 | 2.22E-01 | 2.50E-01 |
| miR-148a | 1.23 ± 1.27 | 2.17 ± 0.58 | 1.83 ± 0.7 | −0.94 | −0.6 | 0.35 | 2.86E-02 | 1.68E-01 | 2.01E-01 |
| miR-148b | 3 ± 0.63 | 3.52 ± 0.4 | 2.86 ± 0.69 | −0.52 | 0.13 | 0.66 | 2.40E-02 | 6.22E-01 | 9.19E-03 |
| miR-149 | 10.77 ± 3.1 | 11.35 ± 4.45 | 11.33 ± 3.71 | −0.58 | −0.56 | 0.03 | 7.21E-01 | 7.01E-01 | 9.88E-01 |
| miR-151 | 2.06 ± 0.97 | 2.59 ± 0.53 | 1.61 ± 1.16 | −0.53 | 0.45 | 0.98 | 1.08E-01 | 3.12E-01 | 1.37E-02 |

TABLE 7-continued

Normalized qRT-PCR data for quantification of 329 miRNAs in serum from PrCa patients, BPH patients, and normal donors (norm).

| miRNA | Avg BPH | Avg Norm | Avg PrCa | BPH − norm | BPH − PrCa | norm − PrCa | p value (BPH vs norm) | p value (BPH vs PrCa) | p value (Norm vs PrCa) |
|---|---|---|---|---|---|---|---|---|---|
| miR-152 | 5.95 ± 0.68 | 6.15 ± 0.58 | 5.5 ± 1.06 | −0.2 | 0.45 | 0.66 | 4.37E−01 | 2.23E−01 | 7.13E−02 |
| miR-153 | 13.13 ± 3.98 | 13.45 ± 3.98 | 14.9 ± 4.36 | −0.32 | −1.77 | −1.45 | 8.95E−01 | 5.49E−01 | 5.39E−01 |
| miR-154 | 11.38 ± 1.97 | 12.22 ± 2.42 | 10.36 ± 1.75 | −0.84 | 1.02 | 1.86 | 3.90E−01 | 2.50E−01 | 6.56E−02 |
| miR-154* | 11.22 ± 1.47 | 10.99 ± 1.31 | 11.98 ± 3.68 | 0.23 | −0.76 | −0.99 | 7.23E−01 | 5.96E−01 | 4.17E−01 |
| miR-155 | 4.9 ± 0.59 | 4.79 ± 0.44 | 4.82 ± 0.57 | 0.11 | 0.08 | −0.03 | 6.08E−01 | 7.53E−01 | 8.68E−01 |
| miR-15a | 4.37 ± 0.69 | 4.79 ± 0.38 | 4.74 ± 1.01 | −0.43 | −0.38 | 0.05 | 7.59E−02 | 2.99E−01 | 8.77E−01 |
| miR-15b | 1.54 ± 0.24 | 1.18 ± 0.35 | 1.95 ± 0.56 | 0.36 | −0.42 | −0.77 | 7.86E−03 | 2.61E−02 | 4.92E−04 |
| miR-16 | −5.17 ± 0.66 | −6.02 ± 0.38 | −5.01 ± 1.18 | 0.85 | −0.16 | −1.01 | 8.82E−04 | 6.79E−01 | 9.85E−03 |
| miR-17-3p | 6.95 ± 0.95 | 7.78 ± 0.83 | 6.39 ± 0.82 | −0.82 | 0.56 | 1.38 | 3.47E−02 | 1.36E−01 | 4.68E−04 |
| miR-17-5p | 2.01 ± 0.57 | 1.52 ± 0.29 | 2.17 ± 0.39 | 0.49 | −0.16 | −0.65 | 1.42E−02 | 4.33E−01 | 1.28E−04 |
| miR-181a | 3.58 ± 1.04 | 3.88 ± 0.93 | 3.58 ± 1.07 | −0.3 | 0 | 0.29 | 4.71E−01 | 9.92E−01 | 4.84E−01 |
| miR-181b | 3.43 ± 0.86 | 3.59 ± 0.46 | 3.09 ± 0.82 | −0.16 | 0.34 | 0.5 | 5.74E−01 | 3.37E−01 | 8.17E−02 |
| miR-181c | 6.43 ± 0.81 | 6.62 ± 0.39 | 6.81 ± 0.94 | −0.19 | −0.39 | −0.2 | 4.68E−01 | 2.92E−01 | 5.12E−01 |
| miR-181d | 3.39 ± 0.79 | 3.29 ± 0.55 | 2.93 ± 0.82 | 0.1 | 0.46 | 0.36 | 7.33E−01 | 1.76E−01 | 2.14E−01 |
| miR-182 | 5.05 ± 1.33 | 4.16 ± 0.72 | 5.19 ± 1.32 | 0.89 | −0.15 | −1.04 | 5.39E−02 | 7.90E−01 | 2.65E−02 |
| miR-182* | 14.6 ± 2.24 | 15.19 ± 4.99 | 14.23 ± 3.21 | −0.59 | 0.37 | 0.96 | 7.76E−01 | 7.99E−01 | 7.03E−01 |
| miR-183 | 10.61 ± 1.48 | 9.99 ± 0.98 | 10.21 ± 0.78 | 0.62 | 0.41 | −0.21 | 2.37E−01 | 4.05E−01 | 5.60E−01 |
| miR-184 | 11.62 ± 3.57 | 14.64 ± 4.17 | 12.13 ± 4.31 | −3.02 | −0.51 | 2.51 | 8.31E−02 | 7.82E−01 | 2.19E−01 |
| miR-185 | 4.56 ± 0.46 | 4.67 ± 0.41 | 4.55 ± 0.88 | −0.12 | 0 | 0.12 | 5.12E−01 | 9.97E−01 | 6.73E−01 |
| miR-186 | 1.23 ± 0.8 | 1.91 ± 0.4 | 1.08 ± 0.85 | −0.67 | 0.15 | 0.82 | 1.64E−02 | 6.59E−01 | 5.97E−03 |
| miR-187 | 11.65 ± 2.54 | 11.72 ± 2.96 | 11.3 ± 2.62 | −0.07 | 0.35 | 0.41 | 9.54E−01 | 7.43E−01 | 7.20E−01 |
| miR-188 | 6.52 ± 1.3 | 6.5 ± 1.45 | 6.55 ± 0.95 | 0.02 | −0.03 | −0.05 | 9.74E−01 | 9.50E−01 | 9.24E−01 |
| miR-189 | 13.71 ± 2.57 | 16.04 ± 1.81 | 13.85 ± 4.45 | −2.34 | −0.14 | 2.19 | 8.11E−02 | 9.49E−01 | 2.68E−01 |
| miR-18a | 3.55 ± 0.51 | 3.5 ± 0.36 | 3.42 ± 0.43 | 0.05 | 0.13 | 0.08 | 7.74E−01 | 5.13E−01 | 6.45E−01 |
| miR-18a* | 5.3 ± 0.8 | 5.06 ± 0.68 | 5.13 ± 0.89 | 0.24 | 0.17 | −0.07 | 4.35E−01 | 6.37E−01 | 8.19E−01 |
| miR-18b | 11.28 ± 2.97 | 12.13 ± 3.31 | 11.68 ± 2.99 | −0.85 | −0.4 | 0.44 | 5.43E−01 | 7.60E−01 | 7.56E−01 |
| miR-190 | 4.84 ± 0.85 | 5.37 ± 0.52 | 4.64 ± 0.74 | −0.53 | 0.2 | 0.73 | 7.83E−02 | 5.53E−01 | 1.10E−02 |
| miR-191 | 1.29 ± 0.45 | 1.08 ± 0.41 | 1.33 ± 0.6 | 0.21 | −0.04 | −0.25 | 2.35E−01 | 8.59E−01 | 2.40E−01 |
| miR-192 | 2.9 ± 0.87 | 3.71 ± 0.47 | 2.56 ± 0.52 | −0.81 | 0.34 | 1.15 | 9.22E−03 | 2.61E−01 | 9.69E−06 |
| miR-193a | 8.15 ± 1.26 | 9.15 ± 1.46 | 8.76 ± 0.61 | −1 | −0.61 | 0.39 | 8.60E−02 | 1.45E−01 | 4.02E−01 |
| miR-193b | 10.22 ± 1.55 | 11.6 ± 0.72 | 10.09 ± 1.58 | −1.38 | 0.12 | 1.5 | 1.06E−02 | 8.52E−01 | 7.33E−03 |
| miR-194 | 4.85 ± 0.64 | 5.22 ± 0.54 | 5.03 ± 0.71 | −0.37 | −0.17 | 0.19 | 1.42E−01 | 5.35E−01 | 4.58E−01 |
| miR-195 | 1.48 ± 0.77 | 0.49 ± 0.36 | 1.82 ± 1.29 | 0.99 | −0.34 | −1.33 | 5.66E−04 | 4.36E−01 | 2.38E−03 |
| miR-196a | 9.99 ± 1.61 | 9.29 ± 0.81 | 10.62 ± 2.48 | 0.7 | −0.63 | −1.33 | 1.94E−01 | 4.70E−01 | 9.21E−02 |
| miR-196b | 6.68 ± 0.77 | 6.45 ± 0.6 | 6.62 ± 0.43 | 0.23 | 0.06 | −0.17 | 4.28E−01 | 8.08E−01 | 4.44E−01 |
| miR-197 | 2.28 ± 0.95 | 2.17 ± 0.52 | 2.46 ± 0.89 | 0.11 | −0.18 | −0.28 | 7.37E−01 | 6.39E−01 | 3.49E−01 |
| miR198 | 8.75 ± 1.9 | 10.4 ± 2.13 | 11.06 ± 1.9 | −1.65 | −2.31 | −0.66 | 5.77E−02 | 7.00E−03 | 4.34E−01 |
| miR-199a | 7.91 ± 1.3 | 8.14 ± 0.77 | 7.79 ± 2.1 | −0.24 | 0.12 | 0.35 | 5.93E−01 | 8.71E−01 | 5.89E−01 |
| miR-199a* | 1.15 ± 0.55 | 1.1 ± 0.4 | 0.84 ± 0.5 | 0.05 | 0.31 | 0.26 | 7.86E−01 | 1.59E−01 | 1.75E−01 |
| miR-199b | 9.7 ± 1.31 | 9.23 ± 0.48 | 8.83 ± 0.93 | 0.47 | 0.87 | 0.4 | 2.57E−01 | 8.31E−02 | 2.01E−01 |
| miR-19a | 0.63 ± 0.64 | 0.99 ± 0.59 | 0.62 ± 0.69 | −0.35 | 0.02 | 0.37 | 1.77E−01 | 9.55E−01 | 1.77E−01 |
| miR-19b | −2.3 ± 0.74 | −1.87 ± 0.58 | −2.44 ± 0.64 | −0.43 | 0.15 | 0.57 | 1.30E−01 | 6.04E−01 | 3.10E−02 |
| miR-502 | 8.7 ± 1.11 | 9.51 ± 0.52 | 8.17 ± 1.02 | −0.81 | 0.53 | 1.34 | 3.23E−02 | 2.38E−01 | 5.35E−04 |
| miR-200a | 9.64 ± 0.79 | 10.54 ± 1.19 | 8.81 ± 1.36 | −0.9 | 0.83 | 1.74 | 3.90E−01 | 8.75E−02 | 4.51E−03 |
| miR-200a* | 14.81 ± 1.83 | 13.79 ± 2.88 | 15.67 ± 4.13 | 1.02 | −0.86 | −1.88 | 3.27E−01 | 5.42E−01 | 2.33E−01 |
| miR-200b | 8.56 ± 0.88 | 8.23 ± 0.67 | 7.93 ± 0.59 | 0.33 | 0.63 | 0.29 | 3.11E−01 | 5.30E−02 | 2.64E−01 |
| miR-200c | 6.42 ± 0.42 | 6.32 ± 0.38 | 5.53 ± 0.68 | 0.1 | 0.89 | 0.79 | 5.57E−01 | 1.03E−03 | 2.19E−03 |
| miR-202 | 7.63 ± 1.44 | 7.99 ± 1.23 | 8.47 ± 1.18 | −0.35 | −0.83 | −0.48 | 5.27E−01 | 1.36E−01 | 3.39E−01 |
| miR-202* | 15.98 ± 2.25 | 12.9 ± 1.23 | 17.59 ± 3.98 | 3.08 | −1.6 | −4.69 | 1.51E−02 | 5.24E−01 | 1.69E−02 |
| miR-203 | 10.41 ± 1.73 | 10.36 ± 0.97 | 10.52 ± 3.77 | 0.05 | −0.11 | −0.17 | 9.30E−01 | 9.27E−01 | 8.94E−01 |
| miR-204 | 8.67 ± 1.21 | 8.6 ± 1.14 | 7.53 ± 0.78 | 0.07 | 1.14 | 1.07 | 8.89E−01 | 1.16E−02 | 1.32E−02 |
| miR-205 | 11.49 ± 3.15 | 11.87 ± 1.46 | 8.94 ± 1.25 | −0.38 | 2.55 | 2.93 | 7.40E−01 | 4.03E−02 | 2.23E−04 |
| miR-206 | 8.83 ± 2.31 | 10.02 ± 1.64 | 7.19 ± 1.17 | −1.18 | 1.64 | 2.82 | 1.62E−01 | 3.88E−02 | 7.34E−05 |
| miR-208 | 14.08 ± 2.36 | 15.81 ± 2.79 | 14.17 ± 1.57 | −1.72 | −0.09 | 1.64 | 1.54E−01 | 9.48E−01 | 2.98E−01 |
| miR-20a | −1.49 ± 0.62 | −2.32 ± 0.39 | −1.33 ± 1.02 | 0.82 | −0.16 | −0.98 | 7.71E−04 | 6.48E−01 | 5.04E−03 |
| miR-20b | 1.97 ± 0.67 | 1.11 ± 0.5 | 1.82 ± 0.93 | 0.86 | 0.15 | −0.71 | 1.74E−03 | 6.52E−01 | 2.98E−02 |
| miR-21 | −0.63 ± 0.59 | 0.35 ± 0.4 | −0.81 ± 0.89 | −0.97 | 0.18 | 1.15 | 1.07E−04 | 5.68E−01 | 4.93E−04 |
| miR-210 | 3.95 ± 0.82 | 4.36 ± 0.32 | 3.79 ± 0.96 | −0.4 | 0.16 | 0.56 | 1.25E−01 | 6.66E−01 | 6.73E−02 |
| miR-211 | 12.01 ± 2.51 | 11.41 ± 1.87 | 11.84 ± 2.29 | 0.6 | 0.17 | −0.44 | 5.12E−01 | 8.74E−01 | 6.27E−01 |
| miR-212 | 8.49 ± 1.6 | 8.24 ± 2.61 | 8.98 ± 0.94 | 0.25 | −0.49 | −0.74 | 7.82E−01 | 3.72E−01 | 3.68E−01 |
| miR-213 | 9.7 ± 1.61 | 10.01 ± 0.69 | 9.99 ± 2.68 | −0.31 | −0.29 | 0.02 | 5.78E−01 | 7.57E−01 | 9.83E−01 |
| miR-214 | 5.88 ± 1.07 | 5.33 ± 1.24 | 5.08 ± 0.88 | 0.56 | 0.81 | 0.25 | 2.53E−01 | 5.54E−02 | 5.69E−01 |
| miR-215 | 9.05 ± 0.54 | 9.47 ± 1.18 | 8.77 ± 2.1 | −0.42 | 0.28 | 0.7 | 2.70E−01 | 6.61E−01 | 3.24E−01 |
| miR-216 | 12.82 ± 2.37 | 13.98 ± 4.03 | 13.67 ± 3.86 | −1.16 | −0.85 | 0.31 | 4.05E−01 | 5.26E−01 | 8.58E−01 |
| miR-217 | 17.88 ± 3.35 | 19.43 ± 3.26 | 13.74± | −1.55 | 4.13 | 5.69 | 4.78E−01 | | |
| miR-218 | 11.27 ± 2.14 | 12.3 ± 2.97 | 10.93 ± 2.62 | −1.03 | 0.35 | 1.38 | 3.42E−01 | 7.25E−01 | 2.41E−01 |
| miR-219 | 13.37 ± 2.83 | 12.87 ± 2.53 | 11.42 ± 1.4 | 0.5 | 1.95 | 1.45 | 7.25E−01 | 1.61E−01 | 2.26E−01 |
| miR-22 | 3.78 ± 1.12 | 4.59 ± 0.9 | 4.69 ± 2.3 | −0.82 | −0.91 | −0.1 | 6.15E−02 | 2.29E−01 | 8.93E−01 |
| miR-220 | 14.41 ± 3.48 | 12.19 ± 1.5 | 16.61 ± 0.54 | 2.22 | −2.2 | −4.42 | 3.67E−02 | 3.40E−01 | 8.68E−03 |
| miR-221 | −0.64 ± 0.83 | −0.8 ± 0.6 | −0.86 ± 0.96 | 0.16 | 0.22 | 0.06 | 5.87E−01 | 5.55E−01 | 8.63E−01 |
| miR-222 | 1.43 ± 0.73 | 1.11 ± 0.51 | 1.37 ± 0.73 | 0.32 | 0.06 | −0.26 | 2.34E−01 | 8.46E−01 | 3.26E−01 |
| miR-223 | −3.65 ± 1.4 | −3.73 ± 0.6 | −3.18 ± 0.55 | 0.08 | −0.47 | −0.55 | 8.62E−01 | 2.89E−01 | 2.99E−02 |
| miR-224 | 7.27 ± 2.04 | 6.34 ± 0.96 | 7.18 ± 0.91 | 0.93 | 0.09 | −0.84 | 1.67E−01 | 8.96E−01 | 4.37E−02 |

TABLE 7-continued

Normalized qRT-PCR data for quantification of 329 miRNAs in serum from PrCa patients, BPH patients, and normal donors (norm).

| miRNA | Avg BPH | Avg Norm | Avg PrCa | BPH – norm | BPH – PrCa | norm – PrCa | p value (BPH vs norm) | p value (BPH vs PrCa) | p value (Norm vs PrCa) |
|---|---|---|---|---|---|---|---|---|---|
| miR-23a | 2.77 ± 0.77 | 3.38 ± 0.38 | 2.9 ± 0.55 | −0.61 | −0.12 | 0.48 | 2.28E−02 | 6.55E−01 | 2.04E−01 |
| miR-23b | 5.26 ± 0.72 | 5.56 ± 0.44 | 4.93 ± 0.45 | −0.29 | 0.33 | 0.63 | 2.43E−01 | 1.92E−01 | 2.53E−03 |
| miR-24 | −1 ± 0.64 | −1.36 ± 0.26 | −0.45 ± 0.53 | 0.36 | −0.55 | −0.91 | 8.39E−02 | 3.22E−02 | 2.59E−05 |
| miR25 | 0.56 ± 0.59 | 0.55 ± 0.32 | 0.15 ± 0.54 | 0.01 | 0.41 | 0.4 | 9.45E−01 | 8.62E−02 | 3.80E−02 |
| miR-26a | −1.87 ± 0.57 | −2.03 ± 0.39 | −1.59 ± 0.56 | 0.16 | −0.29 | −0.44 | 4.43E−01 | 2.28E−01 | 3.45E−02 |
| miR-26b | −1.38 ± 0.56 | −1.63 ± 0.24 | −1.28 ± 0.54 | 0.25 | −0.1 | −0.35 | 1.64E−01 | 6.68E−01 | 5.09E−02 |
| miR-27a | 1.04 ± 0.89 | 1.5 ± 0.46 | 1.29 ± 0.75 | −0.46 | −0.25 | 0.21 | 1.25E−01 | 4.63E−01 | 4.21E−01 |
| miR-27b | 4.07 ± 0.65 | 4.69 ± 0.42 | 4.14 ± 0.82 | −0.62 | −0.07 | 0.55 | 1.11E−02 | 8.21E−01 | 5.10E−02 |
| miR-28 | 5.03 ± 0.4 | 4.78 ± 0.43 | 4.95 ± 0.72 | 0.24 | 0.08 | −0.16 | 1.62E−01 | 7.35E−01 | 5.08E−01 |
| miR-296 | 7.51 ± 0.89 | 7.25 ± 0.81 | 6.9 ± 1.14 | 0.26 | 0.61 | 0.35 | 4.55E−01 | 1.58E−01 | 4.00E−01 |
| miR-299-3p | 17.06 ± 3.67 | 14.94 ± 2.79 | 15.93 ± 2.78 | 2.12 | 1.14 | −0.99 | 2.85E−01 | 5.39E−01 | 5.36E−01 |
| miR-299-5p | 12.21 ± 3.16 | 10.64 ± 1.62 | 10.79 ± 1.66 | 1.57 | 1.42 | −0.15 | 2.03E−01 | 2.50E−01 | 8.48E−01 |
| miR-29a | 0.75 ± 0.92 | 1.76 ± 0.42 | 0.48 ± 1.08 | −1.01 | 0.28 | 1.28 | 2.31E−03 | 5.08E−01 | 8.94E−04 |
| miR-29b | 6.3 ± 1.04 | 7.24 ± 0.89 | 5.9 ± 0.84 | −0.94 | 0.4 | 1.34 | 2.72E−02 | 3.24E−01 | 1.37E−03 |
| miR-29c | 0.95 ± 1.08 | 1.92 ± 0.13 | 0.77 ± 1.01 | −0.97 | 0.18 | 1.15 | 5.32E−03 | 6.75E−01 | 7.46E−04 |
| miR-503 | 12.49 ± 2.37 | 12.46 ± 2.55 | 13.85 ± 3.86 | 0.02 | −1.36 | −1.38 | 9.83E−01 | 3.09E−01 | 3.44E−01 |
| miR-301 | 3.87 ± 0.54 | 3.82 ± 0.23 | 3.87 ± 0.79 | 0.05 | −0.01 | −0.06 | 7.70E−01 | 9.78E−01 | 8.12E−01 |
| miR-302a | 16.93 ± 4.27 | 14.65 ± 2.36 | 16.37 ± 3.94 | 2.28 | 0.56 | −1.72 | 2.14E−01 | 8.35E−01 | 3.60E−01 |
| miR-302a* | 15.69 ± 3.62 | 15.99 ± 3.86 | 16.54 ± 2.89 | −0.3 | −0.85 | −0.55 | 8.64E−01 | 5.76E−01 | 7.21E−01 |
| miR-302b | 18.01± | 22.5± | 20.1± | −4.49 | −2.09 | 2.39 | | | |
| miR-302b* | 16.41 ± 2.09 | 16.93 ± 2.62 | 14.8 ± 2.08 | −0.52 | 1.6 | 2.12 | 7.43E−01 | 2.67E−01 | 1.38E−01 |
| miR-302c | 17.3 ± 4.22 | 15.92 ± 3.93 | ± | 1.38 | | | 6.31E−01 | | |
| miR-302c* | 14.69± | 18.24 ± 1.6 | 16.49± | −3.55 | −1.81 | 1.74 | | | |
| miR-302d | 16.36 ± 3.65 | 14.36 ± 2.39 | 15.67 ± 3.31 | 2 | 0.7 | −1.3 | 2.26E−01 | 7.48E−01 | 4.66E−01 |
| miR-30-a-3p | 6.09 ± 1.15 | 6.27 ± 0.62 | 7.12 ± 3.7 | −0.18 | −1.03 | −0.85 | 6.44E−01 | 3.69E−01 | 4.41E−01 |
| miR-30a-5p | −0.43 ± 0.49 | −0.25 ± 0.38 | −0.56 ± 0.46 | −0.18 | 0.13 | 0.31 | 3.31E−01 | 5.23E−01 | 9.14E−02 |
| miR-30b | 0.79 ± 0.63 | 0.44 ± 0.54 | 1.04 ± 0.72 | 0.35 | −0.25 | −0.6 | 1.59E−01 | 3.80E−01 | 3.38E−02 |
| miR-30c | 0.78 ± 0.55 | 0.56 ± 0.57 | 1.06 ± 0.65 | 0.22 | −0.28 | −0.5 | 3.42E−01 | 2.73E−01 | 5.81E−02 |
| miR-30d | 0.65 ± 0.64 | 0.45 ± 0.32 | 0.73 ± 0.48 | 0.2 | −0.08 | −0.28 | 3.50E−01 | 7.19E−01 | 1.05E−01 |
| miR-30e-3p | 5.11 ± 0.83 | 5.03 ± 0.46 | 5.49 ± 0.63 | 0.08 | −0.37 | −0.46 | 7.59E−01 | 2.28E−01 | 5.48E−02 |
| miR-30e-5p | 1.95 ± 0.8 | 2.56 ± 0.31 | 1.81 ± 0.67 | −0.61 | 0.14 | 0.75 | 2.27E−02 | 6.42E−01 | 1.82E−03 |
| miR-31 | 9.28 ± 1.02 | 8.52 ± 1.13 | 8.54 ± 0.96 | 0.76 | 0.74 | −0.02 | 9.75E−02 | 8.12E−02 | 9.63E−01 |
| miR-32 | 4.39 ± 1.14 | 4.23 ± 0.5 | 4.92 ± 1.2 | 0.16 | −0.53 | −0.69 | 6.67E−01 | 2.80E−01 | 8.14E−02 |
| miR-320 | −0.13 ± 0.75 | 0.18 ± 0.56 | −0.22 ± 0.81 | −0.32 | 0.09 | 0.4 | 2.52E−01 | 7.90E−01 | 1.71E−01 |
| miR-323 | 8.11 ± 1.39 | 7.74 ± 1.04 | 8.2 ± 1.29 | 0.37 | −0.08 | −0.45 | 4.75E−01 | 8.81E−01 | 3.52E−01 |
| miR-324-3p | 3.76 ± 0.8 | 3.95 ± 0.52 | 3.41 ± 1.05 | −0.19 | 0.35 | 0.55 | 4.88E−01 | 3.63E−01 | 1.20E−01 |
| miR-324-5p | 4.54 ± 0.62 | 4.68 ± 0.54 | 4.52 ± 1.34 | −0.14 | 0.02 | 0.16 | 5.65E−01 | 9.65E−01 | 7.09E−01 |
| miR-325 | 16.93 ± 3.41 | 16.14 ± 3.37 | 15.79 ± 4.04 | 0.79 | 1.14 | 0.35 | 6.30E−01 | 5.62E−01 | 8.48E−01 |
| miR-326 | 7.63 ± 0.59 | 8.27 ± 0.85 | 7.92 ± 1.28 | −0.64 | −0.29 | 0.35 | 4.32E−02 | 4.79E−01 | 4.40E−01 |
| miR-328 | 3.82 ± 0.7 | 3.47 ± 0.51 | 3.79 ± 0.84 | 0.35 | 0.03 | −0.31 | 1.77E−01 | 9.13E−01 | 2.84E−01 |
| miR-329 | 12.62 ± 2.88 | 11.06 ± 3.47 | 10.69 ± 1.47 | 1.57 | 1.94 | 0.37 | 3.12E−01 | 1.08E−01 | 7.85E−01 |
| miR-33 | 10.55 ± 3.21 | 11.02 ± 4.27 | 8.93 ± 4.12 | −0.47 | 1.62 | 2.09 | 7.62E−01 | 3.03E−01 | 2.46E−01 |
| miR-330 | 9.67 ± 0.83 | 9.61 ± 0.77 | 9.66 ± 0.82 | 0.07 | 0.02 | −0.05 | 8.37E−01 | 9.58E−01 | 8.78E−01 |
| miR-331 | 4.58 ± 0.8 | 4.18 ± 0.51 | 4.86 ± 0.76 | 0.4 | −0.28 | −0.68 | 1.58E−01 | 3.87E−01 | 1.74E−02 |
| miR-335 | 3.71 ± 0.8 | 3.85 ± 0.94 | 4.33 ± 0.64 | −0.14 | −0.62 | −0.48 | 6.94E−01 | 4.75E−02 | 1.58E−01 |
| miR-337 | 17.3 ± 2.94 | 14.7 ± 2.41 | 14.32 ± 3.49 | 2.6 | 2.98 | 0.38 | 4.93E−02 | 1.50E−01 | 8.13E−01 |
| miR-338 | 5.86 ± 0.94 | 6.63 ± 0.49 | 6.01 ± 0.78 | −0.77 | −0.15 | 0.62 | 1.98E−02 | 6.77E−01 | 3.01E−02 |
| miR-339 | 4.56 ± 0.48 | 5.04 ± 0.73 | 4.58 ± 0.52 | −0.48 | −0.02 | 0.46 | 6.81E−02 | 9.24E−01 | 8.80E−02 |
| miR-340 | 7.57 ± 0.85 | 6.92 ± 0.71 | 8.45 ± 1.6 | 0.65 | −0.88 | −1.53 | 5.25E−02 | 1.10E−01 | 6.56E−03 |
| miR-342 | 3.38 ± 0.81 | 3 ± 0.67 | 3.34 ± 0.83 | 0.38 | 0.04 | −0.33 | 2.24E−01 | 8.96E−01 | 2.89E−01 |
| miR-345 | 2.58 ± 0.77 | 3.12 ± 0.46 | 2.86 ± 0.91 | −0.53 | −0.28 | 0.25 | 5.12E−02 | 4.24E−01 | 3.97E−01 |
| miR-346 | 7.07 ± 1.75 | 6.24 ± 1.8 | 7.13 ± 2.1 | 0.84 | −0.06 | −0.89 | 2.61E−01 | 9.43E−01 | 2.75E−01 |
| miR-34a | 10.85 ± 2.22 | 12.37 ± 2.94 | 8.88 ± 2.38 | −1.52 | 1.97 | 3.5 | 1.73E−01 | 4.74E−02 | 4.84E−03 |
| miR-34b | 12.91 ± 2.65 | 16.2 ± 3.99 | 13.16 ± 0.71 | −3.3 | −0.25 | 3.05 | 1.14E−01 | 8.61E−01 | 1.80E−01 |
| miR-34c | 10.63 ± 2.13 | 10.11 ± 0.9 | 10.03 ± 2.13 | 0.52 | 0.6 | 0.08 | 4.43E−01 | 4.99E−01 | 9.08E−01 |
| miR-361 | 3.25 ± 0.52 | 3.76 ± 0.4 | 3.52 ± 0.8 | −0.51 | −0.27 | 0.24 | 1.35E−02 | 3.38E−01 | 3.74E−01 |
| miR-362 | 6.9 ± 0.64 | 7.12 ± 0.66 | 6.89 ± 1.09 | −0.22 | 0.01 | 0.23 | 4.17E−01 | 9.75E−01 | 5.44E−01 |
| miR-365 | 4.54 ± 1.9 | 4.41 ± 0.89 | 4.68 ± 1.05 | 0.14 | −0.14 | −0.27 | 8.25E−01 | 8.29E−01 | 5.00E−01 |
| miR-367 | 17.27 ± 5.29 | 14.53 ± 2.88 | 19.88± | 2.73 | −2.61 | −5.34 | 4.14E−01 | | |
| miR-368 | 12.7 ± 3.94 | 13.45 ± 3.27 | 10.8 ± 1.73 | −0.75 | 1.9 | 2.65 | 7.06E−01 | 2.66E−01 | 8.28E−02 |
| miR-369-3p | 10.28 ± 1.24 | 9.68 ± 1.17 | 10.16 ± 2.3 | 0.6 | 0.12 | −0.48 | 2.47E−01 | 8.83E−01 | 5.33E−01 |
| miR-369-5p | 14.1 ± 4.47 | 10.29 ± 1.21 | 11.96 ± 3.81 | 3.81 | 2.14 | −1.67 | 2.03E−02 | 3.77E−01 | 2.13E−01 |
| miR-370 | 8.69 ± 1.62 | 9.02 ± 2.84 | 8.19 ± 1.35 | −0.34 | 0.49 | 0.83 | 7.24E−01 | 4.26E−01 | 3.70E−01 |
| miR-371 | 15.41 ± 3.62 | 13.06 ± 3.79 | 12.15 ± 1.91 | 2.34 | 3.26 | 0.91 | 1.66E−01 | 4.26E−02 | 5.71E−01 |
| miR-372 | 15.05 ± 3.63 | 12.67 ± 2 | 15.66 ± 3.76 | 2.38 | −0.61 | −2.99 | 8.60E−02 | 7.31E−01 | 4.53E−02 |
| miR-373 | 14.23 ± 3.01 | 13.03 ± 2.8 | 12.23 ± 1.85 | 1.21 | 2 | 0.79 | 3.52E−01 | 1.41E−01 | 5.19E−01 |
| miR-373* | 13.09 ± 2.34 | 12.58 ± 2.88 | 13.96 ± 4.07 | 0.51 | −0.87 | −1.38 | 6.39E−01 | 5.29E−01 | 3.49E−01 |
| miR-374 | 1.85 ± 0.73 | 2.13 ± 1 | 2.12 ± 0.56 | −0.28 | −0.26 | 0.01 | 4.49E−01 | 3.43E−01 | 9.74E−01 |
| miR-375 | 6.15 ± 1.56 | 6.63 ± 0.88 | 4.31 ± 1.22 | −0.49 | 1.84 | 2.33 | 3.56E−01 | 3.95E−03 | 2.30E−05 |
| miR-376a | 4.18 ± 1.19 | 3.97 ± 0.81 | 3.07 ± 1.16 | 0.21 | 1.11 | 0.9 | 6.22E−01 | 3.01E−02 | 3.77E−02 |
| miR-376a* | 10.52 ± 1.38 | 10.02 ± 1.32 | 9.01 ± 1.52 | 0.5 | 1.51 | 1.01 | 5.08E−01 | 5.04E−02 | 2.10E−01 |
| miR-376b | 13.78 ± 3.96 | 12.66 ± 1.75 | 10.76 ± 2.26 | 1.12 | 3.02 | 1.9 | 4.33E−01 | 1.22E−01 | 7.96E−02 |

TABLE 7-continued

Normalized qRT-PCR data for quantification of 329 miRNAs in serum from PrCa patients, BPH patients, and normal donors (norm).

| miRNA | Avg BPH | Avg Norm | Avg PrCa | BPH – norm | BPH – PrCa | norm – PrCa | p value (BPH vs norm) | p value (BPH vs PrCa) | p value (Norm vs PrCa) |
|---|---|---|---|---|---|---|---|---|---|
| miR-377 | 15.55 ± 3.17 | 16.65 ± 3.46 | 15.56 ± 3.09 | -1.1 | -0.01 | 1.09 | 4.46E-01 | 9.93E-01 | 4.56E-01 |
| miR-378 | 6.58 ± 0.69 | 6.87 ± 0.78 | 6.8 ± 2.29 | -0.3 | -0.22 | 0.07 | 3.31E-01 | 7.49E-01 | 9.17E-01 |
| miR-379 | 8.48 ± 1.27 | 7.14 ± 0.94 | 8.01 ± 1.36 | 1.34 | 0.47 | -0.87 | 7.82E-03 | 3.92E-01 | 8.33E-02 |
| miR-380-3p | 11.99 ± 1.89 | 12.03 ± 2.92 | 12.79 ± 3.33 | -0.04 | -0.81 | -0.76 | 9.76E-01 | 5.88E-01 | 6.71E-01 |
| miR-380-5p | 13.26 ± 2.62 | 13.76 ± 4.91 | 11.26 ± 2.65 | -0.5 | 2 | 2.49 | 8.77E-01 | 3.68E-01 | 3.86E-01 |
| miR-381 | 10.65 ± 1.71 | 10.82 ± 1.62 | 10.23 ± 1.62 | -0.17 | 0.42 | 0.59 | 8.05E-01 | 5.42E-01 | 3.81E-01 |
| miR-382 | 5.85 ± 1.57 | 5.34 ± 0.9 | 5.32 ± 1.52 | 0.5 | 0.53 | 0.03 | 3.47E-01 | 4.11E-01 | 9.59E-01 |
| miR-383 | 10.7 ± 2.02 | 11.24 ± 1.43 | 10.7 ± 1.2 | -0.54 | 0 | 0.54 | 4.55E-01 | 9.97E-01 | 3.26E-01 |
| miR-504 | 9.78 ± 1.19 | 11.27 ± 2.82 | 9.67 ± 1.12 | -1.49 | 0.12 | 1.61 | 1.22E-01 | 8.26E-01 | 1.27E-01 |
| miR-409-5p | 13.14 ± 5.14 | 11.09 ± 3.34 | 10 ± 0.76 | 2.06 | 3.14 | 1.08 | 3.63E-01 | 1.70E-01 | 4.52E-01 |
| miR-410 | 5.53 ± 1.2 | 5.33 ± 1.1 | 5.11 ± 1.32 | 0.2 | 0.42 | 0.22 | 6.69E-01 | 4.19E-01 | 6.63E-01 |
| miR-412 | 13.83 ± 3.34 | 13 ± 4.65 | 15.33 ± 3.71 | 0.83 | -1.5 | -2.33 | 6.31E-01 | 3.43E-01 | 2.16E-01 |
| miR-422a | 7.03 ± 0.97 | 7.56 ± 0.76 | 7.32 ± 1.2 | -0.52 | -0.29 | 0.23 | 1.55E-01 | 5.19E-01 | 5.79E-01 |
| miR-422b | 4.14 ± 0.74 | 4.65 ± 0.38 | 4.53 ± 1 | -0.51 | -0.39 | 0.12 | 4.41E-02 | 2.86E-01 | 6.96E-01 |
| miR-423 | 4.69 ± 1.77 | 3.91 ± 0.61 | 4.15 ± 0.67 | 0.77 | 0.54 | -0.23 | 1.68E-01 | 3.38E-01 | 3.78E-01 |
| miR-424 | 9.01 ± 0.77 | 9.58 ± 1.15 | 9.01 ± 1.09 | -0.57 | 0 | 0.57 | 1.66E-01 | 9.96E-01 | 2.50E-01 |
| miR-425 | 3.68 ± 0.7 | 3.89 ± 0.49 | 3.92 ± 0.9 | -0.21 | -0.24 | -0.03 | 4.01E-01 | 4.67E-01 | 9.14E-01 |
| miR-429 | 14.77 ± 4.71 | 12.99 ± 1.78 | 11.95 ± 3.5 | 1.78 | 2.82 | 1.04 | 2.72E-01 | 1.33E-01 | 4.13E-01 |
| miR-432 | 5.39 ± 1.32 | 4.58 ± 0.98 | 4.71 ± 1.44 | 0.8 | 0.68 | -0.12 | 1.05E-01 | 2.43E-01 | 8.07E-01 |
| miR-432* | 8.68 ± 1.61 | 8.64 ± 2.2 | 9.61 ± 2.74 | 0.04 | -0.93 | -0.97 | 9.60E-01 | 3.23E-01 | 3.51E-01 |
| miR-433 | 6.65 ± 1.24 | 6.36 ± 1.11 | 6.15 ± 1.63 | 0.29 | 0.5 | 0.21 | 5.48E-01 | 4.07E-01 | 7.19E-01 |
| miR-448 | 17.12 ± 3.58 | 16.79 ± 3.27 | 15.78 ± 2.02 | 0.34 | 1.34 | 1.01 | 8.20E-01 | 2.75E-01 | 3.81E-01 |
| miR-449 | 12.85 ± 1.72 | 15.13 ± 4.65 | 16.39 ± 4.47 | -2.28 | -3.55 | -1.27 | 3.25E-01 | 1.54E-01 | 7.43E-01 |
| miR-451 | -3.85 ± 1.05 | -4.24 ± 0.5 | -4.57 ± 0.78 | 0.39 | 0.72 | 0.33 | 2.59E-01 | 7.20E-02 | 2.39E-01 |
| miR-452 | 7.87 ± 0.69 | 7.47 ± 1.48 | 7.7 ± 1.14 | 0.4 | 0.17 | -0.23 | 4.03E-01 | 6.57E-01 | 6.75E-01 |
| miR-452* | 8.93 ± 1.16 | 9.04 ± 1.17 | 9.96 ± 2.88 | -0.11 | -1.03 | -0.92 | 8.21E-01 | 2.65E-01 | 3.18E-01 |
| miR-453 | 9.34 ± 1.49 | 9.18 ± 0.96 | 8.95 ± 1.36 | 0.16 | 0.38 | 0.22 | 7.60E-01 | 5.29E-01 | 6.50E-01 |
| miR-455 | 12.11 ± 2.19 | 14.2 ± 4.35 | 12.05 ± 3.19 | -2.09 | 0.05 | 2.14 | 1.60E-01 | 9.64E-01 | 2.25E-01 |
| miR-483 | 6.89 ± 1.46 | 6.63 ± 1.77 | 4.68 ± 1.4 | 0.26 | 2.21 | 1.95 | 6.96E-01 | 1.03E-03 | 6.69E-03 |
| miR-485-3p | 6.71 ± 1.06 | 5.48 ± 1.19 | 6.29 ± 2.3 | 1.23 | 0.42 | -0.81 | 1.38E-01 | 5.71E-01 | 2.92E-01 |
| miR-485-5p | 8.84 ± 1.46 | 8.35 ± 1.04 | 8.04 ± 1.28 | 0.49 | 0.8 | 0.31 | 3.56E-01 | 1.69E-01 | 5.21E-01 |
| miR-486 | -2.06 ± 0.78 | -2.6 ± 0.59 | -2.68 ± 1.03 | 0.54 | 0.62 | 0.08 | 7.05E-02 | 1.12E-01 | 8.19E-01 |
| miR-487a | 11.16 ± 1.01 | 11.35 ± 3.62 | 10.89 ± 2.38 | -0.19 | 0.27 | 0.46 | 8.76E-01 | 7.46E-01 | 7.51E-01 |
| miR-487b | 6.94 ± 1.19 | 5.96 ± 1.14 | 6.64 ± 1.25 | 0.98 | 0.3 | -0.68 | 5.17E-02 | 5.59E-01 | 1.78E-01 |
| miR-488 | 14.64 ± 5.25 | 12.46 ± 2.38 | 14.19 ± 1.87 | 2.18 | 0.45 | -1.73 | 4.01E-01 | 8.50E-01 | 1.91E-01 |
| miR-489 | 14.94 ± 3.08 | 14.33 ± 3.11 | 16.18 ± 3.85 | 0.61 | -1.24 | -1.84 | 7.11E-01 | 4.89E-01 | 3.31E-01 |
| miR-490 | 10.5 ± 1.7 | 10.97 ± 2.54 | 11.98 ± 3.32 | -0.48 | -1.48 | -1 | 5.96E-01 | 1.84E-01 | 4.15E-01 |
| miR-491 | 7.66 ± 0.94 | 8.72 ± 0.97 | 7.41 ± 1.41 | -1.06 | 0.24 | 1.3 | 1.24E-02 | 6.30E-01 | 1.67E-02 |
| miR-492 | 16.11 ± 3.6 | 12.72 ± 1.97 | 17.03 ± 4.06 | 3.39 | -0.92 | -4.31 | 1.93E-02 | 7.16E-01 | 2.30E-02 |
| miR-493* | 10.16 ± 1.59 | 10.32 ± 1.25 | 10.8 ± 2.44 | -0.16 | -0.64 | -0.48 | 7.92E-01 | 4.74E-01 | 5.69E-01 |
| miR-493 | 9.16 ± 1.22 | 8.67 ± 1.5 | 9.02 ± 2.05 | 0.49 | 0.15 | -0.34 | 3.91E-01 | 8.33E-01 | 6.46E-01 |
| miR-494 | 10.42 ± 1.54 | 10.68 ± 3.36 | 12.44 ± 3.55 | -0.25 | -2.02 | -1.77 | 8.31E-01 | 1.23E-01 | 2.85E-01 |
| miR-495 | 8.86 ± 2.44 | 8.06 ± 1.86 | 7.9 ± 1.55 | 0.8 | 0.97 | 0.16 | 3.75E-01 | 2.59E-01 | 8.16E-01 |
| miR-496 | 9.97 ± 2.12 | 9.9 ± 1.75 | 8.86 ± 1.47 | 0.07 | 1.12 | 1.04 | 9.26E-01 | 1.47E-01 | 1.29E-01 |
| miR-497 | 5.96 ± 1.27 | 6.9 ± 0.75 | 5.2 ± 1.41 | -0.94 | 0.76 | 1.7 | 3.76E-02 | 1.81E-01 | 1.27E-03 |
| miR-498 | 18.24 ± 3.32 | 19.81 ± 2.18 | 16.65 ± 5.13 | -1.57 | 1.59 | 3.16 | 5.31E-01 | 6.94E-01 | 3.90E-01 |
| miR-499 | 20.42 ± 3.07 | 18.58 ± 3.38 | 15.6 ± 4.3 | 1.84 | 4.82 | 2.98 | 3.57E-01 | 1.46E-01 | 3.26E-01 |
| miR-505 | 7.49 ± 0.68 | 7.35 ± 0.63 | 7.17 ± 0.86 | 0.13 | 0.32 | 0.19 | 6.24E-01 | 3.26E-01 | 5.55E-01 |
| miR-510 | 16.17 ± 3.39 | 14.63 ± 3.77 | 16.09 ± 2.95 | 1.54 | 0.08 | -1.47 | 4.58E-01 | 9.68E-01 | 4.58E-01 |
| miR-511 | 9.82 ± 1.31 | 9.42 ± 2.17 | 9.05 ± 2.53 | 0.4 | 0.77 | 0.37 | 5.91E-01 | 3.65E-01 | 7.10E-01 |
| miR-512-5p | 14.48 ± 3.52 | 13.13 ± 2.54 | 14.65 ± 3.4 | 1.35 | -0.17 | -1.51 | 3.47E-01 | 9.20E-01 | 2.83E-01 |
| miR-513 | 16.27 ± 3.99 | 17.16 ± 5.23 | ± | -0.89 | | | 8.40E-01 | | |
| miR-514 | 15.49 ± 3.32 | 15.34 ± 4.79 | 16.6 ± 2.18 | 0.15 | -1.11 | -1.26 | 9.37E-01 | 4.59E-01 | 5.30E-01 |
| miR-515-3p | 13.31 ± 2.69 | 11.14 ± 2.15 | 12.26 ± 3.69 | 2.16 | 1.04 | -1.12 | 4.04E-02 | 4.37E-01 | 3.73E-01 |
| miR-515-5p | 13.56 ± 2.87 | 13.25 ± 2.49 | 16.2 ± 5.5 | 0.3 | -2.64 | -2.94 | 8.72E-01 | 3.81E-01 | 3.67E-01 |
| miR-516-3p | 9.22 ± 2.18 | 9.29 ± 2.29 | 8.93 ± 1.4 | -0.07 | 0.29 | 0.36 | 9.37E-01 | 7.06E-01 | 6.48E-01 |
| miR-516-5p | 14.8 ± 4.72 | 15.07 ± 4.36 | 15.57 ± 2.85 | -0.27 | -0.77 | -0.51 | 9.29E-01 | 7.52E-01 | 8.17E-01 |
| miR-517* | 14.06 ± 2.8 | 14.36 ± 3.08 | 14.09 ± 1.15 | -0.3 | -0.03 | 0.27 | 8.07E-01 | 9.75E-01 | 8.16E-01 |
| miR517a | 17.32 ± 5.4 | 17.81 ± 4.4 | 18.04 ± 0.93 | -0.49 | -0.72 | -0.24 | 9.00E-01 | 8.30E-01 | 9.32E-01 |
| miR-517b | 20.05 ± 3.91 | 17.42 ± 5.56 | ± | 2.64 | | | 5.38E-01 | | |
| miR-517c | 12.57 ± 3.49 | 11.62 ± 2.87 | 10.66 ± 3.54 | 0.95 | 1.91 | 0.96 | 5.37E-01 | 2.67E-01 | 5.38E-01 |
| mir-518a | 15.79 ± 2.8 | 14.62 ± 4.05 | 14.89 ± 4.52 | 1.17 | 0.9 | -0.27 | 4.75E-01 | 6.19E-01 | 8.91E-01 |
| miR-518b | 7.8 ± 1.21 | 6.64 ± 2.28 | 8.54 ± 3.79 | 1.17 | -0.74 | -1.91 | 1.31E-01 | 5.27E-01 | 1.50E-01 |
| miR-518c | 14.23 ± 2.9 | 15.65 ± 2.55 | 19.33± | -1.42 | -5.1 | -3.68 | 3.49E-01 | | |
| miR-518c* | 13.16 ± 3.35 | 14.57 ± 4.29 | 14.12 ± 3.62 | -1.41 | -0.96 | 0.45 | 4.40E-01 | 5.80E-01 | 8.15E-01 |
| miR-518d | 11.64 ± 3.35 | 9.8 ± 2.57 | 12.13 ± 4.36 | 1.84 | -0.49 | -2.33 | 1.52E-01 | 7.70E-01 | 1.29E-01 |
| miR-518e | 10.65 ± 1.98 | 9.61 ± 2.52 | 11.78 ± 3.39 | 1.04 | -1.13 | -2.17 | 2.73E-01 | 3.43E-01 | 1.01E-01 |
| miR-518f | 15.31 ± 3.35 | 14.03 ± 1.96 | 15.52 ± 4.08 | 1.28 | -0.21 | -1.49 | 3.96E-01 | 9.08E-01 | 3.95E-01 |
| miR-519a | ± | 13.69 ± 2.62 | ± | | | | | | |
| miR-519b | ± | 16.24 ± 1.98 | 22.19± | | | -5.95 | | | |
| miR-519c | 16.72 ± 4.13 | 14.29 ± 3.44 | 19.8 ± 2.15 | 2.43 | -3.09 | -5.52 | 3.78E-01 | 2.21E-01 | 3.46E-02 |
| miR-519d | 9.37 ± 2.6 | 8.36 ± 2.7 | 11.37 ± 2.29 | 1.01 | -1.99 | -3 | 3.62E-01 | 5.89E-02 | 7.67E-03 |
| miR-519e | 11.74 ± 2.28 | 9.38 ± 1.37 | 14.02 ± 3.25 | 2.37 | -2.27 | -4.64 | 5.36E-03 | 6.38E-02 | 1.80E-04 |

TABLE 7-continued

Normalized qRT-PCR data for quantification of 329 miRNAs in serum from PrCa patients, BPH patients, and normal donors (norm).

| miRNA | Avg BPH | Avg Norm | Avg PrCa | BPH – norm | BPH – PrCa | norm – PrCa | p value (BPH vs norm) | p value (BPH vs PrCa) | p value (Norm vs PrCa) |
|---|---|---|---|---|---|---|---|---|---|
| miR-519e* | 13.94 ± 2.2 | 14.24 ± 2.94 | 14.64 ± 2.7 | −0.29 | −0.69 | −0.4 | 9.04E−01 | 7.64E−01 | 8.21E−01 |
| miR-520a | 13.36 ± 3.66 | 11.64 ± 3.5 | 10.83 ± 1.87 | 1.72 | 2.52 | 0.81 | 3.11E−01 | 1.80E−01 | 6.42E−01 |
| miR-520a* | 14.3 ± 3.09 | 13.03 ± 1.75 | 18.2 ± 3.23 | 1.28 | −3.89 | −5.17 | 3.37E−01 | 1.40E−01 | 4.55E−03 |
| miR-520b | 13.75 ± 3.07 | 12.39 ± 3.12 | 14.29 ± 3.99 | 1.36 | −0.54 | −1.9 | 3.41E−01 | 7.42E−01 | 2.88E−01 |
| miR-520c | 16.33 ± 4.04 | 16.64 ± 4.56 | 16.39 ± 5.34 | −0.32 | −0.06 | 0.25 | 8.98E−01 | 9.85E−01 | 9.40E−01 |
| miR-520d | 13.69 ± 3.79 | 12.1 ± 2.79 | 13.81 ± 3.64 | 1.58 | −0.12 | −1.71 | 2.71E−01 | 9.38E−01 | 2.32E−01 |
| miR-520d* | 12.21 ± 2.51 | 12.68 ± 3.99 | 13.27 ± 3.2 | −0.47 | −1.06 | −0.59 | 7.44E−01 | 3.92E−01 | 6.93E−01 |
| miR-520e | 15.71 ± 4.27 | 14.83 ± 4.34 | 15.89 ± 2.86 | 0.88 | −0.19 | −1.06 | 6.72E−01 | 9.14E−01 | 5.55E−01 |
| miR-520f | 13.39 ± 3.49 | 15.61 ± 4.62 | 15.64 ± 3.72 | −2.22 | −2.25 | −0.03 | 2.44E−01 | 2.18E−01 | 9.88E−01 |
| miR-520g | 15.13 ± 3.02 | 14.48 ± 3.05 | 14.02 ± 0.84 | 0.64 | 1.11 | 0.46 | 6.50E−01 | 5.55E−01 | 8.04E−01 |
| miR-520h | 14.88 ± 4.78 | 14.61 ± 2.66 | 16.48 ± 3.52 | 0.27 | −1.6 | −1.86 | 8.94E−01 | 4.59E−01 | 2.86E−01 |
| miR-521 | 15.35 ± 3.36 | 13.43 ± 2.5 | 17.05 ± 3 | 1.92 | −1.7 | −3.62 | 2.60E−01 | 5.01E−01 | 7.17E−02 |
| miR-522 | 17.98± | 17.2 ± 4.03 | 11.13± | 0.78 | 6.85 | 6.07 | | | |
| miR-523 | 16.83 ± 3.17 | 16.43 ± 2.83 | 14.79 ± 3.21 | 0.4 | 2.03 | 1.63 | 7.69E−01 | 2.09E−01 | 2.56E−01 |
| miR-525 | 12.24 ± 1.96 | 11.52 ± 1.55 | 12.02 ± 2.08 | 0.72 | 0.22 | −0.5 | 3.26E−01 | 7.91E−01 | 5.08E−01 |
| miR-525* | 13.63 ± 2.49 | 12.75 ± 2.54 | 13.82 ± 2.09 | 0.88 | −0.2 | −1.08 | 4.01E−01 | 8.35E−01 | 2.69E−01 |
| miR-526a | 14.62 ± 3.83 | 12.67 ± 2.2 | 14.47 ± 4.56 | 1.95 | 0.15 | −1.8 | 3.26E−01 | 9.56E−01 | 4.70E−01 |
| miR-526b | 16.82 ± 3.32 | 15.91 ± 3.38 | 17.44 ± 3.04 | 0.91 | −0.62 | −1.53 | 5.30E−01 | 6.84E−01 | 3.25E−01 |
| miR-526b* | 15.6 ± 3.6 | 13.96 ± 3.92 | 11.84 ± 1.36 | 1.63 | 3.75 | 2.12 | 3.67E−01 | 2.24E−02 | 1.91E−01 |
| miR-527 | 11.08 ± 1.79 | 10.84 ± 2.77 | 12.01 ± 3.56 | 0.24 | −0.94 | −1.17 | 8.16E−01 | 4.45E−01 | 4.13E−01 |
| miR-532 | 3.62 ± 0.66 | 3.88 ± 0.63 | 3.33 ± 0.54 | −0.25 | 0.29 | 0.54 | 3.47E−01 | 2.53E−01 | 3.39E−02 |
| miR-539 | 8.2 ± 2.59 | 7.32 ± 1.7 | 7.82 ± 2.45 | 0.88 | 0.38 | −0.5 | 3.36E−01 | 7.18E−01 | 5.65E−01 |
| miR-542-3p | 10.05 ± 1.55 | 10.57 ± 0.87 | 10.76 ± 3.65 | −0.52 | −0.71 | −0.19 | 3.37E−01 | 5.45E−01 | 8.68E−01 |
| miR-542-5p | 12.35 ± 3.47 | 12.79 ± 2.13 | 13.99 ± 4.02 | −0.44 | −1.64 | −1.2 | 7.37E−01 | 3.83E−01 | 4.35E−01 |
| miR-552 | 15.83 ± 3.27 | 14.16 ± 2.28 | 17.49 ± 3.08 | 1.67 | −1.66 | −3.33 | 2.06E−01 | 2.53E−01 | 1.91E−02 |
| miR-561 | 14.42 ± 2.44 | 14.82 ± 3.67 | ± | −0.4 | | | 8.59E−01 | | |
| miR-565 | 6.52 ± 0.99 | 5.83 ± 1.33 | 6.73 ± 1.05 | 0.69 | −0.21 | −0.9 | 1.66E−01 | 6.22E−01 | 8.05E−02 |
| miR-566 | 5.88 ± 1.15 | 5.61 ± 1.42 | 6.01 ± 1.04 | 0.27 | −0.13 | −0.4 | 6.15E−01 | 7.69E−01 | 4.38E−01 |
| miR-575 | 10.44 ± 1.92 | 9.37 ± 2.13 | 10.64 ± 1.69 | 1.07 | −0.2 | −1.27 | 2.10E−01 | 7.85E−01 | 1.19E−01 |
| miR-576 | 7.16 ± 0.83 | 7.3 ± 0.95 | 6.94 ± 0.82 | −0.14 | 0.22 | 0.36 | 7.11E−01 | 5.22E−01 | 3.37E−01 |
| miR-584 | 4.7 ± 0.71 | 4.72 ± 0.39 | 5.27 ± 1.46 | −0.02 | −0.57 | −0.55 | 9.35E−01 | 2.36E−01 | 2.19E−01 |
| miR-592 | 13.84 ± 4.49 | 14.96 ± 4.38 | 12.98 ± 3.71 | −1.12 | 0.86 | 1.99 | 6.40E−01 | 7.03E−01 | 4.16E−01 |
| miR-506 | 17.16 ± 5.46 | 17.59 ± 4.14 | 17.55 ± 5.9 | −0.43 | −0.39 | 0.04 | 8.68E−01 | 9.24E−01 | 9.89E−01 |
| miR-605 | 7.16 ± 2.06 | 6.73 ± 3.27 | 7.3 ± 2.54 | 0.43 | −0.14 | −0.57 | 7.05E−01 | 8.82E−01 | 6.39E−01 |
| miR-618 | 9.63 ± 1.61 | 10.48 ± 2.1 | 10.03 ± 1.17 | −0.85 | −0.4 | 0.45 | 3.07E−01 | 5.01E−01 | 5.29E−01 |
| miR-622 | 11.6 ± 2.18 | 13.79 ± 3.02 | 13.31 ± 3.37 | −2.18 | −1.71 | 0.47 | 6.31E−02 | 1.59E−01 | 7.40E−01 |
| miR-638 | 7.46 ± 1.45 | 6.88 ± 0.92 | 7.49 ± 1.02 | 0.59 | −0.03 | −0.61 | 2.48E−01 | 9.61E−01 | 1.37E−01 |
| miR-652 | 10.94 ± 2 | 10.57 ± 1.62 | 10.99 ± 3.17 | 0.36 | −0.05 | −0.42 | 6.31E−01 | 9.62E−01 | 6.97E−01 |
| mir660 | 1.78 ± 0.63 | 2.18 ± 0.51 | 1.88 ± 0.8 | −0.4 | −0.1 | 0.3 | 1.01E−01 | 7.46E−01 | 2.77E−01 |
| miR-507 | 5.08 ± 1.46 | 4.82 ± 0.73 | 4.52 ± 0.51 | 0.26 | 0.56 | 0.3 | 5.89E−01 | 2.21E−01 | 2.49E−01 |
| miR-7 | 16.44 ± 3.15 | 17.32 ± 3 | 15.93 ± 3.75 | −0.88 | 0.51 | 1.39 | 5.30E−01 | 7.85E−01 | 4.48E−01 |
| miR-508 | 18.75 ± 2.14 | 15.97 ± 2.67 | 16.41 ± 0.47 | 2.77 | 2.33 | −0.44 | 1.80E−01 | 2.44E−01 | 8.35E−01 |
| miR-509 | 15.03 ± 4.43 | 14.85 ± 5.21 | 16.54 ± 2.8 | 0.18 | −1.51 | −1.69 | 9.39E−01 | 4.73E−01 | 4.83E−01 |
| miR-9 | 11.38 ± 1.74 | 9.89 ± 0.78 | 10.18 ± 0.85 | 1.49 | 1.19 | −0.29 | 1.77E−02 | 1.73E−01 | 5.08E−01 |
| miR-9* | 9.23 ± 1.09 | 9.21 ± 0.95 | 9.83 ± 0.67 | 0.02 | −0.6 | −0.62 | 9.56E−01 | 1.47E−01 | 9.65E−02 |
| miR-92 | −4.73 ± 0.65 | −4.77 ± 0.47 | −5.12 ± 0.69 | 0.03 | 0.39 | 0.36 | 8.81E−01 | 1.65E−01 | 1.53E−01 |
| miR-93 | −1.82 ± 0.37 | −2.2 ± 0.49 | −1.82 ± 0.38 | 0.38 | 0 | −0.38 | 4.48E−02 | 9.87E−01 | 4.55E−02 |
| miR-95 | 9.54 ± 1.33 | 10.33 ± 1.84 | 9.17 ± 1.47 | −0.79 | 0.37 | 1.16 | 2.48E−01 | 5.31E−01 | 1.18E−01 |
| miR-96 | 10.38 ± 3.08 | 9.05 ± 0.86 | 8.81 ± 0.98 | 1.32 | 1.57 | 0.25 | 1.66E−01 | 1.39E−01 | 5.36E−01 |
| miR-98 | 4.84 ± 0.78 | 4.1 ± 0.44 | 4.84 ± 1 | 0.74 | 0 | −0.74 | 8.80E−03 | 9.92E−01 | 2.95E−02 |
| miR-99a | 6.25 ± 1.16 | 6.77 ± 0.75 | 5.85 ± 0.77 | −0.52 | 0.4 | 0.92 | 2.09E−01 | 3.32E−01 | 7.32E−03 |
| miR-99b | 5.85 ± 0.61 | 5.86 ± 0.76 | 5.34 ± 1.05 | −0.01 | 0.51 | 0.52 | 9.73E−01 | 1.63E−01 | 1.81E−01 |

Example 2

Combinations of miRNAs that Distinguish Sera of Prostate Cancer Patients from Sera of BPH Patients and Normal Donors The inventors evaluated pairs of miRNA biomarkers for their abilities to distinguish sera of PrCa patients from sera of BPH patients and normal donors. Un-normalized qRT-PCR data generated using the samples described above in Example 1 were used to calculate dCt values for each pair of miRNAs that was evaluated. The dCt values of the various miRNA pairs in PrCa and normal serum samples were analyzed using Receiver-Operator Characteristic (ROC) analysis to identify the miRNA pairs having the ability to distinguish sera of PrCa patients from sera of BPH patients and normal donors.

A Receiver Operator Characteristic (ROC) curve is a graphical plot of the sensitivity vs. specificity for a binary classifier system as its discrimination threshold is varied. ROC analysis provides a tool to select possibly optimal models and to discard suboptimal ones independently from (and prior to specifying) the class distribution. Recently, ROC analysis has been used in selecting and applying biomarkers for the diagnosis of disease (Pepe, 2003; Pepe et al., 2004) since the classification performance can be measured by the area under the ROC curve (AUC). Advantages of the ROC technique include (1) it does not assume a parametric form of the class probability as required in the logistic regression method, (2) it is adaptable to outcome-dependent samplings, e.g. the case-control design, which are widely used in medical studies, and (3) it is relatively straightforward to assign different 'costs' to false positives and false negatives (Pepe, 2003; Pepe et al., 2005).

For the purposes of this invention, ROC curves are used to evaluate the capacities of individual and combinations of biomarker candidates to distinguish patient classes. The abundance(s) of biomarker candidates are measured. The measurements are used to develop classifiers whose true positive and false positive rates are plotted in a ROC curve. The AUC is then calculated for each classifier. An ideal classifier has an ROC AUC value of 1, and classifiers can be ranked based upon how close their ROC AUC is to 1.

Three miRNA pairs (miR-125b+miR-24; miR-125b+miR-26a; miR-432*+miR-483) accurately separated the twelve PrCa patient serum samples from the twelve normal donor serum samples and the twelve BPH patient serum samples (Table 8). Five additional miRNA pairs (miR-125b+miR-335; miR-125b+miR-342; let-7d+miR-125b; miR-125b+miR-197; miR-125b+miR-30c) accurately classified all but one of the 36 samples (ROC AUC>0.98) (Table 8), and 129 miRNA pairs had a ROC AUC score of at least 0.90. Data from 166 independent miRNAs was included at least once in the 221 total miRNA pairs (Table 8). Numerous miRNAs were used in multiple biomarkers pairs, indicating the strength of their variable levels in serums of prostate cancer patients and donors who did not have prostate cancer.

TABLE 8

MicroRNA biomarker pairs for classifying prostate cancer serum.

| Biomarker Pair | ROC AUC |
|---|---|
| miR-125b, miR-24 | 1 |
| miR-125b, miR-26a | 1 |
| miR-432*, miR-483 | 1 |
| miR-125b, miR-335 | 0.996527778 |
| miR-125b, miR-342 | 0.996527778 |
| let-7d, miR-125b | 0.993055556 |
| miR-125b, miR-197 | 0.993055556 |
| miR-125b, miR-30c | 0.993055556 |
| miR-125b, miR-15b | 0.989583333 |
| miR-483, miR-566 | 0.987847222 |
| miR-125b, miR-328 | 0.986111111 |
| miR-125b, miR-331 | 0.986111111 |
| miR-125b, miR-17-5p | 0.982638889 |
| miR-125b, miR-30b | 0.979166667 |
| miR-125b, miR-30e-3p | 0.979166667 |
| miR-125b, miR-340 | 0.979166667 |
| miR-346, miR-483 | 0.979166667 |
| miR-125b, miR-30d | 0.977430556 |
| miR-125b, miR-155 | 0.975694444 |
| let-7f, miR-125b | 0.972222222 |
| miR-125b, miR-132 | 0.972222222 |
| miR-125b, miR-26b | 0.972222222 |
| miR-103, miR-125b | 0.96875 |
| miR-125b, miR-126* | 0.96875 |
| miR-125b, miR-222 | 0.96875 |
| let-7g, miR-125b | 0.965277778 |
| miR-106a, miR-125b | 0.965277778 |
| miR-125b, miR-93 | 0.965277778 |
| miR-125b, miR-126 | 0.961805556 |
| miR-125b, miR-191 | 0.961805556 |
| let-7a, miR-125b | 0.958333333 |
| miR-125b, miR-30a-5p | 0.958333333 |
| miR-125b, miR-195 | 0.954861111 |
| miR-125b, miR-20a | 0.954861111 |
| miR-1, miR-125b | 0.951388889 |
| miR-125b, miR-361 | 0.951388889 |
| miR-200c, miR-24 | 0.951388889 |
| miR-125b, miR-142-5p | 0.947916667 |
| miR-125b, miR-181c | 0.947916667 |
| miR-125b, miR-98 | 0.947916667 |
| miR-125b, miR-18a* | 0.940972222 |
| miR-125b, miR-143 | 0.939236111 |

TABLE 8-continued

MicroRNA biomarker pairs for classifying prostate cancer serum.

| Biomarker Pair | ROC AUC |
|---|---|
| miR-125b, miR-140 | 0.9375 |
| miR-125b, miR-194 | 0.9375 |
| miR-125b, miR-223 | 0.9375 |
| miR-125b, miR-422b | 0.9375 |
| miR-126, miR-24 | 0.9375 |
| miR-125b, miR-196b | 0.935763889 |
| miR-107, miR-125b | 0.934027778 |
| miR-125b, miR-16 | 0.934027778 |
| miR-125b, miR-18a | 0.934027778 |
| miR-125b, miR-20b | 0.934027778 |
| miR-125b, miR-23a | 0.934027778 |
| miR-125b, miR-345 | 0.934027778 |
| miR-139, miR-15b | 0.934027778 |
| miR-181c, miR-375 | 0.934027778 |
| miR-125b, miR-224 | 0.930555556 |
| miR-125b, miR-374 | 0.930555556 |
| miR-125b, miR-565 | 0.930555556 |
| miR-132, miR-375 | 0.930555556 |
| miR-139, miR-24 | 0.930555556 |
| let-7f, miR-10b | 0.927083333 |
| miR-125b, miR-148a | 0.927083333 |
| miR-125b, miR-185 | 0.927083333 |
| miR-125b, miR-423 | 0.927083333 |
| miR-132, miR-200c | 0.927083333 |
| miR-204, miR-340 | 0.927083333 |
| miR-125b, miR-130b | 0.925347222 |
| miR-125a, miR-125b | 0.923611111 |
| miR-125b, miR-28 | 0.923611111 |
| miR-125b, mir660 | 0.923611111 |
| miR-188, miR-483 | 0.923611111 |
| miR-204, miR-24 | 0.923611111 |
| miR-212, miR-375 | 0.923611111 |
| miR-24, miR-375 | 0.923611111 |
| miR-125b, miR25 | 0.921875 |
| miR-125b, miR-130a | 0.920138889 |
| miR-125b, miR-32 | 0.920138889 |
| miR-125b, miR-638 | 0.920138889 |
| miR-125b, miR-15a | 0.916666667 |
| miR-125b, miR-193a | 0.916666667 |
| miR-125b, miR-425 | 0.916666667 |
| miR-125b, miR-576 | 0.916666667 |
| miR-125b, miR-92 | 0.916666667 |
| miR-130a, miR-375 | 0.916666667 |
| miR-30e-3p, miR-375 | 0.916666667 |
| miR-340, miR-375 | 0.916666667 |
| miR-204, miR-30c | 0.913194444 |
| miR-206, miR-24 | 0.913194444 |
| miR-206, miR-30e-3p | 0.913194444 |
| miR-206, miR-340 | 0.913194444 |
| miR-375, miR-425 | 0.913194444 |
| miR-130b, miR-375 | 0.913194444 |
| miR-15b, miR-375 | 0.913194444 |
| miR-375, miR-422b | 0.913194444 |
| let-7d, miR-375 | 0.909722222 |
| miR-103, miR-375 | 0.909722222 |
| miR-10b, miR-30b | 0.909722222 |
| miR-125b, miR-23b | 0.909722222 |
| miR-125b, miR-339 | 0.909722222 |
| miR-125b, miR-365 | 0.909722222 |
| miR-125b, miR-584 | 0.909722222 |
| miR-155, miR-24 | 0.909722222 |
| miR-15b, miR-200c | 0.909722222 |
| miR-15b, miR-204 | 0.909722222 |
| miR-10b, miR-195 | 0.907986111 |
| miR-10b, miR-335 | 0.907986111 |
| miR-199a*, miR-24 | 0.907986111 |
| miR-204, miR-30b | 0.907986111 |
| let-7d, miR-200c | 0.90625 |
| let-7d, miR-206 | 0.90625 |
| let-7f, miR-204 | 0.90625 |
| miR-10b, miR-24 | 0.90625 |
| miR-10b, miR-32 | 0.90625 |
| miR-125b, miR-145 | 0.90625 |
| miR-125b, miR-199a* | 0.90625 |
| miR-15a, miR-375 | 0.90625 |
| miR-30b, miR-375 | 0.90625 |

TABLE 8-continued

MicroRNA biomarker pairs for classifying prostate cancer serum.

| Biomarker Pair | ROC AUC |
|---|---|
| let-7c, miR-125b | 0.902777778 |
| let-7d, miR-204 | 0.902777778 |
| miR-125b, miR-19a | 0.902777778 |
| miR-125b, miR-214 | 0.902777778 |
| miR-125b, miR-301 | 0.902777778 |
| miR-146a, miR-375 | 0.902777778 |
| miR-17-5p, miR-375 | 0.902777778 |
| miR-361, miR-375 | 0.902777778 |
| miR-483, miR-584 | 0.902777778 |
| miR-15b, miR-483 | 0.901041667 |
| miR-30c, miR-375 | 0.901041667 |

The five miRNAs appearing most commonly in biomarker pairs were miR-125b, miR-375, miR-24, miR-340, and miR-483 (Table 9).

TABLE 9

Prevalence of serum biomarkers in paired analysis.

| miRNA | Pairs |
|---|---|
| miR-125b | 69 |
| miR-375 | 13 |
| miR-24 | 7 |
| miR-340 | 4 |
| miR-483 | 4 |
| miR-132 | 3 |
| miR-15b | 3 |
| miR-204 | 3 |
| miR-206 | 3 |
| miR-30e-3p | 3 |
| let-7d | 2 |
| let-7f | 2 |
| miR-103 | 2 |
| miR-10b | 2 |
| miR-126 | 2 |
| miR-130a | 2 |
| miR-130b | 2 |
| miR-139 | 2 |
| miR-181c | 2 |
| miR-200c | 2 |
| miR-30b | 2 |
| miR-30c | 2 |
| miR-422b | 2 |
| miR-425 | 2 |
| let-7a | 1 |
| let-7g | 1 |
| miR-1 | 1 |
| miR-106a | 1 |
| miR-107 | 1 |
| miR125a | 1 |
| miR-126* | 1 |
| miR-140 | 1 |
| miR-142-5p | 1 |
| miR-143 | 1 |
| miR-148a | 1 |
| miR-155 | 1 |
| miR-15a | 1 |
| miR-16 | 1 |
| miR-17-5p | 1 |
| miR-185 | 1 |
| miR-188 | 1 |
| miR-18a | 1 |
| miR-18a* | 1 |
| miR-191 | 1 |
| miR-193a | 1 |
| miR-194 | 1 |
| miR-195 | 1 |
| miR-196b | 1 |
| miR-197 | 1 |
| miR-20a | 1 |
| miR-20b | 1 |
| miR-212 | 1 |
| miR-222 | 1 |
| miR-223 | 1 |
| miR-224 | 1 |
| miR-23a | 1 |
| miR-23b | 1 |
| miR-25 | 1 |
| miR-26a | 1 |
| miR-26b | 1 |
| miR-28 | 1 |
| miR-30a-5p | 1 |
| miR-30d | 1 |
| miR-32 | 1 |
| miR-328 | 1 |
| miR-331 | 1 |
| miR-335 | 1 |
| miR-342 | 1 |
| miR-345 | 1 |
| miR-346 | 1 |
| miR-361 | 1 |
| miR-374 | 1 |
| miR-423 | 1 |
| miR-432* | 1 |
| miR-565 | 1 |
| miR-566 | 1 |
| miR-576 | 1 |
| miR-638 | 1 |
| miR660 | 1 |
| miR-92 | 1 |
| miR-93 | 1 |
| miR-98 | 1 |

The miRNA pairs in Table 8 and the individual miRNA biomarkers in Table 9 are all possible targets for diagnosing prostate cancer using serum.

Example 3

Validation of Prostate Cancer Serum Biomarkers

To assess the performances of the prostate cancer biomarkers, the inventors selected fourteen miRNAs (miR-24, miR-125b, miR-340, miR-375, miR-15b, miR-204, miR-205, miR-206, miR-122a, miR-483, let-7d, let-7f, miR-191, and miR-26a) identified in Example 1 and quantified those miRNAs in the sera of 12 PrCa patients, 12 BPH patients, and 12 normal donors (Table 10) using qRT-PCR. Patient and normal serum samples were purchased from ProteoGenex, Inc. (Culver City, Calif., USA). Serum preparation and serum RNA isolation were performed as described in Example 1.

TABLE 10

Histopathological data and patient information.

| Patient Diagnosis | Patient Age | PSA | Stage (*Greene* et al., 2002) | Gleason Score |
|---|---|---|---|---|
| BPH | 46 | 8.3 | NA | NA |
| BPH | 47 | 7.3 | NA | NA |
| BPH | 49 | 7 | NA | NA |
| BPH | 50 | 7.5 | NA | NA |
| BPH | 51 | 7.4 | NA | NA |
| BPH | 52 | 8.6 | NA | NA |
| BPH | 55 | 5.5 | NA | NA |
| BPH | 61 | 4.5 | NA | NA |
| BPH | 61 | 5.5 | PIN I-II | NA |
| BPH | 63 | 5.1 | NA | NA |
| BPH | 66 | 5.2 | PIN I-II | NA |

TABLE 10-continued

Histopathological data and patient information.

| Patient Diagnosis | Patient Age | PSA | Stage (Greene et al., 2002) | Gleason Score |
|---|---|---|---|---|
| BPH | 71 | 9.2 | NA | NA |
| PrCa | 61 | 4.4 | T2 | 5 |
| PrCa | 61 | 22.9 | T1c | 6 |
| PrCa | 65 | 7.4 | T1c | ND |
| PrCa | 65 | 30 | T3 | 7 |
| PrCa | 66 | 43 | T2 | 7 |
| PrCa | 68 | 11.8 | T1c | ND |
| PrCa | 69 | 6.4 | T1c | 5 |
| PrCa | 69 | 26 | T2 | ND |
| PrCa | 71 | 11 | T2 | 6 |
| PrCa | 73 | 13.5 | T1c | 7 |
| PrCa | 74 | 12.4 | T1c | ND |
| PrCa | Unknown | Unknown | Unknown | Unknown |
| Normal | 48 | 0.36 | NA | NA |
| Normal | 50 | 0.36 | NA | NA |
| Normal | 50 | 0.45 | NA | NA |
| Normal | 50 | 0.42 | NA | NA |
| Normal | 50 | 0.44 | NA | NA |
| Normal | 51 | 0.85 | NA | NA |
| Normal | 51 | 0.36 | NA | NA |
| Normal | 51 | 0.38 | NA | NA |
| Normal | 51 | 0.26 | NA | NA |
| Normal | 52 | 0.55 | NA | NA |
| Normal | 52 | 0.31 | NA | NA |
| Normal | 52 | 0.24 | NA | NA |

NA, not available;
ND, not determined.

microRNA levels were determined by qRT-PCR using TaqMan® MicroRNA Assays (Applied Biosystems; Foster City, Calif., USA) specific for each miRNA. Reverse transcription (RT) reaction components were assembled on ice, as shown above in Example 1 (Table 5), prior to the addition of RNA template. Serum RNA (0.25 μl per reaction) was added and mixed. RT reactions were incubated in a 384-well GeneAmp® PCR System 9700 (Applied Biosystems) at 4° C. for 30 minutes, then at 16° C. for 30 minutes, then at 42° C. for 30 minutes, then at 85° C. for 5 minutes. RT reactions were then frozen at −20° C.

PCR components (Table 11) were assembled on ice prior to the addition of cDNA (4 μl) from the RT reaction. Reactions were incubated in an ABI PRISM™ 7900HT Fast Real-Time PCR system (Applied Biosystems) at 95° C. for 1 minute, then for 50 cycles at 95° C. for 5 seconds and 60° C. for 30 seconds. Results were analyzed with the 7900HT Fast Real-Time PCR system SDS V2.3 software (Applied Biosystems). All reaction components were as provided by the manufacturer (Applied Biosystems; Foster City, Calif., USA) unless otherwise specified.

TABLE 11

PCR components.

| Component | μl per 15 μl rxn | Final Concentration |
|---|---|---|
| Nuclease-free water | 5.8 | |
| $MgCl_2$ (50 mM) | 1.5 | 5 mM |
| 10X Platinum PCR Buffer, Minus Mg (Invitrogen Corp.; Carlsbad, CA, USA) | 1.5 | 1X |
| dNTP mix (2.5 mM each) (Ambion, Inc.; Austin, TX USA) | 1.5 | 0.25 mM each |
| 20X TaqMan Assay Buffer | 0.3 | 0.4X |
| 50X ROX Internal Marker | 0.3 | 1X |
| Platinum ® Taq DNA Polymerase (5 U/μl) (Invitrogen) | 0.1 | 0.033 U/μl |
| cDNA from RT reaction | 4.0 | | qRT-PCR data were initially assessed for outliers. All miRNAs in a given sample with raw Ct readings of 50 were eliminated from further analysis. miR-103 served as an internal control, and its Ct was subtracted from the raw Ct readings for each miRNA in the corresponding sample to produce a dCt for each miRNA that was detected. Normalized values were used to estimate the relative abundance of each miRNA in the samples.

Average dCt values for each miRNA in the normal donor, BPH patient, and PrCa patient samples were calculated. Average dCt values for PrCa patient samples were subtracted from average dCt values for normal donor samples and BPH patient samples to determine the variance in the levels of the miRNAs between the patient sets. Student's t-test was then used to determine the potential of various miRNAs to distinguish the sera of PrCa patients from sera of normal donors and BPH patients. Table 12 shows average dCt values for the three sample types, and the difference between PrCa samples and normal or BPH samples.

TABLE 12 miRNA serum biomarkers for prostate cancer.

| miRNA | Avg Norm | SD Norm | Avg BPH | SD BPH | Avg PrCa | SD PrCa | p-value Norm/PrCa | p-value BPH/PrCa | PrCa-Norm | PrCa-BPH |
|---|---|---|---|---|---|---|---|---|---|---|
| miR-24 | −1.88 | 0.54 | −2.26 | 1.28 | −1.74 | 0.37 | 4.74E−01 | 1.92E−01 | 0.14 | 0.52 |
| miR-125b | 5.92 | 1.30 | 4.92 | 0.87 | 2.32 | 1.30 | 4.87E−06 | 8.28E−06 | −3.60 | −2.61 |
| miR-340 | 6.76 | 0.54 | 6.23 | 0.95 | 6.72 | 1.03 | 9.06E−01 | 2.50E−01 | −0.04 | 0.49 |
| miR-375 | 6.03 | 1.41 | 5.48 | 1.59 | 2.97 | 1.51 | 5.94E−05 | 6.67E−04 | −3.06 | −2.50 |
| miR-15b | 0.26 | 0.73 | 0.00 | 0.80 | 0.59 | 0.99 | 3.58E−01 | 1.20E−01 | 0.33 | 0.59 |
| miR-204 | 8.33 | 0.65 | 7.40 | 0.97 | 6.47 | 0.91 | 4.99E−05 | 2.66E−02 | −1.86 | −0.93 |
| miR-205 | 10.71 | 2.33 | 10.08 | 1.49 | 8.39 | 2.35 | 3.08E−02 | 5.75E−02 | −2.32 | −1.69 |
| miR-206 | 7.27 | 3.35 | 6.73 | 2.18 | 5.76 | 2.02 | 1.99E−01 | 2.68E−01 | −1.52 | −0.98 |
| miR-122a | 10.21 | 1.64 | 8.81 | 2.24 | 5.99 | 2.35 | 4.27E−05 | 6.50E−03 | −4.21 | −2.82 |
| miR-483 | 6.36 | 1.95 | 4.68 | 1.82 | 4.15 | 1.83 | 1.06E−02 | 4.96E−01 | −2.21 | −0.53 |
| let-7d | 1.56 | 0.72 | 2.13 | 0.61 | 2.32 | 1.06 | 5.25E−02 | 6.02E−01 | 0.76 | 0.19 |
| let-7f | 1.68 | 0.70 | 2.18 | 1.02 | 2.32 | 1.38 | 1.64E−01 | 7.73E−01 | 0.64 | 0.14 |
| miR-191 | 0.35 | 0.54 | −0.36 | 1.08 | −0.31 | 0.55 | 7.34E−03 | 8.71E−01 | −0.66 | 0.06 |
| miR-26a | −2.18 | 0.40 | −2.69 | 0.83 | −2.51 | 0.42 | 6.36E−02 | 4.99E−01 | −0.33 | 0.18 |

SD, standard deviation.

Example 4

Validation of Prostate Cancer Serum Biomarkers

To assess the robustness of the prostate cancer biomarkers in diagnosing prostate cancer, the inventors selected 11 miRNA biomarkers (miR-24, miR-125b, miR-375, miR-204, miR-205, miR-206, miR-122a, let-7d, miR-10b, miR-99b, miR-22) and 11 internal control miRNAs (miR-191, miR-16, miR-181a, miR-21, miR-26a, miR-106a, miR-155, miR-30a-5p, let-7a, let-7c, miR-222) and quantified those miRNAs, using qRT-PCR, in the sera of 25 PrCa patients and 25 normal donors (Table 13), which were independent from those serum samples previously described.

TABLE 13

Histopathological data and patient information.

| Patient Diagnosis | Patient Age | PSA | Gleason Score |
|---|---|---|---|
| PrCa | 65 | 2.6 | 6 |
| PrCa | 62 | 6.9 | 8 |
| PrCa | 60 | 5.8 | 6 |
| PrCa | 61 | 4.2 | 6 |
| PrCa | 64 | 3.6 | 6 |
| PrCa | 57 | 2.2 | 6 |
| PrCa | 54 | 3.8 | 6 |
| PrCa | 64 | 0.5 | 6 |
| PrCa | 56 | 4.9 | 6 |
| PrCa | 61 | ND | 7 |
| PrCa | 58 | 6.2 | 7 |
| PrCa | 61 | 3.6 | 6 |
| PrCa | 50 | 3.55 | 7 |
| PrCa | 59 | 6.4 | 7 |
| PrCa | 57 | 4.6 | 7 |
| PrCa | 56 | ND | 9 |
| PrCa | 57 | ND | 6 |
| PrCa | 55 | ND | 6 |
| PrCa | 61 | ND | 7 |
| PrCa | 60 | 3.6 | 6 |
| PrCa | 59 | ND | 7 |
| PrCa | 54 | 7.8 | 6 |
| PrCa | 51 | 7.7 | 7 |
| PrCa | 61 | 3.2 | 6 |
| PrCa | 62 | 4.3 | 6 |
| Normal | 63 | ND | NA |
| Normal | 61 | ND | NA |
| Normal | 56 | ND | NA |
| Normal | 56 | ND | NA |
| Normal | 61 | ND | NA |
| Normal | 61 | ND | NA |
| Normal | 61 | ND | NA |
| Normal | 64 | ND | NA |
| Normal | 61 | ND | NA |
| Normal | 62 | ND | NA |
| Normal | 50 | ND | NA |
| Normal | 51 | ND | NA |
| Normal | 62 | ND | NA |
| Normal | 59 | ND | NA |
| Normal | 57 | ND | NA |
| Normal | 56 | ND | NA |
| Normal | 60 | ND | NA |
| Normal | 60 | ND | NA |
| Normal | 54 | ND | NA |
| Normal | 55 | ND | NA |
| Normal | 59 | ND | NA |
| Normal | 57 | ND | NA |
| Normal | 54 | ND | NA |
| Normal | 58 | ND | NA |
| Normal | 57 | ND | NA |

ND, not determined;
NA, not available.

PrCa patient and normal donor serum samples for this Example were purchased from a different vendor (ProMedDx, LLC; Norton, Mass., USA), than those samples used for screening and validation in Examples 1, 2, and 3 (ProteoGenex, Inc.). In addition, the two vendors use different methods for serum preparation from patient samples. For these samples purchased from ProMedDx, ten (10) ml of whole blood was collected using a BD Vacutainer™ SST™ plastic serum tube (Becton, Dickinson and Company; Franklin Lakes, N.J., USA; cat. no. 367985). The tubes were incubated at room temperature for 10 to 60 minutes to allow the blood to clot. The tubes were centrifuged for 10 minutes at 3000-3500 RPM. Serum was transferred to a new tube using a serological pipette and frozen at −80° C. until it was subjected to RNA isolation. Serum RNA was purified as described in Example 1.

MicroRNA levels were determined by qRT-PCR using TaqMan® MicroRNA Assays (Applied Biosystems; Foster City, Calif., USA) specific for each miRNA. Reverse transcription (RT) reaction components were assembled on ice prior to the addition of RNA template (Table 14). Serum RNA (1 μl per reaction) was added and mixed. RT reactions were incubated in a 384-well GeneAmp® PCR System 9700 (Applied Biosystems) at 4° C. for 30 minutes, then at 16° C. for 30 minutes, then at 42° C. for 30 minutes, then at 85° C. for 5 minutes. RT reactions were then frozen at −20° C. All reaction components were as provided by the manufacturer (Applied Biosystems; Foster City, Calif., USA) unless otherwise specified.

TABLE 14

Reverse transcription reaction components.

| Component | μl per 10 μl rxn | Final Concentration |
|---|---|---|
| Nuclease-free water | 5.1 | |
| 10X Reverse Transcription Buffer | 1.0 | 1X |
| dNTP mix (100 mM) | 0.1 | 1 mM |
| 1.25X RT Primer | 2.0 | 0.25X |
| RNase Inhibitor (20 U/μl) | 0.13 | 0.26 U/μl |
| Multiscribe ™ Recombinant Moloney Murine Leukemia Virus Reverse Transcriptase (MMLV-RT) (50 U/ul) | 0.67 | 3.35 U/μl |
| Human Serum RNA | 1.0 | |

PCR components (Table 15) were assembled on ice prior to the addition of cDNA (4 μl) from the RT reaction. Reactions were incubated in an ABI PRISM™ 7900HT Fast Real-Time PCR system (Applied Biosystems) at 95° C. for 1 minute, then for 50 cycles at 95° C. for 5 seconds and 60° C. for 30 seconds. Results were analyzed with SDS V2.3 (Applied Biosystems). All reaction components were as provided by the manufacturer (Applied Biosystems; Foster City, Calif., USA) unless otherwise specified.

TABLE 15

PCR components.

| Component | μl per 15 μl rxn | Final Concentration |
|---|---|---|
| Nuclease-free water | 5.8 | |
| MgCl$_2$ (50 mM) | 1.5 | 5 mM |
| 10X Platinum PCR Buffer, Minus Mg (Invitrogen Corp.; Carlsbad, CA, USA) | 1.5 | 1X |
| dNTP mix (2.5 mM each) (Ambion, Inc.; Austin, TX USA) | 1.5 | 0.25 mM each |
| 20X TaqMan Assay Buffer | 0.3 | 0.4X |

TABLE 15-continued

PCR components.

| Component | µl per 15 µl rxn | Final Concentration |
|---|---|---|
| 50X ROX Internal Marker | 0.3 | 1X |
| Platinum ® Taq DNA Polymerase (5 U/µl) (Invitrogen) | 0.1 | 0.033 U/µl |
| cDNA from RT reaction | 4.0 | | qRT-PCR data for each miRNA in each sample was normalized by subtracting the Ct value for miR-103 from the Ct value for the miRNA from the same sample. The resulting values, called dCt, were used to calculate the average dCt values for each miRNA in the normal donor and PrCa patient samples. Average dCt values for PrCa patient samples were subtracted from average dCt values for normal donor samples to determine the variance in the levels of the miRNAs between the patient sets. Student's t-test was then used to determine the potential of various miRNAs to distinguish the sera of PrCa patients from sera of normal donors. Table 16 shows average dCt values for the three sample types, and the difference between PrCa samples and normal or BPH samples.

TABLE 16

Prostate cancer biomarkers.

| miRNA | Avg PrCa | SD | Avg Norm | StDev | PrCa-Norm | p-value (PrCa vs Norm) |
|---|---|---|---|---|---|---|
| miR-16 | −5.05 | 0.56 | −6.91 | 0.70 | 1.86 | 2.68E−12 |
| miR-22 | 3.15 | 0.63 | 2.31 | 0.47 | 0.84 | 1.45E−05 |
| let-7d | 2.83 | 0.54 | 2.13 | 0.47 | 0.70 | 4.72E−05 |
| miR-99b | 3.46 | 0.87 | 4.34 | 0.85 | −0.89 | 1.54E−03 |
| miR-181a | 1.95 | 1.04 | 2.73 | 0.54 | −0.79 | 3.89E−03 |
| miR-26a | −3.38 | 0.43 | −2.98 | 0.43 | −0.40 | 3.91E−03 |
| miR-122a | 7.44 | 2.37 | 9.34 | 1.65 | −1.90 | 4.42E−03 |
| miR-155 | 2.58 | 0.76 | 3.19 | 0.60 | −0.61 | 6.06E−03 |
| miR-10b | 3.20 | 1.43 | 4.27 | 1.14 | −1.08 | 9.81E−03 |
| miR-30a-5p | −0.62 | 0.71 | −1.12 | 0.47 | 0.50 | 1.10E−02 |
| miR-125b | 3.53 | 1.73 | 4.63 | 0.83 | −1.10 | 1.32E−02 |
| miR-205 | 6.17 | 7.05 | 10.27 | 3.15 | −4.11 | 2.04E−02 |
| let-7a | −0.65 | 0.47 | −0.31 | 0.48 | −0.33 | 2.70E−02 |
| miR-204 | 6.42 | 1.53 | 7.37 | 1.23 | −0.95 | 3.08E−02 |
| let-7c | 3.09 | 0.89 | 3.51 | 0.48 | −0.42 | 6.68E−02 |
| miR-375 | 6.10 | 1.37 | 5.43 | 0.91 | 0.66 | 7.21E−02 |
| miR-21 | −2.15 | 0.74 | −1.81 | 0.46 | −0.35 | 7.53E−02 |
| miR-222 | 0.53 | 0.43 | 0.79 | 0.62 | −0.26 | 1.16E−01 |
| miR-206 | 7.79 | 2.33 | 8.52 | 1.83 | −0.73 | 2.63E−01 |
| miR-106a | 0.30 | 0.22 | 0.36 | 0.19 | −0.06 | 3.83E−01 |
| miR-191 | −0.58 | 0.32 | −0.65 | 0.35 | 0.06 | 5.33E−01 |
| miR-24 | −1.54 | 0.33 | −1.58 | 0.51 | 0.04 | 7.46E−01 |

SD, standard deviation.

Example 5 qRT-PCR for Evaluation of MicroRNA Levels in Plasma Samples from Prostate Cancer Patients To identify miRNAs present in plasma that may be useful markers for diagnosis of prostate cancer and for establishing patient prognosis, the inventors evaluated miRNA levels in plasma samples from seven PrCa patients and nineteen normal donors (Table 17). Plasma samples were purchased from ProteoGenex Inc. (Culver City, Calif., USA).

TABLE 17

Histopathological data and patient information.

| Diagnosis | Patient Age/Sex | TNM Staging Score | PSA |
|---|---|---|---|
| PrCa Adenocarcinoma | NA/M | NA | 21.2 |
| PrCa Adenocarcinoma | 40/M | T3NxM0 | 14.2 |
| PrCa Adenocarcinoma | 58/M | NA | 7.3 |
| PrCa Adenocarcinoma | 52/M | NA | 86.48 |
| PrCa Adenocarcinoma | 52/M | T3NxM0 | 1.6 |
| PrCa Adenocarcinoma | 56/M | T2N1M1 | 1.4 |
| PrCa Adenocarcinoma | 50/M | T4N1M0 | 40.49 |
| Normal | 39/F | NA | NA |
| Normal | 44/M | NA | NA |
| Normal | 58/F | NA | NA |
| Normal | 59/F | NA | NA |
| Normal | 61/M | NA | NA |
| Normal | 52/M | NA | NA |
| Normal | 59/M | NA | NA |
| Normal | 57/F | NA | NA |
| Normal | 59/F | NA | NA |
| Normal | 56/M | NA | NA |
| Normal | 52/F | NA | NA |
| Normal | 62/F | NA | NA |
| Normal | 61/F | NA | NA |
| Normal | 57/M | NA | NA |
| Normal | 53/F | NA | NA |
| Normal | 60/M | NA | NA |
| Normal | 59/F | NA | NA |
| Normal | NA | NA | NA |
| Normal | 53 | NA | NA |

NA, not available.

For plasma preparation, 10 ml whole blood was collected into a lavender top veinous blood collection tube (Becton, Dickinson and Company; Franklin Lakes, N.J., USA). The sample was allowed to incubate at room temperature for up to two hours, then centrifuged at 2,000×g for 15 minutes. Following centrifugation, plasma was removed to a fresh tube. Plasma RNA was purified using the organic extraction of the mirVana PARIS™ Kit (Part No. AM1556; Applied Biosystems/Ambion; Austin, Tex., USA), with the following modifications. Following the addition of acid phenol:chloroform and vortexing, samples were incubated on ice for five minutes then centrifuged at 13,000×g for 15 minutes at 4° C. The aqueous layer was removed, 3M NaOAc (¹/₁₀ volume), glycogen (5 mg/ml), and 100% ethanol (1.5 volume) were added to the samples, and samples were mixed by inversion. Lysate/ethanol mixtures were passed through a mirVana PARIS™ filter cartridge, and filters were washed once with 650 µl of Wash 1 buffer and twice with 650 µl of Wash ⅔ buffer. RNA was eluted with nuclease free water (50 µl) and stored at −80° C.

Levels of 319 miRNAs were determined by qRT-PCR using TaqMan® MicroRNA Assays (Applied Biosystems; Foster City, Calif., USA) specific for each miRNA. Reverse transcription (RT) reaction components (Table 18) were assembled on ice prior to the addition of RNA template. Plasma RNA (0.25 µl per reaction) was added and mixed. RT reactions were incubated in a 384-well GeneAmp® PCR System 9700 (Applied Biosystems) at 16° C. for 30 minutes, then at 42° C. for 30 minutes, then at 85° C. for 5 minutes. RT reactions were then frozen at −20° C.

TABLE 18

Reverse transcription reaction components. All reaction components were as provided by the manufacturer (Applied Biosystems; Foster City, CA, USA) unless otherwise specified.

| Component | μl per 10 μl rxn | Final Concentration |
|---|---|---|
| Nuclease-free water | 5.6 | |
| 10X Reverse Transcription Buffer | 1.0 | 1X |
| dNTP mix (2.5 mM each, Ambion) | 1.0 | 0.25 mM each |
| 1.25X RT Primer | 2.0 | 0.25X |
| RNase Inhibitor (40 U/μl, Promega, Corp., Madison, WI, USA) | 0.1 | 0.4 U/μl |
| Multiscribe ™ Recombinant Moloney Murine Leukemia Virus Reverse Transcriptase (MMLV-RT) (200 U/μl, Invitrogen) | 0.0.05 | 1 U/μl |
| Human Plasma RNA | 0.25 | |

PCR components (Table 19) were assembled on ice prior to the addition of cDNA (2 μl) from the RT reaction. Reactions were incubated in an ABI PRISM™ 7900HT Fast Real-Time PCR system (Applied Biosystems) at 95° C. for 1 minute, then for 50 cycles at 95° C. for 5 seconds and 60° C. for 30 seconds. Results were analyzed with SDS V2.3 (Applied Biosystems).

TABLE 19

PCR components. All reaction components were as provided by the manufacturer (Applied Biosystems; Foster City, CA, USA) unless otherwise specified.

| Component | μl per 15 μl rxn | Final Concentration |
|---|---|---|
| Nuclease-free water | 6.1 | |
| MgCl$_2$ (50 mM) | 1.5 | 5 mM |
| 10X Platinum PCR Buffer, Minus Mg (Invitrogen Corp., Carlsbad, CA, USA) | 1.5 | 1X |
| dNTP mix (2.5 mM each, Ambion) | 1.5 | 0.25 mM each |
| 3X TaqMan Assay (AB) | 2.0 | 0.4X |
| 50X ROX Internal marker | 0.3 | 1X |
| Platinum ® Taq DNA Polymerase (5 U/μl) (Invitrogen) | 0.1 | 0.033 U/μl |
| cDNA from RT reaction | 2.0 | |

The qRT-PCR data were initially assessed for outliers. All miRNAs in a given sample with raw Ct readings of 50 were eliminated from further analysis. All data from samples with fewer than 150 miRNAs having raw Ct values <50 were eliminated. The average raw Ct values for 50 miRNAs detected in each sample were calculated for each individual sample. The average Ct for a given sample was subtracted from the raw Ct values for each miRNA in the corresponding sample to produce a dCt for each miRNA that was detected. Table 20 provides the normalized values for samples from normal donors and prostate cancer patients, and shows the difference in level of miRNAs between the sample types. miRNAs that have elevated or reduced levels in plasma samples from prostate disease patients are listed in Table 20.

TABLE 20

Normalized qRT-PCR data for quantification of 278 miRNAs in plasma from PrCa patients and normal donors (Norm).

| miRNA | Avg Norm | SD Norm | Avg PrCa | SD PrCa | PrCa-Norm | p-value (PrCa vs Norm) |
|---|---|---|---|---|---|---|
| miR-95 | 8.80 | 1.64 | 6.77 | 0.41 | −2.03 | 2.01E−04 |
| let-7b | −0.85 | 0.90 | −2.12 | 0.49 | −1.27 | 2.05E−04 |
| miR-492 | 16.43 | 3.80 | 11.09 | 0.79 | −5.34 | 2.89E−04 |
| let-7c | 2.88 | 1.55 | 1.21 | 0.47 | −1.67 | 3.29E−04 |
| miR-145 | 2.38 | 0.62 | 6.18 | 1.29 | 3.80 | 5.26E−04 |
| let-7e | 8.44 | 1.85 | 6.79 | 0.40 | −1.65 | 1.40E−03 |
| miR-183 | 8.89 | 1.50 | 7.12 | 0.94 | −1.78 | 2.22E−03 |
| miR-214 | 6.07 | 1.24 | 5.05 | 0.49 | −1.02 | 6.41E−03 |
| miR-542-3p | 9.61 | 1.58 | 8.31 | 0.64 | −1.30 | 6.56E−03 |
| miR-133b | 1.76 | 0.77 | 3.73 | 1.37 | 1.97 | 7.88E−03 |
| miR-453 | 13.54 | 3.75 | 17.24 | 2.55 | 3.71 | 1.11E−02 |
| let-7g | 0.03 | 0.69 | −0.64 | 0.47 | −0.67 | 1.18E−02 |
| miR-148b | 2.43 | 0.52 | 2.82 | 0.21 | 0.39 | 1.35E−02 |
| miR-153 | 16.45 | 5.17 | 9.77 | 2.29 | −6.69 | 1.42E−02 |
| miR-132 | 2.72 | 0.36 | 2.33 | 0.30 | −0.39 | 1.53E−02 |
| miR-9 | 7.24 | 0.80 | 6.20 | 0.88 | −1.04 | 2.11E−02 |
| miR-152 | 2.14 | 0.75 | 1.64 | 0.28 | −0.49 | 2.20E−02 |
| miR-514 | 12.84 | 3.63 | 17.74 | 3.75 | 4.90 | 2.23E−02 |
| miR-30e-3p | 2.19 | 0.71 | 2.97 | 0.67 | 0.78 | 2.44E−02 |
| miR-520d* | 15.47 | 4.33 | 11.91 | 0.12 | −3.55 | 2.90E−02 |
| miR-223 | −6.98 | 0.71 | −6.44 | 0.43 | 0.54 | 2.95E−02 |
| miR-129 | 14.72 | 2.58 | 12.35 | 2.03 | −2.37 | 2.96E−02 |
| miR-370 | 4.71 | 0.67 | 5.29 | 0.53 | 0.58 | 3.94E−02 |
| miR-182 | 4.38 | 1.35 | 3.17 | 1.17 | −1.21 | 4.32E−02 |
| miR-29c | 0.94 | 1.08 | 0.04 | 0.85 | −0.90 | 4.45E−02 |
| miR-383 | 9.59 | 1.45 | 8.29 | 1.28 | −1.30 | 4.72E−02 |
| miR-30e-5p | 1.90 | 0.94 | 1.13 | 0.75 | −0.78 | 4.82E−02 |
| miR-339 | 1.86 | 0.79 | 3.37 | 1.65 | 1.51 | 5.27E−02 |
| miR-140 | −0.19 | 0.88 | −0.68 | 0.35 | −0.49 | 5.51E−02 |
| miR-98 | 3.44 | 1.27 | 2.74 | 0.45 | −0.70 | 5.54E−02 |
| miR-100 | 5.72 | 0.70 | 5.01 | 0.77 | −0.72 | 5.64E−02 |
| miR-150 | −0.78 | 1.29 | −1.97 | 1.25 | −1.19 | 5.66E−02 |
| miR-224 | 3.64 | 0.82 | 4.96 | 1.47 | 1.32 | 5.68E−02 |
| miR-424 | 8.73 | 3.28 | 6.98 | 0.92 | −1.75 | 5.69E−02 |
| miR-106b | 0.25 | 2.93 | −1.17 | 0.52 | −1.41 | 5.71E−02 |
| miR-34c | 8.40 | 2.50 | 7.02 | 1.03 | −1.38 | 5.81E−02 |
| miR-134 | 1.91 | 0.84 | 3.06 | 1.28 | 1.15 | 5.92E−02 |
| miR-182* | 15.22 | 3.87 | 11.39 | 1.17 | −3.83 | 5.98E−02 |
| miR-520d | 11.61 | 3.06 | 14.97 | 3.73 | 3.37 | 6.21E−02 |
| miR-365 | 4.93 | 1.03 | 3.97 | 1.05 | −0.96 | 6.25E−02 |
| miR-491 | 4.71 | 0.94 | 5.48 | 0.84 | 0.77 | 6.84E−02 |
| miR-362 | 4.49 | 0.70 | 5.26 | 0.89 | 0.77 | 6.84E−02 |
| miR-379 | 7.10 | 2.33 | 5.85 | 1.00 | −1.25 | 6.85E−02 |
| miR-517c | 12.94 | 4.57 | 9.74 | 0.46 | −3.21 | 6.96E−02 |
| miR-197 | −0.95 | 1.15 | −2.05 | 1.26 | −1.10 | 7.09E−02 |
| miR-25 | 0.03 | 0.92 | 0.57 | 0.51 | 0.54 | 7.35E−02 |
| miR-141 | 8.23 | 2.00 | 6.94 | 1.20 | −1.29 | 7.44E−02 |
| miR-191 | −2.76 | 0.51 | −2.27 | 0.58 | 0.49 | 7.53E−02 |
| miR-450 | 11.85 | 4.12 | 9.29 | 1.33 | −2.56 | 8.48E−02 |
| miR-222 | −1.44 | 0.83 | −2.02 | 0.66 | −0.59 | 8.53E−02 |
| miR-448 | 12.67 | 3.22 | 15.12 | 2.83 | 2.45 | 8.55E−02 |
| miR-520h | 14.33 | 4.64 | 9.24 | 2.17 | −5.09 | 8.74E−02 |
| miR-9* | 7.62 | 1.19 | 6.63 | 1.22 | −0.99 | 9.41E−02 |
| miR-192 | 2.01 | 0.99 | 1.47 | 0.56 | −0.54 | 9.63E−02 |
| miR-107 | 5.31 | 0.54 | 4.91 | 0.49 | −0.40 | 9.83E−02 |
| miR-199a* | −1.23 | 0.56 | −0.36 | 1.17 | 0.88 | 9.85E−02 |
| miR-497 | 6.53 | 0.87 | 5.91 | 0.78 | −0.62 | 1.06E−01 |
| miR-195 | −0.39 | 1.36 | −1.18 | 0.90 | −0.79 | 1.06E−01 |
| miR-429 | 8.33 | 2.21 | 7.18 | 1.12 | −1.15 | 1.09E−01 |
| miR-101 | 1.54 | 0.97 | 0.82 | 0.95 | −0.73 | 1.12E−01 |
| miR-96 | 10.03 | 1.89 | 8.13 | 2.04 | −1.90 | 1.14E−01 |
| miR-212 | 6.92 | 0.79 | 10.79 | 4.36 | 3.87 | 1.18E−01 |
| miR-539 | 2.76 | 0.85 | 3.15 | 0.39 | 0.40 | 1.19E−01 |
| miR-10b | 6.41 | 1.56 | 5.55 | 0.98 | −0.86 | 1.19E−01 |
| miR-323 | 5.74 | 0.48 | 6.26 | 0.74 | 0.52 | 1.22E−01 |
| miR-200a* | 13.78 | 3.25 | 17.55 | 2.83 | 3.77 | 1.27E−01 |
| miR-518b | 8.55 | 1.45 | 7.01 | 2.26 | −1.54 | 1.34E−01 |
| miR-432 | 2.11 | 0.71 | 1.64 | 0.67 | −0.47 | 1.42E−01 |
| miR-146b | −1.45 | 0.52 | −1.82 | 0.53 | −0.36 | 1.46E−01 |
| miR-155 | 1.81 | 0.81 | 1.37 | 0.57 | −0.44 | 1.51E−01 |
| miR-127 | 1.08 | 0.53 | 1.70 | 0.98 | 0.62 | 1.52E−01 |
| miR-376a | 2.76 | 0.65 | 3.13 | 0.52 | 0.38 | 1.52E−01 |
| miR-213 | 6.84 | 1.92 | 7.90 | 1.45 | 1.06 | 1.53E−01 |

TABLE 20-continued

Normalized qRT-PCR data for quantification of 278 miRNAs in plasma from PrCa patients and normal donors (Norm).

| miRNA | Avg Norm | SD Norm | Avg PrCa | SD PrCa | PrCa-Norm | p-value (PrCa vs Norm) |
|---|---|---|---|---|---|---|
| miR-423 | 2.73 | 0.48 | 2.51 | 0.26 | −0.22 | 1.53E-01 |
| miR-377 | 13.01 | 2.30 | 14.85 | 2.78 | 1.84 | 1.53E-01 |
| miR-410 | 3.31 | 0.82 | 3.73 | 0.57 | 0.42 | 1.60E-01 |
| miR-32 | 3.18 | 0.85 | 2.63 | 0.83 | −0.55 | 1.63E-01 |
| miR-320 | −1.08 | 1.07 | −0.38 | 1.07 | 0.70 | 1.67E-01 |
| miR-520a | 14.92 | 3.79 | 9.77 | 4.44 | −5.15 | 1.69E-01 |
| miR-505 | 3.50 | 0.64 | 3.99 | 0.78 | 0.49 | 1.69E-01 |
| miR-135a | 5.76 | 0.74 | 7.53 | 2.43 | 1.77 | 1.80E-01 |
| miR-138 | 11.69 | 3.02 | 16.08 | 3.94 | 4.39 | 1.83E-01 |
| miR-34a | 8.34 | 2.55 | 9.36 | 1.21 | 1.02 | 1.84E-01 |
| miR-509 | 13.03 | 3.73 | 11.21 | 2.41 | −1.82 | 1.88E-01 |
| miR-92 | −5.27 | 0.97 | −5.81 | 0.84 | −0.54 | 1.89E-01 |
| miR-199b | 7.82 | 1.11 | 9.11 | 2.25 | 1.29 | 1.90E-01 |
| miR-30a-3p | 4.75 | 2.35 | 3.99 | 0.51 | −0.76 | 1.97E-01 |
| miR-137 | 13.89 | 2.93 | 12.40 | 1.30 | −1.49 | 1.97E-01 |
| miR-523 | 15.92 | 2.39 | 18.00 | 2.46 | 2.08 | 1.98E-01 |
| miR-496 | 6.69 | 0.60 | 7.14 | 0.78 | 0.45 | 1.98E-01 |
| let-7d | 1.75 | 1.21 | 1.34 | 0.37 | −0.41 | 1.99E-01 |
| miR-181a | 2.11 | 0.75 | 2.52 | 0.66 | 0.41 | 2.00E-01 |
| miR-512-5p | 16.62 | 2.90 | 14.68 | 2.29 | −1.94 | 2.06E-01 |
| miR-15a | 2.24 | 0.75 | 1.82 | 0.69 | −0.41 | 2.09E-01 |
| miR-451 | −2.31 | 1.41 | −3.01 | 1.11 | −0.70 | 2.10E-01 |
| miR-142-5p | −0.89 | 0.39 | −1.08 | 0.29 | −0.19 | 2.12E-01 |
| miR-324-5p | 2.31 | 0.89 | 2.64 | 0.43 | 0.33 | 2.24E-01 |
| miR-126* | −3.22 | 0.58 | −3.51 | 0.50 | −0.29 | 2.27E-01 |
| miR-301 | 0.89 | 0.45 | 1.18 | 0.52 | 0.29 | 2.29E-01 |
| miR-483 | 8.75 | 1.86 | 7.67 | 1.97 | −1.08 | 2.35E-01 |
| miR-508 | 16.75 | 3.31 | 13.20 | 3.75 | −3.54 | 2.37E-01 |
| miR-139 | 5.63 | 0.68 | 9.20 | 6.58 | 3.57 | 2.42E-01 |
| miR-93 | −3.55 | 0.44 | −2.92 | 1.29 | 0.63 | 2.48E-01 |
| miR-493 | 7.31 | 1.62 | 9.40 | 3.98 | 2.09 | 2.60E-01 |
| miR-519d | 9.38 | 1.70 | 10.52 | 2.28 | 1.14 | 2.64E-01 |
| miR-154 | 10.36 | 2.13 | 9.68 | 0.28 | −0.68 | 2.64E-01 |
| miR-296 | 5.66 | 0.73 | 6.45 | 1.66 | 0.79 | 2.65E-01 |
| miR-299-5p | 8.68 | 1.37 | 11.00 | 4.95 | 2.31 | 2.67E-01 |
| miR-125a | 1.13 | 0.51 | 0.83 | 0.62 | −0.31 | 2.70E-01 |
| miR-422b | 3.82 | 1.23 | 3.47 | 0.40 | −0.35 | 2.79E-01 |
| miR-130a | 1.11 | 1.13 | 2.23 | 2.43 | 1.12 | 2.79E-01 |
| miR-126 | −3.61 | 0.64 | −4.11 | 1.06 | −0.50 | 2.81E-01 |
| miR-381 | 10.13 | 1.61 | 11.47 | 2.37 | 1.35 | 2.84E-01 |
| miR-27a | 0.28 | 0.84 | 0.56 | 0.43 | 0.28 | 2.84E-01 |
| miR-135b | 10.34 | 2.69 | 11.85 | 2.92 | 1.51 | 2.93E-01 |
| miR-30b | −3.26 | 0.74 | −2.32 | 2.14 | 0.94 | 2.94E-01 |
| miR-16 | −7.00 | 1.03 | −7.52 | 1.10 | −0.53 | 2.96E-01 |
| let-7f | 1.14 | 1.42 | 0.54 | 1.19 | −0.60 | 3.02E-01 |
| miR-376a* | 8.79 | 1.64 | 11.86 | 4.95 | 3.07 | 3.04E-01 |
| miR-181d | 1.25 | 0.78 | 1.58 | 0.65 | 0.32 | 3.06E-01 |
| miR-206 | 8.77 | 1.73 | 7.99 | 1.62 | −0.78 | 3.06E-01 |
| miR-340 | 3.88 | 1.07 | −1.10 | 11.98 | −4.99 | 3.14E-01 |
| miR-193a | 8.90 | 0.97 | 9.70 | 1.69 | 0.80 | 3.14E-01 |
| miR-374 | −0.89 | 0.46 | −1.22 | 0.76 | −0.33 | 3.14E-01 |
| miR-507 | 5.95 | 1.25 | 5.45 | 1.03 | −0.51 | 3.20E-01 |
| miR-103 | −0.27 | 0.64 | −0.51 | 0.48 | −0.24 | 3.21E-01 |
| miR-199a | 6.79 | 1.58 | 6.34 | 0.68 | −0.45 | 3.23E-01 |
| miR-525* | 13.87 | 3.67 | 15.68 | 2.33 | 1.81 | 3.25E-01 |
| miR-455 | 8.88 | 11.66 | 13.80 | 5.75 | 4.92 | 3.26E-01 |
| miR-542-5p | 13.54 | 3.76 | 11.19 | 2.45 | −2.34 | 3.28E-01 |
| miR-487a | 10.13 | 2.12 | 1.62 | 17.14 | −8.52 | 3.29E-01 |
| miR-517* | 17.19 | 3.26 | 15.41 | 2.31 | −1.78 | 3.31E-01 |
| miR-130b | 1.79 | 0.78 | 1.56 | 0.37 | −0.22 | 3.40E-01 |
| miR-485-5p | 6.06 | 0.57 | 6.67 | 1.41 | 0.61 | 3.44E-01 |
| miR-380-5p | 9.52 | 11.03 | 13.16 | 4.77 | 3.64 | 3.46E-01 |
| miR-99b | 2.49 | 0.47 | 3.40 | 2.37 | 0.91 | 3.51E-01 |
| miR-338 | 7.12 | 1.29 | 7.51 | 0.74 | 0.39 | 3.55E-01 |
| miR-133a | 4.40 | 0.86 | 4.78 | 0.89 | 0.38 | 3.59E-01 |
| miR-143 | 8.85 | 1.37 | 8.19 | 1.46 | −0.65 | 3.61E-01 |
| miR-504 | 17.16 | 1.74 | 16.17 | 1.77 | −0.99 | 3.62E-01 |
| miR-501 | 5.89 | 0.81 | 7.58 | 4.56 | 1.69 | 3.65E-01 |
| miR-189 | 10.85 | 1.88 | 14.56 | 5.55 | 3.70 | 3.67E-01 |
| miR-519c | 17.01 | 3.47 | 14.23 | 5.12 | −2.77 | 3.69E-01 |
| miR-346 | 11.30 | 3.01 | 9.89 | 2.86 | −1.42 | 3.69E-01 |
| miR-190 | 4.51 | 0.70 | 5.12 | 1.64 | 0.61 | 3.76E-01 |
| miR-218 | 11.86 | 3.64 | 10.59 | 2.51 | −1.27 | 3.76E-01 |
| miR-30d | −1.18 | 0.45 | −0.75 | 1.20 | 0.43 | 3.86E-01 |
| miR-520f | 16.98 | 3.03 | 14.26 | 6.13 | −2.72 | 3.88E-01 |
| miR-452* | 5.49 | 8.60 | 7.29 | 0.42 | 1.80 | 3.88E-01 |
| miR-368 | 11.49 | 1.98 | 14.50 | 4.78 | 3.01 | 3.89E-01 |
| miR-193b | 9.95 | 1.99 | 11.61 | 4.24 | 1.66 | 3.93E-01 |
| miR-15b | −0.98 | 0.67 | −0.74 | 0.61 | 0.24 | 3.94E-01 |
| miR-518d | 10.89 | 2.98 | 11.97 | 2.39 | 1.08 | 3.94E-01 |
| miR-185 | 5.77 | 1.28 | 5.32 | 1.11 | −0.44 | 4.04E-01 |
| miR-375 | 5.42 | 1.39 | 5.87 | 1.13 | 0.45 | 4.09E-01 |
| miR-30c | −2.57 | 0.66 | −2.12 | 1.37 | 0.45 | 4.27E-01 |
| miR-492 | 9.10 | 12.10 | 11.93 | 0.87 | 2.84 | 4.40E-01 |
| miR-128b | 13.46 | 3.51 | 12.36 | 2.70 | −1.10 | 4.41E-01 |
| miR-31 | 7.29 | 1.14 | 6.59 | 2.02 | −0.70 | 4.49E-01 |
| miR-99a | 5.46 | 0.80 | 5.82 | 1.15 | 0.36 | 4.61E-01 |
| miR-29a | 0.51 | 0.66 | 0.29 | 0.68 | −0.23 | 4.64E-01 |
| miR-203 | 9.39 | 0.71 | 8.86 | 1.74 | −0.53 | 4.66E-01 |
| miR-20a | −4.20 | 0.76 | −4.47 | 0.83 | −0.27 | 4.66E-01 |
| miR-154* | 10.01 | 2.48 | 9.39 | 1.51 | −0.62 | 4.69E-01 |
| miR-516-3p | 9.70 | 2.20 | 10.18 | 1.07 | 0.47 | 4.73E-01 |
| miR-142-3p | −4.06 | 0.48 | −4.37 | 1.03 | −0.30 | 4.74E-01 |
| miR-1 | 4.25 | 1.59 | 3.85 | 1.07 | −0.40 | 4.78E-01 |
| miR-10a | 5.02 | 0.90 | 4.69 | 1.04 | −0.33 | 4.81E-01 |
| miR-329 | 10.26 | 1.85 | 11.49 | 3.44 | 1.22 | 4.82E-01 |
| miR-526b | 14.62 | 2.22 | 16.83 | 4.46 | 2.21 | 4.83E-01 |
| miR-18a | 3.16 | 0.54 | 3.36 | 0.63 | 0.20 | 4.84E-01 |
| miR-494 | 7.23 | 0.96 | 7.96 | 2.60 | 0.74 | 4.89E-01 |
| miR-204 | 6.35 | 0.81 | 6.69 | 1.13 | 0.34 | 4.90E-01 |
| miR-217 | 16.70 | 3.02 | 15.07 | 2.19 | −1.63 | 4.91E-01 |
| miR-518c* | 12.69 | 3.32 | 11.84 | 2.00 | −0.85 | 4.91E-01 |
| miR-489 | 8.62 | 1.61 | 11.75 | 6.50 | 3.14 | 4.92E-01 |
| miR-382 | 2.12 | 0.54 | 2.45 | 1.13 | 0.32 | 4.96E-01 |
| miR-425 | 2.76 | 0.89 | 2.97 | 0.61 | 0.21 | 4.96E-01 |
| miR-221 | −2.47 | 1.12 | −2.20 | 0.77 | 0.27 | 4.99E-01 |
| miR-376b | 10.40 | 3.17 | 14.98 | 6.58 | 4.58 | 5.02E-01 |
| miR-525 | 12.71 | 2.88 | 11.75 | 3.01 | −0.96 | 5.12E-01 |
| miR-373* | 14.60 | 3.64 | 16.22 | 5.03 | 1.62 | 5.16E-01 |
| miR-122a | 10.40 | 2.64 | 9.35 | 3.11 | −1.05 | 5.22E-01 |
| miR-326 | 4.75 | 0.72 | 4.52 | 0.79 | −0.23 | 5.23E-01 |
| miR-28 | 1.55 | 0.92 | 1.39 | 0.34 | −0.16 | 5.28E-01 |
| miR-432* | 9.34 | 1.67 | 8.86 | 1.71 | −0.49 | 5.34E-01 |
| miR-33 | 10.30 | 1.98 | 11.30 | 3.92 | 1.00 | 5.41E-01 |
| miR-184 | 14.32 | 4.25 | 12.90 | 4.06 | −1.41 | 5.43E-01 |
| miR-526b* | 17.77 | 2.90 | 16.88 | 2.67 | −0.89 | 5.43E-01 |
| miR-409-5p | 9.49 | 1.58 | 8.88 | 1.70 | −0.61 | 5.46E-01 |
| miR-23b | 4.63 | 3.44 | 4.13 | 0.59 | −0.49 | 5.54E-01 |
| miR-148a | 2.50 | 0.44 | 2.63 | 0.50 | 0.13 | 5.60E-01 |
| miR-422a | 5.65 | 0.91 | 5.92 | 1.03 | 0.26 | 5.63E-01 |
| miR-503 | 11.15 | 2.75 | 5.66 | 19.49 | −5.49 | 5.64E-01 |
| miR-23a | 3.01 | 0.81 | 3.18 | 0.58 | 0.18 | 5.64E-01 |
| miR-187 | 9.21 | 1.15 | 5.70 | 15.72 | −3.51 | 5.77E-01 |
| miR-208 | 17.01 | 2.79 | 16.13 | 2.46 | −0.88 | 5.82E-01 |
| miR-105 | 14.00 | 3.07 | 15.04 | 4.12 | 1.04 | 5.91E-01 |
| miR-378 | 6.51 | 0.89 | 6.33 | 0.66 | −0.18 | 5.91E-01 |
| miR-200c | 3.08 | 0.51 | 3.21 | 0.54 | 0.13 | 5.95E-01 |
| miR-181c | 4.99 | 0.73 | 5.26 | 1.22 | 0.27 | 5.96E-01 |
| miR-202 | 8.14 | 2.03 | 7.78 | 1.26 | −0.36 | 6.01E-01 |
| miR-211 | 9.57 | 1.66 | 9.90 | 1.20 | 0.33 | 6.10E-01 |
| let-7i | 1.00 | 1.22 | 1.25 | 1.16 | 0.26 | 6.32E-01 |
| miR-18a* | 4.22 | 0.87 | 4.05 | 0.77 | −0.17 | 6.37E-01 |
| miR-485-3p | 3.74 | 0.83 | 4.03 | 1.51 | 0.29 | 6.45E-01 |
| miR-26b | −3.51 | 0.87 | −3.21 | 1.65 | 0.30 | 6.57E-01 |
| miR-20b | −0.36 | 0.75 | −0.48 | 0.53 | −0.12 | 6.57E-01 |
| miR-515-3p | 14.75 | 4.05 | 13.95 | 3.24 | −0.79 | 6.60E-01 |
| miR-488 | 14.36 | 2.29 | 13.48 | 2.06 | −0.88 | 6.62E-01 |
| miR-527 | 14.67 | 2.93 | 13.76 | 3.50 | −0.91 | 6.63E-01 |
| miR-520e | 14.45 | 3.18 | 13.38 | 4.73 | −1.07 | 6.65E-01 |
| miR-196a | 6.62 | 0.87 | 7.07 | 2.56 | 0.45 | 6.65E-01 |
| miR-302b* | 14.00 | 1.88 | 13.20 | 1.96 | −0.80 | 6.71E-01 |
| miR-181b | 2.21 | 0.91 | 2.05 | 0.78 | −0.16 | 6.72E-01 |
| miR-302a | 16.16 | 3.73 | 14.23 | 5.00 | −1.94 | 6.81E-01 |
| miR-302d | 14.22 | 2.09 | 16.32 | 5.45 | 2.10 | 6.82E-01 |
| miR-486 | −3.96 | 1.32 | −3.71 | 1.45 | 0.26 | 6.92E-01 |
| miR-361 | 4.11 | 0.99 | 3.96 | 0.81 | −0.15 | 6.92E-01 |

TABLE 20-continued

Normalized qRT-PCR data for quantification of 278 miRNAs in plasma from PrCa patients and normal donors (Norm).

| miRNA | Avg Norm | SD Norm | Avg PrCa | SD PrCa | PrCa-Norm | p-value (PrCa vs Norm) |
|---|---|---|---|---|---|---|
| miR-24 | −4.26 | 0.54 | −4.34 | 0.43 | −0.08 | 6.92E−01 |
| miR-328 | 1.35 | 0.77 | 1.21 | 0.79 | −0.14 | 6.96E−01 |
| miR-493* | 7.66 | 2.13 | 8.23 | 3.55 | 0.57 | 7.02E−01 |
| miR-342 | 0.43 | 0.55 | 0.54 | 0.63 | 0.11 | 7.02E−01 |
| miR-507 | 15.72 | 1.95 | 16.13 | 2.49 | 0.41 | 7.03E−01 |
| miR-19b | −5.05 | 0.61 | −4.95 | 0.59 | 0.10 | 7.11E−01 |
| miR-186 | −1.49 | 0.85 | −1.40 | 0.35 | 0.09 | 7.12E−01 |
| miR-518e | 13.05 | 3.97 | 12.22 | 4.29 | −0.83 | 7.15E−01 |
| miR-511 | 8.55 | 1.81 | 9.22 | 4.61 | 0.68 | 7.18E−01 |
| miR-337 | 12.83 | 2.94 | 12.31 | 2.49 | −0.52 | 7.19E−01 |
| miR-146a | −3.80 | 0.64 | −3.91 | 0.68 | −0.11 | 7.24E−01 |
| miR-380-3p | 11.12 | 2.43 | 11.91 | 4.80 | 0.79 | 7.38E−01 |
| miR-510 | 16.10 | 3.11 | 14.80 | 5.75 | −1.30 | 7.39E−01 |
| miR-106a | −0.40 | 0.59 | −0.47 | 0.49 | −0.08 | 7.45E−01 |
| miR-216 | 12.98 | 2.78 | 12.28 | 2.31 | −0.70 | 7.47E−01 |
| miR-215 | 8.29 | 1.47 | 8.07 | 1.49 | −0.22 | 7.48E−01 |
| miR-210 | 2.63 | 0.91 | 2.55 | 0.32 | −0.07 | 7.66E−01 |
| miR-372 | 15.95 | 5.58 | 13.43 | 9.47 | −2.51 | 7.74E−01 |
| miR-149 | 11.04 | 3.22 | 10.70 | 1.92 | −0.34 | 7.75E−01 |
| miR-30a-5p | −2.03 | 0.62 | −1.93 | 0.83 | 0.10 | 7.77E−01 |
| miR-331 | 1.00 | 0.79 | 1.07 | 0.43 | 0.07 | 7.80E−01 |
| miR-490 | 9.17 | 1.52 | 9.37 | 1.73 | 0.20 | 7.94E−01 |
| miR-335 | 1.37 | 0.73 | 1.43 | 0.40 | 0.06 | 7.95E−01 |
| miR-520b | 14.24 | 3.88 | 13.40 | 5.75 | −0.84 | 7.98E−01 |
| miR-26a | −4.67 | 0.77 | −4.74 | 0.60 | −0.07 | 7.98E−01 |
| miR-125b | 4.76 | 0.50 | 4.66 | 0.99 | −0.10 | 8.03E−01 |
| miR-188 | 6.73 | 1.48 | 6.89 | 1.40 | 0.16 | 8.04E−01 |
| miR-136 | 11.82 | 1.15 | 11.62 | 2.02 | −0.19 | 8.17E−01 |
| miR-22 | 3.05 | 1.02 | 2.98 | 0.63 | −0.07 | 8.31E−01 |
| miR-19a | −3.50 | 0.67 | −3.43 | 0.65 | 0.06 | 8.36E−01 |
| miR-506 | 15.76 | 3.26 | 16.35 | 4.96 | 0.59 | 8.41E−01 |
| miR-198 | 11.07 | 3.74 | 11.37 | 3.40 | 0.30 | 8.49E−01 |
| miR-151 | −0.51 | 0.64 | −0.47 | 0.44 | 0.04 | 8.53E−01 |
| miR-519e | 13.57 | 3.68 | 13.85 | 2.40 | 0.28 | 8.56E−01 |
| miR-452 | 8.66 | 3.24 | 8.46 | 2.31 | −0.21 | 8.59E−01 |
| miR-29b | 5.50 | 1.28 | 5.37 | 1.71 | −0.13 | 8.60E−01 |
| miR-196b | 3.90 | 0.95 | 3.96 | 0.65 | 0.06 | 8.63E−01 |
| miR-433 | 3.90 | 0.62 | 3.84 | 0.85 | −0.06 | 8.66E−01 |
| miR-449 | 10.31 | 4.55 | 10.76 | 4.96 | 0.44 | 8.67E−01 |
| miR-18b | 13.77 | 4.29 | 13.38 | 5.17 | −0.39 | 8.73E−01 |
| miR-373 | 15.03 | 4.77 | 15.59 | 5.14 | 0.57 | 8.73E−01 |
| let-7a | 0.31 | 1.91 | 0.11 | 3.10 | −0.20 | 8.75E−01 |
| miR-205 | 10.05 | 3.22 | 9.67 | 5.07 | −0.38 | 8.81E−01 |
| miR-369-5p | 7.95 | 0.93 | 7.87 | 1.16 | −0.08 | 8.89E−01 |
| miR-128a | 9.47 | 1.57 | 9.37 | 1.54 | −0.11 | 8.97E−01 |
| miR-412 | 13.33 | 3.32 | 13.08 | 3.43 | −0.25 | 9.02E−01 |
| miR-495 | 6.50 | 3.55 | 6.61 | 0.64 | 0.11 | 9.03E−01 |
| miR-324-3p | 1.63 | 0.54 | 1.66 | 0.54 | 0.03 | 9.07E−01 |
| miR-17-5p | −0.81 | 0.92 | −0.78 | 0.54 | 0.03 | 9.14E−01 |
| miR-330 | 5.89 | 0.79 | 5.94 | 1.03 | 0.05 | 9.17E−01 |
| miR-369-3p | 8.91 | 1.33 | 8.84 | 1.85 | −0.07 | 9.33E−01 |
| miR-500 | 8.45 | 3.41 | 8.41 | 0.93 | −0.05 | 9.58E−01 |
| miR-520g |  | 5.84 | 15.61 | 2.49 | 15.61 | 9.64E−01 |
| miR-345 | 1.25 | 0.69 | 1.24 | 0.73 | −0.01 | 9.81E−01 |
| miR-487b | 3.60 | 1.14 | 3.61 | 0.58 | 0.01 | 9.82E−01 |
| miR-27b | 2.50 | 0.67 | 2.50 | 0.67 | −0.01 | 9.83E−01 |
| miR-502 | 7.25 | 2.64 | 7.27 | 1.11 | 0.02 | 9.83E−01 |
| miR-200a | 8.54 | 2.41 | 8.55 | 1.02 | 0.01 | 9.87E−01 |
| miR-21 | −2.75 | 0.67 | −2.75 | 0.75 | 0.00 | 9.99E−01 |

Example 6 miRNA Combinations that Distinguish Plasma of Prostate Cancer Patients from Plasma of Normal Donors The un-normalized qRT-PCR data generated as described in Example 5 was used to calculate dCts for each pair of miRNAs that was quantified. The dCt values for the miRNA pairs from plasma samples of PrCa patients and normal donors were analyzed using Receiver-Operator Characteristic (ROC) analysis to determine which miRNA pairs have the potential to distinguish plasma samples from those two groups. One miRNA pair (let-7c:miR-326) (Table 21) accurately classified the 14 PrCa patient samples and 12 normal donor samples that were analyzed. Twenty additional miRNA pairs accurately classified all but one of the 26 samples (ROC AUC>0.98) (Table 21) and 221 miRNA pairs had an ROC AUC score of at least 0.93. Data from 166 independent miRNAs was included at least once in the 221 total miRNA pairs (Table 22). Several miRNAs were used in multiple biomarkers pairs, indicating that they are present at significantly different levels in the plasmas of prostate cancer patients and normal donors. The six miRNAs appearing most commonly in biomarker pairs were miR-10b, miR-192, miR-206, miR-101, miR-205, and miR-16 (Table 22). The miRNA pairs in Table 21 and the individual miRNA biomarkers in Table 22 are all possible targets for diagnosing prostate cancer using plasma.

TABLE 21 miRNA biomarker pairs that can be used to identify plasma from prostate cancer patients.

| miRNA Pair | p-value | ROC AUC |
|---|---|---|
| let7:miR-326 | 3.76E−06 | 1 |
| miR-326:miR-507 | 5.72E−07 | 0.994048 |
| miR-206:miR-491 | 5.58E−06 | 0.994048 |
| miR-339:miR-375 | 5.77E−06 | 0.994048 |
| miR-30a-3p:miR-326 | 8.26E−08 | 0.988095 |
| miR-151:miR-206 | 8.06E−07 | 0.988095 |
| miR-10b:miR-30b | 5.06E−07 | 0.988095 |
| miR-330:miR-375 | 8.51E−07 | 0.988095 |
| miR-134:miR-206 | 4.50E−06 | 0.988095 |
| miR-432*:miR-491 | 1.66E−06 | 0.988095 |
| miR-181d:miR-375 | 6.74E−06 | 0.988095 |
| miR-191:miR-200c | 2.71E−05 | 0.988095 |
| miR-23a:miR-326 | 0.000328 | 0.988095 |
| miR-181a:miR-218 | 3.87E−07 | 0.982143 |
| miR-151:miR-218 | 6.72E−07 | 0.982143 |
| miR-491:miR-512-5p | 3.08E−06 | 0.982143 |
| miR-326:miR-375 | 1.27E−06 | 0.982143 |
| miR-200c:miR-326 | 3.03E−06 | 0.982143 |
| miR-20b:miR-30b | 1.88E−05 | 0.982143 |
| miR-491:miR-516-3p | 2.50E−05 | 0.982143 |
| miR-125b:miR-146a | 0.000188 | 0.982143 |

TABLE 22 miRNA biomarkers that can be used in combination to identify plasma from prostate cancer patients.

| miRNA | Pairs |
|---|---|
| miR-10b | 65 |
| miR-192 | 62 |
| miR-206 | 61 |
| miR-101 | 58 |
| miR-205 | 52 |
| miR-16 | 50 |
| miR-151 | 44 |
| miR-137 | 43 |
| miR-215 | 43 |
| miR-181a | 42 |
| miR-218 | 42 |
| miR-126* | 41 |
| miR-125b | 39 |
| miR-326 | 39 |
| miR-100 | 38 |
| miR-31 | 36 |
| miR-197 | 35 |
| miR-222 | 34 |
| miR-191 | 32 |

TABLE 22-continued miRNA biomarkers that can be used in combination to identify plasma from prostate cancer patients.

| miRNA | Pairs |
|---|---|
| miR-200c | 32 |
| miR-186 | 31 |
| miR-145 | 30 |
| miR-155 | 30 |
| miR-29c | 30 |
| let-7c | 28 |
| miR-181c | 27 |
| miR-125a | 26 |
| miR-134 | 25 |
| miR-181d | 25 |
| let-7b | 24 |
| miR-127 | 24 |
| miR-146a | 24 |
| miR-139 | 23 |
| miR-152 | 23 |
| miR-190 | 23 |
| miR-30e-5p | 23 |
| miR-106b | 22 |
| miR-10a | 22 |
| miR-132 | 21 |
| miR-148a | 21 |
| miR-213 | 21 |
| miR-29a | 21 |
| miR-375 | 21 |
| miR-133b | 19 |
| miR-15a | 18 |
| miR-107 | 17 |
| miR-148b | 17 |
| miR-19a | 17 |
| miR-106a | 15 |
| miR-130a | 15 |
| miR-17-3p | 15 |
| miR-18a | 15 |
| miR-195 | 15 |
| miR-20b | 15 |
| miR-301 | 15 |
| miR-339 | 15 |
| miR-410 | 15 |
| miR-188 | 14 |
| miR-193a | 14 |
| let-7g | 13 |
| let-7i | 13 |
| miR-140 | 13 |
| miR-181b | 13 |
| miR-25 | 13 |
| miR-328 | 13 |
| miR-133a | 12 |
| miR-150 | 12 |
| miR-17-5p | 12 |
| miR-21 | 12 |
| miR-214 | 12 |
| miR-370 | 12 |
| miR-383 | 12 |
| miR-130b | 11 |
| miR-199a | 11 |
| miR-212 | 11 |
| miR-221 | 11 |
| miR-27b | 11 |
| miR-30e-3p | 11 |
| miR-338 | 11 |
| miR-361 | 11 |
| miR-141 | 10 |
| miR-142-5p | 10 |
| miR-30a-3p | 10 |
| miR-30a-5p | 10 |
| miR-451 | 10 |
| miR-142-3p | 9 |
| miR-146b | 9 |
| miR-15b | 9 |
| miR-18a | 9 |
| miR-210 | 9 |
| miR-296 | 9 |
| miR-323 | 9 |
| miR-362 | 9 |
| let-7a | 8 |
| miR-196b | 8 |
| miR-223 | 8 |
| miR-29b | 8 |
| miR-324-5p | 8 |
| miR-376a | 8 |
| miR-379 | 8 |
| miR-491 | 8 |
| let-7d | 7 |
| miR-126 | 7 |
| miR-182 | 7 |
| miR-185 | 7 |
| miR-204 | 7 |
| miR-23a | 7 |
| miR-27a | 7 |
| miR-324-3p | 7 |
| miR-342 | 7 |
| miR-34c | 7 |
| miR-382 | 7 |
| miR-425 | 7 |
| miR-432* | 7 |
| miR-103 | 6 |
| miR-193b | 6 |
| miR-196a | 6 |
| miR-199a* | 6 |
| miR-199b | 6 |
| miR-28 | 6 |
| miR-30d | 6 |
| miR-330 | 6 |
| miR-423 | 6 |
| miR-433 | 6 |
| miR-485-5p | 6 |
| miR-20a | 5 |
| miR-23b | 5 |
| miR-26a | 5 |
| miR-30b | 5 |
| miR-30c | 5 |
| miR-320 | 5 |
| miR-345 | 5 |
| miR-422b | 5 |
| miR-335 | 4 |
| miR-365 | 4 |
| miR-486 | 4 |
| miR-24 | 3 |
| miR-26b | 3 |
| miR-331 | 3 |
| miR-340 | 3 |
| miR-34a | 3 |
| miR-374 | 3 |
| miR-452 | 3 |
| miR-483 | 3 |
| miR-512-5p | 3 |
| let-7e | 2 |
| miR-32 | 2 |
| miR-422a | 2 |
| miR-424 | 2 |
| miR-432 | 2 |
| miR-485-3p | 2 |
| miR-487b | 2 |
| miR-496 | 2 |
| miR-505 | 2 |
| miR-507 | 2 |
| miR-202 | 1 |
| miR-369-3p | 1 |
| miR-495 | 1 |
| miR-502 | 1 |
| miR-511 | 1 |
| miR-516-3p | 1 |
| miR-517c | 1 |
| miR-92 | 1 |
| miR-93 | 1 |
| miR-99a | 1 |
| miR-99b | 1 |

Example 7

Serum Biomarkers of Prostate Cancer Aggressiveness

A key issue associated with prostate cancer patients is determining whether treatment is necessary. Many patients are diagnosed at very early stages of disease. Because most cases of prostate cancer are unlikely to progress to metastatic disease, it is often unnecessary to subject an individual, especially one of advanced age, to aggressive treatment. Distinguishing patients with relatively benign prostate cancer from patients with an aggressive form of the disease is vital to determining the appropriate level of therapeutic intervention.

Histopathological methods have been developed that are reasonably accurate in estimating the aggressiveness of a tumor. The Gleason score corresponds with tumor aggressiveness; higher Gleason scores correspond with more aggressive tumors. To determine if individual miRNAs in serum can distinguish prostate cancer patients with high Gleason scores (>6) from those with low Gleason scores (≤6) or from patients with BPH, the inventors further analyzed the qRT-PCR data from Example 1.

All miRNAs in a given sample with raw Ct values of 50 were eliminated from further analysis. Data from serum samples with fewer than 150 miRNAs that had raw Ct values <50 were also eliminated. Un-normalized qRT-PCR data were used to calculate dCts for each pair of miRNAs that were evaluated. The dCt values for miRNA pairs measured in serum samples from PrCa and BPH patients were used to identify those pairs that distinguished serum samples from PrCa patients with high Gleason scores from those with low Gleason scores and from serum samples of BPH patients. Thirty-five (35) miRNA pairs were capable of distinguishing those serum samples (Table 23; low, samples from PrCa patients with Gleason scores 56; High, samples from PrCa patients with Gleason scores >6.). These miRNA pairs are useful for predicting aggressiveness of prostate cancer using patient serum samples.

TABLE 23

Biomarker pairs that can be used to identify serum from prostate cancer patients with high Gleason scores.

| miRNA Pair | Avg Low | Avg High | Avg Norm | Avg BPH | p-value Low/High | p-value High/BPH |
|---|---|---|---|---|---|---|
| miR-27a, miR-495 | −7.484 | −5.033 | −6.558 | −6.944 | 0.0021 | 0.0054 |
| miR-27b, miR-495 | −4.594 | −2.413 | −3.374 | −3.985 | 0.0021 | 0.0019 |
| miR-152, miR-495 | −2.79 | −1.065 | −1.907 | −2.096 | 0.0035 | 0.0294 |
| miR-133b, miR-495 | −4.636 | −1.915 | −3.195 | −3.554 | 0.0039 | 0.0335 |
| miR-29a, miR-495 | −8.584 | −5.345 | −6.303 | −7.162 | 0.0057 | 0.0453 |
| miR-199b, miR-495 | 0.264 | 2.2267 | 1.1717 | 1.424 | 0.0064 | 0.1453 |
| miR-29c, miR-495 | −8.102 | −5.213 | −6.137 | −6.952 | 0.007 | 0.0454 |
| miR-146a, miR-495 | −9.466 | −7.72 | −8.814 | −9.01 | 0.009 | 0.0265 |
| miR-106b, miR-495 | −9.584 | −7.19 | −8.031 | −8.4 | 0.0111 | 0.1064 |
| miR-15a, miR-495 | −3.692 | −1.673 | −3.268 | −3.594 | 0.0122 | 0.0129 |
| miR-142-3p, miR-495 | −9.064 | −7.518 | −8.524 | −8.819 | 0.0137 | 0.0309 |
| miR-135a, miR-495 | 0.266 | 1.99 | 0.8182 | 0.964 | 0.0139 | 0.1192 |
| miR-146b, miR-495 | −7.842 | −6.41 | −7.317 | −7.494 | 0.0144 | 0.0412 |
| miR-218, miR-432 | 4.246 | 2.885 | 5.5986 | 5.209 | 0.016 | 0.0016 |
| miR-23a, miR-495 | −5.526 | −3.68 | −4.68 | −5.135 | 0.0189 | 0.0367 |
| miR-148a, miR-495 | −6.878 | −4.63 | −5.887 | −6.629 | 0.0203 | 0.0281 |
| miR-148b, miR-495 | −5.556 | −3.825 | −4.53 | −5.057 | 0.0217 | 0.0652 |
| let-7c, miR-154* | −7.45 | −5.297 | −6.99 | −6.721 | 0.0237 | 0.0623 |
| miR-194, miR-495 | −3.73 | −1.315 | −2.839 | −3.059 | 0.0266 | 0.0692 |
| miR-130b, miR-495 | −5.782 | −3.743 | −5.171 | −5.529 | 0.0291 | 0.0432 |
| miR-181c, miR-495 | −1.884 | 0.37 | −1.443 | −1.591 | 0.0292 | 0.0435 |
| miR-199a*, miR-495 | −7.494 | −6.02 | −6.963 | −6.905 | 0.036 | 01678 |
| miR-223, miR-495 | −11.46 | −9.883 | −11.79 | −11.49 | 0.0374 | 0.0356 |
| miR-221, miR-495 | −8.992 | −7.745 | −8.858 | −8.76 | 0.0382 | 0.0816 |
| miR-155, miR-495 | −3.598 | −2.018 | −3.273 | −2.99 | 0.0384 | 0.1573 |
| miR-28, miR-495 | −3.258 | −1.795 | −3.244 | −2.937 | 0.0426 | 0.092 |
| miR-187, miR-618 | 0.23 | −1.33 | 0.7333 | 0.6914 | 0.0432 | 0.0368 |
| miR-301, miR-495 | −4.46 | −2.83 | −4.244 | −4.503 | 0.0444 | 0.0994 |
| miR-218, miR-378 | 3.806 | 2.35 | 3.6157 | 3.581 | 0.0533 | 0.0837 |
| miR-142-5p, miR-495 | −5.088 | −3.045 | −4.418 | −4.732 | 0.0549 | 0.0865 |
| miR-132, miR-495 | −3.674 | −2.035 | −3.857 | −3.2 | 0.0554 | 0.1165 |
| miR-130a, miR-495 | −7.102 | −5.148 | −6.668 | −6.766 | 0.0558 | 0.0904 |
| miR-188, miR-218 | −2.944 | −1.505 | −4.453 | −3.824 | 0.057 | 0.0126 |
| miR-181d, miR-495 | −5.248 | −3.805 | −4.768 | −4.639 | 0.0606 | 0.2255 |
| miR-146a, miR-539 | −9.648 | −7.603 | −8.07 | −8.367 | 0.0752 | 0.3664 |

Example 8

Validation of Prostate Cancer Serum Biomarkers

The inventors assessed the performance of 29 miRNAs (Table 24) that were identified as prostate cancer biomarkers in Example 1 by quantifying those miRNAs in the sera of 12 PrCa patients and 12 normal donors (purchased from Proteo-Genex, Inc.) and in the sera of 8 PrCa patients, 8 BPH patients, and 8 normal donors (purchased from ProMedDx, LLC) (Table 25) using qRT-PCR. Serum RNA was purified as described in Example 1.

TABLE 24 miRNAs assayed.

| miRNA Assayed |
| --- |
| hsa-miR-125b |
| hsa-miR-99b |
| hsa-miR-10b |
| hsa-miR-205 |
| hsa-miR-206 |
| hsa-miR-29a |
| hsa-miR-29c |
| hsa-miR-122a |
| hsa-miR-16 |
| hsa-miR-138 |
| hsa-miR-34a |
| hsa-miR-200a |
| hsa-miR-200c |
| hsa-miR-20a |
| hsa-miR-195 |
| hsa-miR-15b |
| hsa-miR-22 |
| hsa-miR-17-5p |
| hsa-miR-24 |
| hsa-miR-139 |
| hsa-miR-192 |
| hsa-miR-155 |
| hsa-miR-181 |
| hsa-let-7d |
| hsa-let-7f |
| hsa-let-7g |
| hsa-miR-103 |
| hsa-miR-191 |
| hsa-miR-26a |

TABLE 25

Histopathological data and patient information.

| Patient Diagnosis | Patient Age | PSA | Gleason Score | Smoking History (Total Years) | Source |
| --- | --- | --- | --- | --- | --- |
| PrCa | 60 | 5.8 | 6 | No | 1 |
| PrCa | 57 | 2.2 | 6 | Past (10) | 1 |
| PrCa | 64 | 0.5 | 6 | Past (25) | 1 |
| PrCa | 56 | 4.9 | 6 | No | 1 |
| PrCa | 58 | 6.2 | 7 | No | 1 |
| PrCa | 51 | 7.7 | 7 | Present (1) | 1 |
| PrCa | 61 | 3.2 | 6 | Present (50) | 1 |
| PrCa | 61 | 3.6 | 6 | No | 1 |
| PrCa | 50 | 3.55 | 7 | No | 1 |
| PrCa | 57 | ND | 7 | Past (20) | 1 |
| PrCa | 55 | ND | 9 | Past (30) 0 | 1 |
| PrCa | 59 | ND | 7 | Present (40) | 1 |
| Normal | 57 | ND | ND | ND | 1 |
| Normal | 56 | ND | ND | ND | 1 |
| Normal | 56 | ND | ND | ND | 1 |
| Normal | 56 | ND | ND | ND | 1 |
| Normal | 61 | ND | ND | ND | 1 |
| Normal | 60 | ND | ND | ND | 1 |
| Normal | 60 | ND | ND | ND | 1 |
| Normal | 61 | ND | ND | ND | 1 |
| Normal | 64 | ND | ND | ND | 1 |
| Normal | 62 | ND | ND | ND | 1 |
| Normal | 50 | ND | ND | ND | 1 |
| Normal | 62 | ND | ND | ND | 1 |
| | | | | Smoking History Years Amount | |
| PrCa | 62 | 10.6 | 4(2 + 2) | No | 2 |
| PrCa | 61 | 4.39 | 5(2 + 3) | No | 2 |
| PrCa | 68 | 11.8 | N/A | No | 2 |
| PrCa | 66 | 43 | 7(4 + 3) | 40 years 1 pack/day | 2 |
| PrCa | 65 | 30 | 7(3 + 4) | No | 2 |
| PrCa | 67 | 12 | 4(2 + 2) | No | 2 |
| PrCa | 71 | 11 | 6(3 + 3) | No | 2 |
| PrCa | 61 | 52.64 | 8(4 + 4) | No | 2 |
| BPH | 66 | 4 | ND | 50 years 1 pack/day | 2 |
| BPH | 61 | 4.5 | ND | 50 years 1 pack/day | 2 |
| BPH | 61 | 5.5 | ND | 30 years 1.5 pack/day | 2 |
| BPH | 53 | 4 | ND | 25 years 1 pack/day | 2 |
| BPH | 63 | 5.1 | ND | No | 2 |
| BPH | 45 | 9.02 | ND | No | 2 |
| BPH | 49 | 7.03 | ND | 20 years 1 pack/day | 2 |
| BPH | 51 | 9.15 | ND | No | 2 |
| Normal | 51 | 0.85 | ND | No | 2 |
| Normal | 48 | 0.36 | ND | No | 2 |
| Normal | 52 | 0.55 | ND | No | 2 |
| Normal | 47 | 0.42 | ND | No | 2 |
| Normal | 50 | 0.45 | ND | No | 2 |
| Normal | 46 | 0.47 | ND | 20 years 1 pack/day | 2 |
| Normal | 51 | 0.36 | ND | No | 2 |
| Normal | 53 | 0.47 | ND | No | 2 |

ND, not determined
Source1, ProteoGenex, INc.;
Source 2, ProMedDx, LLC.

miRNA levels were determined by qRT-PCR using Taq-Man® MicroRNA Assays (Applied Biosystems; Foster City, Calif., USA) specific for each miRNA. Reverse transcription (RT) reaction components (Table 26) were assembled on ice prior to the addition of RNA template. Serum RNA (1.0 µl per reaction) was added and mixed. RT reactions were incubated in a 384-well GeneAmp® PCR System 9700 (Applied Biosystems) at 4° C. for 30 minutes, 16° C. for 30 minutes, 42° C. for 30 minutes, and 85° C. for 5 minutes. RT reactions were then frozen and stored at −20° C. All reaction components were as provided by the manufacturer (Applied Biosystems; Foster City, Calif., USA) unless otherwise specified.

TABLE 26

Reverse transcription reaction components.

| Component | µl per 10 µl rxn | Final Concentration |
| --- | --- | --- |
| Nuclease-free water | 5.1 | |
| 10X Reverse Transcription Buffer | 1.0 | 1X |
| dNTP mix (100 mM) | 0.1 | 1 mM |

TABLE 26-continued

Reverse transcription reaction components.

| Component | μl per 10 μl rxn | Final Concentration |
|---|---|---|
| 1.25X RT Primer | 2.0 | 0.25X |
| RNase Inhibitor (20 U/ul) | 0.13 | 0.26 U/μl |
| Multiscribe ™ Recombinant Moloney Murine Leukemia Virus Reverse Transcriptase (MMLV-RT) (50 U/ul) | 0.67 | 3.35 U/μl |
| Human Serum RNA | 1.0 | |

PCR components (Table 27) were assembled on ice prior to the addition of cDNA (4 μl) from the RT reaction. Reactions were incubated in an ABI PRISM™ 7900HT Fast Real-Time PCR system (Applied Biosystems) at 95° C. for 1 minute, then for 50 cycles at 95° C. for 5 seconds, then at 60° C. for 30 seconds. Data were extracted and exported with SDS V2.3 (Applied Biosystems). The data were analyzed with Microsoft Excel (Microsoft Corporation). All reaction components were as provided by the manufacturer (Applied Biosystems; Foster City, Calif., USA) unless otherwise specified.

TABLE 27

PCR components.

| Component | μl per 15 μl rxn | Final Concentration |
|---|---|---|
| Nuclease-free water | 4.1 | |
| MgCl$_2$ (50 mM) | 1.5 | 5 mM |
| 10X Platinum PCR Buffer, Minus Mg (Invitrogen Corp.; Carlsbad, CA, USA) | 1.5 | 1X |
| dNTP mix (2.5 mM each) (Ambion, Inc.; Austin, TX USA) | 1.5 | 0.25 mM each |
| 3X TaqMan Assay Buffer | 2.0 | 0.4X |
| 50X ROX Internal Marker | 0.3 | 1X |
| Platinum ® Taq DNA Polymerase (5 U/μl) (Invitrogen) | 0.1 | 0.033 U/μl |
| cDNA from RT reaction | 4.0 | |

The qRT-PCR data were initially assessed for outliers. All miRNAs in a given sample with raw Ct readings of ≥40 were eliminated from further analyses. qRT-PCR data for each miRNA in each sample were normalized by subtracting the Ct value for miR-103 from the Ct value for the miRNA in the same sample. The resulting dCt values, were used to calculate the average dCt values for each miRNA in the normal donor and PrCa patient samples. Average dCt values for PrCa patient samples were subtracted from average dCt values for normal donor samples to determine the variance in the levels of the miRNAs between the patient sets. Student's t-test was then used to determine the potential of various miRNAs to distinguish the sera of PrCa patients from sera of normal donors. Table 28 lists the difference in average Ct between normal and prostate cancer samples, as well as p-values for PrCa samples compared to normal or BPH samples, and normal samples compared to BPH samples. These miRNAs are biomarkers of prostate cancer that can be used to diagnose prostate cancer using the serum from a patient.

TABLE 28

Prostate cancer biomarkers.

| miRNA | ddCt (Norm − PrCa) | p (Norm vs PrCa) | p (BPH vs PrCa) | p (Norm vs BPH) |
|---|---|---|---|---|
| miR-16 | −1.46 | 2.27E−05 | 6.83E−03 | 6.80E−01 |
| let-7d | −1.35 | 1.55E−02 | 3.93E−01 | 2.21E−02 |
| miR-195 | −1.25 | 1.72E−04 | 1.92E−02 | 7.38E−01 |
| miR-138 | −0.79 | 2.43E−01 | 6.48E−01 | 7.02E−01 |
| mir-15b | −0.61 | 8.19E−03 | 9.52E−01 | 7.24E−02 |
| miR-20a | −0.60 | 3.26E−02 | 2.28E−01 | 6.71E−01 |
| miR-17-5p | −0.35 | 3.49E−02 | 6.80E−01 | 3.07E−01 |
| let-7g | −0.34 | 2.87E−01 | 9.83E−01 | 4.28E−01 |
| let-7f | −0.32 | 3.86E−01 | 8.31E−01 | 2.14E−01 |
| miR-24 | −0.19 | 2.11E−01 | 3.79E−02 | 8.26E−02 |
| miR-22 | −0.18 | 5.53E−01 | 4.87E−02 | 1.50E−02 |
| miR-29c | 0.13 | 7.31E−01 | 5.97E−01 | 2.88E−01 |
| miR-191 | 0.23 | 9.72E−02 | 6.04E−02 | 2.89E−02 |
| miR-29a | 0.35 | 2.84E−01 | 8.20E−01 | 2.95E−01 |
| miR-192 | 0.39 | 2.30E−01 | 2.33E−01 | 9.62E−03 |
| miR-26a | 0.51 | 6.40E−03 | 6.13E−01 | 3.00E−01 |
| miR-181 | 0.87 | 2.16E−03 | 1.49E−01 | 3.12E−01 |
| miR-155 | 0.90 | 1.25E−04 | 9.09E−01 | 9.21E−02 |
| miR-200c | 1.01 | 4.32E−05 | 8.55E−01 | 3.69E−02 |
| miR-200a | 1.16 | 6.56E−04 | 2.09E−02 | 5.72E−01 |
| miR-99b | 1.19 | 1.30E−04 | 4.98E−02 | 3.65E−01 |
| miR-139 | 1.30 | 4.66E−06 | 2.34E−04 | 3.62E−01 |
| miR-10b | 1.47 | 1.72E−03 | 3.67E−04 | 1.69E−02 |
| miR-34a | 1.85 | 5.12E−03 | 2.89E−01 | 1.93E−01 |
| miR-206 | 1.89 | 3.09E−03 | 7.95E−02 | 6.38E−01 |
| miR-125b | 2.02 | 6.00E−06 | 9.73E−04 | 9.59E−01 |
| miR-205 | 2.18 | 3.65E−02 | 1.00E+00 | 6.90E−02 |
| miR-122a | 2.34 | 1.53E−04 | 1.45E−02 | 2.70E−01 |

The inventors used the data for the same miRNA biomarkers to identify pairs of miRNAs with the capacity to distinguish sera of PrCa patients from sera of BPH patients and normal donors. Un-normalized qRT-PCR data were used to calculate dCt values for each pair of miRNAs that was evaluated. The dCt values of the various miRNA pairs in PrCa and normal serum samples were analyzed using Receiver-Operator Characteristic (ROC) analysis to identify the miRNA pairs having the ability to distinguish sera of PrCa patients from sera of BPH patients and normal donors. Data from the best biomarker pairs are presented in Table 29. Numerous miRNAs were used in multiple biomarkers pairs, indicating the strength of their variable levels in sera of prostate cancer patients and normal donors.

TABLE 29

MicroRNA biomarker pairs for classifying prostate cancer serum.

| Biomarker Pair | Classify AUC.ROC Estimate |
|---|---|
| miR-139, let-7d | 0.983928571 |
| miR-125b, miR-16 | 0.980357143 |
| miR-125b, miR-195 | 0.976785714 |
| miR-125b, let-7d | 0.973214286 |
| miR-16, miR-139 | 0.951785714 |
| miR-195, miR-139 | 0.947321429 |
| miR-17-5p, miR-139 | 0.946428571 |
| miR-125b, mir-15b | 0.941964286 |
| miR-10b, mir-15b | 0.933928571 |
| miR-125b, miR-17-5p | 0.930357143 |
| miR-10b, miR-195 | 0.923214286 |
| mir-15b, miR-139 | 0.923214286 |
| miR-10b, let-7d | 0.922321429 |
| miR-125b, miR-20a | 0.921428571 |
| miR-20a, miR-139 | 0.917857143 |
| miR-125b, miR-191 | 0.916964286 |
| miR-125b, let-7g | 0.916071429 |

TABLE 29-continued

MicroRNA biomarker pairs for classifying prostate cancer serum.

| Biomarker Pair | Classify AUC.ROC Estimate |
|---|---|
| miR-16, miR-200a | 0.914285714 |
| miR-99b, miR-16 | 0.908035714 |
| miR-24, miR-139 | 0.90625 |
| miR-125b, miR-103 | 0.905357143 |
| miR-16, miR-155 | 0.905357143 |
| miR-125b, miR-24 | 0.903571429 |
| miR-10b, let-7f | 0.903571429 |
| miR-139, let-7g | 0.903571429 |
| miR-16, miR-200c | 0.898214286 |
| miR-125b, miR-22 | 0.896428571 |
| miR-122a, miR-16 | 0.896428571 |
| miR-139, miR-103 | 0.896428571 |
| miR-10b, miR-16 | 0.892857143 |
| mir-15b, miR-26a | 0.891964286 |
| miR-125b, miR-192 | 0.889285714 |
| miR-200a, miR-195 | 0.884821429 |
| miR-200a, let-7d | 0.882142857 |
| miR-99b, miR-195 | 0.880357143 |
| miR-122a, miR-195 | 0.880357143 |
| let-7d, miR-26a | 0.878571429 |
| miR-10b, miR-20a | 0.875 |
| miR-122a, let7d | 0.875 |
| miR-16, miR-26a | 0.875 |
| miR-200c, let-7d | 0.875 |
| miR-125b, miR-26a | 0.873214286 |
| miR-10b, let-7g | 0.873214286 |
| miR-206, miR-16 | 0.871428571 |
| miR-125b, let-7f | 0.869642857 |
| miR-195, miR-26a | 0.869642857 |
| miR-155, let-7d | 0.86875 |
| mir-15b, miR-155 | 0.865178571 |
| miR-122a, miR-192 | 0.864285714 |
| miR-125b, miR-155 | 0.863392857 |
| miR-206, miR-22 | 0.8625 |
| miR-125b, miR-29a | 0.861607143 |
| miR-99b, let7d | 0.860714286 |
| miR-181, let7d | 0.860714286 |
| miR-16, miR-181 | 0.858928571 |
| miR-10b, miR-17-5p | 0.858035714 |
| miR-125b, miR-29c | 0.85625 |
| miR-195, miR-17-5p | 0.85625 |
| miR-155, miR-191 | 0.85625 |
| miR-200a, miR-22 | 0.853571429 |
| miR-122a, miR-22 | 0.852678571 |
| miR-16, miR-34a | 0.85 |
| miR-16, miR-103 | 0.85 |
| miR-139, miR-191 | 0.848214286 |
| miR-34a, miR-195 | 0.846428571 |
| miR-195, miR-155 | 0.846428571 |
| miR-206, let-7d | 0.844642857 |
| miR-16, miR-17-5p | 0.844642857 |
| miR-99b, miR-24 | 0.842857143 |
| miR-99b, miR-191 | 0.842857143 |
| miR-200c, mir-15b | 0.840178571 |
| miR-200a, mir-15b | 0.839285714 |
| miR-195, miR-181 | 0.839285714 |
| miR-99b, miR-20a | 0.8375 |
| miR-16, miR-192 | 0.8375 |
| miR-200a, miR-20a | 0.8375 |
| miR-200c, miR-195 | 0.8375 |
| miR-206, miR-195 | 0.835714286 |
| miR-139, let-7f | 0.835714286 |
| miR-20a, miR-26a | 0.833035714 |
| miR-206, miR-29a | 0.832142857 |
| miR-99b, mir-15b | 0.830357143 |
| miR-122a, mir-15b | 0.830357143 |
| miR-122a, miR-17-5p | 0.830357143 |
| miR-16, miR-191 | 0.830357143 |
| miR-200a, miR-17-5p | 0.830357143 |
| miR-200a, miR-103 | 0.830357143 |
| miR-139, miR-26a | 0.829464286 |
| miR-200a, miR-24 | 0.828571429 |
| miR-29a, miR-16 | 0.828571429 |
| miR-20a, miR-155 | 0.828571429 |
| miR-206, mir-15b | 0.827678571 |
| miR-29c, miR-122a | 0.826785714 |
| miR-122a, miR-20a | 0.826785714 |
| miR-206, miR-29c | 0.825892857 |
| miR-22, miR-139 | 0.825892857 |
| miR-10b, miR-24 | 0.825 |
| miR-29c, miR-200a | 0.822321429 |
| miR-206, miR-20a | 0.821428571 |
| miR-206, miR-24 | 0.821428571 |

Example 9

Validation of Prostate Cancer Serum Biomarker Pair

To further assess the specificity and sensitivity of the combination of miR-125b and miR-24 in diagnosing prostate cancer patients using serum samples, miR-125b and miR-24 were quantified in the sera of 50 normal male donors, 40 patients with benign prostatic hyperplasia (BPH), 16 patients with prostate cancer who were undergoing hormone treatment and/or chemotherapy, and 33 untreated prostate cancer patients.

For serum preparation, 10 ml of whole blood were collected from patients and normal donors using a BD Vacutainer® glass serum tube (Becton, Dickinson and Company; Franklin Lakes, N.J., USA; cat. no. 366441). Following blood collection, tubes were incubated at room temperature for up to 2.5 hours to allow the blood to clot, then centrifuged for 10 minutes at 2,000×g. Serum was transferred to a new tube using a serological pipette and frozen at −80° C. until it was processed for RNA isolation.

Serum RNA was purified using the organic extraction of the mirVana PARIS™ Kit (Part No. AM1556; Applied Biosystems/Ambion; Austin, Tex., USA), with the following modifications. Following the addition of acid phenol:chloroform and vortexing, samples were incubated on ice for 5 min then centrifuged at 13,000×g for 10 min at 4° C. The aqueous layer was removed, extracted with chloroform, and centrifuged again. The aqueous layer was removed from the second extraction, and 3M NaOAc (1/10 volume), glycogen (5 mg/ml), and 100% ethanol (1.5 volume) were added to the samples. Lysate/ethanol mixtures were passed through a mirVana PARIS filter cartridge, and filters were washed once with 650 µl of Wash 1 buffer and twice with 650 µl of Wash 2/3 buffer. RNA was eluted with two aliquots of nuclease free water (50 µl) and stored at −80° C.

Levels of miR-125b and miR-24 were determined by qRT-PCR using TaqMan® MicroRNA Assays (Applied Biosystems; Foster City, Calif., USA) specific for each miRNA. Reverse transcription (RT) reaction components were assembled on ice prior to the addition of RNA template (Table 30). Serum RNA (1 µl per reaction) was added and mixed. RT reactions were incubated in a 384-well GeneAmp® PCR System 9700 (Applied Biosystems) at 4° C. for 30 minutes, then at 16° C. for 30 minutes, then at 42° C. for 30 minutes, then at 85° C. for 5 minutes. RT reactions were then frozen at −20° C. All reaction components were as provided by the manufacturer (Applied Biosystems; Foster City, Calif., USA) unless otherwise specified. Thus, the assays are useful to monitor patients' response to treatment.

TABLE 30

Reverse transcription reaction components.

| Component | μl per 10 μl rxn | Final Concentration |
|---|---|---|
| Nuclease-free water | 5.1 | |
| 10X Reverse Transcription Buffer | 1.0 | 1X |
| dNTP mix (100 mM) | 0.1 | 1 mM |
| 1.25X RT Primer | 2.0 | 0.25X |
| RNase Inhibitor (20 U/μl) | 0.13 | 0.26 U/μl |
| Multiscribe ™ Recombinant Moloney Murine Leukemia Virus Reverse Transcriptase (MMLV-RT) (50 U/μl) | 0.67 | 3.35 U/μl |
| Human Serum RNA | 1.0 | |

PCR components (Table 31) were assembled on ice prior to the addition of cDNA (4 μl) from the RT reaction. Reactions were incubated in an ABI PRISM™ 7900HT Fast Real-Time PCR system (Applied Biosystems) at 95 C for 1 minute, then for 50 cycles at 95° C. for 5 seconds and 60° C. for 30 seconds. Results were analyzed with SDS V2.3 software (Applied Biosystems). All reaction components were as provided by the manufacturer (Applied Biosystems; Foster City, Calif., USA) unless otherwise specified.

TABLE 31

PCR components.

| Component | μl per 15 μl rxn | Final Concentration |
|---|---|---|
| Nuclease-free water | 5.8 | |
| MgCl₂ (50 mM) | 1.5 | 5 mM |
| 10X Platinum PCR Buffer, Minus Mg (Invitrogen Corp.; Carlsbad, CA, USA) | 1.5 | 1X |
| dNTP mix (2.5 mM each) (Ambion, Inc.; Austin, TX USA) | 1.5 | 0.25 mM each |
| 20X TaqMan MicroRNA Assay | 0.3 | 0.4X |
| 50X ROX Reference Dye | 0.3 | 1X |
| Platinum ® Taq DNA Polymerase (5 U/μl) (Invitrogen) | 0.1 | 0.033 U/μl |
| cDNA from RT reaction | 4.0 | |

The Ct values for miR-24 in each sample were subtracted from those for miR-125b in the corresponding sample to produce a dCt value for each sample (Table 32). Smaller dCt values correspond to serum samples with relatively higher miR-125b levels and/or lower miR-24 levels.

A diagnostic threshold of 6.00 dCt or 7.00 dCt was used to classify serum samples from donors. Using a threshold of 6.00 dCt to identify serum from prostate cancer patients (i.e., a serum sample with dCt<6.00 is indicative of prostate cancer), the miR-125b/miR-24 dCt value correctly identified 25 out of 33 untreated prostate cancer patients (76% sensitivity) and mis-identified 2 out of 50 normal male donors (96% specificity) and 0 out of 40 benign prostatic hyperplasia patients (100% specificity). Three (3) of 16 prostate cancer patients undergoing treatment were classified as positive using the 6 dCt cutoff.

Using a threshold of 7.00 dCt to identify serum from prostate cancer patients (i.e., a serum sample with dCt <7.00 is indicative of prostate cancer), the miR-125b/miR-24 dCt value correctly identified 32 out of 33 prostate cancer patients (97% sensitivity) and mis-identified 5 out of 50 normal male donors (90% specificity) and 4 out of 40 benign prostatic hyperplasia patients (90% specificity). Nine (9) of the 16 prostate cancer patients undergoing treatment had dCt values ranging from 6.00 to 6.99 and three other treated patients had dCt values ranging from 7.00 to 7.10, indicating that treatment was changing the serum levels of one or both miRNA biomarkers.

Table 32 shows miR-125b/miR-24 dCt following qRT-PCR quantification of miR-125b and miR-24 in serum samples from normal male donors (Normal), benign prostatic hyperplasia patients (BPH), treated prostate cancer patients (Tr-PrCa), and untreated prostate cancer patients (PrCa). Values marked with * denote serum samples with dCt values less than 6.00. Values marked with # denote serum samples with dCt values ranging from 6.00 to 6.99. Unmarked values denote samples with dCt values ≥7.00.

TABLE 32 miR-125b/miR-24 dCt

| Serum Sample | miR-125b-miR-24 | Serum Sample | miR-125b-miR-24 | Serum Sample | miR-125b-miR-24 |
|---|---|---|---|---|---|
| Normal | 8.98 | BPH | 7.30 | Tr-PrCa | 6.59# |
| Normal | 10.01 | BPH | 7.50 | Tr-PrCa | 5.27* |
| Normal | 9.10 | BPH | 7.61 | Tr-PrCa | 7.56 |
| Normal | 9.15 | BPH | 7.89 | Tr-PrCa | 6.94# |
| Normal | 9.81 | BPH | 8.52 | Tr-PrCa | 5.47* |
| Normal | 8.92 | BPH | 10.33 | Tr-PrCa | 6.49# |
| Normal | 5.21* | BPH | 8.86 | Tr-PrCa | 7.08 |
| Normal | 8.41 | BPH | 6.72# | Tr-PrCa | 6.34# |
| Normal | 7.82 | BPH | 7.57 | Tr-PrCa | 7.09 |
| Normal | 5.63* | BPH | 8.80 | Tr-PrCa | 4.94* |
| Normal | 7.08 | BPH | 7.53 | Tr-PrCa | 6.30# |
| Normal | 7.58 | BPH | 8.14 | Tr-PrCa | 7.00 |
| Normal | 9.58 | BPH | 10.43 | Tr-PrCa | 6.36# |
| Normal | 8.94 | BPH | 15.24 | Tr-PrCa | 6.44# |
| Normal | 8.50 | BPH | 7.02 | Tr-PrCa | 6.34# |
| Normal | 9.87 | BPH | 7.52 | Tr-PrCa | 6.19# |
| Normal | 9.28 | BPH | 7.42 | | |
| Normal | 9.39 | BPH | 8.88 | PrCa | 5.63* |
| Normal | 9.31 | BPH | 7.64 | PrCa | 4.10* |
| Normal | 9.15 | BPH | 7.02 | PrCa | 5.68* |
| Normal | 6.38# | BPH | 6.36# | PrCa | 5.03* |
| Normal | 7.11 | BPH | 7.63 | PrCa | 6.79# |
| Normal | 9.14 | BPH | 8.06 | PrCa | 4.60* |
| Normal | 8.02 | BPH | 7.52 | PrCa | 3.34* |
| Normal | 7.83 | BPH | 7.90 | PrCa | 4.27* |
| Normal | 6.77# | BPH | 7.26 | PrCa | 4.41* |
| Normal | 8.42 | BPH | 8.00 | PrCa | 4.63* |
| Normal | 9.15 | BPH | 9.30 | PrCa | 3.46* |
| Normal | 9.46 | BPH | 8.01 | PrCa | 6.48# |
| Normal | 8.54 | BPH | 7.16 | PrCa | 5.68* |
| Normal | 8.36 | BPH | 8.71 | PrCa | 6.61# |
| Normal | 8.28 | BPH | 8.86 | PrCa | 3.32* |
| Normal | 8.39 | BPH | 6.61# | PrCa | 4.54* |
| Normal | 7.72 | BPH | 9.33 | PrCa | 6.02# |
| Normal | 7.86 | BPH | 7.76 | PrCa | 4.64* |
| Normal | 7.19 | BPH | 8.81 | PrCa | 5.44* |
| Normal | 10.26 | BPH | 7.17 | PrCa | 3.39* |
| Normal | 7.86 | BPH | 7.98 | PrCa | 4.10* |
| Normal | 8.26 | BPH | 8.81 | PrCa | 7.10 |
| Normal | 7.45 | BPH | 6.20# | PrCa | 6.66# |
| Normal | 6.83# | | | PrCa | 6.70# |
| Normal | 8.09 | | | PrCa | 5.39* |
| Normal | 8.70 | | | PrCa | 5.03* |
| Normal | 8.71 | | | PrCa | 5.55* |
| Normal | 8.65 | | | PrCa | 4.10* |
| Normal | 8.98 | | | PrCa | 5.58* |
| Normal | 8.64 | | | PrCa | 6.58# |
| Normal | 9.10 | | | PrCa | 4.06* |
| Normal | 8.90 | | | PrCa | 4.14* |
| Normal | 8.16 | | | PrCa | 4.38* |

All references cited herein are incorporated herein by reference in their entirety. To the extent publications and patents or patent applications incorporated by reference contradict the invention contained in the specification, the specification will supersede any contradictory material.

What is claimed is:

1. A method for characterizing whether a prostate disease in a patient is prostate cancer or benign prostatic hyperplasia (BPH), comprising the steps of:
   a. reverse transcribing a first miRNA and in a serum sample;
   b. amplifying the first miRNA and the second miRNA;
   c. measuring the level of the first miRNA and the second miRNA, wherein the first miRNA is miR-125b;
   d. detecting whether the level of miR-125b is elevated; and
   e. further detecting whether the level of the second miRNA is elevated or reduced,
   thereby characterizing the prostate disease in the patient as prostate cancer or BPH.

2. The method of claim 1, wherein the second miRNA is miR-24, miR-1, miR-15a, miR-15b, miR-16, miR-17-5p, miR-18a, miR-18a, miR-19a, miR-20a, miR-20b, miR-22, miR-23a, miR-23b, miR-25, miR-26a, miR-26b, miR-28, miR-29a, miR-29c, miR-30a-5p, miR-30b, miR-30c, miR-30d, miR-30e-3p, miR-32, miR-92, miR-93, miR-98, miR-103, miR-106a, miR-107, miR-125a, miR-126, miR-130a, miR-130b, miR-132, miR-140, miR-142-5p, miR-143, miR-145, miR-148a, miR-155, miR-181c, miR-185, miR-191, miR-192, miR-193a, miR-194, miR-195, miR-196b, miR-197, miR-199a, miR-214, miR-222, miR-223, miR-224, miR-301 miR-328, miR-331, miR-335, miR-339, miR-340, miR-342, miR-345, miR-361, miR-365, miR-374, miR-422b, miR-423, miR-425, miR-565, miR-576, miR-584, miR-638, miR-660 let-7a let-7d, let-7f, or let-7g.

3. The method of claim 1, wherein the stage of the prostate cancer is characterized based on the level of the first miRNA and the second miRNA.

4. The method of claim 1, wherein the amplification is by quantitative reverse transcriptase polymerase chain reaction.

5. The method of claim 1, wherein the first miRNA is expressed at elevated levels in patients with prostate cancer, and the second miRNA is expressed at reduced levels in patients with prostate cancer.

6. The method of claim 1, wherein the first and the second miRNAs are expressed at elevated levels in patients with prostate cancer.

7. The method of claim 1, wherein the progression of prostate cancer is characterized based on the level of the first miRNA and the second miRNA.

8. The method of claim 1, wherein the aggressiveness of the prostate cancer is evaluated based on the level of the first miRNA and the second miRNA.

9. The method of claim 1, wherein the second miRNA is miR-24.

* * * * *

UNITED STATES PATENT AND TRADEMARK OFFICE
CERTIFICATE OF CORRECTION

PATENT NO. : 8,597,892 B2  
APPLICATION NO. : 12/785216  
DATED : December 3, 2013  
INVENTOR(S) : Jeffrey Shelton et al.

Page 1 of 1

It is certified that error appears in the above-identified patent and that said Letters Patent is hereby corrected as shown below:

In the Claims

Claim 1, col. 187, lines 5-6,
"a. reverse transcribing a first miRNA and in a serum sample;" should read
--a. reverse transcribing a first miRNA and a second miRNA in a serum sample;--.

Claim 2, col. 188, line 4,
"miR-660let-7a let-7d," should read --miR-660, let-7a, let-7d,--.

Signed and Sealed this  
Twenty-ninth Day of April, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,597,892 B2
APPLICATION NO. : 12/785216
DATED : December 3, 2013
INVENTOR(S) : Shelton et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 486 days.

Signed and Sealed this
Thirty-first Day of March, 2015

Michelle K. Lee
*Director of the United States Patent and Trademark Office*

SEQUENCE LISTING

<160> NUMBER OF SEQ ID NOS: 340

<210> SEQ ID NO 1
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugggaugagg uaguagguug uauaguuuua ggucacacc caccacuggg agauaacuau      60
acaaucuacu gucuuccua                                                 80

<210> SEQ ID NO 2
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agguugaggu aguagguugu auaguuuaga auuacaucaa gggagauaac uguacagccu     60
ccuagcuuuc cu                                                        72

<210> SEQ ID NO 3
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggugaggua guagguugua uaguuugggg cucugcccug cuaugggaua acauacaau      60 cuacugucuu uccu                                                      74

<210> SEQ ID NO 4
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cggggugagg uaguagguug uguggguuca gggcagugau guugcccuc ggaagauaac      60 uauacaaccu acugccuucc cug                                            83

<210> SEQ ID NO 5
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gcauccgggu ugagguagua gguuguaugg uuuagaguua cacccuggga guuaacugua     60
caaccuucua gcuuuccuug gagc                                           84

```
<210> SEQ ID NO 6
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ccuaggaaga gguaguaggu ugcauaguuu uagggcaggg auuuugccca caaggaggua      60
acuauacgac cugcugccuu ucuuagg                                          87

<210> SEQ ID NO 7
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cccgggcuga gguaggaggu uguauaguug aggaggacac ccaaggagau cacuauacgg      60
ccuccuagcu uuccccagg                                                   79

<210> SEQ ID NO 8
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ucagagugag guaguagauu guauaguugu gggguaguga uuuuacccug uucaggagau      60
aacuauacaa ucuauugccu ucccuga                                          87

<210> SEQ ID NO 9
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugugggauga gguaguagau uguauaguuu uagggucaua ccccaucuug gagauaacua      60
uacagucuac ugucuuuccc acg                                              83

<210> SEQ ID NO 10
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
aggcugaggu aguaguuugu acaguuugag ggucuaugau accacccggu acaggagaua      60
acuguacagg ccacugccuu gcca                                             84

<210> SEQ ID NO 11
<211> LENGTH: 84
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 11
cuggcugagg uaguaguuug ugcuguuggu cgguuguga cauugcccgc uguggagaua    60
acugcgcaag cuacugccuu gcua                                          84

<210> SEQ ID NO 12
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ugggaaacau acuucuuuau augcccauau ggaccugcua agcuauggaa uguaaagaag    60
uauguaucuc a                                                        71

<210> SEQ ID NO 13
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
accuacucag aguacauacu ucuuuaugua cccauaugaa cauacaaugc uauggaaugu    60
aaagaaguau guauuuuugg uaggc                                         85

<210> SEQ ID NO 14
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ccuguugcca caaacccgua gauccgaacu ugugguauua guccgcacaa gcuuguaucu    60
auagguaugu gucuguuagg                                               80

<210> SEQ ID NO 15
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ugcccuggcu caguuaucac agugcugaug cugucuauuc uaaagguaca guacugugau    60
aacugaagga uggca                                                    75

<210> SEQ ID NO 16
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16

```
acuguccuuu uucgguuauc augguaccga ugcuguauau cugaaaggua caguacugug    60
auaacugaag aaugguggu                                                 79

<210> SEQ ID NO 17
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uacugcccuc ggcuucuuua cagugcugcc uuguugcaua uggaucaagc agcauuguac    60
agggcuauga aggcauug                                                  78

<210> SEQ ID NO 18
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uugugcuuuc agcuucuuua cagugcugcc uuguagcauu caggucaagc agcauuguac    60
agggcuauga aagaacca                                                  78

<210> SEQ ID NO 19
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ugugcaucgu ggucaaaugc ucagacuccu gggugggcug cucaugcacc acggauguuu    60
gagcaugugc uacggugucu a                                              81

<210> SEQ ID NO 20
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ugugcaucgu ggucaaaugc ucagacuccu gggugggcug cuuaugcacc acggauguuu    60
gagcaugugc uauggugucu a                                              81

<210> SEQ ID NO 21
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ccuuggccau guaaaagugc uuacagugca gguagcuuuu ugagaucuac ugcaauguaa    60
gcacuucuua cauuaccaug g                                              81
```

```
<210> SEQ ID NO 22
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ccugccgggg cuaaagugcu gacagugcag auagugguuc ucuccgugcu accgcacugu      60 gggacuugc ugcuccagca gg                                                82

<210> SEQ ID NO 23
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
cucucugcuu ucagcuucuu uacaguguug ccuuguggca uggaguucaa gcagcauugu      60
acagggcuau caaagcacag a                                                81

<210> SEQ ID NO 24
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 24
gaucugucug ucuucuguau uacccuguua gauccgaauu uguguaagga auuuugugggu     60 cacaaauucg uaucuagggg aauauguagu ugacauaaac acuccgcucu                110

<210> SEQ ID NO 25
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 25
ccagagguug uaacguuguc uauauauacc cuguagaacc gaauuugugu gguauccgua      60
uagucacaga uucgauucua ggggaauaua uggucgaugc aaaaacuuca               110

<210> SEQ ID NO 26
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ccuuagcaga gcugguggagu gugacaaugg uguuugaugc uaaacuauca aacgccauua    60
ucacacuaaa uagcuacugc uaggc                                           85

<210> SEQ ID NO 27
<211> LENGTH: 85
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 27
aggccucucu cuccguguuc acagcggacc uugauuuaaa uguccauaca auuaaggcac    60
gcggugaaug ccaagaaugg ggcug                                        85

<210> SEQ ID NO 28
<211> LENGTH: 109
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 28
aucaagauua gaggcucugc ucccguguu cacagcggac cuugauuuaa ugucauacaa    60
uuaaggcacg cggugaaugc caagagcgga gccuacggcu gcacuugaa              109

<210> SEQ ID NO 29
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ugagggcccc ucugcguguu cacagcggac cuugauuuaa ugucuauaca auuaaggcac    60
gcggugaaug ccaagagagg cgccucc                                      87

<210> SEQ ID NO 30
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugccagucuc uagguccug agacccuuua accgugagg cauccaggg ucacagguga    60 gguucuuggg agccuggcgu cuggcc                                      86

<210> SEQ ID NO 31
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugcgcuccuc ucagucccug agacccuaac uugugauguu uaccguuuaa auccacgggu    60
uaggcucuug ggagcugcga gucgugcu                                    88

<210> SEQ ID NO 32
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32

```
accagacuuu uccuaguccc ugagacccua acuugugagg uauuuuagua acaucacaag    60
ucaggcucuu gggaccuagg cggagggga                                      89

<210> SEQ ID NO 33
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cgcuggcgac gggacauuau uacuuuuggu acgcgcugug acacuucaaa cucguaccgu    60
gaguaauaau gcgccgucca cggca                                          85

<210> SEQ ID NO 34
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ugugaucacu gucuccagcc ugcugaagcu cagagggcuc ugauucagaa agaucaucgg    60
auccgucuga gcuuggcugg ucggaagucu caucauc                             97

<210> SEQ ID NO 35
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ugagcuguug gauucggggc cguagcacug ucugagaggu uuacauuucu cacagugaac    60
cggucucuuu uucagcugcu uc                                             82

<210> SEQ ID NO 36
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ugugcagugg gaagggggc cgauacacug uacgagagug aguagcaggu cucacaguga    60 accgucucu uucccuacug uguc                                            84

<210> SEQ ID NO 37
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ggaucuuuuu gcggucuggg cuugcuguuc cucucaacag uagucaggaa gcccuuaccc    60
caaaaaguau cu                                                        72
```

```
<210> SEQ ID NO 38
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ugcccuucgc gaaucuuuuu gcggucuggg cuugcuguac auaacucaau agccggaagc    60 ccuuaccccca aaaagcauuu gcggagggcg                                   90

<210> SEQ ID NO 39
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugcugcuggc cagagcucuu uucacauugu gcuacugucu gcaccuguca cuagcagugc    60
aauguuaaaa gggcauuggc cguguagug                                     89

<210> SEQ ID NO 40
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ggccugcccg acacucuuuc ccuguugcac uacuauaggc cgcugggaag cagugcaaug    60
augaaagggc aucggucagg uc                                            82

<210> SEQ ID NO 41
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 41
ccgcccccgc gucuccaggg caaccguggc uuucgauugu uacuguggga acuggaggua    60
acagucuaca gccauggucg ccccgcagca cgcccacgcg c                      101

<210> SEQ ID NO 42
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
acaaugcuuu gcuagagcug guaaaaugga accaaaucgc cucuucaaug gauuuggucc    60 ccuucaaccca gcuguagcua ugcauuga                                     88

<210> SEQ ID NO 43
<211> LENGTH: 102
<212> TYPE: RNA
<213> ORGANISM: Artificial Sequence
<220> FEATURE:
```

```
<223> OTHER INFORMATION: Description of Artificial Sequence: Synthetic
      polynucleotide

<400> SEQUENCE: 43
gggagccaaa ugcuuugcua gagcugguaa aauggaacca aaucgacugu ccaauggauu    60 uggucccuu caaccagcug uagcugugca uugauggcgc cg                      102

<210> SEQ ID NO 44
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 44
ccucagaaga aagaugcccc cugcucuggc uggucaaacg gaaccaaguc cgucuuccug    60
agagguuugg uccccuucaa ccagcuacag cagggcuggc aaugcccagu ccuuggaga   119

<210> SEQ ID NO 45
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cagggugugu gacugguuga ccagaggggc augcacugug uucacccugu gggccaccua    60
gucaccaacc cuc                                                      73

<210> SEQ ID NO 46
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aggccucgcu guucucuaug gcuuuuauu ccuaugugau ucuacugcuc acucauauag     60
ggauuggagc cguggcgcac ggcggggaca                                    90

<210> SEQ ID NO 47
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 47
agauaaauuc acucuagugc uuuauggcuu uuuauuccua ugugauagua auaaagucuc    60
auguagggau ggaagccaug aaauacauug ugaaaaauca                        100

<210> SEQ ID NO 48
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
```

```
cacucugcug uggccuaugg cuuuucauuc cuaugugauu gcugucccaa acucauguag    60
ggcuaaaagc caugggcuac agugaggggc gagcucc                            97

<210> SEQ ID NO 49
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ugagcccucg gaggacucca uuuguuuga ugauggauuc uuaugcucca ucaucgucuc     60
aaaugagucu ucagaggguu cu                                            82

<210> SEQ ID NO 50
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 50
gguccucuga cucucuucgg ugacgggugu ucuuggugg auaauacgga uuacguuguu    60
auugcuuaag aauacgcgua gucgaggaga guaccagcgg ca                     102

<210> SEQ ID NO 51
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cccuggcaug gugguggg gcagcuggug uugugaauca ggccguugcc aaucagagaa     60
cggcuacuuc acaacaccag ggccacacca cacuacagg                          99

<210> SEQ ID NO 52
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cguugcugca gcugguguug ugaaucaggc cgacgagcag cgcauccucu uacccggcua   60
uuucacgaca ccagghuugc auca                                          84

<210> SEQ ID NO 53
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
guguauucua cagugcacgu gucuccagug uggcucggag gcuggagacg cggcccuguu   60
ggaguaac                                                            68
```

```
<210> SEQ ID NO 54
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 54
ugugucucuc ucuguguccu gccaguggun uuacccuaug guagguuacg ucaugcuguu     60
cuaccacagg guagaaccac ggacaggaua ccggggcacc                         100

<210> SEQ ID NO 55
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
cggccggccc uggguccauc uuccaguaca guguuggaug gucuaauugu gaagcuccua     60
acacugucug guaaagaugg cucccggguy gguuc                               95

<210> SEQ ID NO 56
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gacagugcag ucacccauaa aguagaaagc acuacuaaca gcacuggagg guguagvguu     60
uccuacuuua uggaugagug uacugug                                        87

<210> SEQ ID NO 57
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 57
gcgcagcgcc cugucuccca gccugaggug cagugcugca ucucuggvca guugggaguc     60
ugagaugaag cacuguagcu caggaagaga gaaguuguuc ugcagc                  106

<210> SEQ ID NO 58
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
caccuugucc ucacggucca guuucccag gaaucccuua gaugcuaaga uggggauucc       60
uggaaauacu guucuugagg ucaugguu                                       88

<210> SEQ ID NO 59
<211> LENGTH: 99
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 59
ccgaugugua uccucagcuu ugagaacuga auuccauggg uugugucagu gucagaccuc      60
ugaaauucag uucuucagcu gggauaucuc ugucaucgu                            99

<210> SEQ ID NO 60
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ccuggcacug agaacugaau uccauaggcu gugagcucua gcaaugcccu guggacucag      60
uucuggugcc cgg                                                        73

<210> SEQ ID NO 61
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aaucuaaaga caacauuucu gcacacacac cagacuaugg aagccagugu guggaaaugc      60
uucugcuaga uu                                                         72

<210> SEQ ID NO 62
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uauaaaucua guggaaacau uucugcacaa acuagauucu ggacaccagu gugcggaaau      60
gcuucugcua cauuuuuagg                                                 80

<210> SEQ ID NO 63
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gaggcaaagu ucugagacac uccgacucug aguaugauag aagucagugc acuacagaac      60
uuugucuc                                                              68

<210> SEQ ID NO 64
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64

```
caagcacgau uagcauuuga ggugaaguuc uguuauacac ucaggcugug gcucucugaa    60
agucagugca ucacagaacu uugucucgaa agcuuucua                          99

<210> SEQ ID NO 65
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
gccggcgccc gagcucuggc uccgugucuu cacucccgug cuugccgag gagggaggga    60 gggacggggg cugugcuggg gcagcugga                                     89

<210> SEQ ID NO 66
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cuccccaugg cccugucucc caacccuugu accagugcug ggcucagacc cugguacagg    60 ccuggggac agggaccugg ggac                                           84

<210> SEQ ID NO 67
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uuuccugccc ucgaggagcu cacagucuag uaugcucau ccccuacuag acugaagcuc    60
cuugaggaca gggaugguca uacucaccuc                                    90

<210> SEQ ID NO 68
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uguccccccc ggcccagguu cugugauaca cuccgacucg ggcucuggag cagucagugc    60
augacagaac uugggcccgg aaggacc                                       87

<210> SEQ ID NO 69
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cucacagcug ccagugucau uuugugauc ugcagcuagu auucucacuc caguugcaua    60
gucacaaaag ugaucauugg caggguggc                                     90
```

```
<210> SEQ ID NO 70
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
agcgguggcc agugucauuu uugugauguu gcagcuagua auaugagccc aguugcauag    60
ucacaaaagu gaucauugga aacugug                                       87

<210> SEQ ID NO 71
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gugguacuug aagauagguu auccguguug ccuucgcuuu auuugugacg aaucauacac    60
gguugaccua uuuuucagua ccaa                                          84

<210> SEQ ID NO 72
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
cuguuaaugc uaaucgugau agggguuuuu gccuccaacu gacuccuaca uauuagcauu    60
aacag                                                               65

<210> SEQ ID NO 73
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73 ccuuggaagua aaguagcagc acauaauggu uugguggauuu ugaaaaggug caggccauau   60
ugugcugccu caaaaauaca agg                                           83

<210> SEQ ID NO 74
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uugaggccuu aaaguacugu agcagcacau cauggguuuac augcuacagu caagaugcga    60
aucauuauuu gcugcucuag aaauuuaagg aaauucau                           98

<210> SEQ ID NO 75
<211> LENGTH: 89
<212> TYPE: RNA
<213> ORGANISM: Artificial Sequence
<220> FEATURE:
```

<223> OTHER INFORMATION: Description of Artificial Sequence: Synthetic
    oligonucleotide

<400> SEQUENCE: 75
gucagcagug ccuuagcagc acguaaauau uggcguuaag auucuaaaau uaucuccagu    60
auuaacugug cugcugaagu aagguugac                                     89

<210> SEQ ID NO 76
<211> LENGTH: 81
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 76
guuccacucu agcagcacgu aaauauuggc guagugaaau auauauuaaa caccaauauu    60
acugugcugc uuuaguguga c                                             81

<210> SEQ ID NO 77
<211> LENGTH: 84
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 77
gucagaauaa ugucaaagug cuuacagugc agguagugau augugcaucu acugcaguga    60
aggcacuugu agcauuaugg ugac                                          84

<210> SEQ ID NO 78
<211> LENGTH: 110
<212> TYPE: RNA
<213> ORGANISM: Artificial Sequence
<220> FEATURE:
<223> OTHER INFORMATION: Description of Artificial Sequence: Synthetic
    polynucleotide

<400> SEQUENCE: 78
ugaguuuuga gguugcuuca gugaacauuc aacgcugucg gugaguuugg aauuaaaauc    60
aaaaccaucg accguugauu guacccuaug gcuaaccauc aucuacucca              110

<210> SEQ ID NO 79
<211> LENGTH: 110
<212> TYPE: RNA
<213> ORGANISM: Artificial Sequence
<220> FEATURE:
<223> OTHER INFORMATION: Description of Artificial Sequence: Synthetic
    polynucleotide

<400> SEQUENCE: 79
agaagggcua ucaggccagc cuucagagga cuccaaggaa cauucaacgc ugucggugag    60
uuugggauuu gaaaaaacca cugaccguug acuguaccuu gggguccuua              110

<210> SEQ ID NO 80
<211> LENGTH: 110
<212> TYPE: RNA
<213> ORGANISM: Artificial Sequence
<220> FEATURE:
<223> OTHER INFORMATION: Description of Artificial Sequence: Synthetic
    polynucleotide

<400> SEQUENCE: 80

```
ccugugcaga gauuauuuuu uaaaagguca caaucaacau ucauugcugu cggugggung      60
aacugugugg acaagcucac ugaacaauga augcaacugu ggccccgcuu                110
```

<210> SEQ ID NO 81
<211> LENGTH: 89
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 81

```
cugauggcug cacucaacau ucauugcugu cgguggguuu gagucugaau caaucucacug     60 aucaaugaau gcaaacugcg gaccaaaca                                        89
```

<210> SEQ ID NO 82
<211> LENGTH: 110
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 82

```
cggaaaauuu gccaaggguu uggggaaca uucaaccugu cggugaguuu gggcagcuca       60
ggcaaaccau cgaccguuga guggacccug aggccuggaa uugccauccu                110
```

<210> SEQ ID NO 83
<211> LENGTH: 137
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 83

```
gucccucccc cuaggccaca gccgagguca caaucaacau ucauuguugu cggugggung      60
ugaggacuga ggccagaccc accggggau gaaugucacu guggcugggc cagacacggc     120
uuaaggggaa uggggac                                                   137
```

<210> SEQ ID NO 84
<211> LENGTH: 110
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 84

```
gagcugcuug ccucccccg uuuuuggcaa ugguagaacu cacacuggug agguaacagg       60
auccgguggu ucuagacuug ccaacuaugg ggcgaggacu cagccggcac                110
```

<210> SEQ ID NO 85
<211> LENGTH: 110
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 85

```
ccgcagagug ugacuccugu ucuguguaug gcacugguag aauucacugu gaacagucuc      60
agucagugaa uuaccgaagg gccauaaaca gagcagagac agauccacga                110
```

<210> SEQ ID NO 86
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ccagucacgu cccuuauca cuuuccagc ccagcuuugu gacuguaagu guuggacgga      60
gaacugauaa ggguagguga uuga                                          84

<210> SEQ ID NO 87
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87 aggggcgag ggauuggaga gaaaggcagu uccugauggu ccccuccca ggggcuggcu      60 uuccucuggu ccuucccucc ca                                            82

<210> SEQ ID NO 88
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ugcuuguaac uuuccaaaga auucuccuuu ugggcuuucu gguuuuauuu uaagcccaaa    60
ggugaauuuu uugggaaguu ugagcu                                        86

<210> SEQ ID NO 89
<211> LENGTH: 109
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 89
ggucgggcuc accaugacac agugugagac cucgggcuac aacacaggac ccgggcgcug    60
cucugacccc ucgugucuug uguugcagcc ggagggacgc agguccgca               109

<210> SEQ ID NO 90
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ugcucccucu cucacauccc uugcauggug gagggugagc uuucugaaaa ccccucccac    60 augcagggu ugcaggaugg cgagcc                                         86

<210> SEQ ID NO 91
<211> LENGTH: 71
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 91
uguucuaagg ugcaucuagu gcagauagug aaguagauua gcaucuacug cccuaagugc    60
uccuucuggc a                                                        71

<210> SEQ ID NO 92
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uguguuaagg ugcaucuagu gcaguuagug aagcagcuua gaaucuacug cccuaaaugc    60
cccuucuggc a                                                        71

<210> SEQ ID NO 93
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
ugcaggccuc ugugugauau guuugauaua uuagguuguu auuuaaucca acuauauauc    60
aaacauauuc cuacaguguc uugcc                                         85

<210> SEQ ID NO 94
<211> LENGTH: 92
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
cggcuggaca gcgggcaacg gaaucccaaa agcagcuguu gucccagag cauuccagcu     60 gcgcuuggau uucguccccu gcucuccugc cu                                 92

<210> SEQ ID NO 95
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 95
gccgagaccg agugcacagg gcucugaccu augaauugac agccagugcu cucgucuccc    60
cucuggcugc caauuccaua ggucacaggu auguucgccu caaugccagc               110

<210> SEQ ID NO 96
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 96
cgaggauggg agcugagggc ugggucuuug cgggcgagau gagggugucg gaucaacugg    60
ccuacaaagu cccaguucuc ggcccccg                                       88

<210> SEQ ID NO 97
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
guggucucag aaucggggu uugagggcga gaugaguuua uguuuauccc aacuggcccu    60
caaagucccg cuuuuggggu cau                                            83

<210> SEQ ID NO 98
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
augguguuau caaguguaac agcaacucca uguggacugu guaccaauuu ccaguggaga    60
ugcuguuacu uuugaugguu accaa                                          85

<210> SEQ ID NO 99
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ugguccccgc ccccuguaac agcaacucca uggaagug cccacugguu ccaguggggc    60
ugcuguuauc uggggcgagg gccag                                          85

<210> SEQ ID NO 100
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
agcuucccug gcucuagcag cacagaaaua uuggcacagg gaagcgaguc ugccaauauu    60
ggcugugcug cuccaggcag gguggug                                        87

<210> SEQ ID NO 101
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gugaauuagg uaguuucaug uuguugggcc uggguuucug aacacaacaa cauuaaacca    60
cccgauucac                                                           70
```

<210> SEQ ID NO 102
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 102
ugcucgcuca gcugaucugu ggcuuaggua guuucauguu guugggauug aguuuugaac    60
ucggcaacaa gaaacugccu gaguuacauc agucgguuuu cgucgagggc               110

<210> SEQ ID NO 103
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
acuggucggu gauuuaggua guuccuguu guugggaucc accuucucu cgacagcacg      60 acacugccuu cauuacuuca guug                                            84

<210> SEQ ID NO 104
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
ggcugugccg gguagagagg gcagugggag guaagagcuc uucacccuuc accaccuucu    60
ccacccagca uggcc                                                      75

<210> SEQ ID NO 105
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
ucauuggucc agaggggaga uagguuccug ugauuuuucc uucuucucua agaauaaau     60 ga                                                                    62

<210> SEQ ID NO 106
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gccaacccag uguucagacu accuguucag gaggcucuca auguguacag uagucugcac    60
auugguuagg c                                                          71

<210> SEQ ID NO 107
<211> LENGTH: 110
<212> TYPE: RNA

```
<213> ORGANISM: Artificial Sequence
<220> FEATURE:
<223> OTHER INFORMATION: Description of Artificial Sequence: Synthetic
      polynucleotide

<400> SEQUENCE: 107
aggaagcuuc uggagauccu gcuccgucgc cccaguguuc agacuaccug uucaggacaa    60
ugccguugua caguagucug cacauugguu agacugggca agggagagca              110

<210> SEQ ID NO 108
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 108
ccagaggaca ccuccacucc gucuacccag uguuuagacu aucuguucag gacucccaaa    60
uuguacagua gucugcacau ugguuaggcu gggcugggu agaccccucgg              110

<210> SEQ ID NO 109
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109 gcagccucucu guuaguuuug cauaguugca cuacaagaag aauguaguug ugcaaaucua    60
ugcaaaacug augguggccu gc                                            82

<210> SEQ ID NO 110
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
cacuguucua ugguuaguuu ugcagguuug cauccagcug ugugauauuc ugcugugcaa    60
auccaugcaa aacugacugu gguagug                                       87

<210> SEQ ID NO 111
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
acauugcuac uuacaauuag uuuugcaggu uugcauuuca gcguauauau guauaugugg    60
cugugcaaau ccaugcaaaa cugauuguga uaaugu                             96

<210> SEQ ID NO 112
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 112 ccgggcccu gugagcaucu uaccggacag ugcuggauuu cccagcuuga cucuaacacu      60
gucugguaac gauguucaaa ggugacccgc                                      90

<210> SEQ ID NO 113
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ccagcucggg cagccguggc caucuuacug ggcagcauug gauggaguca ggucucuaau      60
acugccuggu aaugaugacg gcggagcccu gcacg                                95

<210> SEQ ID NO 114
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
cccucgucuu acccagcagu guugggugc gguugggagu cucuaauacu gccgggaauu       60
gauggagg                                                              68

<210> SEQ ID NO 115
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 115
cgccucagag ccgcccgccg uuccuuuuuc cuaugcauau acuucuuuga ggaucuggcc      60
uaaagaggua uagggcaugg gaaaacgggg cggucggguc cuccccagcg                110

<210> SEQ ID NO 116
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 116
guguugggga cucgcgcgcu ggguccagug guucuuaaca guucaacagu ucuguagcgc      60
aauugugaaa uguuuaggac cacuagaccc ggcgggcgcg gcgacagcga                110

<210> SEQ ID NO 117
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 117
ggcuacaguc uuucuucaug ugacucgugg acuccccuuu gcauccuau gccugagaau       60 auaugaagga ggcugggaag gcaaagggac guucaauugu caucacuggc                110
```

<210> SEQ ID NO 118
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 118
aaagauccuc agacaaucca ugugcuucuc uguccuuca uuccaccgga gucugucuca      60
uacccaacca gauuucagug gagugaaguu caggaggcau ggagcugaca              110

<210> SEQ ID NO 119
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
ugcuucccga ggccacaugc uucuuuauau ccccauaugg auuacuuugc uauggaaugu      60
aaggaagugu gugguuucgg caagug                                          86

<210> SEQ ID NO 120
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ugacgggcga gcuuuggcc cggguuauac cugaugcuca cguauaagac gagcaaaaag      60
cuuguugguc a                                                          71

<210> SEQ ID NO 121
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
guagcacuaa agugcuuaua gugcaggguag uguuuaguua ucuacugcau uaugagcacu      60
uaaaguacug c                                                          71

<210> SEQ ID NO 122
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
aguaccaaag ugcucauagu gcagguaguu uuggcaugac cuacuguag uaugggcacu      60 uccaguacu                                                             69

<210> SEQ ID NO 123
<211> LENGTH: 72
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 123
ugucggguag cuuaucagac ugauguugac uguugaaucu cauggcaaca ccagucgaug    60
ggcugucuga ca                                                        72

<210> SEQ ID NO 124
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 124
acccggcagu gccuccaggc gcagggcagc cccugcccac cgcacacugc gcugcccag     60 acccacugug cgugugacag cggcugaucu gugccugggc agcgcgaccc               110

<210> SEQ ID NO 125
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 125
ucaccuggcc augugacuug ugggcuuccc uuugucaucc uucgccuagg gcucugagca    60
gggcagggac agcaaagggg ugcucaguug ucacuuccca cagcacggag               110

<210> SEQ ID NO 126
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 126
cggggcaccc cgcccggaca gcgcgccggc accuuggcuc uagacugcuu acugcccggg    60
ccgcccucag uaacagucuc cagucacggc caccgacgcc uggccccgcc               110

<210> SEQ ID NO 127
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 127
ggccuggcug gacagaguug ucaugugucu gccugucuac acuugcugug cagaacaucc    60
gcucaccugu acagcaggca cagacaggca gucacaugac aacccagccu               110

<210> SEQ ID NO 128
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide
```

<400> SEQUENCE: 128
aucauucaga aauggauauac aggaaaauga ccuaugaauu gacagacaau auagcugagu     60
uugucuguca uuucuuuagg ccaauauucu guaugacugu gcuacuucaa                110

<210> SEQ ID NO 129
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 129
gauggcugug aguuggcuua aucucagcug gcaacuguga gauguucaua caaucccuca     60
caguggucuc ugggauuaug cuaaacagag caauuuccua gcccucacga                110

<210> SEQ ID NO 130
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 130
aguauaauua uuacauaguu uuugaugucg cagauacugc aucaggaacu gauuggauaa     60
gaaucaguca ccaucaguuc cuaaugcauu gccuucagca ucuaaacaag                110

<210> SEQ ID NO 131
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 131
gugauaaugu agcgagauuu ucuguugugc uugaucuaac caugugguug cgagguauga     60
guaaaacaug guuccgucaa gcaccaugga acgucacgca gcuuucuaca                110

<210> SEQ ID NO 132
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 132
gaccagucgc ugcggggcuu uccuuugugc uugaucuaac caugguggug aacgauggaa     60
acggaacaug guucugucaa gcaccgcgga aagcaccgug cucuccugca                110

<210> SEQ ID NO 133
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 133
ccgccccggg ccgcggcucc ugauugucca aacgcaauuc ucgagcuau ggcuccggcc      60 gagaguugag ucuggacguc ccgagccgcc gcccccaaac cucgagcggg               110

<210> SEQ ID NO 134
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
acucaggggc uucgccacug auuguccaaa cgcaauucuu guacgagucu gcggccaacc      60
gagaauugug gcuggacauc uguggcugag cuccggg                              97

<210> SEQ ID NO 135
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ggcugagccg caguaguucu ucaguggcaa gcuuuauguc cugacccagc uaaagcugcc      60
aguugaagaa cguugcccu cugcc                                            85

<210> SEQ ID NO 136
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 136
gacagugugg cauuguaggg cuccacaccg uaucugacac uuugggcgag ggcaccaugc      60 ugaaggguu caugaugcgg ucugggaacu ccucacggau cuuacugaug               110

<210> SEQ ID NO 137
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 137
ugaacaucca ggucuggggc augaaccugg cauacaaugu agauuucugu guucguuagg      60
caacagcuac auugucugcu ggguuucagg cuaccuggaa acauguucuc              110

<210> SEQ ID NO 138
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 138
gcugcuggaa gguguaggua cccucaaugg cucaguagcc aguguagauc cugucuuucg      60
uaaucagcag cuacaucugg cuacugggguc ucgauggca ucuucuagcu              110

<210> SEQ ID NO 139
<211> LENGTH: 110
<212> TYPE: RNA

```
<213> ORGANISM: Artificial Sequence
<220> FEATURE:
<223> OTHER INFORMATION: Description of Artificial Sequence: Synthetic
      polynucleotide

<400> SEQUENCE: 139
ccuggccucc ugcagugcca cgcuccgugu auuugacaag cugaguugga cacuccaugu    60
gguagagugu caguuuguca aauaccccaa gugcggcaca ugcuuaccag              110

<210> SEQ ID NO 140
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gggcuuucaa gucacuagug guuccguuua guagaugauu ugcauuguu ucaaaauggu    60 gcccuaguga cuacaaagcc c                                             81

<210> SEQ ID NO 141
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ggccggcugg gguuccuggg gaugggauuu gcuuccuguc acaaaucaca uugccaggga    60
uuuccaaccg acc                                                      73

<210> SEQ ID NO 142
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
cucaggugcu cuggcugcuu ggguuccugg caugcugauu ugugacuuaa gauuaaaauc    60
acauugccag ggauuaccac gcaaccacga ccuuggc                            97

<210> SEQ ID NO 143
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
cuccggugcc uacugagcug auaucaguuc ucauuuaca cacuggcuca guucagcagg    60
aacaggag                                                            68

<210> SEQ ID NO 144
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 144
cucugccucc cgugccuacu gagcugaaac acaguugguu uguguacacu ggcucaguuc    60
agcaggaaca ggg                                                     73

<210> SEQ ID NO 145
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ggccaguguu gagaggcgga gacuugggca auugcuggac gcugcccugg gcauugcacu    60
ugucucgguc ugacagugcc ggcc                                         84

<210> SEQ ID NO 146
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
guggccucgu ucaaguaauc caggauaggc ugugcagguc ccaaugggcc uauucuuggu    60
uacuugcacg gggacgc                                                 77

<210> SEQ ID NO 147
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ggcuguggcu ggauucaagu aauccaggau aggcuguuuc caucugugag gccuauucuu    60
gauuacuugu uucggaggc agcu                                          84

<210> SEQ ID NO 148
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ccgggaccca guucaaguaa uucaggauag guugugugcu guccagccug uucuccauua    60
cuuggcucgg ggaccgg                                                 77

<210> SEQ ID NO 149
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
cugaggagca gggcuuagcu gcuugugagc aggguccaca ccaagucgug uucacagugg    60
cuaaguuccg cccccccag                                               78
```

<210> SEQ ID NO 150
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
accucucuaa caaggugcag agcuuagcug auuggugaac agugauuggu uccgcuuug    60 uucacagugg cuaaguucug caccugaaga gaaggug                            97

<210> SEQ ID NO 151
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gguccuugcc cucaaggagc ucacagucua uugaguuacc uuucugacuu ucccacuaga    60
uugugagcuc cuggagggca ggcacu                                        86

<210> SEQ ID NO 152
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
aggacccuuc cagagggccc ccccucaauc cuguugugcc uaauucagag gguugggugg    60
aggcucuccu gaagggcucu                                               80

<210> SEQ ID NO 153
<211> LENGTH: 63
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
aagaaauggu uuaccguccc acauacauuu ugaauaugua ugugggaugg uaaaccgcuu    60
cuu                                                                 63

<210> SEQ ID NO 154
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
augacugauu ucuuugggug uucagaguca auauaauuuu cuagcaccau cugaaaucgg    60
uuau                                                                64

<210> SEQ ID NO 155
<211> LENGTH: 81
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 155
cuucaggaag cugguuucau auggugguuu agauuuaaau agugauuguc uagcaccauu    60
ugaaaucagu guucuugggg g                                              81

<210> SEQ ID NO 156
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
cuucuggaag cugguuucac augguggcuu agauuuuccc aucuuuguau cuagcaccau    60
uugaaaucag uguuuuagga g                                              81

<210> SEQ ID NO 157
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
aucucuuaca caggcugacc gauuucuccu ggguucaga gucuguuuuu gucuagcacc     60
auuugaaauc gguuaugaug uaggggga                                       88

<210> SEQ ID NO 158
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
acugcuaacg aaugcucuga cuuuauugca cuacuguacu uuacagcuag cagugcaaua    60
guauugucaa agcaucugaa agcagg                                         86

<210> SEQ ID NO 159
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ccaccacuua aacguggaug uacuugcuuu gaaacuaaag aaguaagugc uuccauguuu    60
uggugaugg                                                            69

<210> SEQ ID NO 160
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 160
gcucccuuca acuuaacau ggaagugcuu ucgugacuu uaaaaguaag ugcuuccaug    60
uuuuaguagg agu                                                    73

<210> SEQ ID NO 161
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ccuuugcuuu aacauggggg uaccugcugu gugaaacaaa aguaagugcu uccauguuuc   60
aguggagg                                                           68

<210> SEQ ID NO 162
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ccucuacuuu aacauggagg cacuugcugu gacaugacaa aaauaagugc uuccauguuu   60
gagugugg                                                           68

<210> SEQ ID NO 163
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
gcgacuguaa acauccucga cuggaagcug ugaagccaca gaugggcuuu cagucggaug   60
uuugcagcug c                                                       71

<210> SEQ ID NO 164
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
accaaguuuc aguucaugua aacauccuac acucagcugu aauacaugga uuggcuggga   60
gguggauguu uacuucagcu gacuugga                                     88

<210> SEQ ID NO 165
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
accaugcugu agugugugua aacauccuac acucucagcu gugagcucaa gguggcuggg   60
agaggguugu uuacuccuuc ugccaugga                                    89
```

<210> SEQ ID NO 166
<211> LENGTH: 72
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 166
agauacugua aacauccuac acucucagcu guggaaagua agaaagcugg gagaaggcug    60
uuuacucuuu cu    72

<210> SEQ ID NO 167
<211> LENGTH: 70
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 167
guuguuguaa caucccega cuggaagcug uaagacacag cuaagcuuuc agucagaugu    60
uugcugcuac    70

<210> SEQ ID NO 168
<211> LENGTH: 92
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 168
gggcagucuu ugcuacugua aacauccuug acuggaagcu guaagguguu cagaggagcu    60
uucagucgga uguuuacagc ggcaggcugc ca    92

<210> SEQ ID NO 169
<211> LENGTH: 71
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 169
ggagaggagg caagaugcug gcauagcugu ugaacuggga accugcuaug ccaacauauu    60
gccaucuuuc c    71

<210> SEQ ID NO 170
<211> LENGTH: 70
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 170
ggagauauug cacauuacua aguugcaugu ugcacggcc ucaaugcaau uuagugugug    60
ugauauuuc    70

<210> SEQ ID NO 171
<211> LENGTH: 82
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 171
gcuucgcucc ccuccgccuu cucuucccgg uucuucccgg agucgggaaa agcuggguug      60
agagggcgaa aaaggaugag gu                                              82

<210> SEQ ID NO 172
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
uugguacuug gagagaggug guccguggcg cguucgcuuu auuuauggcg cacauuacac      60
ggucgaccuc uuugcaguau cuaauc                                          86

<210> SEQ ID NO 173
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
cugacuaugc cuccccgcau ccccuagggc auugguguaa agcuggagac ccacugcccc      60
aggugcugcu gggguugua guc                                              83

<210> SEQ ID NO 174
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
auacagugcu ugguuccuag uaggugucca guaaguguuu gugacauaau uuguuuauug      60
aggaccuccu aucaaucaag cacugugcua ggcucugg                             98

<210> SEQ ID NO 175
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
cucaucuguc uguugggcug gaggcagggc cuuugugaag gcggguggug cucagaucgc      60
cucugggccc uuccuccagc cccgaggcgg auuca                                95

<210> SEQ ID NO 176
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 176 uggaguggggg gggcaggagg ggcucaggga gaaagugcau acagcccug gcccucucug    60 cccuuccguc cccug                                                   75

<210> SEQ ID NO 177
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
gguaccugaa gagagguuuu cuggguuucu guuucuuuaa ugaggacgaa acacaccugg    60
uuaaccucuu uuccaguauc                                              80

<210> SEQ ID NO 178
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
gugguaccug aagagagguu uucuggguuu cuguuucuuu auugaggacg aaacacaccu    60
gguuaaccuc uuuuccagua ucaa                                         84

<210> SEQ ID NO 179
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
cuguggugca uuguaguugc auugcauguu cuggugguac ccaugcaaug uuccacagu     60 gcaucacag                                                          69

<210> SEQ ID NO 180
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
cuuuggcgau cacugccucu cugggccugu gucuuaggcu cugcaagauc aaccgagcaa    60
agcacacggc cugcagagag gcagcgcucu gccc                              94

<210> SEQ ID NO 181
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
gaguuugguu uuguugggu uuguucuagg uauggucccca gggaucccag aucaaaccag    60
gccccugggc cuauccuaga accaaccuaa gcuc                              94
```

-continued

```
<210> SEQ ID NO 182
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uguuuugagc gggggucaag agcaauaacg aaaaauguuu gucauaaacc guuuuucauu     60
auugcuccug accuccucuc auuugcuaua uuca                                94

<210> SEQ ID NO 183
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
guagucagua guuggggggu gggaacggcu ucauacagga guugaugcac aguuauccag     60
cuccuauaug augccuuucu caucccccuu caa                                 93

<210> SEQ ID NO 184
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
ucuccaacaa uauccuggug cugagugaug acucaggcga cuccagcauc agugauuuug     60
uugaaga                                                              67

<210> SEQ ID NO 185
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
cggggcggcc gcucucccug uccuccagga gcucacugu gccugccugu gagcgccucg      60
acgacagagc cggcgccugc cccagugucu gcgc                                94

<210> SEQ ID NO 186
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uuguaccugg ugugauuaua aagcaaugag acugauuguc auaugucguu ugugggaucc     60
gucucaguua cuuuauagcc auaccuggua ucuua                               95

<210> SEQ ID NO 187
<211> LENGTH: 99
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 187
gaaacugggc ucaaggugag gggugcuauc ugugauugag ggacaugguu aauggaauug    60
ucucacacag aaaucgcacc cgucaccuug gccuacuua                           99

<210> SEQ ID NO 188
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
acccaaaccc uaggucugcu gacuccuagu ccagggcucg ugauggcugg ugggcccuga    60
acgagggguc uggaggccug gguuugaaua ucgacagc                            98

<210> SEQ ID NO 189
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
ggucucugug uugggcgucu gucugcccgc augccugccu cucuguugcu cugaaggagg    60
caggggcugg gccugcagcu gccugggcag agcgg                               95

<210> SEQ ID NO 190
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 190
ggccagcugu gaguguuucu uuggcagugu cuuagcuggu uguugugagc aauaguaagg    60
aagcaaucag caaguauacu gcccuagaag ugcugcacgu uguggggccc               110

<210> SEQ ID NO 191
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
gugcucgguu uguaggcagu gucauuagcu gauuguacug uggugguuac aaucacuaac    60
uccacugcca ucaaaacaag gcac                                           84

<210> SEQ ID NO 192
<211> LENGTH: 77
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
agucuaguua cuaggcagug uaguuagcug auugcuaaua guaccaauca cuaaccacac    60
ggccagguaa aaagauu                                                  77

<210> SEQ ID NO 193
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
ggagcuuauc agaaucucca ggguacuuu auaauuucaa aaguccccc aggugugauu     60 cugauuugcu uc                                                        72

<210> SEQ ID NO 194
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
cuugaauccu uggaaccuag gugugagugc uauuucagug caacacaccu auucaaggau    60
ucaaa                                                                65

<210> SEQ ID NO 195
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
accgcaggga aaugaggga cuuuggggg cagaugoguu uccauccac uaucauaaug       60 ccccuaaaaa uccuuauugc ucuugca                                        87

<210> SEQ ID NO 196
<211> LENGTH: 111
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 196
agaguguuca aggacagcaa gaaaaaugag ggacuuucag gggcagcugu guuuucugac    60
ucagucauaa ugccccuaaa aauccuuauu guucuugcag ugugcaucgg g            111

<210> SEQ ID NO 197
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
ccauuacugu ugcuaauaug caacucuguu gaauauaaau uggaauugca cuuuagcaau    60
ggugaugg                                                             68

<210> SEQ ID NO 198
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
uugaagggag aucgaccgug uuauauucgc uuuauugacu ucgaauaaua caugguugau    60
cuuucucag                                                           70

<210> SEQ ID NO 199
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
agacagagaa gccaggucac gucucugcag uuacacagcu cacgagugcc ugcuggggug    60
gaaccugguc ugucu                                                    75

<210> SEQ ID NO 200
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
guggcacuca aacugugggg gcacuuucug cucucuggug aaagugccgc caucuuuga    60 guguuac                                                             67

<210> SEQ ID NO 201
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
gugggccuca aauguggagc acuauucuga uguccaagug gaaagugcug cgacauuuga    60
gcgucac                                                             67

<210> SEQ ID NO 202
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
gggauacuca aaugggggc gcuuccuuu uugucuguac ugggaagugc uucgauuuug    60
ggguguccc                                                           69

<210> SEQ ID NO 203
<211> LENGTH: 72
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 203
uacaucggcc auuauaauac aaccugauaa guguuauagc acuuaucaga uuguauugua     60
auugucugug ua                                                        72

<210> SEQ ID NO 204
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
ccccgcgacg agccccucgc acaaaccgga ccugagcguu uuguucguuc ggcucgcgug     60
aggc                                                                 64

<210> SEQ ID NO 205
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uaaaagguag auucuccuuc uaugaguaca uuauuuauga uuaaucauag aggaaaaucc     60
acguuuuc                                                             68

<210> SEQ ID NO 206
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
gguauuuaaa agguagauuu uccuucuaug guuacguguu ugaugguuaa ucauagagga     60
aaauccacgu uuucaguauc                                                80

<210> SEQ ID NO 207
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 207
caguccuucu uugguauuua aaacguggau auuccuucua uguuuacgug auccugguu      60 aaucauagag gaaaauccau guuuucagua ucaaaugcug                         100

<210> SEQ ID NO 208
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 208
aaaaggugga uauuccuucu auguuuaugu uauuuauggu uaaacauaga ggaaauucca    60
cguuuu    66

<210> SEQ ID NO 209
<211> LENGTH: 69
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
uugagcagag guugcccuug gugaauucgc uuuauuuaug uugaaucaca caaaggcaac    60
uuuuguuug    69

<210> SEQ ID NO 210
<211> LENGTH: 66
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
agggcuccug acuccagguc cuguguguua ccuagaaaua gcacuggacu uggagucaga    60
aggccu    66

<210> SEQ ID NO 211
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
agagauggua gacuauggaa cguaggcguu augauuucug accauaguaa caugguccac    60
uaacucu    67

<210> SEQ ID NO 212
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
aagaugguug accauagaac augcgcuauc ucugugucgu auguaauaug guccacaucu    60
u    61

<210> SEQ ID NO 213
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
uacuuaaagc gagguugccc uuuguauauu cgguuuauug acauggaaua uacaagggca    60
agcucucugu gagua    75

```
<210> SEQ ID NO 214
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
uacuugaaga gaaguuguuc gugguggauu cgcuuuacuu augacgaauc auucacggac    60
aacacuuuuu ucagua                                                   76

<210> SEQ ID NO 215
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
cuccucagau cagaagguga uuguggcuuu ggguggauau uaaucagcca cagcacugcc    60
uggucagaaa gag                                                      73

<210> SEQ ID NO 216
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
ugguacucgg ggagagguua cccgagcaac uuugcaucug gacgacgaau guugcucggu    60
gaaccccuuu ucgguauca                                                79

<210> SEQ ID NO 217
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
gguaccugag aagagguugu cugugaugag uucgcuuuua uuaaugacga auauaacaca    60
gauggccugu uuucaguacc                                               80

<210> SEQ ID NO 218
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
cugggguacg gggauggaug gucgaccagu uggaaaguaa uuguuucuaa uguacuucac    60
cugguccacu agccguccgu auccgcugca g                                  91

<210> SEQ ID NO 219
<211> LENGTH: 90
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 219
gagagaagca cuggacuuag ggucagaagg ccugagucuc ucugcugcag augggcucuc     60
ugucccugag ccaagcuuug uccucccugg                                     90

<210> SEQ ID NO 220
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
auaaaggaag uuaggcugag gggcagagag cgagacuuuu cuauuuucca aaagcucggu     60
cugaggcccc ucagucuugc uuccuaaccc gcgc                                94

<210> SEQ ID NO 221
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221 cgagggaua cagcagcaau ucauguuuug aaguguucua aaugguucaa aacgugaggc     60
gcugcuauac ccccucgugg ggaagguaga aggugggg                            98

<210> SEQ ID NO 222
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
gaaagcgcuu uggaaugaca cgaucacucc cguugagugg gcacccgaga agccaucggg     60
aaugucgugu ccgcccagug cucuuuc                                        87

<210> SEQ ID NO 223
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
cgccggccga ugggcgucuu accagacaug guuagaccug gcccucuguc uaauacuguc     60
ugguaaaacc guccauccgc ugc                                            83

<210> SEQ ID NO 224
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 224
ugacuccucc aggucuugga guaggucauu ggguggaucc ucuauuuccu uacgugggcc      60
acuggauggc uccuccaugu cuggaguag auca                                   94

<210> SEQ ID NO 225
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ccggggagaa guacggugag ccugucauua uucagagagg cuagauccuc uguguugaga      60
aggaucauga ugggcuccuc ggguucucc agg                                    93

<210> SEQ ID NO 226
<211> LENGTH: 111
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 226
gccgggaggu ugaacauccu gcauagugcu gccaggaaau cccuauuuca uauaagaggg      60
ggcuggcugg uugcauaugu aggaugucc aucucccagc ccacuucguc a               111

<210> SEQ ID NO 227
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
cuguguguga ugagcuggca guguauuguu agcugguuga auaugugaau ggcaucggcu      60
aacaugcaac ugcugucuua uugcauauac a                                    91

<210> SEQ ID NO 228
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
aaacgauacu aaacuguuuu ugcgaugugu uccuaauaug cacuauaaau auauugggaa      60
cauuuugcau guauaguuuu guaucaauau a                                    91

<210> SEQ ID NO 229
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 229
ccaaagaaag augcuaaacu auuuuugcga uguguuccua auauguaaua uaaauguauu      60
ggggacauuu ugcauucaua guuuuguauc aauaauaugg                          100
```

<210> SEQ ID NO 230
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
cuugggaaug gcaaggaaac cguuaccauu acugaguuua guaaugguaa ugguucucuu    60
gcuauaccca ga                                                       72

<210> SEQ ID NO 231
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
gcuaagcacu uacaacuguu ugcagaggaa acugagacuu uguaacuaug ucucagucuc    60
aucugcaaag aaguaagugc uuugc                                         85

<210> SEQ ID NO 232
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
gcaggaaugc ugcgagcagu gccaccucau gguacucgga gggagguugu ccguggugag    60
uucgcauuau uuaaugaugc                                               80

<210> SEQ ID NO 233
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ucccuggcgu gaggguaugu gccuuuggac uacaucgugg aagccagcac caugcagucc    60
augggcauau acacuugccu caaggccuau gucauc                             96

<210> SEQ ID NO 234
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234 gaggggaag acgggaggaa agaagggagu gguuccauca cgccuccuca cuccucuccu     60
cccgucuucu ccucuc                                                   76

<210> SEQ ID NO 235
<211> LENGTH: 73
<212> TYPE: RNA

<213> ORGANISM: Artificial Sequence
<220> FEATURE:
<223> OTHER INFORMATION: Description of Artificial Sequence: Synthetic
     oligonucleotide

<400> SEQUENCE: 235
acuuggagag aggcuggccg ugaugaauuc gauucaucaa agcgagucau acacggcucu    60
ccucucuuuu agu                                                      73

<210> SEQ ID NO 236
<211> LENGTH: 68
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 236
gcauccugua cugagcugcc ccgaggcccu ucaugcugcc cagcucgggg cagcucagua    60
caggauac                                                            68

<210> SEQ ID NO 237
<211> LENGTH: 80
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 237
gguacuugaa gagugguuau cccugcugug uucgcuuaau uuaugacgaa ucauacaggg    60
acauccaguu uuucaguauc                                               80

<210> SEQ ID NO 238
<211> LENGTH: 84
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 238
uugguacuug gagagugguu aucccugucc uguucguuuu gcucaugucg aaucguacag    60
ggucauccac uuuuucagua ucaa                                          84

<210> SEQ ID NO 239
<211> LENGTH: 83
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 239
gagaaucauc ucucccagau aauggcacuc ucaaacaagu uccaaauug uuugaaaggc    60 uauuucuugg ucagaugacu cuc                                           83

<210> SEQ ID NO 240
<211> LENGTH: 84
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 240
guggcagcuu gguggucgua ugugugacgc cauuuacuug aaccuuuagg agugacauca      60
cauauacggc agcuaaacug cuac                                             84

<210> SEQ ID NO 241
<211> LENGTH: 128
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 241
uggaggccuu gcugguuugg aaaguucauu guucgacacc auggaucucc aggugguca       60 aguuuagaga ugcaccaacc uggaggacuc caugcuguug agcuguucac aagcagcgga     120
cacuucca                                                              128

<210> SEQ ID NO 242
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
uugacuuagc uggguagugg ggaacccuuc caugaggagu agaacacucc uuaugcaaga      60
uucccuucua ccuggcuggg uugg                                             84

<210> SEQ ID NO 243
<211> LENGTH: 116
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 243
caacuacagc cacuacuaca ggaccaucga ggaccugcgg gacaagauuc uuggugccac      60
cauugagaac gccaggauug uccugcagau caacaaugcu caacuggcug cagaug         116

<210> SEQ ID NO 244
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
cuggccucca gggcuuugua caugguaggc uuucauucau ucguuugcac auucggugaa      60
ggucuacugu gugccaggcc cugugccag                                        89

<210> SEQ ID NO 245
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
gauacucgaa ggagagguug uccguguugu cuucucuuua uuuaugauga aacauacacg      60

```
ggaaaccucu uuuuuaguau c                                             81

<210> SEQ ID NO 246
<211> LENGTH: 82
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
ugguaccuga aagaaguug cccauguuau uuucgcuuua uaugugacga aacaaacaug     60
gugcacuucu uuucgguau ca                                             82

<210> SEQ ID NO 247
<211> LENGTH: 102
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 247
cccaagucag guacucgaau ggagguuguc caugugugu ucauuuuauu uaugaugagu     60
auuacauggc caaucuccuu ucgguacuca auucuucuug gg                     102

<210> SEQ ID NO 248
<211> LENGTH: 112
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 248
ccaccccggu ccugcucccg ccccagcagc acacugggu uuguacggca cuguggccac     60
guccaaacca cacugguug uuagagcgag ggugggggag gcaccgccga gg            112

<210> SEQ ID NO 249
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 249
aacccuccuu gggaagugaa gcucaggcug ugauuucaag ccaggggcg uuuuucuaua     60 acuggaugaa aagcaccucc agagcuugaa gcucacaguu ugagagcaau cgucaagga   120 aguu                                                               124

<210> SEQ ID NO 250
<211> LENGTH: 122
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 250
gcccuguccc cugugccuug ggcgggcggc uguuaagacu ugcagugaug uuuaacuccu     60
cuccacguga acaucacagc aagucugugc ugcuucccgu cccuacgcug ccugggcagg   120
```

```
gu                                                                  122

<210> SEQ ID NO 251
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251 gcuccccuc ucuaauccuu gcuaccuggg ugagagugcu gucugaaugc aaugcaccug     60
ggcaaggauu cugagagcga gagc                                          84

<210> SEQ ID NO 252
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
gcucuuccuc ucuaauccuu ugcccuggg ugagagugcu uucugaaugc aaugcacccg     60
ggcaaggauu cugagagggu gagc                                          84

<210> SEQ ID NO 253
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253 ugcuccccu cucuaauccu ugcuaucugg gugcuagugc uggcucaaug caaugcaccu     60
gggcaaggau ucagagaggg ggagcu                                        86

<210> SEQ ID NO 254
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
ugcccuagca gcgggaacag uucugcagug agcgaucggu gcucggggu auuguuccg      60 cugccagggu a                                                        71

<210> SEQ ID NO 255
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gcugcuguug ggagacccug gucugcacuc uaucuguauu cuuacugaag ggagugcagg    60
gcagggcuuc ccaucacagag ggc                                          83

<210> SEQ ID NO 256
<211> LENGTH: 84
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
gaugcaccca gugggggagc caggaaguau ugauguuucu gccaguuuag cgucaacacu    60
ugcugguuuc cucucuggag cauc                                          84

<210> SEQ ID NO 257
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 257
gccaccacca ucagccauac uauguguagu gccuuauuca ggaagguguu acuuaauaga    60
uuaauauuug uaaggcaccc uucugaguag aguaaugugc aacauggaca acauuugugg  120
uggc                                                               124

<210> SEQ ID NO 258
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
gugcugugug uagugcuuca cuucaagaag ugccaugcau gugucuagaa auauguuuug    60
caccuuuugg agugaaauaa ugcacaacag auac                               94

<210> SEQ ID NO 259
<211> LENGTH: 115
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 259
ccaccuucag cugaguguag ugcccuacuc cagagggcgu cacucaugua aacuaaaaca    60
ugauuguagc cuuuuggagu agaguaauac acaucacgua acgcauauuu ggugg       115

<210> SEQ ID NO 260
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
caugcugugu gugguacccu acugcagaca gugggcaauca uguauaauua aaaaugauug    60
guacgucugu ggguagagua cugcaugaca caug                               94

<210> SEQ ID NO 261
<211> LENGTH: 91
<212> TYPE: RNA
<213> ORGANISM: Artificial Sequence
<220> FEATURE:
```

<223> OTHER INFORMATION: Description of Artificial Sequence: Synthetic
     oligonucleotide

<400> SEQUENCE: 261
caugcugugu gugguacccu acugcagaca guggcaauca uguauaauua aaaugauug    60 guacgucugu ggguagagua cugcaugaca c    91

<210> SEQ ID NO 262
<211> LENGTH: 75
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 262
gugguacccu acugcagacg uggcaaucau guauaauuaa aaaugauugg uacgucugug    60
gguagaguac ugcau    75

<210> SEQ ID NO 263
<211> LENGTH: 74
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 263
gugguguccu acucaggaga guggcaauca cauguaauua ggugugauug aaaccucuaa    60
gaguggagua acac    74

<210> SEQ ID NO 264
<211> LENGTH: 87
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 264
caauagacac ccaucguguc uuuugcucug cagucaguaa auauuuuuuu gugaaugugu    60
agcaaaagac agaauggugg uccauug    87

<210> SEQ ID NO 265
<211> LENGTH: 87
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 265
caauagacac ccaucguguc uuuugcucug cagucaguaa auauuuuuuu gugaaugugu    60
agcaaaagac agaauggugg uccauug    87

<210> SEQ ID NO 266
<211> LENGTH: 84
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 266
ucucagucug uggcacucag ccuugagggc acuuucuggu gccagaauga aagugcuguc    60
auagcugagg uccaaugacu gagg                                           84

<210> SEQ ID NO 267
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
gguacuucuc agucuguggc acucagccuu gagggcacuu ucuggugcca gaaugaaagu    60
gcugucauag cugaggucca augacugagg cgagcacc                            98

<210> SEQ ID NO 268
<211> LENGTH: 129
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 268
gggaugccac auucagccau ucagcguaca gugccuuuca cagggaggug ucauuuaugu    60
gaacuaaaau auaaauuuca ccuuucugag aaggguaaug uacagcaugc acugcauaug   120
ugguguccc                                                           129

<210> SEQ ID NO 269
<211> LENGTH: 127
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 269
ggaugccaca uucagccauu cagugugcag ugccuuucac agggaggugu cauuuaugug    60
aacuaaaaua uaaauuucac cuuucugaga aggguaaugu acagcaugca cugcauaugu   120
ggugucc                                                             127

<210> SEQ ID NO 270
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
aacauguugu cuggguacc cuacucugga gagugacaau cauguauaau uaaauuugau    60
ugacacuucu gugaguagag uaacgcauga cacguacg                            98

<210> SEQ ID NO 271
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
guugucugug guacccuacu cuggagagug acaaucaugu auaacuaaau uugauugaca    60

```
cuucugugag uagaguaacg caugacac                                      88

<210> SEQ ID NO 272
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
guugucugug guacccuacu cuggagagug acaaucaugu auaacuaaau uugauugaca    60
cuucugugag uagaguaacg caugacac                                      88

<210> SEQ ID NO 273
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
ucucaugcag ucauucucca aaagaaagca cuuucuguug ucgaaagca gagugccuuc     60 uuuuggagcg uuacuguuug aga                                           83

<210> SEQ ID NO 274
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
ucucaugcag ucauucucca aaagaaagca cuuucuguug ucgaaagca gagugccuuc     60 uuuuggagcg uuacuguuug aga                                           83

<210> SEQ ID NO 275
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
ucucaggcug ugaccuucuc gaggaaagaa gcacuuucug uugucugaaa gaaaagaaag    60
ugcuuccuuu cagaggguua cgguuugaga                                    90

<210> SEQ ID NO 276
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
ucucagguug ugaccuucuc gaggaaagaa gcacuuucug uugucugaaa gaaaagaaag    60
ugcuuccuuu cagaggguua cgguuugaga                                    90

<210> SEQ ID NO 277
```

```
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
ucucaggcag ugacccucua gauggaagca cugucuguug uauaaaagaa aagaucgugc      60
aucccuuuag aguguuacug uuugaga                                         87

<210> SEQ ID NO 278
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
gugacccucu agauggaagc acugucuguu gucuaagaaa agaucgugca ucccuuuaga      60
guguuac                                                               67

<210> SEQ ID NO 279
<211> LENGTH: 95
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gaagaucuca ggcagugacc cucuagaugg aagcacuguc uguugcuaa gaaaagaucg       60 ugcauccuuu uagaguguua cuguuugaga aaauc                                95

<210> SEQ ID NO 280
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
ucucaagcug ugacugcaaa gggaagcccu uucuguuguc ugaaagaaga gaaagcgcuu      60
cccuuugcug gauuacgguu ugaga                                           85

<210> SEQ ID NO 281
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ucucaagcug ugggucugca aagggaagcc cuuucuguug ucuaaaagaa gagaaagcgc      60
uucccuuugc uggauuacgg uuugaga                                         87

<210> SEQ ID NO 282
<211> LENGTH: 83
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 282
ucaugcugug gcccuccaga gggaagcgcu uucuguuguc ugaaagaaaa caaagcgcuc    60
cccuuuagag guuuacgguu uga    83

<210> SEQ ID NO 283
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 283
gcgagaagau cucaugcugu gacucucugg agggaagcac uuucuguugu cugaaagaaa    60
acaaagcgcu ucucuuuaga guguuacggu uugagaaaag c    101

<210> SEQ ID NO 284
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
ucccaugcug ugacccucua gagggaagca cuuucuguug ucugaaagaa accaaagcgc    60
uucccuuugg agcguuacgg uuugaga    87

<210> SEQ ID NO 285
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
ucucaggcug ugacccucua gagggaagcg cuuucuguug gcuaaaagaa aagaaagcgc    60 uuccccuucag aguguuaacg cuuugaga    88

<210> SEQ ID NO 286
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ucucaugcug ugacccucua gagggaagca cuuucucuug ucuaaaagaa aagaaagcgc    60
uucucuuuag aggauuacuc uuugaga    87

<210> SEQ ID NO 287
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
cucaggcugu gacacucuag agggaagcgc uuucuguugu cugaaagaaa ggaaagugca    60

```
uccuuuuaga guguuacugu uugag                                         85

<210> SEQ ID NO 288
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
ucucaggcug ugucccucua cagggaagcg cuuucuguug ucugaaagaa aggaaagugc    60
auccuuuuag aguguuacug uuugaga                                       87

<210> SEQ ID NO 289
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
caugcuguga cccucuagag ggaagcgcuu ucuguugucu gaaagaaaag aaagugcauc    60
cuuuuagagg uuuacuguuu g                                             81

<210> SEQ ID NO 290
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
ucucagccug ugacccucua gagggaagcg cuuucuguug ucugaaagaa aagaaagugc    60
aucuuuuuag aggauuacag uuugaga                                       87

<210> SEQ ID NO 291
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ucccaugcug ugacccucca aagggaagcg cuuucuguuu guuucucuu aaacaaagug     60 ccucccuuua gaguguuacc guuuggga                                      88

<210> SEQ ID NO 292
<211> LENGTH: 84
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
ucucaugcag ucauucucca aagggagca cuuucuguuu gaaagaaaac aaagugccuc     60
cuuuuagagu guuacuguuu gaga                                          84

<210> SEQ ID NO 293
```

<211> LENGTH: 85
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 293
cucaggcugu gacccuccag agggaaguac uuucuguugu cugagagaaa agaaagugcu    60 uccccuuugga cuguuucggu uugag                                        85

<210> SEQ ID NO 294
<211> LENGTH: 61
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 294
cccucuacag ggaagcgcuu ucuguugucu gaaagaaaag aaagugcuuc cuuuuagagg    60
g                                                                   61

<210> SEQ ID NO 295
<211> LENGTH: 87
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 295
ucucaggcug ucguccucua gagggaagca cuuucuguug ucugaaagaa agaaagugc     60 uuccuuuuag aggguuaccg uuugaga                                       87

<210> SEQ ID NO 296
<211> LENGTH: 87
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 296
ucucaagcug ugagucuaca aagggaagcc cuuucuguug ucuaaaagaa agaaagugc     60 uucucuuugg uggguuacgg uuugaga                                       87

<210> SEQ ID NO 297
<211> LENGTH: 87
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 297
ucuccugcug ugacccucaa gauggaagca guuucuguug ucugaaagga agaaagugc     60 uuccuuuuug aggguuacug uuugaga                                       87

<210> SEQ ID NO 298
<211> LENGTH: 87
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 298
ucucaggcug ugacccucua aagggaagcg cuuucugugg ucagaaagaa aagcaagugc    60
uuccuuuuag aggguuaccg uuuggga                                       87

<210> SEQ ID NO 299
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
ucccaugcug ugacccucua gaggaagcac uuucuguuug uugucugaga aaaacaaag    60 ugcuucccuu uagaguguua ccguuuggga                                    90

<210> SEQ ID NO 300
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
ucccaugcug ugacccucua gaggaagcac uuucuguuug uugucugaga aaaacaaag    60 ugcuucccuu uagaguuacu guuuggga                                      88

<210> SEQ ID NO 301
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ucucaggcug ugacccucca aagggaagaa cuuucuguug ucuaaaagaa aagaacgcac    60
uucccuuuag aguguuaccg ugugaga                                       87

<210> SEQ ID NO 302
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
ucucgggcug ugacucucca aagggaagaa uuuucucuug ucuaaaagaa aagaacgcac    60
uucccuuuag aguguuaccg ugugaga                                       87

<210> SEQ ID NO 303
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ucucaggcug ugucccucua gagggaagcg cuuucuguug ucugaaagaa aagaaaaugg    60

```
uucccuuuag aguguuacgc uuugaga                                       87

<210> SEQ ID NO 304
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ucucaugcug ugacccucua gagggaagcg cuuucuguug ucugaaagaa aagaacgcgc   60
uucccuauag aggguuaccc uuugaga                                       87

<210> SEQ ID NO 305
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
cucaagcugu gacucuccag agggaugcac uuucucuuau gugaaaaaaa agaaggcgcu   60
ucccuuuaga gcguuacggu uuggg                                         85

<210> SEQ ID NO 306
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
cucaggcugu gacccucuag agggaagcac uuucuguugc uugaaagaag agaaagcgcu   60
uccuuuuaga ggauuacucu uugag                                         85

<210> SEQ ID NO 307
<211> LENGTH: 65
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gugacccucu agagggaagc acuuucuguu gaaagaaaag aacaugcauc cuuucagagg   60
guuac                                                               65

<210> SEQ ID NO 308
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
ucaggcugug acccucuuga gggaagcacu uucuguuguc ugaaagaaga gaaagugcuu   60
ccuuuuagag gcuuacuguc uga                                           83

<210> SEQ ID NO 309
```

```
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
ucucaagcug ugacugcaaa gggaagcccu uucuguuguc uaaaagaaaa gaaagugcuu    60
cccuuuggug aauuacgguu ugaga                                         85

<210> SEQ ID NO 310
<211> LENGTH: 91
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
cgacuugcuu ucucuccucc augccuugag uguaggaccg uuggcaucuu aauuacccuc    60
ccacacccaa ggcuugcaaa aaagcgagcc u                                  91

<210> SEQ ID NO 311
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
auacuugagg agaaauuauc cuuggugugu ucgcuuuauu uaugaugaau cauacaagga    60
caauuucuuu uugaguau                                                 78

<210> SEQ ID NO 312
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
cagaucucag acaucucggg gaucaucaug ucacgagaua ccagugugca cuugugacag    60
auugauaacu gaaaggucug ggagccacuc aucuuca                            97

<210> SEQ ID NO 313
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
aaccauucaa auauaccaca guuuguuuaa ccuuuugccu guuggugaa gaugccuuuc    60 aacaggugac ugguuagaca aacugugggua uauaca                            96

<210> SEQ ID NO 314
<211> LENGTH: 97
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 314
cuucauccac caguccucca ggaacaucaa ggaucuuaaa cuuugccaga gcuacaaagg     60
caaaguuuaa gauccuugaa guuccugggg gaaccau                              97

<210> SEQ ID NO 315
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
ccaguggcgc aauggauaac gcgucugacu acggaucaga agauucuagg uucgacuccu     60
ggcuggcucg cgaugucugu uuugccacac uugaccc                              97

<210> SEQ ID NO 316
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
gcuaggcgug guggcgggcg ccugugaucc caacuacuca ggaggcuggg gcagcagaau     60
cgcuugaacc cgggaggcga agguugcagu gagc                                 94

<210> SEQ ID NO 317
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
aauucagccc ugccacuggc uuaugucaug accuugggcu acucaggcug ucugcacaau     60
gagccaguug gacaggagca gugccacuca acuc                                 94

<210> SEQ ID NO 318
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uacaauccaa cgaggauucu aauuucucca cgucuuuggu aauaagguuu ggcaaagaug     60
uggaaaaauu ggaauccuca uucgauuggu uauaacca                             98

<210> SEQ ID NO 319
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
uagggugacc agccauuaug guuugccugg gacugaggaa uuugcuggga uaugucaguu     60

```
ccaggccaac caggcugguu ggucucccug aagcaac                                    97

<210> SEQ ID NO 320
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
uauuaugcca ugacauugug ucaauaugcg augaugeguu gugauggcac agcgucauca          60
cguggugacg caacaucaug acguaagacg ucacaac                                   97

<210> SEQ ID NO 321
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
gcccuagcuu gguucuaaau cccauggugc cuucuccuug ggaaaaacag agaaggcacu          60
augagauuua gaaucaaguu agg                                                  83

<210> SEQ ID NO 322
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
cucuuguuca cagccaaacu cuacuugucc uucugagugu aauuacguac augcaguagc          60
ucaggagaca agcagguuua cccuguggau gagucuga                                  98

<210> SEQ ID NO 323
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
agagaagcug acaaguacu ggucucagca gauugaggag agcaccacag uggucaucac           60
acagucugcu gagguuggag cugcugagau gacacu                                    96

<210> SEQ ID NO 324
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 324
gugagcgggc gcggcaggga ucgcgggcgg guggcggccu agggcgcgga gggcggaccg          60
ggaauggcgc gccgugcgcc gccggcguaa cugcggcgcu                                100

<210> SEQ ID NO 325
```

```
<211> LENGTH: 98
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
acgaauggcu augcacugca caacccuagg agagggugcc auucacauag acuauaauug        60
aauggcgcca cuaggguugu gcagugcaca accuacac                               98

<210> SEQ ID NO 326
<211> LENGTH: 97
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
cugcuccuuc ucccauaccc auugcauauc ggaguuguga auucucaaaa caccuccugu        60
gugcauggau uacaggaggg ugagccuugu caucgug                                97

<210> SEQ ID NO 327
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 327
uuggauguug gccuaguucu guguggaaga cuagugauuu uguuguuuuu agauaacuaa        60
aucgacaaca aaucacaguc ugccauaugg cacaggccau gccucuacag                 110

<210> SEQ ID NO 328
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 328
cuggauacag aguggaccgg cuggccccau cuggaagacu agugauuuug uuguugucuu        60
acugcgcuca acaacaaauc ccagucuacc uaauggugcc agccaucgca                 110

<210> SEQ ID NO 329
<211> LENGTH: 110
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 329
agauuagagu ggcugugguc uagugcugug uggaagacua gugauuuugu uguucugaug        60
uacuacgaca caagucaca gccggccuca uagcgcagac ucccuucgac                  110

<210> SEQ ID NO 330
<211> LENGTH: 89
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 330
cggggauggu uguuaucuuu gguuaucuag cuguaugagu ggugugggagu cuucauaaag      60 cuagauaacc gaaaguaaaa auaacccca                                         89

<210> SEQ ID NO 331
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
ggaagcgagu uguuaucuuu gguuaucuag cuguaugagu guauuggucu ucauaaagcu      60
agauaaccga aaguaaaaac uccuuca                                           87

<210> SEQ ID NO 332
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
ggaggcccgu uucucucuuu gguuaucuag cuguaugagu gccacagagc cgucauaaag      60
cuagauaacc gaaaguagaa augauucuca                                        90

<210> SEQ ID NO 333
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
cuuucuacac agguugggau cgguugcaau gcuguguuuc uguaugguau ugcacuuguc      60
ccggccuguu gaguuugg                                                     78

<210> SEQ ID NO 334
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
ucaucccugg gugggauuu guugcauuac uuguguucua auaaaguau ugcacuuguc        60 ccggccugug gaaga                                                        75

<210> SEQ ID NO 335
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335 cuggggcuc caaagugcug uucgugcagg uagugugauu acccaaccua cugcugagcu       60

```
agcacuuccc gagccccgg                                                    80
```

<210> SEQ ID NO 336
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336

```
aacacagugg gcacucaaua aaugucuguu gaauugaaau gcguuacauu caacggguau      60
uuauugagca cccacucugu g                                                81
```

<210> SEQ ID NO 337
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337

```
uggccgauuu uggcacuagc acauuuuugc uugugucucu ccgcucugag caaucaugug      60
cagugccaau augggaaa                                                    78
```

<210> SEQ ID NO 338
<211> LENGTH: 119
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 338

```
aggauucugc ucaugccagg gugagguagu aaguuguauu guuguggggu agggauauua      60
ggccccaauu agaagauaac uauacaacuu acuacuuucc cuggugugug gcauauuca     119
```

<210> SEQ ID NO 339
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339

```
cccauuggca uaaacccgua gauccgaucu uguggugaag uggaccgcac aagcucgcuu      60
cuaugggucu gugucagugu g                                                81
```

<210> SEQ ID NO 340
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340

```
ggcacccacc cguagaaccg accuugcggg gccuucgccg cacacaagcu cgugucugug      60
gguccguguc                                                             70
```